US012241066B2

(12) United States Patent
Cox et al.

(10) Patent No.: US 12,241,066 B2
(45) Date of Patent: Mar. 4, 2025

(54) GENE THERAPY OF THE FAAH PSEUDOGENE

(71) Applicant: UCL BUSINESS LTD, London (GB)

(72) Inventors: James John Cox, London (GB); Devjit Srivastava, Inverness (GB)

(73) Assignee: UCL Business Ltd., London (GB)

( * ) Notice: Subject to any disclaimer, the term of this patent is extended or adjusted under 35 U.S.C. 154(b) by 651 days.

(21) Appl. No.: 16/969,278

(22) PCT Filed: Feb. 12, 2019

(86) PCT No.: PCT/GB2019/050368
§ 371 (c)(1),
(2) Date: Aug. 12, 2020

(87) PCT Pub. No.: WO2019/158909
PCT Pub. Date: Aug. 22, 2019

(65) Prior Publication Data
US 2021/0002648 A1  Jan. 7, 2021

(30) Foreign Application Priority Data
Feb. 13, 2018  (GB) .................................. 1802326.7

(51) Int. Cl.
*C12N 9/80* (2006.01)
*C12N 9/22* (2006.01)
*C12N 15/113* (2010.01)

(52) U.S. Cl.
CPC ...... *C12N 15/1137* (2013.01); *C12N 2310/11* (2013.01); *C12N 2310/14* (2013.01); *C12N 2310/20* (2017.05)

(58) Field of Classification Search
None
See application file for complete search history.

(56) References Cited

U.S. PATENT DOCUMENTS

| 9,920,317 B2 * | 3/2018 | Lee | ..................... C12N 15/113 |
| 2007/0004741 A1 | 1/2007 | Apodaca et al. | |
| 2007/0129423 A1 | 6/2007 | Di Marzo et al. | |
| 2017/0037396 A1 * | 2/2017 | Lee | ..................... C12N 15/113 |

FOREIGN PATENT DOCUMENTS

| WO | 2012/106569 A1 | 8/2012 |
| WO | 2013/028570 A2 | 2/2013 |

OTHER PUBLICATIONS

Otrubova et al., The Discovery and Development of Inhibitors of Fatty Acid Amide Hydrolase (FAAH), Bioorganic Medicinal Chemistry Letters, 2011, 21, 4674-4685. (Year: 2011).*

Ahn K et. al, Chem Biol. Apr. 24, 2009;16(4):411-20. doi: 10.1016/j.chembiol.2009.02.013. PMID: 19389627; PMCID: PMC2692831. (Year: 2009).*

IASP, Pain Terms and Definitions, 2020, International Association for the Study of Pain, 2020, 1-10. (Year: 2020).*

Sloan, M., Thesis, Severity of Alcohol Dependence is Associated with the Fatty Acid Amide Hydrolase Pro129Thr Missense Variant, McGill University, Montreal, Canada, 2016, 1-53. (Year: 2016).*

Mallet C. et al. FAAH inhibitors in the limelight, but regrettably. Int J Clin Pharmacol Ther. Jul. 2016;54(7):498-501. doi: 10.5414/CP202687. PMID: 27191771; PMCID: PMC4941643. (Year: 2016).*

Winkler K. et al. Fatty acid amide hydrolase inhibitors confer anti-invasive and antimetastatic effects on lung cancer cells. Oncotarget. Mar. 22, 2016;7(12):15047-64. doi: 10.18632/oncotarget.7592. PMID: 26930716; PMCID: PMC4924770. (Year: 2016).*

Dincheva, I. et al. FAAH genetic variation enhances fronto-amygdala function in mouse and human. Nat Commun 6, 6395 (2015). (Year: 2015).*

Cajanus K. et al. Effect of endocannabinoid degradation on pain: role of FAAH polymorphisms in experimental and postoperative pain in women treated for breast cancer. Pain. Feb. 2016;157(2):361-369. (Year: 2016).*

Siegmund, S. et al. The Journal of Biological Chemistry, 2006, 281(15), 10431-10438; (Year: 2006).*

Li H. et al. Inhibition of fatty acid amide hydrolase activates Nrf2 signalling and induces heme oxygenase 1 transcription in breast cancer cells. Br J Pharmacol. Oct. 2013;170(3):489-505. doi: 10.1111/bph.12111. PMID: 23347118; PMCID: PMC3791989. (Year: 2013).*

Caplen NJ. et al. Specific inhibition of gene expression by small double-stranded RNAs in invertebrate and vertebrate systems. Proc Natl Acad Sci U S A. Aug. 14, 2001;98(17):9742-7. doi: 10.1073/pnas.171251798. Epub Jul. 31, 2001. PMID: 11481446; PMCID: PMC55523. (Year: 2001).*

Deutsch DG et al. The fatty acid amide hydrolase (FAAH). Prostaglandins Leukot Essent Fatty Acids. Feb.-Mar. 2002;66(2-3):201-10. doi: 10.1054/plef.2001.0358. Erratum in: Prostaglandins Leukot Essent Fatty Acids.Jan. 2003;68(1):69. PMID: 12052036. (Year: 2002).*

Sun L. et al. The CRISPR/Cas9 system for gene editing and its potential application in pain research. Transl Perioper Pain Med. 2016;1(3):22-33. PMID: 27500183; PMCID: PMC4971521 (Year: 2016).*

Sadhasivam S. et al. Novel associations between FAAH genetic variants and postoperative central opioid-related adverse effects. Pharmacogenomics J. Oct. 2015;15(5):436-42. doi: 10.1038/tpj.2014.79. Epub Jan. 6, 2015. PMID: 25558980; PMCID: PMC4492912. (Year: 2015).*

Cajanus, K., et al., "Effect of Endocannabinoid Degradation on Pain: Role of FAAH Polymorphisms in Experimental and Postoperative Pain in Women Treated for Breast Cancer," Pain 157(2):361-369, Feb. 2016.

(Continued)

Primary Examiner — Tracy Vivlemore
Assistant Examiner — Vyoma Shubham Tiwari
(74) Attorney, Agent, or Firm — Christensen O'Connor Johnson Kindness PLLC

(57) ABSTRACT

The present invention relates to analgesic treatments to reduce pain through use of an inhibitor of fatty-acid amide hydrolase pseudogene (FAAH-OUT).

3 Claims, 12 Drawing Sheets
Specification includes a Sequence Listing.

(56) References Cited

OTHER PUBLICATIONS

Chang, L., et al., "Inhibition of Fatty Acid Amide Hydrolase Produces Analgesia by Multiple Mechanisms, " British Journal of Pharmacology 148(1):102-113, May 2006.
Chiang, K.P., et al., "Reduced Cellular Expression and Activity of the P129T Mutant of Human Fatty Acid Amide Hydrolase: Evidence for a Link Betweeen Defects in the Endocannabinoid System and Problem Drug Use," Human Molecular Genetics 13(18):2113-2119, Sep. 2004.
Clapper, J.R., et al., "Anandamide Suppresses Pain Initiation Through a Peripheral Endocannabinoid Mechanism," Nature Neuroscience 13(10):1265-1270, Oct. 2010.
Cravatt, B.F., et al., "Supersensitivity to Anandamide and Enhanced Endogenous Cannabinoid Signaling in Mice Lacking Fatty Acid Amide Hydrolase," Proceedings of the National Academy of Sciences of the United States of America 98(16):9371-9376, Jul. 2001.
Dincheva, I., et al., "FAAH Genetic Variation Enhances Fronto-Amygdala Function in Mouse and Human," Nature Communications 6:6395, Mar. 2015.
Greenbaum, L., et al., "Contribution of Genetic Variants to Pain Susceptibility in Parkinson Disease," European Journal of Pain 16(9):1243-1250, Oct. 2012.
Habib, A.M., et al., "A Novel Human Pain Insensitivity Disorder Caused by a Point Mutation in ZFHX2," Brain: A Journal of Neurology 141(2):365-376, Feb. 2018.
Huggins, J.P., et al., "An Efficient Randomised, Placebo-Controlled Clinical Trial With the Irreversible Fatty Acid Amide Hydrolase-1 Inhibitor PF-04457845, Which Modulates Endocannabinoids but Fails to Induce Effective Analgesia in Patients with Pain Due to Osteoarthritis of the Knee," PAIN® 153(9):1837-1846, Sep. 2012.
Kim, H., et al., "Genetic Predictors for Acute Experimental Cold and Heat Pain Sensitivity in Humans, " Journal of Medical Genetics 43(8):e40, Aug. 2006.
Li, H., et al., "Inhibition of Fatty Acid Amide Hydrolase Activates Nrf2 Signalling and Induces Heme Oxygenase 1 Transcription in Breast Cancer Cells," British Journal of Pharmacology 170(3):489-505, Oct. 2013.
Lichtman, A.H., et al., "Mice Lacking Fatty Acid Amide Hydrolase Exhibit a Cannabinoid Receptor-Mediated Phenotypic Hypoalgesia," PAIN 109(3):319-327, Jun. 2004.
Pillarisetti, S., et al., "Pain and Beyond: Fatty Acid Amides and Fatty Acid Amide Hydrolase Inhibitors in Cardiovascular and Metabolic Diseases," Drug Discovery Today 14(23-24):1098-1111, Dec. 2009.
Prabhakar, B., et al., "Exploiting Long Noncoding RNAs as Pharmacological Targets to Modulate Epigenetic Diseases," Yale Journal of Biology and Medicine 90(1):73-86, Mar. 2017.
Salaga, M., et al., "Inhibition of Fatty Acid Amid Hydrolase (FAAH) as a Novel Therapeutic Strategy in the Treatment of Pain and Inflammatory Diseases in the Gastrointestinal Tract," European Journal of Pharmaceutical Sciences 52:173-179, Feb. 2014.
Spagnolo, P.A., et al., "FAAH Gene Variation Moderates Stress Response and Symptom Severity in Patients With Post-Traumatic Stress Disorder and Comorbid Alcohol Dependence," Alcoholism, Clinical and Experimental Research 40(11):2426-2434, Nov. 2016.
Van Esbroeck, A.C.M, et al., "Activity-Based Protein Profiling Reveals Off-Target Proteins of the FAAH Inhibitor BIA 10-2474," Science 356(6342):1084-1087, Jun. 2017.
Westbrook, I., and P. Roxby, "The Family That Doesn't Feel Pain," BBC News, Dec. 16, 2017, <http://www.bbc.co.uk/news/health-42322225> [retrieved Dec. 27, 2017], 5 pages.
Search Report mailed Sep. 28, 2018, issued in GB Application No. 1802326.7, filed Feb. 13, 2018, 1 page.
International Search Report and Written Opinion mailed Apr. 12, 2019, issued in International Application No. PCT/GB2019/050368, filed Feb. 12, 2019, 15 pages.

\* cited by examiner

A
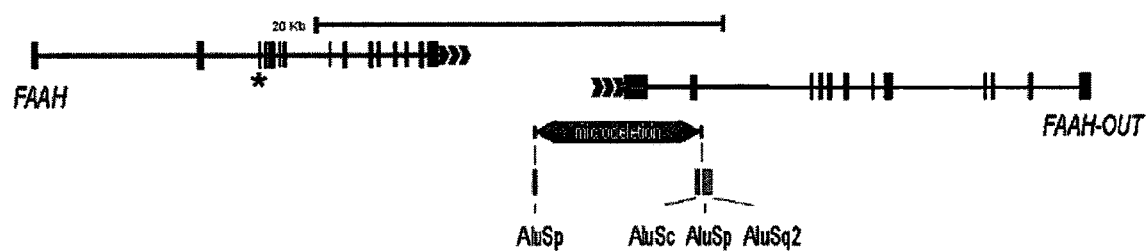
B
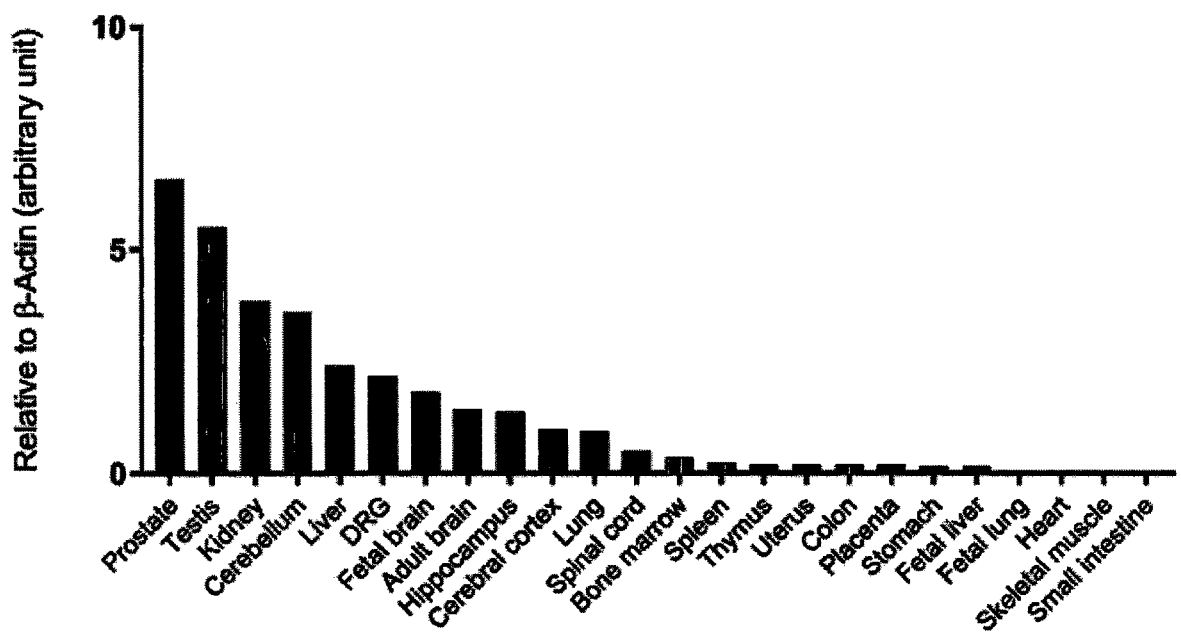
Figure 1

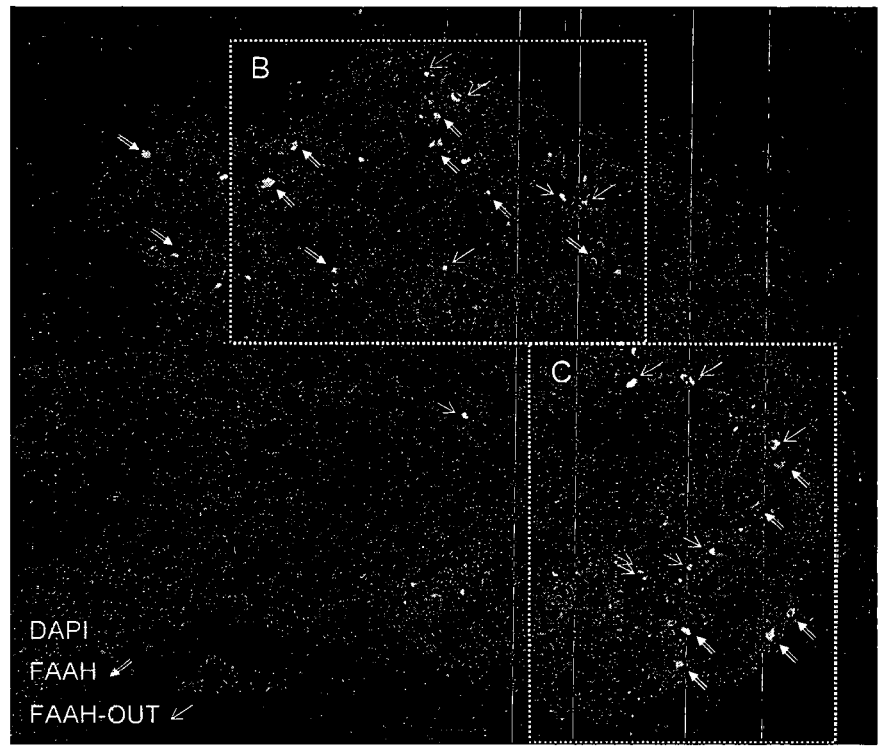
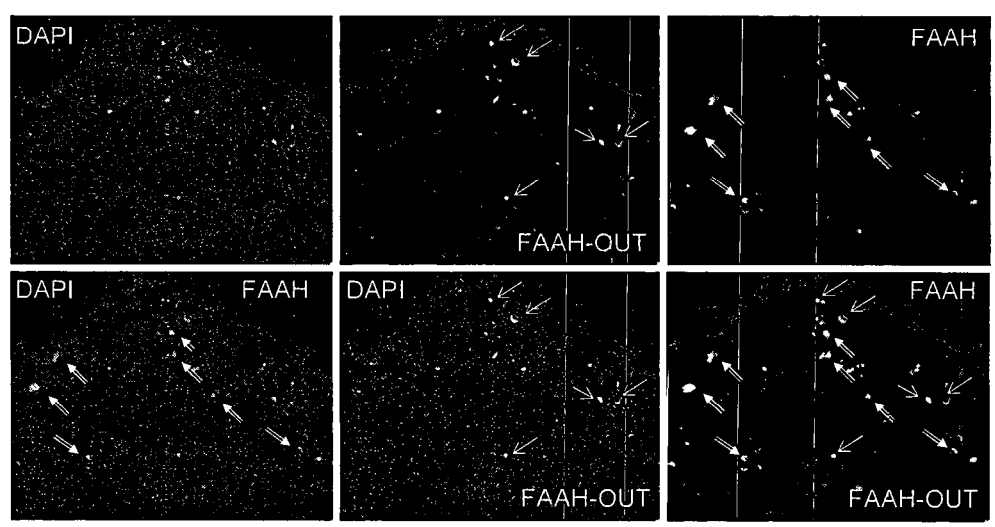
Figure 2

```
A  FAAH       476  GGCCTGCTCTATGGCGTCCCTGTGAGCCTCAAGGAGTGCTTCACCTACAAGGGCCAGGAC
                   |||||  ||||||||  |||||  ||||||||||||||  ||    |  ||  ||||||  |||
   FAAH-OUT  1363  GGCCTTCTCTATGGGGTCCCCATGAGCCTCAAGGACACCTATGACAGCATGGGCCATGAC

FAAH       536  TC--CACGC----TGGGCTTGAGCCTGAATGAAGGGGTGCCGGCGGAGTGCGACAGCGTA
                   |    || ||    ||| || |  |||| | ||||    ||| | |  ||   ||| | ||
   FAAH-OUT  1423  TGTGCATGCCGCCTGGCCTAGTTCCTGGA-GAAGCC-TGC-GACCAAG----GACGGGTC

FAAH       590  GTGGTGCATGTGCTGAAGCTGCAGGGTGCCGTGCCCTTCGTGCACACCAATGTTCCACAG
                   |   ||  |   |||||| |||  ||  || | |||  ||  ||||||   |   ||||  |
   FAAH-OUT  1477  ATTATGAAAGTGCTCAAGGCCCAAGGAGCCATCCCCTTTGTTAAGACCAACATCCCACTG

FAAH       650  TCCATGTTCAGCTATGACTGCAGTAACCCCC-TCTTTGGCCAGACCGTGAACCCATGGAA
                   |   || ||||||| ||| ||| |  ||| ||| ||||||||||    |||  ||||   |||
   FAAH-OUT  1537  ACGCTGCTCAGCTTTGAATGCGGCAACTCCCATCTATGGCCAGATGTTGAGCCCACTGAA

FAAH       709  GTCCTCCAAAAGCCCAG--GGGGCTCCTCAGGGGGTGAAGGGGCCCTCATCGGGTCTGGA
                   |    |   | |||  |   |  |||||||||||||||||||||| ||||| ||   |  |        |
   FAAH-OUT  1597  CT--TAAAGAAGACATGTGGGGGCTCCTCAGGGGGTGA-GGGGCTCTGCTGGCAGAAAGG

FAAH       767  GGCTCCCCCCTGGGCTTAGGCACTGATATCGGAGGCAGCATCCGCTTCCCCTCCTCCTTC
                   || |||   ||| |||   |  ||||||| |   || |  ||||||||  ||  ||  ||||
   FAAH-OUT  1654  GGGTCCATCCTAGGCATGGGTACTGACACAGGTGACAGCATCTGCATACCAGCCAGCTTC

FAAH       827  TGCGGCATCTGCGGCCTCAAGCCCACAGGGAACCGCCTCAGCAAGAGTGGCCTGAAGGGC
                   ||  ||     | |  ||||||  | ||||||||||||||||| |  |||   |    ||
   FAAH-OUT  1714  TGTGGTGTTTATGGCCTCTGGACCACAGGTTCCCGCCTCAGCTACACTGGAATT---GCC

FAAH       887  TGTG---TCTATGG-ACAGGAGGCAGTGCGTCTCTCCGTGG---GCCCCATGGCCCGGGA
                   | ||   || | ||  |   | ||    | ||||   | ||||   ||||||||||| |||
   FAAH-OUT  1771  TCTGCCATCAAGGGGAAAAAAATCGGTGAC---CACGGTGGCTGGCCCCATGGCCCAGGA

FAAH       940  CGTGGAGAGCCTGGCACTGTGCCTGCGAGCCCTGCTGTGCGAGGACATGTTCCGCTTGGA
                   |||||||||||||||| ||||||||||| ||||||||||| | || ||||||  |   ||||
   FAAH-OUT  1828  CGTGGAGAGCCTGGCGCTGTGCCTGCAAGCCCTGCTGAGTGAAGACATGTACCGACTGGA

FAAH      1000  CCCCACTGTGCCTCCCTTGCCCTTCAGAGAAGAGGT
                   |||||||||||||  |    |||'|||| || || |||||              68% identity
   FAAH-OUT  1888  CCCCACTGTGCTCCAGATGCCCTTTAGGGAGGAGGT FAAH      1568  CTGTACAACTGCCTGGACTTCCCTGCAGGGGTGGTGCCTGTCACCACGGTGACTGCTGAG
                   ||||||||  |||||||||| |||   ||  ||||||||||||||| |||||| |||||   ||
   FAAH-OUT  2216  CTGTACAACCTCCTGGACTTTCCCGCGGGCGTGGTGCCTGTCACTATCGTGACACTACAG FAAH      1628  GACGAGGCCCAGATGGAACATTACAGGGGCTACTTTGGGGATA--TCTGGGACAAGATGC
                   |||||||    |  |||    |||| |||  || || ||  ||  ||||  |  ||   | |
   FAAH-OUT  2276  GACGAGGAGGAACTGGCCTTCTACAAGGGGTGCTACGGAGATAGTTCTGACAAAAATTTC FAAH      1686  TGCAGAAGGGCATGAAGAAGA-GTGTGGGGCTGCCGGTGGCCGTGCAGTGTGTGGCTCTG
                   |  |||| ||   |||||  ||| ||  || || ||| ||||||||| | ||||||| ||
   FAAH-OUT  2336  T-CAGA--GGCGGTAAGAGGATCCGTCGGACTTCTGGTGACTGTGCAGTGCATTGCTTTG FAAH      1745  CCCTGGCAAGAAGAGTTGTGTCTGCGGTTCATGCGGGAGGTGGA
                   || |||  |||| |||||||||| ||||||||||||  ||||||||||
   FAAH-OUT  2393  CCATGGGAAGAGGAGCTGTGTCTCCGGTTCATGAAGGAGGTGGA
                                                                                   71% identity
```

MLSPVCFLPLLDTSCFGFLAIWSHSLTPKKLWEQHTAVEEYEQEFIAKWR
SLDLDVLLVPVLGSAFYIGSSSLASESQSYVTLYNLLDFPAGVVPVTIVT
LQDEEELAFYKGCYGDSSDKNFSEAVRGSVGLLVTVQCIALPWEEELCLR
FMKEVDTLVKNQRGPK

C

69% homology

```
FAAH      438  SRSAGKLWELQHEIEVYRKTVIAQWRALDLDVVLTPMLAPALDLNAPGRATGAVSYTMLY
               S  +   KLWE    +E Y  +   IA+WR+LDLDV+L P+L  A  + +    A+ + SY   LY
FAAH-OUT   25  SLTPKKLWEQHTAVEEYEQEFIAKWRSLDLDVLLVPVLGSAFYIGSSSLASESQSYVTLY

FAAH      498  NCLDFPAGVVPVTTVTAEDEAQMEHYRGYFGDIWDKMLQKGMKKSVGLPVAVQCVALPWQ
               N LDFPAGVVPVT VT +DE ++   Y+G +GD  DK     + ++ SVGL V VQC+ALPW+
FAAH-OUT   85  NLLDFPAGVVPVTIVTLQDEEELAFYKGCYGDSSDKNFSEAVRGSVGLLVTVQCIALPWE

FAAH      558  EELCLRFMREVERLMTPEK
               EELCLRFM+EV+ L+   ++
FAAH-OUT  145  EELCLRFMKEVDTLVKNQR
```

Figure 7 (cont)

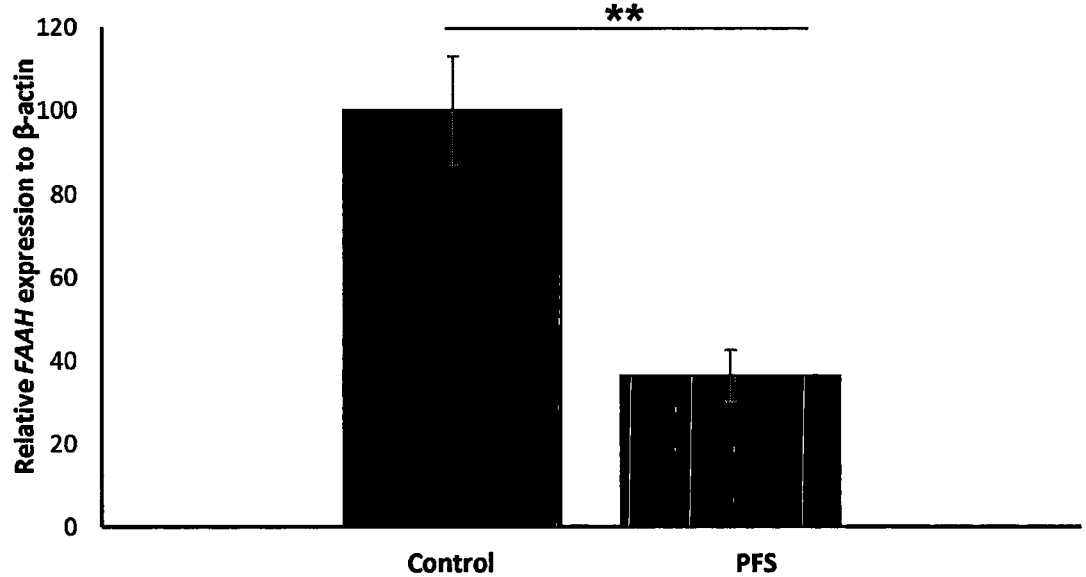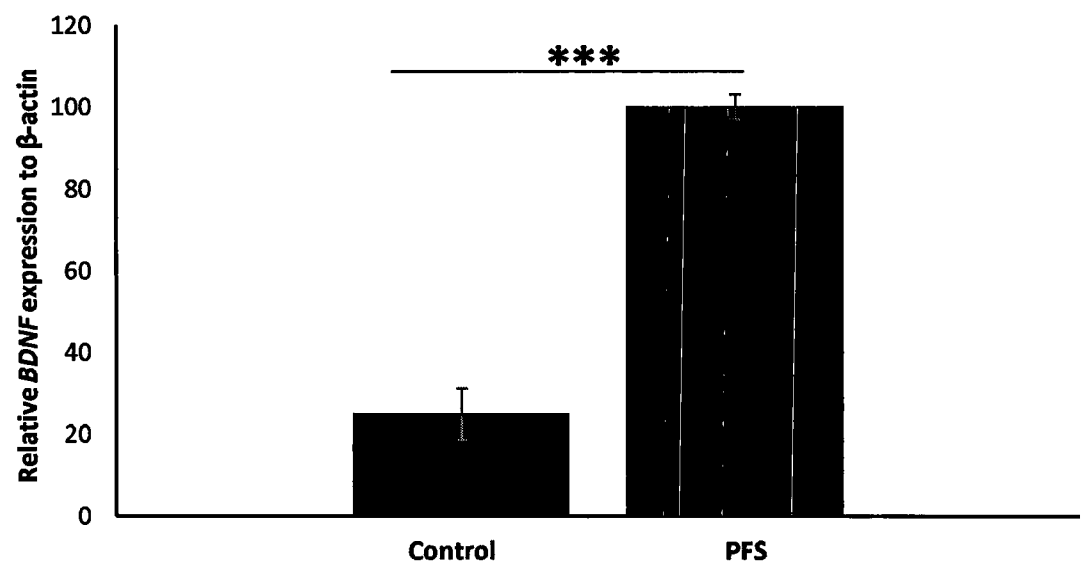
Figure 8

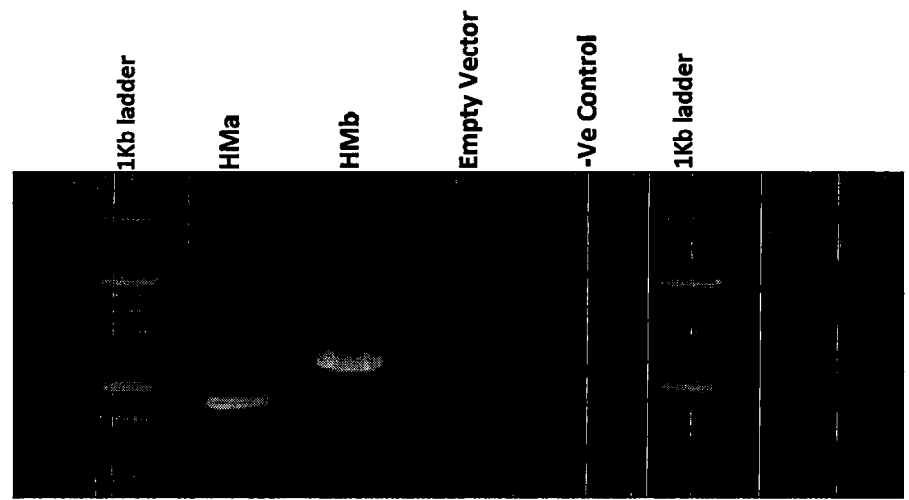
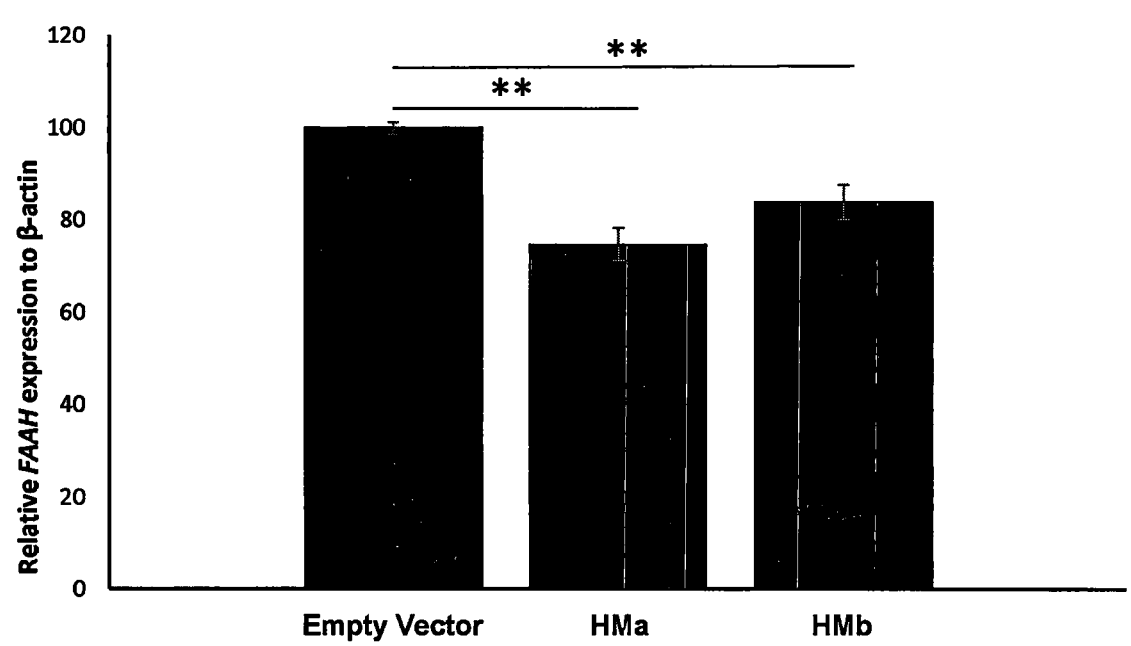
Figure 9

SEQUENCE LISTING

<160> NUMBER OF SEQ ID NOS: 41

<210> SEQ ID NO 1
<211> LENGTH: 2105
<212> TYPE: DNA
<213> ORGANISM: Homo sapiens

<400> SEQUENCE: 1

```
tccgggtttt gcggcggagc gggcgggctg cgcgtgcggc ggcttcaact gtcgcggtag        60
gcagcagcag gctgaaggga tcatggtgca gtacgagctg tgggccgcgc tgcctggcgc       120
ctccggggtc gccctggcct gctgcttcgt ggcggcggcc gtggccctgc gctggtccgg       180
gcgccggacg gcgcggggcg cggtggtccg ggcgcgacag aggcagcgag cgggcctgga       240
gaacatggac agggcggcgc agcgcttccg gctccagaac ccagacctgg actcagaggc       300
gctgctagcc ctgccccctgc ctcagctggt gcagaagtta cacagtagag agctggcccc       360
tgaggccgtg ctcttcacct atgtgggaaa ggcctgggaa gtgaacaaag ggaccaactg       420
tgtgacctcc tatctggctg actgtgagac tcagctgtct caggccccaa ggcagggcct       480
gctctatggc gtccctgtga gcctcaagga gtgcttcacc tacaagggcc aggactccac       540
gctgggcttg agcctgaatg aaggggtgcc ggcggagtgc gacagcgtag tggtgcatgt       600
gctgaagctg cagggtgccg tgcccttcgt gcacaccaat gttccacagt ccatgttcag       660
ctatgactgc agtaaccccc tctttggcca gaccgtgaac ccatggaagt cctccaaaag       720 cccaggggc tcctcagggg gtgaagggc cctcatcggg tctggaggct ccccctggg       780 cttaggcact gatatcggag gcagcatccg cttcccctcc tccttctgcg gcatctgcgg       840
cctcaagccc acagggaacc gcctcagcaa gagtggcctg aagggctgtg tctatggaca       900
ggaggcagtg cgtctctccg tgggccccat ggcccgggac gtggagagcc tggcactgtg       960
cctgcgagcc ctgctgtgcg aggacatgtt ccgcttggac cccactgtgc ctcccttgcc      1020
cttcagagaa gaggtctaca ccagctctca gcccctgcgt gtgggtact atgagactga      1080 caactatacc atgccctccc cggccatgag gcgggccgtg ctggagacca acagagcct      1140 tgaggctgcg gggcacacgc tggttccctt cttgccaagc aacataccc atgctctgga      1200 gaccctgtca acaggtgggc tcttcagtga tggtggccac accttcctac agaacttcaa      1260
aggtgatttc gtggacccct gcctggggga cctggtctca attctgaagc ttccccaatg      1320
```

| | |
|---|---:|
| gcttaaagga ctgctggcct tcctggtgaa gcctctgctg ccaaggctgt cagctttcct | 1380 |
| cagcaacatg aagtctcgtt cggctggaaa actctgggaa ctgcagcacg agatcgaggt | 1440 |
| gtaccgcaaa accgtgattg cccagtggag ggcgctggac ctggatgtgg tgctgacccc | 1500 |
| catgctggcc cctgctctgg acttgaatgc cccaggcagg gccacagggg ccgtcagcta | 1560 |
| cactatgctg tacaactgcc tggacttccc tgcaggggtg gtgcctgtca ccacggtgac | 1620 |
| tgctgaggac gaggcccaga tggaacatta caggggctac tttggggata tctgggacaa | 1680 |
| gatgctgcag aagggcatga agaagagtgt ggggctgccg gtggccgtgc agtgtgtggc | 1740 |
| tctgccctgg caagaagagt tgtgtctgcg gttcatgcgg gaggtggagc gactgatgac | 1800 |
| ccctgaaaag cagtcatcct gatggctctg gctccagagg acctgagact cacactctct | 1860 |
| gcagcccagc ctagtcaggg cacagctgcc ctgctgccac agcaaggaaa tgtcctgcat | 1920 |
| ggggcagagg cttccgtgtc ctctccccca accccctgca agaagcgccg actccctgag | 1980 |
| tctggacctc catccctgct ctggtcccct ctcttcgtcc tgatccctcc accccatgt | 2040 |
| ggcagcccat gggtatgaca taggccaagg cccaactaac agtcaagaaa cagctaaaaa | 2100 |
| aaaaa | 2105 |

<210> SEQ ID NO 2
<211> LENGTH: 2105
<212> TYPE: DNA
<213> ORGANISM: Homo sapiens

<400> SEQUENCE: 2

| | |
|---|---:|
| tccgggtttt gcggcggagc gggcgggctg cgcgtgcggc ggcttcaact gtcgcggtag | 60 |
| gcagcagcag gctgaaggga tcatggtgca gtacgagctg tgggccgcgc tgcctggcgc | 120 |
| ctccggggtc gccctggcct gctgcttcgt ggcggcggcc gtggccctgc gctggtccgg | 180 |
| gcgccggacg gcgcggggcg cggtggtccg ggcgcgacag aggcagcgag cgggcctgga | 240 |
| gaacatggac agggcggcgc agcgcttccg gctccagaac ccagacctgg actcagaggc | 300 |
| gctgctagcc ctgcccctgc tcagctggt gcagaagtta cacagtagag agctggcccc | 360 |
| tgaggccgtg ctcttcacct atgtgggaaa ggctgggaa gtgaacaaag ggaccaactg | 420 |
| tgtgacctcc tatctggctg actgtgagac tcagctgtct caggccacaa ggcagggcct | 480 |
| gctctatggc gtccctgtga gcctcaagga gtgcttcacc tacaagggcc aggactccac | 540 |
| gctgggcttg agcctgaatg aaggggtgcc ggcggagtgc gacagcgtag tggtgcatgt | 600 |
| gctgaagctg cagggtgccg tgccccttcgt gcacaccaat gttccacagt ccatgttcag | 660 |
| ctatgactgc agtaaccccc tctttggcca gaccgtgaac ccatggaagt cctccaaaag | 720 |
| cccagggggc tcctcagggg gtgaagggc cctcatcggg tctggaggct cccccctggg | 780 |
| cttaggcact gatatcggag gcagcatccg cttcccctcc tccttctgcg gcatctgcgg | 840 |
| cctcaagccc acaggaacc gcctcagcaa gagtggcctg aagggctgtg tctatggaca | 900 |
| ggaggcagtg cgtctctccg tgggccccat ggcccggac gtggagagcc tggcactgtg | 960 |
| cctgcgagcc ctgctgtgcg aggacatgtt ccgcttggac cccactgtgc ctcccttgcc | 1020 |
| cttcagagaa gaggtctaca ccagctctca gcccctgcgt gtggggtact atgagactga | 1080 |
| caactatacc atgccctccc cggccatgag gcgggccgtg ctggagacca aacagagcct | 1140 |
| tgaggctgcg gggcacacgc tggttcccctt cttgccaagc aacataccc atgtctctgga | 1200 |
| gaccctgtca acaggtgggc tcttcagtga tggtggccac accttcctac agaacttcaa | 1260 |
| aggtgatttc gtggacccct gcctggggga cctggtctca attctgaagc ttccccaatg | 1320 |

```
gcttaaagga ctgctggcct tcctggtgaa gcctctgctg ccaaggctgt cagctttcct    1380
cagcaacatg aagtctcgtt cggctggaaa actctgggaa ctgcagcacg agatcgaggt    1440
gtaccgcaaa accgtgattg cccagtggag ggcgctggac ctggatgtgg tgctgacccc    1500
catgctggcc cctgctctgg acttgaatgc cccaggcagg gccacagggg ccgtcagcta    1560
cactatgctg tacaactgcc tggacttccc tgcaggggtg gtgcctgtca ccacggtgac    1620
tgctgaggac gaggcccaga tggaacatta caggggctac tttggggata tctgggacaa    1680
gatgctgcag aagggcatga agaagagtgt ggggctgccg gtggccgtgc agtgtgtggc    1740
tctgccctgg caagaagagt tgtgtctgcg gttcatgcgg gaggtggagc gactgatgac    1800
ccctgaaaag cagtcatcct gatggctctg ctccagagg  acctgagact cacactctct    1860
gcagcccagc ctagtcaggg cacagctgcc ctgctgccac agcaaggaaa tgtcctgcat    1920
ggggcagagg cttccgtgtc ctctccccca accccctgca agaagcgccg actccctgag    1980
tctggacctc catccctgct ctggtcccct ctcttcgtcc tgatccctcc accccatgt    2040 ggcagcccat gggtatgaca taggccaagg cccaactaac agtcaagaaa cagctaaaaa    2100
aaaaa                                                                2105
```

<210> SEQ ID NO 3
<211> LENGTH: 2845
<212> TYPE: DNA
<213> ORGANISM: Homo sapiens

<400> SEQUENCE: 3

```
ggcaaaggcg ccattctcct gggtacagtg acttgcagtc tcagtgatga ccattgagat      60
ggagactgga tggaggcccc tgaggagagc agaatggttc ccacatcagg gcccctctgc     120 accactttc cagtctcctc atgtcttctc tgttcctcgt ctgggaagtc atctccctta     180 ccccccacaac tccctccac cagcaggag agtcaataga ctggggaggc tggaacccca     240
gatcagagtc atggccttgc tttggagtca agggggaagc ccagctgggc gggctggtct     300
catgtcctgg catcatctcc cctggggtgg atgcctgatg agccctgccc gctcctccag     360
gtgttctttc cttttcctctc ttcctgtccc ccagaacctc cactctaggc aaacatggcc     420
tgttcagttc cacctccatg cgtctgctta tgcggaacaa aggagctttg ggagaatcct     480
gaaggcaatg ggaaccccag gagcaacccc atccataact cctgagggtt ggagtaggga     540
atctgagggg tgggatctga gaggtaggat gggtgggagt aggatgtgac agaggtgagg     600
tcagctgccc agctgcaggc ttgggcccct tccaggctc gcctgctaaa gcctcttcct     660
ctgcatggcc cgggagatag gggttttgtc gccaggaagt ccagatgggg taagaactag     720
gaggaggttg atcactgcca cacccagggc ccgagatgtg cgtgggtgcc ctggcagcat     780
cgctgacaaa tactcctgag gaaacagcag ctggattcac acaggtcgtg caatacctaa     840
ggtggcttgg ctgtttgact ccctgatgat gctacttctg ctggccctgc tggggctgg     900 cctactgggg gcttccctgc tcacctcgtg gcatgctcca gcccggaaca agatccccag     960
ggcccagaag tggagggagg tagcactgca gaagatggag gacctggccc agtgactccg    1020
gcagcagacg gagtctcact ttgttgccca ggctggagtg cagtggcctg atctcagctc    1080
cctgcaacct ccacctcccg agttgaagca attctcttgc ctcagcctcc agagtagctg    1140
ggattacagg agccagatct ggaccccaag ccaatcctgg agctgcccct ggcagagctg    1200
gcccagcagc ttcggaccga agagctgagt ctggagagca tcctctgtag ctacttaaag    1260
```

```
caggcactga aggtgcacca ggaggtgaac tgcctgatgg atttcctggg ggaatgtgag    1320
gaggaactgc aggcattaaa gaagcttaag aagagtgaga gaggccttct ctatggggtc    1380
cccatgagcc tcaaggacac ctatgacagc atgggccatg actgtgcatg ccgcctggcc    1440
tagttcctgg agaagcctgc gaccaaggac ggggtcatta tgaaagtgct caaggcccaa    1500
ggagccatcc cctttgttaa gaccaacatc ccactgacgc tgctcagctt tgaatgcggc    1560
aactcccatc tatggccaga tgttgagccc actgaactta agaagacat gtggggctc     1620 ctcaggggt gagggctct gctggcagaa aggggtcca tcctaggcat gggtactgac      1680
acaggtgaca gcatctgcat accagccagc ttctgtggtg tttatggcct ctggaccaca    1740
ggttcccgcc tcagctacac tggaattgcc tctgccatca aggggaaaaa aatcggtgac    1800
cacggtggct ggccccatgg cccaggacgt ggagagcctg cgctgtgcc tgcaagccct     1860 gctgagtgaa gacatgtacc gactggaccc cactgtgctc cagatgccct ttagggagga    1920
ggtgaagacc ccctttccca ccccaggctg cagtgagtga aagcccaca tgctcagtcc     1980 agtttgtttc cttcccctgc tggacaccag ctgctttggc ttcttggcta tctggagcca    2040
tagcttgaca cccaagaaac tgtgggaaca gcacacagca gtggaggaat atgagcaaga    2100
gttcatagcc aagtggaggt ccctggacct ggatgtgctg ctggtgccag ttctgggctc    2160
tgccttctat ataggctctt cctccctagc atcagaaagt cagtcttatg tgaccctgta    2220
caacctcctg gactttcccg cgggcgtggt gcctgtcact atcgtgacac tacaggacga    2280
ggaggaactg gccttctaca aggggtgcta cggagatagt tctgacaaaa atttctcaga    2340
ggcggtaaga ggatccgtcg gacttctggt gactgtgcag tgcattgctt tgccatggga    2400
agaggagctg tgtctccggt tcatgaagga ggtggacacc ttggtcaaga atcagagggg    2460
gcccaagtga taggctcctg gaatggagta acagctcatg aaacacgggg ctggttgtgg    2520
tggctcatac ttgtaatccc agcagttcag gaggcagagg ctggcagatc gcttgaggcc    2580
acgagtttga gaccaacctg gcaacatag tgagaccctg cttctaaagc attttcttgg     2640
tgttactcct gtagatcctc acccaagtgt gctcctgatg cccttcctt ctcatgaata     2700 ccatgtccac cttatgtctc ctccttctgg aacccacca ggttccttt ctttgttggt      2760 ccctctgtgt gggtgctcaa tattcctcag atgggcccag gatggggagc agggtgagga    2820
gctcaataaa cattttctga ctggc                                          2845
```

<210> SEQ ID NO 4
<211> LENGTH: 1696
<212> TYPE: DNA
<213> ORGANISM: Homo sapiens

<400> SEQUENCE: 4

```
gagccagatc tggaccccaa gccaatcctg gagctgcccc tggcagagct ggcccagcag     60
cttcggaccg aagagctgag tctggagagc atcctctgta gctacttaaa gcaggcactg    120
aaggtgcacc aggaggtgaa ctgcctgatg gatttcctgg gggaatgtga ggaggaactg    180
caggcattaa agaagcttaa gaagagtgag agaggccttc tctatggggt ccccatgagc    240
ctcaaggaca cctatgacag catgggccat gactgtgcat gccgcctggc ctagttcctg    300
gagaagcctg cgaccaagga cggggtcatt atgaaagtgc tcaaggccca aggagccatc    360
ccctttgtta agaccaacat cccactgacg ctgctcagct ttgaatgcgg caactcccat    420
ctatggccag atgttgagcc cactgaactt aagaagacat gtgggggct cctcagggg      480 tgagggctc tgctggcaga aagggggtcc atcctaggca tgggtactga cacaggtgac     540
```

```
agcatctgca taccagccag cttctgtggt gtttatggcc tctggaccac aggttcccgc      600
ctcagctaca ctggaattgc ctctgccatc aaggggaaaa aaatcggtga ccacggtggc      660
tggccccatg gcccaggacg tggagagcct ggcgctgtgc ctgcaagccc tgctgagtga      720
agacatgtac cgactggacc ccactgtgct ccagatgccc tttagggagg aggtgaagac      780
cccctttccc accccaggct gcagtgagtg agaagcccac atgctcagtc cagtttgttt      840
ccttcccctg ctggacacca gctgctttgg cttcttggct atctggagcc atagcttgac      900
acccaagaaa ctgtgggaac agcacacagc agtggaggaa tatgagcaag agttcatagc      960
caagtggagg tccctggacc tggatgtgct gctggtgcca gttctgggct ctgccttcta     1020
tataggctct tcctccctag catcagaaag tcagtcttat gtgaccctgt acaacctcct     1080
ggactttccc gcgggcgtgg tgcctgtcac tatcgtgaca ctacaggacg aggaggaact     1140
ggccttctac aagggtgct acggagatag ttctgacaaa aatttctcag aggcggtaag     1200
aggatccgtc ggacttctgg tgactgtgca gtgcattgct ttgccatggg aagaggagct     1260
gtgtctccgg ttcatgaagg aggtggacac cttggtcaag aatcagaggg ggcccaagtg     1320
ataggctcct ggaatggagt aacagctcat gaaacacggg gctggttgtg gtggctcata     1380
cttgtaatcc cagcagttca ggaggcagag gctggcagat cgcttgaggc cacgagtttg     1440
agaccaacct gggcaacata gtgagaccct gcttctaaag catttcttg gtgttactcc     1500 tgtagatcct cacccaagtg tgctcctgat gccccttcct tctcatgaat accatgtcca     1560
ccttatgtct cctccttctg gaaccccacc aggttccttt tctttgttgg tccctctgtg     1620
tgggtgctca atattcctca gatgggccca ggatggggag cagggtgagg agctcaataa     1680
acattttctg actggc                                                    1696
```

<210> SEQ ID NO 5
<211> LENGTH: 26960
<212> TYPE: DNA
<213> ORGANISM: Homo sapiens

<400> SEQUENCE: 5

```
tttcgctctt gttgtgcagg ctggagtgca atggcgagat ctcagctcac tgcaacctct       60
gcctaccgga ttcaagtgat tctcctgcct cagcctcccg agtatctggg attacaggcg      120
tgtgccacca tgcccagcta attttgtatt tttagtagag atgggatttc tccatgttag      180
tcaggctggt cttgaactcc tgacctcagg tgatctgcct gccttggcct cccaaagtgc      240
tgggattaca ggcgtgagcc actgtgcccg gcctgccaca gcttttttgcc tcgcttccct      300 gggctccaga ctggacatct ccaacaatct ttcacatggc agttaggcaa tctcatgctt      360
aaaatctttg gactcacttg tgccaagtcc agaagcttg ttatgacctg caaggccatg      420
attaacctga ccctgcagct ggcccctgcg gcctcatctc ctgcccttcc tcagtgctca      480
cagcccggcc acgtggcctg caggtaatgt tcagaacacc gagtgatctc ccgcctccac      540 gcccttttgct cttggtgctt gctgtgcctg gagtgttgtt cctggggtct ccacctaaag      600
accacctact cgtccaaggt gagggcaatt gctcttccaa ctctgtcagg ctgtgttgaa      660
agagcttctt tgtgcttctg cacgtggtca aaagcaaggt ctgtgtatta atagaaccca      720
acatctgtta ggctgtggag ttgaataccc attatctcat tggaaagtg gcattacta      780 tttccattta aaaaatttat ttatttattt attttttgag acagagtctc tctctgtcgc      840
ccaggctgga gttcaatggc acgatcttgg ctcactgcaa cctctgtctc tgggttcaag      900
```

```
tgattctcct gcctcagcct cccaagtagc tgggattaca ggcgcctgcc actgtgcccg      960
gctatgtttt gtatttgtag tagagatggg gtttcaccac gttggccagg ctggtttcga     1020
actcccgacc tcaggtggtc cacctgcctt ggccaaagtg ctgggattac aggcgtgagc     1080
cactgcgcct ggcctttttt cttttctttt tctttgagat ggcgtcttcc tctgccaccc     1140
aggctggagt gcagtggtgc gatctcagct cactgcagcc tccgcctcct ggcttcaagc     1200
gattttcctg cctcagactc ccgagtatag ctgggactcc aggcgcctgc caccatgcct     1260
ggctatgttt tgtatttgtg gtagagatgg ggtttcacta tgttggccag gctggtcctc     1320
aactcctgat ctcaagtgat ccgcccgcct tggcctccca aagtgctgag attacaggtg     1380
tgagctaccg tgtctggccc tattatttcc attttataca taaggaaact gaagttcaga     1440
ggggattgct gacttgttga aggctgatca ttatgggtta cagagaagac ttgaaaccca     1500
cacgctcaac tctaaactta ctgtgacttc ctcatttgta caatcatcac aagaacatgc     1560
attcaacatt cttcggacac cagcctctgt gctaggcgac cacaaacactt tgaagacaga    1620 agcagtcctg tgtactgtgc acctctgcca atatctgttt acaggagata gctgccatgt     1680
ccctgtccac cctcccttt ctcctctggc gattgcgata ttggagtttt aggacacagc      1740
cagagcactt gtcatttgtt cctgttggac accattttta ggattatccc aagagctctg     1800 gctgttctg ctcttcctcc caacatgtgc ttatccacaa atctgagcac tggacctctg      1860
caacttcatc caagtcaccc ataaacctat ggatcacagc agaccaagga aagggcgtga     1920 cctacacccct taacagacag acacataacc gagttttgag cttcccagcc agatgtatct    1980
ttagttcaca tttctctggc tgggcttagc tgggccctcc caagtttcct acacatagat     2040
ttggggtggc ggccctgggc acctcaggaa ggtgaagcca cttgggatcg ggctgtgtat     2100
gctcagcacc cagcatggtg cctggtactc agtgggtacc cagagaaggc ttgttgaatg     2160
gagcaatggg tgacttgtta ttagggaacc cattttggtc cattctgatt acttcctctt     2220
ctcacctcca atagggaatt ttccaatcag tccctgaccc tttgctcctt tcacatttat     2280
tgtatctacc tccatgatct tttttttttt tttttttgag atggagtctt gcactgttgc     2340
ccaggctgga gtgcaatggc aggatctcgg cttactgcaa cctctgcctc ctgggttcaa     2400
gcgattttcc tgcctcagcc tccggagtag ctgggattat aggcgcctgc caccacgccc     2460
agctaatttt ttgtatttat agtagagatg gggtttcact atgttggcta ggctggtctc     2520
gaactcttga cctcaggcaa tccacctgcc tcagcctccc aaaatgctag gagccatgat     2580
cttgattagt gcccatgagg acaaataatt cccagtctac attcaaccta tagctttctc     2640
ctggtctgta gatcctcatc tatccacttc tctcatcctc ttaactcctt catctctctc     2700
aggctgttga aagagcttct ttgtgcttct gcacttggta gaaagcaggg actgtgtctt     2760
aatagaatcc aacatccgtt aggctgtgga gttgaaccca ttatctcctt tgtaaaatgg     2820
gcttattatt tccatttcat atataaggaa actgaaattc agagagggtt gctctctgaa     2880
caacaatgga gggttgctcc ctccattcat cctcccatcc atgcaataaa atatattgaat    2940 tcttcccaca gtatgttcag ggtaaccaat cagaaatagt ccctgcctga atggagcttc     3000
cattctacca ggaaacagac atcaaatgta gaattacaca gaaacactcg ttagaagtgc     3060
aatcaagcag aagccctggg tattatgaga ataaaccacg tgggatctga tccagcctga    3120
gatgtgtgta tgtgtgtgtc agggaatgct tcctggagga agtaacattg aagctgaaaa     3180
ctgcattgtc acctgagcca aggaatgagt gtgtttcaag gagggtgaag ctgacaactc     3240
taaatgctgc tgatttactc ttgaggagat cactgggatg atataggcac aagccagact     3300
```

```
ttgttgggtg ggggagtgag tgaaaggtga agaagtaaag gcagcccgtg tagaaaactg    3360
gaaaagttca ggaagcggac aaaagacgtg gtagtagtta gggagggtgt aaatctgagg    3420
gaatcatccc tcatccccca agataggaga gacttagcat gttaaatgct gctaggaaag    3480
agctagcagc aacgcacaga ggggggaagt caaggtagga atggagggct caacctgcca    3540
tcatttcttc actgaagaga taccattgaa cacataccat gtgccaggtg ttttgaaaaa    3600
ggctgacaag gtctatgctc ccccaacccc ccagctaatt ttttgcatt ttctgtagag     3660 atggggtctt gccgtgttgt ccaggttgag ctcaaactcc tgagctcaat tgatccgccc    3720
aaagtgctgg gattacaggc gtgagccact gtgcctggcc tcgtctgtgc ttttacggag    3780
cttattttct agggagggag gcaggaggtg agttacagat caacaagaaa acttcagcta    3840
atgataagtg taatgatgag ataaaatgag gtatgtggta acggaagggt gtaacccagg    3900
aaaaggtgag gtcacgaggc ctagagtgct gtgccgtggg atgtggtgcg ggtgacaagt    3960
ggcctggggg agctgaagat atgggggaga gctggagttc atgaaggtgg agtgggggct    4020
atggaagaaa atggtcagaa agaggcaga aggacagagg agggctggtc tggaggcccc      4080
agggagatga cagagtgtta cagagtgggc aacttcaggg tcacccttag tcaactgctg    4140
acctcgcatc tgttccttta gaccctcggg tactcagact caacattacc aaccatgaat    4200
tcagttcctt cccaccctaa cctgctgctg ccctggcttc ctggtctgga gggcaaaggc    4260
gccattctcc tgggtacagt gacttgcagt ctcagtgatg accattgaga tggagactgg    4320
atggaggccc ctgaggagag cagaatggtt cccacatcag ggcccctctg caccactttt    4380
ccagtctcct catgtcttct ctgttcctcg tctgggaagt catctcctt accccacaa      4440 ctcccctcca ccagcaggga gagtcaatag actggggagg ctggaacccc ggatcagagt    4500
catggccttg ctttggagtc aagggggaag cccagctggg cgggctggtc tcatgtcctg    4560
gcatcatctc ccctggggtg gatgcctgat gagccctgcc cgctcctcca ggtgttcttt    4620
cctttcctct cttcctgtcc cccagaacct ccactctagg caaacatggc ctgttcagtt    4680
ccacctccat gcgtctgctt atgcggaaca aaggagcttt gggagaatcc tgaaggcaat    4740
gggaacccca ggagcaaccc catccataac tcctgagggt tggagtaggg aatctgaggg    4800
gtgggatctg agaggtagga tgggtgggag taggatgtga cagaggtgag gtcagctgcc    4860
cagctgcagg cttgggccct tcttcaggct cgcctgctaa agcctcttcc tctgcatggc    4920
ccgggagata ggggttttgt cgccaggaag tccagatggg gtaagaacta ggaggaggtt    4980
gatcactgcc acacccaggg cccgagatgt gcgtgggtgc cctggcagca tcgctgacaa    5040
atactcctga ggaaacagca gctggattca cacaggtcgt gcaataccta aggtggcttg    5100
gctgtttgac tccctgatga tgctacttct gctggccctg ctggggctg gcctactggg      5160 ggcttccctg ctcacctcgt ggcatgctcc agcccggaac aagatcccca gggcccagaa    5220
gtggagggag gtagcactgc agaagatgga ggacctggcc cagtgactcc ggcagcaggt    5280
gagtcgacac gggtcccgga ggcccccagc cacagggggc cttggccctc aatcccaaca    5340
ggaggactac acctcaggat gcccctcccg tccatgaccc cagcccccgc agacacaggg    5400
agcaggtggg cacttcccca cccccagttc tcccccatg ccagctctgt gtgtggttgt      5460
cagttctcct ccatccccgg cctttgagac cctggagatt gggggcagtg tattctttct    5520
ctgttctccc agcacttggc acgtggctca gtaacatggg aggtgcccac ttagggtatt    5580
tgcggaaata agataaactg atggaggcca ttggaggagg gaggctcgat ctcttttagc    5640
```

```
ccctgagcac tccaaaatcc cccaagacag gaaccctagt ctacctgtcc cctcctacct   5700
ccacccatt  cagctctgaa aacacttgct gagccctgat aagtgcagag catggggggc    5760
tggggatggg gtctcccagg aagctgcagg tcttcagagg cagctttggc aactcggagt   5820
gggggtattt cactgggata gcctctgtgg ctggctgggc tgagactggc aggcgaagtg   5880
gctgagccat agatgtatca gcaaagcctg ccccaggtgg cagagagaag ggcgggaagg   5940
agggacatgg agacaaacat agactgagcc tgggatttgc tgtgtggcct ggaggatgtg   6000
acaacccgtc tctgggcctt ggactcccca gctgtctgag gggggatggg ctcatggtct   6060
ctcggggtct ccagctttgg ttgatgatgg tggactcagt ctgggagccc ggaggtaggg   6120
gctggggcta gtgcctgagg tgctgttccc atgctttgga gttcctgagt gtcctctgct   6180
gtcccctgga tggtgattga tggccccaat gggcagcttc tctgtctgag ttgctgcagt   6240
tgctgagtat gtgtattaat attaattagg ctaattagt  tggataaatc aatctgcccc   6300
cagagagcag ctgcccctcc ctggttgatg aggaggaagt ctgggctaat ggttgcagt    6360
ggtgaatggg catgatggag gcgtcctgtg tgcgtgtgga ggcccatct  gtgtgcggtg   6420
gtgggtatag cttcctttac tgcggacgag ggcctgcttt cttgtgcctc ctgctggcat   6480
ttcattgtgt tgtggttggt tgtgtgtctg gtctggctgt gtggttatgt gcctggctgg   6540
gtgtgcatgt gttgggttat tggttggagt gtgtacatct agctatgtgt ggctggtgtg   6600
ggtctgaatg tctggtagag agtgtttgtg tgtggttgtg tgtctgatgt gtgggggcag   6660
ctggtttggt atgtgtctgg gcatctggtt ggtgaacatg tggatgtctg ggctgttggg   6720
ctggggacct ggaggggta  tatgtctgga tggctggagg agtggaagag gttttgggt    6780
gaggtcactc atggtgtctc cagcctccca ttgtggtttc aggcttcttg gctctcagca   6840
ccttgctgtc tccccaacaa gctatacagg tctgtcctgg gcaccttctc agtcatgtca   6900
ccctctctct gccagtgaca acctcgagac ctcaggtgtc caccttatg  tcccggggag   6960
gtgcaaggct gggacacagg tcaaaccctc acaggctcag caaacaaatt caattctgct   7020
gagtttagta aaatttccca gggaatttct ccaggtcttg ccctgtgctg agctctgggg   7080
acacattcat tataaagatg aatctgaccc ctgactcaca cttgtgctaa aaatgttccc   7140
aacctgggag gggcgtggtg gagatagagc tgtgcagact atgcagggca gcagcacggc   7200
agagtgtggt gaggccagat gcccacagaa ctggtgactt ggcaggaggg tggctggtct   7260
gtctggagag gatcatgttg ggagggctcc ccagacgggt ggtgagtgag ctgaacctca   7320
tggcacctgt aggactttc  tgaaaggaga aacgagaaag gcagtaccag ggagggagaa   7380
gccccagatg aggcagtgtt tctgtagaac gtatagaaaa taatattcct aggacccatt   7440
gggtaaatgg accagctgct catggctgga actgctcaag ctactcatgg ccaggaagct   7500
ctgctcacct caggcagagc ctggccacct tgagagttga cggtttttat gatactaaac   7560
atttaaccac cacattggaa ttttttttt  tttcagacgg agtctcactt tgttgcccag   7620
gctggagtgc agtggcctga tctcagctcc ctgcaacctc cacctcccga gttgaagcaa   7680
ttctcttgcc tcagcctcca gagtagctgg gattacaggc aagtcccacc aagcccaact   7740
aattttgta  ttttttcgtag acatggggtt tcaccatgtt ggccaggatg gtcttgatct   7800
cttgacctcg tgatcctccc accttggcct cccaaagtgc tgggattaca ggcgtgagcc   7860
accgtgcccg gccataaata ttaataatac attgattcac taaaaacttt aaattacatt   7920
tttttgttt  ttcaaactag gctggaggca gcacccgag  tacagagaag gctggatgtc   7980
cgtggggctg tgggatggag ctggagggaa gggttagctc caaactaaat tacatattaa   8040
```

```
aaagtgatat aacttgaggc tcaattttc atcaaattat tcaaataatt tgttgatttt    8100 tagcttttt ttttttttt tggagacgga gtttcgctct tgttgcccag gctggagtgc    8160
aatggcatga tctcggctca ccgcaacctc cgcctcccag attcaagcaa ttctcctatc    8220
tcagcctccc aagtagctgg gattacaggc atgcaccacc acgcccagct aattttgtat    8280
ttttagtaga gatggggttt ctccatgttg aggctggtct cgaactcctg acctcaggtg    8340
atctgcccac ctcggcctcc caaagtgctg gattacagg cgtaagtcac cgcgcccggc    8400 ctttttctc tttctttttt tttttttga cacagagttt tgctcttgtt gctcatgctg    8460
gagtgcaatg gcgcaatctt ggctcactgc aatctccgcc tcccgggttc aagtgattct    8520
cctgcctcag cctcctaggt agctgggatt acaggcgctc accaccatgc ccggctaaat    8580
tttttttttt ttggatttg agtagaaacg gggtttcacc atgttagtct cgaactcctg    8640
accacaggtg atccgcccgc tttggcctcc caaagtgctg ggattacaga tgctcgccac    8700
tgcgcctggc taatttgttg attttttagaa tttgttgtga ggatcctgtg atgtggctat    8760
catcttttga aagttgtccc tgtctttcaa agcgctcctg atacattgga gtcattaggt    8820
cacttgcagt ctgattaagg agagtctttc tcttaacgtt agtgatattg ttccgtgggt    8880
ggagtcctct ctcagctttt gctgaaccag tagcaattac actcacaatt ttctagcttt    8940
tctaatacag tgttagattt catgtagtta agcatctctg ttgtcaatta agtaataaac    9000
attgttatta gaatgtcatt aacactaatt agaagttgtc tagcatggca gctaagagtg    9060
tggcttctgt tgttgggctg gctgtttgaa tcctgactct tgacttttt tattttgttt    9120 gattttatca ttttacattg tcttgaactc ctggcctcaa gcaatcctcc cacctcagac    9180
tcccaaagtg ctagcattac aggcgtgagc caccaaaccc agcaaacact tacacttaaa    9240
tgactactct gtatcttaac ttcttcatct ctacaatggt atgatgattg taatgatagc    9300
actcaaacaa gttaataaat gtttacagtg gtgcctggta cacagcaaac accatacaga    9360
tgctcctcga cttaccgtgg ggcttcatcc tgataaactc atcctaaatt gaaaatattg    9420
taagttgaaa atgcacttaa tacatacaac ccacccaaca tcatagctta gcctagcctt    9480
tttgaaacat gctcagaaca cttacattag cccacggttg ggcaaaatca cctggcaaca    9540
cagtaccctg tagaggattc actgtttccc ttgtgatttt gtggctgact gggagctagt    9600
cttgctggca ctgtccagta tcgagaatca agagagtatc ttactgcttt ttttttttt    9660 tttcttttt ttgagacgga gtctggctct gtctcccagg ctggagtgca gtggcgcagt    9720
ctcagctcac tgcaacctct gcctcccagg ttcaagagat tctcctgcct catcctcccg    9780
agtagctggg attacaggtg tgcgccacca cgcccggcta acttttgtat ttttagtaga    9840
gacagggttt tgccatgttg gccaggctgg tcttgaactc ctgacctcag gtgatccccc    9900
caccttggcc tcccaaagtg ctggaattac aggcgtgagc aaacgtgccc ggccttttac   9960
tgctttccga tgaatgtata tcaatcgctt ttgcgctacc gtaaagtcaa agattgtaag   10020
ttgaaccatg gtaagttggg actgtctgta caagtgatag ttctcacttt aggaatgaag   10080
ctactgttgt tgtccatggt gagtgggtat tttgggtgag cagaatatgt tctattagat   10140
ggatgtgaca ttcgtcctc ccaggtccct ggagcgcctg ctgtggtctc agcagccacc   10200
tgcagaggtc acattagcca ctcccccaacc cctgcccttg cctgctcttc ccacctctcc   10260
ccaagctccc tgagagtcaa agtgcccccag aggctgccat tccacaaat ggccatgcaa   10320 ggacagctgc aggggaaggc tagcctcagg ggcccagagg gacacattgg gcacttgccc   10380
```

```
atgggctgcc accaggggtg ttgtctctcc aggtagaaat atagaaatgg gggctggtgt    10440
gcagctgctg atgtctctgg ggtgcgtctg gggacctgtg agtgcaggga ggtccctggc    10500
ggggcccgct agggctcctt agggttggag ggcgcagggc aagggatgaa cccaggctgg    10560
ccctccacag tccctatgcc tagagggtcc ctgctgggct gagcattaac tttacttgct    10620
ggactgtgta gagagggtgg agtcctgggg aggggctagg acaactaggg tggtgggggg    10680
tgcccagcag agcagctttt tgccaagtga ctcagaaatg tttcagtagt ttagccactg    10740
gcatggctgt ggtggtgcat cctggctgaa tgctagccct gtccaaggga tctgtgtctg    10800
gaccctcctg agagtccctg tggcacacca gctggggagc tctgagctga ggcacagcaa    10860
ggaaagggac tggacagtgt ggctggagca gcatgcatgg gagaggctga gagagacagg    10920
cccactggac ccaagcaggg aaagaccctg gtccagtgcc tggcacctta aaaagcctcc    10980
cttccacaag atgccccaag agccaggaga gggtagtggt taaggtatgg acggcctggg    11040
tttaagccca ggctcccctg tcctctgacc ttgggcaaga gagttagtct ctccgggtct    11100
cagttgcctt cactggggaa atggaaacag taataacagc acttagccaa gggttttttgt   11160 gaggatttaa tgaaacggtg cagtaaaggg cttgagaggg tttccagccc cacagtgata    11220
ctctgaatac ttggtcaatg ggaattgtgt acatcgaagc aagaacccat gttacacatt    11280
tacagtgaag gctttgcaag tggtgctggt gagaatggtg ctgcaatgtt atcctgaggg    11340
ctactgggac ctattttcag agtgggcctt ataagatctt aaaaggattg cccaggctgc    11400
agtgaagagg ctgagttgga ggagtggagg ccaagccgtg gaggccaagc caaggaggcc    11460
agtgaggagg ccaatgagcc aacagagaga ggtccttagg caggcaagag gcctgagggt    11520
ccgaggtggg agatacgaag gagtagaacc acctgcaggc agtgtgtgca gttaagaatg    11580
tggtcactgg tgttggactg cctgggtcca gctctgccac ttactggctg tgtatcctcg    11640
ggcaaagagg aggaggtctc tgtgcctcag tgttgtcttc tgctgtgaaa tgagaaaacg    11700
atgtgaccta cctcttaggg ttgttacaat taaaaattgt aaattttttaa tttacaattt    11760 tcttggagac agggtctcat gtcatccagg ctggaatgca gcagtgagat catagctcac    11820
tgcagcctca aactcctggc ttcaagaaat cctcccacct cggccttcca aaattcatta    11880
taggcaatga ctgattatat gcaaagtgtc tggaataggg cctggcacta ttaagtgtta    11940
gaacacatcc tagtgtgatt atgttagcta gtgtaactat tatcagaact tgggtgtgag    12000
ggaggaccta ggatgattct gaggtttgtt gctttggtga catgcatgtc atcaattggg    12060
aatttcaaga agaacagatt tggctgaaag aaggtgagtc ctggggagtc tgtgtatatg    12120
tgggtaggta aaggggtctg agtcctggcg gaagagaggc ctaggttaga gaaacaggtg    12180
gcctgcttat ccttggggtg cacctggctg ccgaggtcac ccatggagag tgggcaggca    12240
gggagagaaa aggtcatgcc ctgaggaaca ccaacatttc aggcaactga aaggagcca    12300 cctgagggtg ggaggaggcc agcagagttg ggggcataga gagctttggg agggagagtg    12360
tcagacgctg ctgaggagag tgagatgaag actaacccga atccataaga tttagtaacc    12420
gagaagtctt gatgcccttg gtgagaaggg gcccagtgca gaggggagga cagatgtcag    12480
actggttgct ttgaggaatg aaagaagaca gactggagcc aggggatcct aacctccaag    12540
ggaaatttat ttgtctccac cttcccccac ctccaggacc aagaaaagcc cacttcttgc    12600
ccaacccata ctccagcttg gaggcatcgg ggtcttaacc agagctgagg ggggcaagag    12660
gaagagaact ttgcccttcct gagtgcctgc tgtgtgctag acctttgtca tgtcacactt    12720
gcccagggcg gcagtcctga gggcctggta tcagacctcc cctcatatcc tgaaggacgg    12780
```

```
ggctcagagc agttgagggg ctgactcagg atggactcct agtccttccc tctctgagga   12840
gacctaggcc atgggaggag cagagaacca cctccagtta cccagctgac caagggcgcg   12900
gccaagatgg tgctaactct cttgccaccc atgctggact cctgcctccc taaagtcagc   12960
tcagcagggg gaggactggg tagggaggag aggtgggatg cctgggatgc ccctgaaggc   13020
cagccaccca gggctgaact tcacttccat aacctccagt ctcatgatgt cacatgtgga   13080
gtcaccccca ctccagttgt gacccttctg aagagcagca tgaaggggca ggcccttctc   13140
cacgccaggc cctgggctgg ccactggggg cagaggcaga ggagaacatc gtgcccttgg   13200
agggttttca tgacaacctg gagacacaac agatgttttt agtgctaagc atgagtgccg   13260
gaacatgtac cgagagacat gggcgtgtgt gcagctgtgc atagggagt ctggggtgtg   13320
atgtggagtg tgtgggagtg ggccttagcg ggtccatctt ggatatctgc ctactccatc   13380
tcatttctgc aggagccaga tctggacccc aagccaatcc tggagctgcc cctggcagag   13440
ctggcccagc agcttcggac cgaagagctg agtctggaga gcatcctctg tagctactta   13500
aagcaggtgg tggccagggc acaggatcca agcccggggc tctgggctgg agtggggat   13560
gtcacttgtc attgttttac tcagaggagc tgaggggcag gtgtaactct gccactgact   13620
tgggaggtgg cacatgccac agttacctca gggtggcagg aggggctggg gcaaccgagt   13680
gccctgcttt ggtcctggcc tcacctgggg ctgttgtctg ctgtcttcac tgttgtgcag   13740
gcactgaagg tgcaccagga ggtgaactgc ctgatggatt cctgggggga atgtgaggag   13800
gaactgcagg cattaaagaa gcttaagaag agtgagagag gccttctcta tgggtcccc   13860
atgagcctca aggacaccta tgacagcatg gtgagcctgg ggtgtacatg cacacgaatg   13920
tgcatatgca cgcttgtgcc accagcctgg agcttggtgt gtgacactgg ggggctcagt   13980
gtgtgacaat gggtgagtca tttaaaactg cacagctacg aagcggcaaa ctgaggttta   14040
tacccagaat ttgggttcca aaccccaaat tctcagccac cacactcttt tgccatccgt   14100
gaagtgctgc gcttgtgtcc ccaggggtgt gagagtgtgt gtgaggggg tggaatgggg   14160
ctgaaaatca gccagctggc tggttccacc ctgaccccca tggctggagg caatgttcct   14220
tccctgcagg gccatgactg tgcatgccgc ctggcctagt tcctggagaa gcctgcgacc   14280
aaggacgggg tcattatgaa agtgctcaag gcccaaggag ccatccccct tgttaagacc   14340
aacatcccac tgacgctgct caggtctctg aagcgggcta gctggggtcg ggggctgggc   14400
taagcccagg gctgaaacag ctctttgaag tcctgattca gggcagaggg tgaggagggg   14460
gctagtcata cagacttcaa agaccagggt tcttgggcca gccccttctg tccccggggc   14520
tgagtttctt tatcacagaa catgtggatg gactccacag tctgtaaggg cccttcgggc   14580
tccaaggttc tgtaaagcta cactctttt ctatcccagt ttctctctca aattgttcta   14640
tttctaccca ggcttctctc tttgattgtt ctccccatcg cttattctct cccttctcta   14700
ctcagcctgt agtgcatctg tgtttcgtga ggaacatgtt ctcagttctg atggcagagc   14760
tgtgggctct ttggtcctga tattaggagt catggctggt gtctgatctt ggtctttctt   14820
gcagcagcag cccctcaccc cagctggaag ggagcccagg aagcctcagc cttagggagg   14880
agctcatgga gcccaggaag ccctgggtt gactctggag ggtggttggc ccccatatgg   14940
ggagaggtct gccgagtgag gctttcaccc tcagctcatt ttcttctgct tcccttagct   15000
ttgaatgcgg caactcccat ctatggccag atgttgagcc cactgaactt aaagaagaca   15060
tgtgggggct cctcaggggg tgaggggctc tgctggcaga aaggggtcc atcctaggca   15120
```

```
tgggtactga cacaggtgac agcatctgca taccagccag cttctgtggt gtttatggcc   15180
tctggaccac aggttcccgc ctcaggtact cattgatggt ggtggtgggg tgggctcgga   15240
cctgcctaag ggaactagag ggtggggaag tagaggggtc tgctcctccc atcaactttc   15300
atctacccaa ctcagtacta ggggaagtgg gtaggagggc ttcaaataac tcctgcagta   15360
gccatgctaa acataccata ttttccagg tggcagtaga atagaccttc cactcattaa    15420
ctcatcagct cattaattca ttaatctata cagctatcca tccacatacc ccttctctta   15480
ctcatcaatc tgtccatgta tctatctgtc cttcatccat tcaatcaccc acatggtcat   15540
catctcagtc tctatccatc aatcaatttt accattcatc cactatttat ttaaaagatt   15600
tctattgact atttactgtg tcagacacaa cagctccttg ggtactagct acttgggtta   15660
cttcggtgaa caaagagac aaatatctca gcccttgaaa aacttacaca tactcttcct    15720
tccaaccatt tatccatcca tctttccatc catccatttg tgtatccatc catcaatcca   15780
catttgtatc tctccatcca tccatccatc catccatcca tccatccatc catccatcca   15840
tccatccgtt catcgtatat gcatgcatgc atccacccat ctctcaaccc ctctctgtgt   15900
acccacacca tggcccctat tctggggaca tagaccactc ttggacccag cccctgcccc   15960
tgctgtgctc ttagacacac aaatgagtta gtcagaaagt gatcaggtct gtaagagagg   16020
gtcaaagctt acaagaggaa gctgacattt tctttaacag agatttatta aaagcttata   16080
ctcttgactt tcagaggcag ggcaagggaa gggaaggatt cctggaggag gcagcatttg   16140
agcgtggttt tgagggccag acatgccaag atgatgtggc gtctagaagg ctgtaagatt   16200
gtttgtaagc ggctgacttt gcctgcagca atatgcacgt gtggaagggc tagaagggga   16260
agccatggag agttagagtc ttgaaaagca gtcaaagaga tcagactatg ctgtgggcag   16320
cagagggtca gggaatgttg aagcagctcc tattttgtg ggctgcgccc tgggggagca    16380
catcgcctgg gtgctcaagc tcctagcac ccaggcccct cccttcacat gctgagctgg    16440
gctctgggtc ggaatgtttt gcagctacac tggaattgcc tctgccatca agggaaaaa    16500 aatcgggtaa gtcctggtct gtgcctgtgg ccaccccatt taaagatgaa actgccagtc   16560
tttctcccaa ggacattttg ctcagctcat atctccagac agatcagccc cacagatgat   16620
gactgagagg gcagactgca tggttcccac ctggcctccc cttgtccagt gactcttggc   16680
cctctgagaa gggcttttgt cctgctatct agctttaatc tcttccttcg tcctgaccat   16740
gaccctggaa cccaccctct gaggccaggc agttgggatc cccagggcac aacaaatgag   16800
aggtgcttgc tgggcgcagt ggctcatgcc tgtaatccca gcactttggg aggctgaggt   16860
gggcgatcac ttgaggtcag gaattcgaga ccagcctggc caacatggtg aaaccccgtc   16920
tctactagaa atacaaaaat tagccaggtg tggtggcggg cacctgtaat tccagctact   16980
ggggaggctg aggcaggaga atcacttgaa cccgggaggt ggaggttgta gtaagcagag   17040
atggtgccac tgcactccag cctgggtgac agagaaaaac ttcgtctcaa aaccaacaa    17100 acaaaaaaca aaacacaaca agcaaacaaa acgagaggtg cctgcctctc tcccctcctc   17160
tttgtgcagt gaccacggtg gctggcccca tgcccagga cgtggagagc ctggcgctgt    17220
gcctgcaagc cctgctgagt gaagacatgt accgactgga ccccactgtg ctccagatgc   17280
cctttaggga ggaggtaagc caggtgggag agcagacctg ggggtttcct tgccccccac   17340
catcattcct ccctgacctg tctgccatct taccttccca ggtgaagacc ccctttccca   17400
ccccaggctg cagtgagtga gaagcccaca tgctcagtcc agtttgtttc cttccctgc    17460 tggacaccag ctgctttggc ttcttggcta tctggagcca tagcttgtaa gtgccccaa    17520
```

```
agagggcctc cagtgccata tacccaaccc atgcagttag aatactcagc aagtgtggtt    17580
gagagggtgt ggcatccagt taagctgggt ttttaaccct ctaggtaacc ctggccaagt    17640
cacatctctt ctttcagcct tagcctcccc atcaatacaa taaagaggtt aggctgggag    17700
attactccac acccttctgt ctacagcagc cttcattttat tcgttaattc attcaacaac    17760
atttgcttgt accagttgtg tgccaggctc tgcgtgtctc atcctaacac tctatagagt    17820
gagcagtgct cctcccattt acagctgggg agactgaggg gaagtgaaat gacttgccta    17880
agatcatgta gttagtaact ggcagagctg gctttgaacc cagccctatc taactgcaga    17940
accctctcca tagggcagtt tctgtctacg tcccggcaat gtctgttcct cggattccct    18000
acacccctcc tagcattatc aacctgagat cattgtatat catccatgat ttgcccctac    18060
aaacatgtgt tgtgtgacgg gtgaggggcg gctgcctttc tggcagcacc ccacttccca    18120
ggactagggg ccctccatct cagaccctgg tctgggtatt tgtccctata gatctccagc    18180
ctcatattct cctaacattt ctttagctta aagatatttg agtctatgca tgacttactc    18240
acctgcccac ccactcaact ccaaccatcc attcaccccac tcacccacat atgcattcaa    18300
ccctctgccc acccaactac ccaccatctc atacatacat ccaccccaccc acccaggagt    18360 ctgtctacca tctatctact atccacccca tctgcccaac cacccatctc atccatttct    18420
ctttcctcca ggggtttccg cagagcacct agagcctgga gagtatatag ggaggctccc    18480
agggggtctt ggggtgtcca catggattcc cccctttgtg aggacagctg tagaccaagg    18540
ccctgcccct aaagtctggc tcctggatag agtggggcca ccttgtcccc agcacaatct    18600
ctcctccgag ctccatccag cccctttgtgc cctaggttt acaccagtaa ccggccccttt    18660 cgaattggct actatgaatc agatggttac atccagccat cccctagcat ggccagggct    18720
gtgcagctca cctcctggct gctccaggat gcttgacacc aggtagtctc acctggtcct    18780
gggtgagaga gagtctgggc cagtgcgagg atgctgggcg gggccatcct tggagacaaa    18840
ggtggctaca tctgcgtttg aggtgctgag ataactgtgt tcccctatg cttcctggag     18900 aagactgatg ggatggaggt ggggatagg gtgagccctac cctagaagga aggcattaag     18960
cttttgtgct tcctccttcg gtggtggaga ttcagggact cactcctata attccttcag    19020
cttgggtctc tgttgcctcc atcaagtggc cgtaaggagc tttctgtctc caaaatccct    19080
accttagccc tacccccaaac tcccctgccc ccagtggctt gtcctggcct cacttccct    19140 ttgagattct accatgtgat cttgggctag cctttttaacc tctctgggct tgttttctac    19200
ccaatgcggt ggctgtgaag attaaatgtg gttccataga taaagcactt ggcacgctgg    19260
ctggatcaca gtgaagcatg aaggaaatga gggctgctct cgttctgttc tgtcacatct    19320
gtgtgtgagg gtgagggagt ggggtggcag gagagcaacc agtgacacag gcctcccatg    19380
ccatgctgag gcgctgaggt ggacggagat gcacgagatg atgtggcatc cttcttgaaa    19440
tcttggggga tgcagagaca gagaaccagg cagggtcggg gaagctccag acactgactc    19500
tgcctctgcc tccccaggtt atccccttct ccatccccca ggcagaatac gccatcaaag    19560
acttgtacac gggggggatgt ttactgatgg aggggccact cttctagaga agctatacgt    19620
tatctgctgg gactcagggg tggggcatgg tggaaacaag gtaggggagt gggctggagc    19680
caacctgagt cccaggaggg aaactggggg cctgggctgg ggtgcctctg cctaatagtg    19740
tgaccttatg ccgcaaacca cacactgggc ctgtctttag gatgcacctg ttccgggggt    19800
ggggcagaag tacatctttg ggtttggcct ccttcttgtc tacggcgtgg aagttgggtg    19860
```

```
gctgtggggg caggccactg gctaagggct gtgacttacc catctgcgac tggttcctca   19920
gagaggggga cattgtggat cccagcataa agggcatggt caaccagctc tgcctgccag   19980
accccttcaa atgtttcttg gcctggatcc caaagtacat agtaagtgca ggccctagtc   20040
agggagggct ttggaagggc agggagcaca gggagtagga ggggctcaga aagcagaggg   20100
agctcacaga aggagtggaa gtggggtcag agaggaggat gaggcccaga gaatggtggt   20160
agctcagaga ggggttcaaa atggggaaga agaatgaagg gctgggtgca cagtggctca   20220
tgtatgtaat cccagcactt tgggaggcca aggtaggaag atcacttgag cccaggagtc   20280
tgagaccagc ctgggcaaca tagtgagact ccattctcta aaagaatgg aaaaaaaat    20340
agctgggcat ggtggtgcat gcctgtggtc ccagctactc aggaggctga ggtgggagta   20400
tcacttgagc ccagaagatc aaggctgcag tgagctgaga ttatgcactg cactccagct   20460
tgggtgacaa gtaagactct gactcaaaaa aaataaaaaa aaattaatta aaacaaataa   20520
tgaaagaagg ggatgggct aaaagagtag ggtgctcaca gagaggggag ggggtttcag    20580
agaggaggct cagaaagggg gaagggcatt tggagggcta cagggccagt gtgagctcag   20640
ggcttggtga agtggtgtag gcttgttgag gatcggaggg ttccacgtca gtgcgttgag   20700
caatgctacc cttcttggac cccctcctgg gcaggctgac tgtttccctg tgggttctga   20760
agttggactc cccctctcag cccccctcta ggatccccaa actagccagc atcttgaaga   20820
gattcgtgga gtggggtgag tctccctagg gccagctctt gctccaatgg ttgtccatgg   20880
gatggtggga attgaggagg ggcatgaggc tagagctggt atccactaag gggggatcta   20940
tttagatttc ggactctaat tagggtttta ggatcatgcc tgacattagc ttagattgag   21000
acttttgatt ggtgttggga ctttatttgg agttaagatc tgaattaagg ccgggtgtgg   21060
tggctcatgc ctgtaatccc agcactttgg gaggctgagc ggggaggatc acttgaggcc   21120
aggggttcaa gaccagccag gacaacatga tgaaaccctg tccctactaa aaatacaaaa   21180
atcagcgggt gtggtggtat gtgtctttat cccagctact cggggaggctg aggcacgaga   21240
atcacttgaa cccaggaggt ggagcttgca gtgggccaag atggtgccac tgcactctag   21300
cctgggtgat agagatagac tctgtctcaa gggaaaaaaa aatctgaatt aaggctaggt   21360
tgaggtaaaa tttgggactg aagttgagat taggttttat ttggggatgg gcttaagact   21420
gaggctgggg ttggagttgg tttgagttgg ggttggtggg gcgaagatag atttggaaga   21480
gggttgggac tgaggctgga gttggggtgg ggctagagtt agggttagag atgaggttgg   21540
gagaggctgg tatgggcttg ggtttgctgt tgggcttggc ctggtgggt tggcatgaag    21600
atgctgggca gaattgggct ggagtggact gagggctaac tgggtgcctc acagattagg   21660
gtaaggagcc tgtggccttt gaggcagccc atgagttcct gtgactggtg aatgggggg    21720
tagattgacc agaggatgtg tgctcttggg gaccttgagc aggcaagatg tcttggccag   21780
gggacaagac acgggtcac tcccagccca tcagctgatt tgcagcgtgc actgaggcct    21840
tggttgtcat gtccccattt gtataaaagg gttccctccc atgctgacct ttgaacttgt   21900
cagagtcttc ctcattcttt caggacaccc aagaaactgt gggaacagca cacagcagtg   21960
gaggtaatgc ctgtctggga agaccttgag gggctgctgg agctgggct gcagacacct    22020
gggtagtgcc ctgagtggtc agagttatga actggcctgc agagaaggcc cagctggacc   22080
tgggtggggg ggcttggtga cctcagaagt tattctagtc catctcccta gagcattgtc   22140
cccaaatcct tgtgacctga aattcagctt cccatccctt cacctctgtc cctgggaaga   22200
tcctgaacct ccacaggtat ctcaggctga agcttatagc ctgagacttc ctcctggtgt   22260
```

```
gcaactcagt gctgcctggc agcatctgac cttgtctggc aaacagtaac ccctgccttc   22320
ctacccctcc catccctcac tgtccctgca ggaatatgag caagagttca tagccaagtg   22380
gaggtccctg gacctggatg tgctgctggt gccagttctg ggctctgcct tctatatagg   22440
ctcttcctcc ctagcatcag gtgagagcac actgggtctt ggtggggttg agattgggag   22500
tccgggactc ctgagtcctg ccccagcttc tgtgatcttg ccctctatct ccattaactt   22560
tttaaaaata tttcttaaat tgagataaaa gtcagataac acaaacttac cattttaaag   22620
tgtacaatta agtggttttt aatatttcaa aatgtcgtgc aaccaccacc attatctaat   22680
gtctgaacat ttctgttacc ctgaaaggaa aacttgtacc tgttagcaat ttccattcac   22740
tttaaaaatg aactttatgg aagtataatt tacatgcaat aaaattcacc gattttaagt   22800
ataatttgat gaattttgac aaatgtatac tgttgtataa ccaccactat aatcagaaat   22860
acagaacaga atatatttt agattttaca gatacatgtt ccatcacccc caaatttccc   22920
tcatgtctct gcagttcact ctatccctaa ccccagtaac cactgatctg ctttctgtca   22980
ccatagtttt gccttttcta gaatttcata caaatggaat caaagggtat gaagcttttg   23040
tgtttggctt cttccaccta gcacatccat ttactgtttt tttttttttt tttttttttt   23100
tttttttttt tttgagacag agtcttgctc tgtcacccag gctggagcgc agtggcatga   23160
tctcagctca ctgcaacctc ctctgcctcc tgatttcaag caattctcct gcctcagcct   23220
cccaagtagc tggaattaca ggtgtgtgcc accacgtcca gctaatcttt gcatttttag   23280
tagagacggg gttgcgccat gttggctagg ctggtctcaa actcctaacc tcaggtgatc   23340
cacccacctc agcctcccaa agtcctggca ttacaggcgt gagccactgt gcccagccca   23400
tccatttact cttaacatgc cctctgctgc cctacttcaa aagggtctt cagcccagcc   23460 tgtccaaaac atgggctcag gacagggtaa tatctgggcc atccctgggt cccatgcaca   23520
ggtactggtc tcaaaggtgc tacccaaggc aggataaaac tcagttccaa acctgagcct   23580
ggactcctct cccctgacct taagaacatg tcctcctggg tcccccgact gtggccagcc   23640
aaaggctcat cccacgcctg actctccctg cacacatgtg gctgctgcag aagagctgtc   23700
ctttcaactc caggtggcgc tgtacaccct tactatcttg aagtccggta cacaggaggg   23760
cgtgggctga atcctctgcc atccactagc tgtgtagcct tagaaaaggc taatcctgcc   23820
cctaatcctg ccacctcgat ttcctcactt gtacacagtc aatagtaatc cacacctcac   23880
agagtggaga ggattcaagg gatcagcaat gtgatgaggc cagcacagtg cctggcactg   23940
agtgaggctt ctgcaatgca gattccgtcc ttccctccac cctggggaga gcatgaggcc   24000
attgtcaaga tgacccctga cacaaattgg ctagtccgag cccagagcgc tgaagttccc   24060
agaaggaccg ggagggggcg cccacccaca ttcttcccca cctgagtctg cgctgacgat   24120
ttcctgggct tatctggatc ttcctgcaga aagtcagtct tatgtgaccc tgtacaacct   24180
cctggacttt cccgcgggcg tggtgcctgt cactatcgtg acactacagg acgaggagga   24240
actggccttc tacaaggggt gctacggaga tagttctgac aaaaatttct cagaggtcag   24300
tttccttctc cgagcctctc ccggagcggg gacaaaccag ggctggttct ctccgggttg   24360
gggcccctga cggtagtggt ggagagagta gggcgggact ggtcattcct ggtgttcacc   24420
ctttggcact tatgctagtt tcaccccaac cctgaggaca catcatttga cctccttgtc   24480
agccccatcc atgtcagggg agaaaacttt gcaaaaccag tggttttctt tgtatttctt   24540
ctgcctcctc ctcctccccc tcccctccc cctcttcctc cttctcctcc tctcttcct   24600
```

```
cctcctcctc cttctccccc tccttcttct ttttcttctt ctcctcctcc tcctcctcct    24660
cctcctcctt ctccccctcc ttctccttct ccttcttcct cctttccttt ctccttctcc    24720
ttctccttct tcctccttttt ccttctcctt ctccttcttt tttgagacag agtcttgctc   24780
tatcgcccag gctggagtgc agtggcacga tctcggctca ctgcaacctc tgcctcctgg    24840
gttcaagtga ttctcctgcc tcagcctccc aagtagctgg gattacaggc acctgccacc    24900
acgcccggct aatttttttt tttttttttg agatggaatc tcactctttt gcccaggctg    24960
atgtgcagtg gtgcaatctc agctcactgc aacctccaca tcctgagttt gagccatcct    25020
cctgcctctc agcctcccaa gtagctggga ctacaggcat gcaccaccat gctcggctaa    25080
tttttgtaat tttagtagag acacggtttc accatgttgg tcaggctggt ctcaaactcc    25140
tggcctcaag tgatctgcct gcctcggcct cccaatgtgc tgggattaca ggtgtgagcc    25200
attgcgcccg gccttctttg cattgctgta ggtaaaaatg atctcagagg cagggagggc    25260
agagcagggc aaaagccgct ggttatgagc ttactgtgta tctgctctgg atatgacctc    25320
tcttgggacc tctgtttctt caccaggaaa atgggaataa aaacatctac tttgtagggt    25380
tgtgctaaag gttaattaat ttgaaaaagt gaatgaagca atttgcataa ggtcttgtgt    25440
gtaggaagtg ttcgataaat actatgatta gtaagtcaga gtggtttcat aaagaaaat    25500
attaccaaat atttaactgc agggtctaaa ataacacacc tgactttggt gagagagaga    25560
aggagagaga ggaagagaaa gaggccgact ctgaaacata tgcacgtatc tgagtcagac    25620
attaagtaac ttactttttc tggaaattga ttttagtgct agagttaccc agtggaactg    25680
ctgacctgaa ttctgagaaa ataacaataa tgacactatc tcatgtgtct tgagcactta    25740
ctctgttcca ggagctgttt aaaagtgccg tgtataaata ttaaatcatt aaattcaata    25800
actctcctgt gaggtttttt aaatgaggaa aatggaggca cagacagatt aagggactgg    25860
gccaaagcca cacagccaat tgaagtggag gagctaggac ttgaaacagg tgatctgact    25920
ccagagacaa aggcaaataa agcctcaaat gatatcatca caaagcaaag aaaacaggtt    25980
tgaattccta caaggacgtt tggatttcgt ggcagggact caggcttagc ccccatgttc    26040
ctgggcctgt tttgggccaa ggcaatgctt tcactgtgga agggtaacca ggctctggat    26100
cagggattag catgctcttc tttctcttgc ttgaacattg agtggatgct cggctttctc    26160
tttcgtcatt ataatcagca ttctgcacag ggagcaagtt ttacatgtta accctgaaga    26220
actatgggca ataaaatcag aacagtcttt tcaggtttca ctgagagctg aggaagcctg    26280
gaattctgag atctaggtca ttttttacctt aatatagatt gggaaaggga tgtttggact    26340
aaagcatacc tagaccaacc gttggtacgg aggcccagaa tagcatgggt gatgaacaga    26400
gccaggcaag gggcctgtga agcaggctct gagttcccga ccttctctac tggcaggcgg    26460
taagaggatc cgtcggagtt ctggtgactg tgcagtgcat tgctttgcca tgggaagagg    26520
agctgtgtct ccggttcatg aaggaggtgg acaccttggt caagaatcag aggggggccca   26580
agtgataggc tcctggaatg gagtaacagc tcatgaaaca cggggctggt tgtggtggct    26640
catacttgta atcccagcag ttcaggaggc agaggctggc agatcgcttg aggccacgag    26700
tttgagacca acctgggcaa catagtgaga ccctgcttct aaagcatttt cttggtgtta    26760
ctcctgtaga tcctcaccca agtgtgctcc tgatgcccct tccttctcat gaataccatg    26820
tccaccttat gtctcctcct tctggaaccc caccaggttc cttttctttg ttggtccctc    26880
tgtgtgggtg ctcaatattc ctcagatggg cccaggatgg ggagcagggt gaggagctca    26940
ataaacattt tctgactggc                                                26960
```

<210> SEQ ID NO 6
<211> LENGTH: 18829
<212> TYPE: DNA
<213> ORGANISM: Homo sapiens

<400> SEQUENCE: 6

```
tttcgctctt gttgcccagg ctggagtgca atggcatgat ctcggctcac cgcaacctcc      60
gcctcccaga ttcaagcaat tctcctatct cagcctccca gtagctggga ttacaggca     120
tgcaccacca cgcccagcta attttgtatt tttagtagag atggggtttc tccatgttga     180
ggctggtctc gaactcctga cctcaggtga tctgcccacc tcggcctccc aaagtgctgg     240
gattacaggc gtaagtcacc gcgcccggcc ttttttctct ttcttttttt ttttttgag     300
acagagtttt gctcttgttg ctcatgctgg agtgcaatgg cgcaatcttg gctcactgca     360
atctccgcct cccgggttca gtgattctc ctgcctcagc ctcctaggta gctgggatta     420
caggcgctca ccaccatgcc cggctaaatt tttttttttt tggattttga gtagaaacgg     480
ggtttcacca tgttagtctc gaactcctga ccacaggtga tccgcccgct ttggcctccc     540
aaagtgctgg gattacagat gctcgccact gcgcctggct aatttgttga tttttagaat     600
ttgttgtgag gatcctgtga tgtggctatc atcttttgaa agttgtccct gtctttcaaa     660
gcgctcctga tacattggag tcattaggtc acttgcagtc tgattaagga gagtctttct     720
cttaacgtta gtgatattgt tccgtgggtg gagtcctctc tcagcttttg ctgaaccagt     780
agcaattaca ctcacaattt tctagctttt ctaatacagt gttagatttc atgtagttaa     840
gcatctctgt tgtcaattaa gtaataaaca ttgttattag aatgtcatta acactaatta     900
gaagttgtct agcatggcag ctaagagtgt ggcttctgtt gttgggctgg ctgtttgaat     960
cctgactctt gacactttt atttgtttg atttatcat tttacattgt cttgaactcc    1020
tggcctcaag caatcctccc acctcagact cccaaagtgc tagcattaca ggcgtgagcc    1080
accaaaccca gcaaacactt acacttaaat gactactctg tatcttaact tcttcatctc    1140
tacaatggta tgatgattgt aatgatagca ctcaaacaag ttaataaatg tttacagtgg    1200
tgcctggtac acagcaaaca ccatacagat gctcctcgac ttaccgtggg gcttcatcct    1260
gataaactca tcctaaattg aaaatattgt aagttgaaaa tgcacttaat acatacaacc    1320
cacccaacat catagcttag cctagccttt ttgaaacatg ctcagaacac ttacattagc    1380
ccacggttgg gcaaaatcac ctggcaacac agtaccctgt agaggattca ctgtttccct    1440
tgtgattttg tggctgactg ggagctagtc ttgctggcac tgtccagtat cgagaatcaa    1500
gagagtatct tactgctttt tttttttttt ttctttttt tgagacggag tctggctctg    1560
tctcccaggc tggagtgcag tggcgcagtc tcagctcact gcaacctctg cctcccaggt    1620
tcaagagatt ctcctgcctc atcctcccga gtagctggga ttacaggtgt gcgccaccac    1680
gcccggctaa cttttgtatt tttagtagag acagggtttt gccatgttgg ccaggctggt    1740
cttgaactcc tgacctcagg tgatccccc accttggcct cccaaagtgc tggaattaca    1800
ggcgtgagca acgtgcccg gcctttact gctttcgat gaatgtatat caatcgcttt     1860
tgcgctaccg taaagtcaaa gattgtaagt tgaaccatgg taagttggga ctgtctgtac    1920
aagtgatagt tctcactttta ggaatgaagc tactgttgtt gtccatggtg agtgggtatt    1980
ttgggtgagc agaatatgtt ctattagatg gatgtgacat tctgtcctcc caggtccctg    2040
gagcgcctgc tgtggtctca gcagccacct gcagaggtca cattagccac tccccaaccc    2100
```

```
ctgcccttgc ctgctcttcc cacctctccc caagctccct gagagtcaaa gtgccccaga    2160
ggctgccatt cccacaaatg gccatgcaag gacagctgca ggggaaggct agcctcaggg    2220
gcccagaggg acacattggg cacttgccca tggggtgcca ccagggtgt tgtctctcca     2280
ggtagaaata tagaaatggg ggctggtgtg cagctgctga tgtctctggg gtgcgtctgg    2340
ggacctgtga gtgcagggag gtccctggcg gggcccgcta gggctcctta gggttggagg    2400
gcgcagggca agggatgaac ccaggctggc cctccacagt ccctatgcct agagggtccc    2460
tgctgggctg agcattaact ttacttgctg gactgtgtag agagggtgga gtcctgggga    2520
ggggctagga caactagggt ggtgggggt gcccagcaga gcagcttttt gccaagtgac     2580
tcagaaatgt ttcagtagtt tagccactgg catggctgtg gtggtgcatc ctggctgaat    2640
gctagccctg tccaagggat ctgtgtctgg accctcctga gagtcccgtgt ggcacaccag   2700
ctggggagct ctgagctgag gcacagcaag gaaagggact ggacagtgtg gctggagcag    2760
catgcatggg agaggctgag agagacaggc ccactggacc caagcaggga aagaccctgg    2820
tccagtgcct ggcaccttaa aaagcctccc ttccacaaga tgccccaaga gccaggagag    2880
ggtagtggtt aaggtatgga cggcctgggt ttaagcccag gctcccctgt cctctgacct    2940
tgggcaagag agttagtctc tccgggtctc agttgccttc actggggaaa tggaaacagt    3000
aataacagca cttagccaag ggttttttgtg aggatttaat gaaacggtgc agtaaagggc   3060
ttgagagggt ttccagcccc acagtgatac tctgaatact tggtcaatgg gaattgtgta    3120
catcgaagca agaacccatg ttacacattt acagtgaagg ctttgcaagt ggtgctggtg    3180
agaatggtgt tgcaatgtta tcctgagggc tactgggacc tattttcaga gtgggcctta    3240
taagatctta aaaggattgc ccaggctgca gtgaagaggc tgagttggag gagtggaggc    3300
caagccgtgg aggccaagcc aaggaggcca gtgaggaggc caatgagcca acagagagag    3360
gtccttaggc aggcaagagg cctgagggtc cgaggtggga gatacgaagg agtagaacca    3420
cctgcaggca gtgtgtgcag ttaagaatgt ggtcactggt gttggactgc ctgggtccag    3480
ctctgccact tactggctgt gtatcctcgg gcaaagagga ggaggtctct gtgcctcagt    3540
gttgtcttct gctgtgaaat gagaaaacga tgtgacctac ctcttagggt tgttacaatt    3600
aaaaattgta aattttttaat ttacaatttt cttggagaca gggtctcatg tcatccaggc   3660
tggaatgcag cagtgagatc atagctcact gcagcctcaa actcctggct tcaagaaatc    3720
ctcccacctc ggccttccaa aattcattat aggcaatgac tgattatatg caaagtgtct    3780
ggaataggc ctggcactat taagtgttag aacacatcct agtgtgatta tgttagctag     3840
tgtaactatt atcagaactt gggtgtgagg gaggacctag gatgattctg aggtttgttg    3900
ctttggtgac atgcatgtca tcaattggga atttcaagaa gaacagattt ggctgaaaga    3960
aggtgagtcc tggggagtct gtgtatatgt gggtaggtaa agggctctga gtcctggcgg    4020
aagagaggcc taggttagag aaacaggtgg cctgcttatc cttggggtgc acctggctgc    4080
cgaggtcacc catggagagt gggcaggcag ggagagaaaa ggtcatgccc tgaggaacac    4140
caacatttca ggcaactgag aaggagccac ctgagggtgg gaggaggcca gcagagttgg    4200
gggcatagag agctttggga gggagagtgt cagacgctgc tgaggagagt gagatgaaga    4260
ctaacccgaa tccataagat ttagtaaccg agaagtcttg atgcccttgg tgagaagggg    4320
cccagtgcag aggggaggac agatgtcaga ctggttgctt tgaggaatga agaagacag     4380
actggagcca ggggatccta acctccaagg gaaatttatt tgtctccacc ttcccccacc    4440
tccaggacca agaaaagccc acttcttgcc caacccatac tccagcttgg aggcatcggg    4500
```

```
gtcttaacca gagctgaggg gggcaagagg aagagaactt tgccttcctg agtgcctgct    4560
gtgtgctaga cctttgtcat gtcacacttg cccagggcgg cagtcctgag ggcctggtat    4620
cagacctccc ctcatatcct gaaggacggg gctcagagca gttgaggggc tgactcagga    4680
tggactccta gtccttccct ctctgaggag acctaggcca tgggaggagc agagaaccac    4740
ctccagttac ccagctgacc aagggcgcgg ccaagatggt gctaactctc ttgccaccca    4800
tgctggactc ctgcctccct aaagtcagct cagcaggggg aggactgggt agggaggaga    4860
ggtgggatgc ctgggatgcc cctgaaggcc agccacccag ggctgaactt cacttccata    4920
acctccagtc tcatgatgtc acatgtggag tcaccccac tccagttgtg acccttctga     4980
agagcagcat gaaggggcag gcccttctcc acgccaggcc ctgggctggc cactgggggc    5040
agaggcagag gagaacatcg tgcccttgga gggttttcat gacaacctgg agacacaaca    5100 gatgtttta gtgctaagca tgagtgccgg aacatgtacc gagagacatg ggcgtgtgtg     5160
cagctgtgca taggggagtc tggggtgtga tgtggagtgt gtgggagtgg gccttagcgg    5220
gtccatcttg gatatctgcc tactccatct catttctgca ggagccagat ctggacccca    5280
agccaatcct ggagctgccc ctggcagagc tgcccagca gcttcggacc gaagagctga     5340
gtctggagag catcctctgt agctacttaa agcaggtggt ggccagggca caggatccaa    5400
gcccggggct ctgggctgga gtgggggatg tcacttgtca ttgttttact cagaggagct    5460
gaggggcagg tgtaactctg ccactgactt gggaggtggc acatgccaca gttacctcag    5520
ggtggcagga ggggctgggg caaccgagtg ccctgctttg gtcctggcct cacctggggc    5580
tgttgtctgc tgtcttcact gttgtgcagg cactgaaggt gcaccaggag gtgaactgcc    5640
tgatggattt cctgggggaa tgtgaggagg aactgcaggc attaaagaag cttaagaaga    5700
gtgagagagg ccttctctat ggggtcccca tgagcctcaa ggacacctat gacagcatgg    5760
tgagcctggg gtgtacatgc acacgaatgt gcatatgcac gcttgtgcca ccagcctgga    5820
gcttggtgtg tgacactggg gggctcagtg tgtgacaatg ggtgagtcat ttaaaactgc    5880
acagctacga agcggcaaac tgaggtttat acccagaatt tgggttccaa accccaaatt    5940
ctcagccacc acactctttt gccatccgtg aagtgctgcg cttgtgtccc caggggtgtg    6000
agagtgtgtg tgagggggt ggaatggggc tgaaaatcag ccagctggct ggttccaccc     6060 tgaccccat ggctggaggc aatgttcctt ccctgcaggg ccatgactgt gcatgccgcc     6120
tggcctagtt cctggagaag cctgcgacca aggacggggt cattatgaaa gtgctcaagg    6180
cccaaggagc catccccttt gttaagacca acatcccact gacgctgctc aggtctctga    6240
agcgggctag ctggggtcgg gggctgggct aagcccaggg ctgaaacagc tctttgaagt    6300
cctgattcag ggcagagggt gaggaggggg ctagtcatac agacttcaaa gaccagggtt    6360
cttgggccag cccccttctgt ccccggggct gagtttcttt atcacagaac atgtggatgg    6420
actccacagt ctgtaaggc ccttcggct ccaaggttct gtaaagctac actctttttc       6480
tatcccagtt tctctctcaa attgttctat ttctacccag gcttctctct ttgattgttc    6540
tccccatcgc ttattctctc ccttctctac tcagcctgta gtgcatctgt gtttcgtgag    6600
gaacatgttc tcagttctga tggcagagct gtgggctctt tggtcctgat attaggagtc    6660
atggctggtg tctgatcttg gtctttcttg cagcagcagc cctcacccc agctggaagg      6720 gagcccagga agcctcagcc ttagggagga gctcatggag cccaggaagc cctgggttg      6780 actctggagg gtggttggcc cccatatggg gagaggtctg ccgagtgagg ctttcaccct    6840
```

```
cagctcattt tcttctgctt cccttagctt tgaatgcggc aactcccatc tatgccaga      6900 tgttgagccc actgaactta aagaagacat gtggggctc ctcagggggt gaggggctct      6960
gctggcagaa aggggtcca tcctaggcat gggtactgac acaggtgaca gcatctgcat      7020
accagccagc ttctgtggtg tttatggcct ctggaccaca ggttcccgcc tcaggtactc      7080
attgatggtg gtggtggggt gggctcggac ctgcctaagg gaactagagg gtggggaagt      7140
agaggggtct gctcctccca tcaactttca tctacccaac tcagtactag ggaagtggg      7200 taggagggct tcaaataact cctgcagtag ccatgctaaa cataccatat ttttccaggt      7260
ggcagtagaa tagaccttcc actcattaac tcatcagctc attaattcat taatctatac      7320
agctatccat ccacataccc cttctcttac tcatcaatct gtccatgtat ctatctgtcc      7380
ttcatccatt caatcaccca catggtcatc atctcagtct ctatccatca atcaattta      7440 ccattcatcc actatttatt taaaagattt ctattgacta tttactgtgt cagacacaac      7500
agctccttgg gtactagcta cttgggttac ttcggtgaac aaaagagaca aatatctcag      7560
cccttgaaaa acttacacat actcttcctt ccaaccattt atccatccat ctttccatcc      7620
atccatttgt gtatccatcc atcaatccac atttgtatct ctccatccat ccatccatcc      7680
atccatccat ccatccatcc atccatccat ccatccgttc atcgtatatg catgcatgca      7740
tccacccatc tctcaacccc tctctgtgta cccacaccat ggcccctatt ctggggacat      7800
agaccactct tggacccagc ccctgccct gctgtgctct tagacacaca aatgagttag      7860
tcagaaagtg atcaggtctg taagagaggg tcaaagctta caagaggaag ctgacatttt      7920
ctttaacaga gatttattaa aagcttatac tcttgacttt cagaggcagg gcaagggaag      7980
ggaaggattc ctggaggagg cagcatttga gcgtggtttt gagggccaga catgccaaga      8040
tgatgtggcg tctagaaggc tgtaagattg tttgtaagcg gctgactttg cctgcagcaa      8100
tatgcacgtg tggaagggct agaaggggaa gccatggaga gttagagtct tgaaaagcag      8160
tcaaagagat cagactatgc tgtgggcagc agagggtcag ggaatgttga agcagctcct      8220 attttttgtgg gctgcgccct gggggagcac atcgcctggg tgctcaagcc tcctagcacc      8280
caggcccctc ccttcacatg ctgagctggg ctctgggtcg gaatgttttg cagctacact      8340
ggaattgcct ctgccatcaa ggggaaaaaa atcgggtaag tcctggtctg tgcctgtggc      8400
caccccattt aaagatgaaa ctgccagtct ttctcccaag gacatttttgc tcagctcata      8460 tctccagaca gatcagcccc acagatgatg actgagaggg cagactgcat ggttcccacc      8520
tggcctcccc ttgtccagtg actcttggcc ctctgagaag ggcttttgtc ctgctatcta      8580
gctttaatct cttccttcgt cctgaccatg accctggaac ccaccctctg aggccaggca      8640
gttgggatcc ccagggcaca acaaatgaga ggtgcttgct gggcgcagtg gctcatgcct      8700
gtaatcccag cactttggga ggctgaggtg ggcgatcact tgaggtcagg aattcgagac      8760
cagcctggcc aacatggtga aaccccgtct ctactagaaa tacaaaaatt agccaggtgt      8820
ggtggcgggc acctgtaatt ccagctactg gggaggctga ggcaggagaa tcacttgaac      8880
ccgggaggtg gaggttgtag taagcagaga tggtgccact gcactccagc ctgggtgaca      8940
gagaaaaact tcgtctcaaa aaccaacaaa caaaaaacaa aacacaacaa gcaaacaaaa      9000
cgagaggtgc ctgcctctct cccctcctct ttgtgcagtg accacggtgg ctggccccat      9060
ggcccaggac gtggagagcc tggcgctgtg cctgcaagcc ctgctgagtg aagacatgta      9120
ccgactggac cccactgtgc tccagatgcc ctttagggag gaggtaagcc aggtgggaga      9180
gcagacctgg gggtttcctt gccccccacc atcattcctc cctgacctgt ctgccatctt      9240
```

```
accttcccag gtgaagaccc cctttcccac cccaggctgc agtgagtgag aagcccacat    9300
gctcagtcca gtttgtttcc ttcccctgct ggacaccagc tgctttggct tcttggctat    9360
ctggagccat agcttgtaag tgcccccaaa gagggcctcc agtgccatat acccaaccca    9420
tgcagttaga atactcagca agtgtggttg agagggtgtg gcatccagtt aagctgggtt    9480
tttaaccctc taggtaaccc tggccaagtc acatctcttc tttcagcctt agcctcccca    9540
tcaatacaat aaagaggtta ggctgggaga ttactccaca cccttctgtc tacagcagcc    9600
ttcatttatt cgttaattca ttcaacaaca tttgcttgta ccagttgtgt gccaggctct    9660
gcgtgtctca tcctaacact ctatagagtg agcagtgctc ctcccatttta cagctgggga   9720
gactgagggg aagtgaaatg acttgcctaa gatcatgtag ttagtaactg gcagagctgg    9780
cttgaacccc agccctatct aactgcagaa ccctctccat agggcagttt ctgtctacgt    9840
cccggcaatg tctgttcctc ggattcccta cacccctcct agcattatca acctgagatc    9900
attgtatatc atccatgatt tgcccctaca aacatgtgtt gtgtgacggg tgaggggcgg    9960
ctgcctttct ggcagcaccc cacttcccag gactaggggc cctccatctc agaccctggt   10020
ctgggtattt gtccctatag atctccagcc tcatattctc ctaacatttc tttagcttaa   10080
agatatttga gtctatgcat gacttactca cctgcccacc cactcaactc caaccatcca   10140
ttcacccact cacccacata tgcattcaac cctctgccca cccaactacc caccatctca   10200
tacatacatc cacccaccca cccaggagtc tgtctaccat ctatctacta tccacccat   10260
ctgcccaacc acccatctca tccatttctc tttcctccag gggtttccgc agagcaccta   10320
gagcctggag agtatatagg gaggctccca gggggtcttg gggtgtccac atggattccc   10380
cccttttgtga ggacagctgt agaccaaggc cctgccctta aagtctggct cctggataga   10440
gtggggccac cttgtcccca gcacaatctc tcctccgagc tccatccagc cccttgtgcc   10500
cctaggttta caccagtaac cggccccttc gaattggcta ctatgaatca gatggttaca   10560
tccagccatc cctagcatg gccagggctg tgcagctcac ctcctggctg ctccaggatg    10620
cttgacacca ggtagtctca cctggtcctg ggtgagagag agtctgggcc agtgcgagga   10680
tgctgggcgg ggccatcctt ggagacaaag gtggctacat ctgcgtttga ggtgctgaga   10740
taactgtgtt ccccctatgc ttcctggaga agactgatgg gatggaggtg gggatagggt   10800
gagccctacc ctagaaggaa ggcattaagc ttttgtgctt cctccttcgg tggtggagat   10860
tcagggactc actcctataa ttccttcagc ttgggtctct gttgcctcca tcaagtggcc   10920
gtaaggagct ttctgtctcc aaaatcccta ccttagccct accccaaact ccctgcccc    10980
cagtggcttg tcctggcctc acttccccttt tgagattcta ccatgtgatc ttgggctagc   11040
cttttaacct ctctgggctt gttttctacc caatgcggtg gctgtgaaga ttaaatgtgg   11100
ttccatagat aaagcacttg gcacgctggc tggatcacag tgaagcatga aggaaatgag   11160
ggctgctctc gttctgttct gtcacatctg tgtgtgaggg tgaggagtg gggtggcagg    11220
agagcaacca gtgacacagg cctcccatgc catgctgagg cgctgaggtg gacggagatg   11280
cacgagatga tgtggcatcc ttcttgaaat cttgggggat gcagagacag agaaccaggc   11340
agggtcgggg aagctccaga cactgactct gcctctgcct cccaggttta tccccttctc   11400
catcccccag gcagaatacg ccatcaaaga cttgtacacg gggggatgtt tactgatgga   11460
ggggccactc ttctagagaa gctatacgtt atctgctggg actcaggggt ggggcatggt   11520
ggaaacaagg taggggagtg ggctggagcc aacctgagtc ccaggaggga aactgggggc   11580
```

```
ctgggctggg gtgcctctgc ctaatagtgt gaccttatgc cgcaaaccac acactgggcc    11640
tgtctttagg atgcacctgt tccggggggtg gggcagaagt acatctttgg gtttggcctc   11700
cttcttgtct acggcgtgga agttgggtgg ctgtgggggc aggccactgg ctaagggctg    11760
tgacttaccc atctgcgact ggttcctcag agaggggggac attgtggatc ccagcataaa   11820
gggcatggtc aaccagctct gcctgccaga ccccttcaaa tgtttcttgg cctggatccc    11880
aaagtacata gtaagtgcag gccctagtca gggagggctt tggaagggca gggagcacag    11940
ggagtaggag gggctcagaa agcagaggga gctcacagaa ggagtggaag tggggtcaga    12000
gaggaggatg aggcccagag aatggtggta gctcagagag gggttcaaaa tggggaagaa    12060
gaatgaaggg ctgggtgcac agtggctcat gtatgtaatc ccagcacttt gggaggccaa    12120
ggtaggaaga tcacttgagc ccaggagtct gagaccagcc tggcaacat agtgagactc      12180
cattctctaa aaagaatgga aaaaaaaata gctgggcatg gtggtgcatg cctgtggtcc    12240
cagctactca ggaggctgag gtgggagtat cacttgagcc cagaagatca aggctgcagt    12300
gagctgagat tatgcactgc actccagctt gggtgacaag taagactctg actcaaaaaa    12360
aataaaaaaa aattaattaa acaaataat gaaagaaggg gatggggcta aaagagtagg     12420
gtgctcacag agaggggagg gggtttcaga gaggaggctc agaaaggggg aagggcattt    12480
ggagggctac agggccagtg tgagctcagg gcttggtgaa gtggtgtagg cttgttgagg    12540
atcggagggt tccacgtcag tgcgttgagc aatgctaccc ttcttggacc ccctcctggg    12600
caggctgact gtttccctgt gggttctgaa gttggactcc ccctctcagc ccccctctag    12660
gatccccaaa ctagccagca tcttgaagag attcgtggag tgggggtgagt ctccctaggg    12720
ccagctcttg ctccaatggt tgtccatggg atggtgggaa ttgaggaggg gcatgaggct    12780
agagctggta tccactaagg ggggatctat ttagatttcg gactctaatt agggttttag    12840
gatcatgcct gacattagct tagattgaga cttttgattg gtgttgggac tttatttgga    12900
gttaagatct gaattaaggc cgggtgtggt ggctcatgcc tgtaatccca gcactttggg    12960
aggctgagcg gggaggatca cttgaggcca ggggttcaag accagccagg acaacatgat    13020
gaaaccctgt ccctactaaa aatacaaaaa tcagcgggtg tggtggtatg tgtctttatc    13080
ccagctactc gggaggctga ggcacgagaa tcacttgaac ccaggaggtg gagcttgcag    13140
tgggccaaga tggtgccact gcactctagc ctgggtgata gagatagact ctgtctcaag    13200
ggaaaaaaaa atctgaatta aggctaggtt gaggtaaaat ttgggactga agttgagatt    13260
aggttttatt tggggatggg cttaagactg aggctgggt tggagttggt ttgagttggg     13320
gttggtgggg cgaagataga tttggaagag ggttgggact gaggctggag ttggggtggg    13380
gctagagtta gggttagaga tgaggttggg agaggctggt atgggcttgg gtttgctgtt    13440
gggcttggcc tggtggggtt ggcatgaaga tgctgggcag aattgggctg gagtggactg    13500
agggctaact gggtgcctca cagattaggg taaggagcct gtggcctttg aggcagccca    13560
tgagttcctg tgactggtgg aatggggggt agattgacca gaggatgtgt gctcttgggg    13620
accttgagca ggcaagatgt cttggccagg ggacaagaca cggggtcact cccagcccat    13680
cagctgattt gcagcgtgca ctgaggcctt ggttgtcatg tccccatttg tataaaaggg    13740
ttccctccca tgctgacctt tgaacttgtc agagtcttcc tcattctttc aggacaccca    13800
agaaactgtg ggaacagcac acagcagtgg aggtaatgcc tgtctgggaa gaccttgagg    13860
ggctgctgga gctgggctg cagacacctg ggtagtgccc tgagtggtca gagttatgaa     13920
ctggcctgca gagaaggccc agctggacct gggtggggg gcttggtgac ctcagaagtt     13980
```

```
attctagtcc atctccctag agcattgtcc ccaaatcctt gtgacctgaa attcagcttc  14040
ccatcccttc acctctgtcc ctgggaagat cctgaacctc acaggtatc tcaggctgaa  14100 gcttatagcc tgagacttcc tcctggtgtg caactcagtg ctgcctggca gcatctgacc  14160
ttgtctggca aacagtaacc cctgccttcc taccctccc atccctcact gtccctgcag  14220
gaatatgagc aagagttcat agccaagtgg aggtccctgg acctggatgt gctgctggtg  14280
ccagttctgg gctctgcctt ctatataggc tcttcctccc tagcatcagg tgagagcaca  14340
ctgggtcttg gtggggttga gattgggagt ccgggactcc tgagtcctgc cccagcttct  14400
gtgatcttgc cctctatctc cattaacttt ttaaaaatat ttcttaaatt gagataaaag  14460
tcagataaca caaacttacc attttaaagt gtacaattaa gtggtttta atatttcaaa  14520 atgtcgtgca accaccacca ttatctaatg tctgaacatt tctgttaccc tgaaaggaaa  14580
acttgtacct gttagcaatt tccattcact ttaaaaatga actttatgga agtataattt  14640
acatgcaata aaattcaccg attttaagta taatttgatg aatttgaca aatgtatact  14700 gttgtataac caccactata atcagaaata cagaacagaa tatattttta gattttacag  14760
atacatgttc catcaccccc aaatttccct catgtctctg cagttcactc tatccctaac  14820
cccagtaacc actgatctgc tttctgtcac catagttttg cctttctag aatttcatac  14880 aaatggaatc aaagggtatg aagcttttgt gtttggcttc ttccacctag cacatccatt  14940
tactgttttt ttttttttt tttttttt tttttttt ttgagacaga gtcttgctct  15000
gtcacccagg ctggagcgca gtggcatgat ctcagctcac tgcaacctcc tctgcctcct  15060
gatttcaagc aattctcctg cctcagcctc ccaagtagct ggaattacag gtgtgtgcca  15120
ccacgtccag ctaatctttg catttttagt agagacgggg ttgcgccatg ttggctaggc  15180
tggtctcaaa ctcctaacct caggtgatcc acccacctca gcctcccaaa gtcctggcat  15240
tacaggcgtg agccactgtg cccagcccat ccatttactc ttaacatgcc ctctgctgcc  15300
ctacttcaaa aggggtcttc agcccagcct gtccaaaaca tgggctcagg acagggtaat  15360
atctgggcca tccctgggtc ccatgcacag gtactggtct caaaggtgct acccaaggca  15420
ggataaaact cagttccaaa cctgagcctg gactcctctc ccctgacctt aagaacatgt  15480
cctcctgggt cccccgactg tggccagcca aaggctcatc ccacgcctga ctctccctgc  15540
acacatgtgc ctgctgcaga agagctgtcc tttcaactcc aggtggcgct gtacacccctt  15600 actatcttga gtccggtac acaggagggc gtgggctgaa tcctctgcca tccactagct  15660
gtgtagcctt agaaaaggct aatcctgccc ctaatcctgc cacctcgatt tcctcacttg  15720
tacacagtca atagtaatcc acacctcaca gagtggagag gattcaaggg atcagcaatg  15780
tgatgaggcc agcacagtgc ctggcactga gtgaggcttc tgcaatgcag attccgtcct  15840
tccctccacc ctggggagag catgaggcca ttgtcaagat gacccctgac acaaattggc  15900
tagtccgagc ccagagcgct gaagttccca aaggaccgg gaggggcgc ccacccacat  15960 tcttccccac ctgagtctgc gctgacgatt tcctgggctt atctggatct tcctgcagaa  16020
agtcagtctt atgtgaccct gtacaacctc ctgactttc ccgcgggcgt ggtgcctgtc  16080
actatcgtga cactacagga cgaggaggaa ctggccttct acaaggggtg ctacgagat  16140 agttctgaca aaaatttctc agaggtcagt ttccttctcc gagcctctcc cggagcgggg  16200
acaaaccagg gctggttctc tccggggttgg ggccctgac ggtagtggtg gagagagtag  16260
ggcgggactg gtcattcctg gtgttcaccc tttggcactt atgctagttt caccccaacc  16320
```

-continued

```
ctgaggacac atcatttgac ctccttgtca gccccatcca tgtcagggga gaaaactttg    16380
caaaaccagt ggttttcttt gtatttcttc tgcctcctcc tcctccccct cccccctccc    16440
ctcttcctcc ttctcctcct cctcttcctc ctcctcctcc ttctccccct ccttcttctt    16500
tttcttcttc tcctcctcct cctcctcctc ctcctccttc tcccccctcct tctccttctc    16560 cttcttcctc cttttccttc tccttctcct tctccttctt cctcctttc cttctccttc    16620 tccttctttt ttgagacaga gtcttgctct atcgcccagg ctggagtgca gtggcacgat    16680
ctcggctcac tgcaacctct gcctcctggg ttcaagtgat tctcctgcct cagcctccca    16740
agtagctggg attacaggca cctgccacca cgcccggcta atttttttttt tttttttga    16800 gatggaatct cactcttttg cccaggctga tgtgcagtgg tgcaatctca gctcactgca    16860
acctccacat cctgagtttg agccatcctc ctgcctctca gcctcccaag tagctgggac    16920
tacaggcatg caccaccatg ctcggctaat ttttgtaatt ttagtagaga cacggtttca    16980
ccatgttggt caggctggtc tcaaactcct ggcctcaagt gatctgcctg cctcggcctc    17040
ccaatgtgct gggattacag gtgtgagcca ttgcgcccgg ccttctttgc attgctgtag    17100
gtaaaaatga tctcagaggc agggagggca gagcagggca aaagccgctg gttatgagct    17160
tactgtgtat ctgctctgga tatgacctct cttgggacct ctgtttcttc accaggaaaa    17220
tgggaataaa acatctact ttgtagggtt gtgctaaagg ttaattaatt tgaaaaagtg    17280
aatgaagcaa tttgcataag gtcttgtgtg taggaagtgt tcgataaata ctatgattag    17340
taagtcagag tggtttcata aaagaaaata ttaccaaata tttaactgca gggtctaaaa    17400
taacacacct gactttggtg agagagagaa ggagagagag gaagagaaag aggccgactc    17460
tgaaacatat gcacgtatct gagtcagaca ttaagtaact tactttttct ggaaattgat    17520
tttagtgcta gagttaccca gtggaactgc tgacctgaat tctgagaaaa taacaataat    17580
gacactatct catgtgtctt gagcacttac tctgttccag gagctgttta aaagtgccgt    17640
gtataaatat taaatcatta aattcaataa ctctcctgtg aggttttta aatgaggaaa    17700 atggaggcac agacagatta agggactggg ccaaagccac acagccaatt gaagtggagg    17760
agctaggact tgaaacaggt gatctgactc cagagacaaa ggcaaataaa gcctcaaatg    17820
atatcatcac aaagcaaaga aaacaggttt gaattcctac aaggacgttt ggatttcgtg    17880
gcagggactc aggcttagcc cccatgttcc tgggcctgtt ttgggccaag gcaatgcttt    17940
cactgtggaa gggtaaccag gctctggatc agggattagc atgctcttct ttctcttgct    18000
tgaacattga gtggatgctc ggctttctct ttcgtcatta taatcagcat tctgcacagg    18060
gagcaagttt tacatgttaa ccctgaagaa ctatgggcaa taaaatcaga acagtctttt    18120
caggtttcac tgagagctga ggaagcctgg aattctgaga tctaggtcat ttttacctta    18180
atatagattg ggaaagggat gtttggacta aagcatacct agaccaaccg ttggtacgga    18240
ggcccagaat agcatgggtg atgaacagag ccaggcaagg ggcctgtgaa gcaggctctg    18300
agttcccgac cttctctact ggcaggcggt aagaggatcc gtcggagttc tggtgactgt    18360
gcagtgcatt gctttgccat gggaagagga gctgtgtctc cggttcatga aggaggtgga    18420
caccttggtc aagaatcaga gggggcccaa gtgataggct cctggaatgg agtaacagct    18480
catgaaacac ggggctggtt gtggtggctc atacttgtaa tcccagcagt tcaggaggca    18540
gaggctggca gatcgcttga ggccacgagt ttgagaccaa cctgggcaac atagtgagac    18600
cctgcttcta aagcattttc ttggtgttac tcctgtagat cctcacccaa gtgtgctcct    18660 gatgccccctt ccttctcatg aataccatgt ccaccttatg tctcctcctt ctggaacccc    18720
```

```
accaggttcc ttttctttgt tggtccctct gtgtgggtgc tcaatattcc tcagatgggc    18780
ccaggatggg gagcagggtg aggagctcaa taaacatttt ctgactggc                18829

<210> SEQ ID NO 7
<211> LENGTH: 8131
<212> TYPE: DNA
<213> ORGANISM: Homo sapiens

<400> SEQUENCE: 7
tttcgctctt gttgtgcagg ctggagtgca atggcgagat ctcagctcac tgcaacctct      60
gcctaccgga ttcaagtgat tctcctgcct cagcctcccg agtatctggg attacaggcg     120
tgtgccacca tgcccagcta attttgtatt tttagtagag atgggatttc tccatgttag     180
tcaggctggt cttgaactcc tgacctcagg tgatctgcct gccttggcct cccaaagtgc     240
tgggattaca ggcgtgagcc actgtgcccg gcctgccaca gcttttttgcc tcgcttccct    300 gggctccaga ctggacatct ccaacaatct ttcacatggc agttaggcaa tctcatgctt     360
aaaatctttg gactcacttg tgccaagtcc agaagccttg ttatgacctg caaggccatg     420
attaacctga ccctgcagct ggcccctgcg gcctcatctc ctgcccttcc tcagtgctca     480
cagcccggcc acgtggcctg caggtaatgt tcagaacacc gagtgatctc ccgcctccac     540 gcccctttgct cttggtgctt gctgtgcctg gagtgttgtt cctggggtct ccacctaaag    600
accacctact cgtccaaggt gagggcaatt gctcttccaa ctctgtcagg ctgtgttgaa     660
agagcttctt tgtgcttctg cacgtggtca aaagcaaggt ctgtgtatta atagaaccca    720
acatctgtta ggctgtggag ttgaataccc attatctcat ttggaaagtg gcattacta     780 tttccattta aaaaatttat ttatttattt attttttgag acagagtctc tctctgtcgc     840
ccaggctgga gttcaatggc acgatcttgg ctcactgcaa cctctgtctc tgggttcaag     900
tgattctcct gcctcagcct cccaagtagc tgggattaca ggcgcctgcc actgtgcccg     960
gctatgtttt gtatttgtag tagagatggg gtttcaccac gttggccagg ctggtttcga    1020
actcccgacc tcaggtggtc cacctgcctt ggccaaagtg ctgggattac aggcgtgagc    1080
cactgcgcct ggcctttttt ctttttcttt tctttgagat ggcgtcttcc tctgccaccc    1140
aggctggagt gcagtggtgc gatctcagct cactgcagcc tccgcctcct ggcttcaagc    1200
gattttcctg cctcagactc ccgagtatag ctgggactcc aggcgcctgc caccatgcct    1260
ggctatgttt tgtatttgtg gtagagatgg ggtttcacta tgttggccag gctggtcctc    1320
aactcctgat ctcaagtgat ccgcccgcct tggcctccca agtgctgag attacaggtg    1380 tgagctaccg tgtctggccc tattatttcc attttataca taaggaaact gaagttcaga    1440
ggggattgct gacttgttga aggctgatca ttatgggtta cagagaagac ttgaaaccca    1500
cacgctcaac tctaaactta ctgtgacttc ctcatttgta caatcatcac aagaacatgc    1560
attcaacatt cttcggacac cagcctctgt gctaggcgac cacaacactt tgaagacaga    1620
agcagtcctg tgtactgtgc acctctgcca atatctgttt acaggagata gctgccatgt    1680
ccctgtccac cctcccttttt ctcctctggc gattgcgata ttggagtttt aggacacagc    1740
cagagcactt gtcatttgtt cctgttggac accatttta ggattatccc aagagctctg     1800
gctgtttctg ctcttcctcc caacatgtgc ttatccacaa atctgagcac tggacctctg    1860
caacttcatc caagtcaccc ataaacctat ggatcacagc agaccaagga aagggcgtga   1920
cctacaccct taacagacag acacataacc gagttttgag cttcccagcc agatgtatct    1980
```

```
ttagttcaca tttctctggc tgggcttagc tgggccctcc caagtttcct acacatagat    2040
ttggggtggc ggccctgggc acctcaggaa ggtgaagcca cttgggatcg ggctgtgtat    2100
gctcagcacc cagcatggtg cctggtactc agtgggtacc cagagaaggc ttgttgaatg    2160
gagcaatggg tgacttgtta ttagggaacc cattttggtc cattctgatt acttcctctt    2220
ctcacctcca atagggaatt ttccaatcag tccctgaccc tttgctcctt tcacatttat    2280
tgtatctacc tccatgatct tttttttttt ttttttgag atggagtctt gcactgttgc     2340
ccaggctgga gtgcaatggc aggatctcgg cttactgcaa cctctgcctc ctgggttcaa    2400
gcgattttcc tgcctcagcc tccggagtag ctgggattat aggcgcctgc caccacgccc    2460
agctaatttt ttgtatttat agtagagatg gggtttcact atgttggcta ggctggtctc    2520
gaactcttga cctcaggcaa tccacctgcc tcagcctccc aaaatgctag agccatgat     2580
cttgattagt gcccatgagg acaaataatt cccagtctac attcaaccta tagctttctc    2640
ctggtctgta gatcctcatc tatccacttc tctcatcctc ttaactcctt catctctctc    2700
aggctgttga aagagcttct ttgtgcttct gcacttggta aaagcaggg actgtgtctt     2760
aatagaatcc aacatccgtt aggctgtgga gttgaaccca ttatctcctt tgtaaaatgg    2820
gcttattatt tccatttcat atataaggaa actgaaattc agagagggtt gctctctgaa    2880
caacaatgga gggttgctcc ctccattcat cctcccatcc atgcaataaa atatattgaat   2940
tcttcccaca gtatgttcag ggtaaccaat cagaaatagt ccctgcctga atggagcttc    3000
cattctacca ggaaacagac atcaaatgta gaattacaca gaaacactcg ttagaagtgc    3060
aatcaagcag aagccctggg tattatgaga ataaccacg tgggatctga tccagcctga    3120
gatgtgtgta tgtgtgtgtc agggaatgct tcctggagga agtaacattg aagctgaaaa    3180
ctgcattgtc acctgagcca aggaatgagt gtgtttcaag gagggtgaag ctgacaactc    3240
taaatgctgc tgatttactc ttgaggagat cactgggatg atataggcac aagccagact    3300
ttgttgggtg gggagtgag tgaaggtga agaagtaaag gcagcccgtg tagaaaactg       3360
gaaaagttca ggaagcggac aaaagacgtg gtagtagtta gggagggtgt aaatctgagg    3420
gaatcatccc tcatccccca agataggaga gacttagcat gttaaatgct gctaggaaag    3480
agctagcagc aacgcacaga ggggggaagt caaggtagga atggagggct caacctgcca    3540
tcatttcttc actgaagaga taccattgaa cacataccat gtgccaggtg ttttgaaaaa    3600
ggctgacaag gtctatgctc ccccaacccc ccagctaatt ttttttgcatt ttctgtagag   3660
atggggtctt gccgtgttgt ccaggttgag ctcaaactcc tgagctcaat tgatccgccc    3720
aaagtgctgg gattacaggc gtgagccact gtgcctggcc tcgtctgtgc ttttacggag    3780
cttatttct agggagggag gcaggaggtg agttacagat caacaagaaa acttcagcta    3840
atgataagtg taatgatgag ataaaatgag gtatgtggta acggaagggt gtaacccagg    3900
aaaaggtgag gtcacgaggc ctagagtgct gtgccgtggg atgtggtgcg ggtgacaagt    3960
ggcctggggg agctgaagat atgggggaga gctggagttc atgaaggtgg agtggggct     4020
atggaagaaa atggtcagaa agaggcagaa aggacagagg agggctggtc tggaggcccc    4080
agggagatga cagagtgtta cagagtgggc aacttcaggg tcacccttag tcaactgctg    4140
acctcgcatc tgttcctttta gaccctcggg tactcagact caacattacc aaccatgaat   4200
tcagttcctt cccaccctaa cctgctgctg ccctggcttc ctggtctgga gggcaaaggc    4260
gccattctcc tgggtacagt gacttgcagt ctcagtgatg accattgaga tggagactgg    4320
atggaggccc ctgaggagag cagaatggtt cccacatcag ggcccctctg caccactttt    4380
```

```
ccagtctcct catgtcttct ctgttcctcg tctgggaagt catctccctt accccacaa    4440
ctcccctcca ccagcaggga gagtcaatag actggggagg ctggaacccc ggatcagagt   4500
catggccttg ctttggagtc aagggggaag cccagctggg cgggctggtc tcatgtcctg   4560
gcatcatctc ccctggggtg gatgcctgat gagccctgcc cgctcctcca ggtgttcttt   4620
cctttcctct cttcctgtcc cccagaacct ccactctagg caaacatggc ctgttcagtt   4680
ccacctccat gcgtctgctt atgcggaaca aaggagcttt gggagaatcc tgaaggcaat   4740
gggaacccca ggagcaaccc catccataac tcctgagggt tggagtaggg aatctgaggg   4800
gtgggatctg agaggtagga tgggtgggag taggatgtga cagaggtgag gtcagctgcc   4860
cagctgcagg cttgggccct tcttcaggct cgcctgctaa agcctcttcc tctgcatggc   4920
ccgggagata ggggttttgt cgccaggaag tccagatggg gtaagaacta ggaggaggtt   4980
gatcactgcc acacccaggg cccgagatgt gcgtgggtgc cctggcagca tcgctgacaa   5040
atactcctga ggaaacagca gctggattca cacaggtcgt gcaataccta aggtggcttg   5100
gctgtttgac tccctgatga tgctacttct gctggccctg ctggggggctg gcctactggg   5160
ggcttccctg ctcacctcgt ggcatgctcc agcccggaac aagatcccca gggcccagaa   5220
gtggagggag gtagcactgc agaagatgga ggacctggcc cagtgactcc ggcagcaggt   5280
gagtcgacac gggtcccgga ggcccccagc cacagggggc cttggccctc aatcccaaca   5340
ggaggactac acctcaggat gcccctcccg tccatgaccc cagccccgc agacacaggg    5400
agcaggtggg cacttcccca cccccagttc tcccccatg ccagctctgt gtgtggttgt    5460
cagttctcct ccatccccgg cctttgagac cctggagatt gggggcagtg tattctttct   5520
ctgttctccc agcacttggc acgtggctca gtaacatggg aggtgcccac ttagggtatt   5580
tgcggaaata agataaactg atggaggcca ttggaggagg gaggctcgat ctcttttagc   5640
ccctgagcac tccaaaatcc cccaagacag gaacccctagt ctacctgtcc cctcctacct  5700
ccaccccatt cagctctgaa aacacttgct gagccctgat aagtgcagag catggggggc   5760
tggggatggg gtctcccagg aagctgcagg tcttcagagg cagctttggc aactcggagt   5820
gggggtattt cactgggata gcctctgtgg ctggctgggc tgagactggc aggcgaagtg   5880
gctgagccat agatgtatca gcaaagcctg ccccaggtgg cagagagaag ggcgggaagg   5940
agggacatgg agacaaacat agactgagcc tgggatttgc tgtgtggcct ggaggatgtg   6000
acaacccgtc tctgggcctt ggactcccca gctgtctgag ggggatggg ctcatggtct    6060
ctcggggtct ccagctttgg ttgatgatgg tggactcagt ctgggagccc ggaggtaggg   6120
gctgggggcta gtgcctgagg tgctgttccc atgctttgga gttcctgagt gtcctctgct  6180
gtccctgga tggtgattga tggccccaat gggcagcttc tctgtctgag ttgctgcagt    6240
tgctgagtat gtgtattaat attaattagg gctaattagt tggataaatc aatctgcccc   6300
cagagagcag ctgcccctcc ctggttgatg aggaggaagt ctgggctaat gggttgcagt   6360
ggtgaatggg catgatggag gcgtcctgtg tgcgtgtgga ggcccatct gtgtgcggtg    6420
gtgggtatag cttcctttac tgcggacgag ggcctgcttt cttgtgcctc ctgctggcat   6480
ttcattgtgt tgtggttggt tgtgtgtctg gtctggctgt gtggttatgt gcctggctgg   6540
gtgtgcatgt gttgggttat tggttggagt gtgtacatct agctatgtgt ggctggtgtg   6600
ggtctgaatg tctggtagag agtgtttgtg tgtggttgtg tgtctgatgt gtgggggcag   6660
ctggtttggt atgtgtctgg gcatctggtt ggtgaacatg tggatgtctg ggctgttggg   6720
```

| | |
|---|---|
| ctggggacct ggaggggta tatgtctgga tggctggagg agtggaagag gttttgggt | 6780 |
| gaggtcactc atggtgtctc cagcctccca ttgtggtttc aggcttcttg gctctcagca | 6840 |
| ccttgctgtc tccccaacaa gctatacagg tctgtcctgg gcaccttctc agtcatgtca | 6900 |
| ccctctctct gccagtgaca acctcgagac ctcaggtgtc cacctttatg tcccggggag | 6960 |
| gtgcaaggct gggacacagg tcaaaccctc acaggctcag caaacaaatt caattctgct | 7020 |
| gagtttagta aaatttccca gggaatttct ccaggtcttg ccctgtgctg agctctgggg | 7080 |
| acacattcat tataaagatg aatctgaccc ctgactcaca cttgtgctaa aaatgttccc | 7140 |
| aacctgggag gggcgtggtg gagatagagc tgtgcagact atgcagggca gcagcacggc | 7200 |
| agagtgtggt gaggccagat gcccacagaa ctggtgactt ggcaggaggg tggctggtct | 7260 |
| gtctggagag gatcatgttg ggagggctcc ccagacgggt ggtgagtgag ctgaacctca | 7320 |
| tggcacctgt aggacttttc tgaaaggaga aacgagaaag gcagtaccag ggagggagaa | 7380 |
| gccccagatg aggcagtgtt tctgtagaac gtatagaaaa taatattcct aggacccatt | 7440 |
| gggtaaatgg accagctgct catggctgga actgctcaag ctactcatgg ccaggaagct | 7500 |
| ctgctcacct caggcagagc ctggccacct tgagagttga cggttttat gatactaaac | 7560 |
| atttaaccac cacattggaa ttttttttt tttcagacgg agtctcactt tgttgcccag | 7620 |
| gctggagtgc agtggcctga tctcagctcc ctgcaacctc cacctccga gttgaagcaa | 7680 |
| ttctcttgcc tcagcctcca gagtagctgg gattacaggc aagtcccacc aagcccaact | 7740 |
| aattttgta ttttcgtag acatgggtt tcaccatgtt ggccaggatg gtcttgatct | 7800 |
| cttgacctcg tgatcctccc accttggcct cccaaagtgc tgggattaca ggcgtgagcc | 7860 |
| accgtgcccg gccataaata ttaataatac attgattcac taaaacttt aaattacatt | 7920 |
| ttttttgttt ttcaaactag gctggaggca gcaccctgag tacagagaag gctggatgtc | 7980 |
| cgtggggctg tgggatggag ctggagggaa gggttagctc caaactaaat tacatattaa | 8040 |
| aaagtgatat aacttgaggc tcaattttc atcaaattat tcaaataatt tgttgatttt | 8100 |
| tagctttttt ttttttttt tggagacgga g | 8131 |

```
<210> SEQ ID NO 8
<211> LENGTH: 22
<212> TYPE: DNA
<213> ORGANISM: Artificial Sequence
<220> FEATURE:
<223> OTHER INFORMATION: Primer sequence

<400> SEQUENCE: 8
```

| | |
|---|---|
| ccaccagtgt gctggtggct ac | 22 |

```
<210> SEQ ID NO 9
<211> LENGTH: 22
<212> TYPE: DNA
<213> ORGANISM: Artificial Sequence
<220> FEATURE:
<223> OTHER INFORMATION: Primer sequence

<400> SEQUENCE: 9
```

| | |
|---|---|
| agcctctggg gcactttgac tc | 22 |

```
<210> SEQ ID NO 10
<211> LENGTH: 25
<212> TYPE: DNA
<213> ORGANISM: Artificial Sequence
<220> FEATURE:
<223> OTHER INFORMATION: Primer sequence
```

-continued

<400> SEQUENCE: 10
ttaatgtctg gagtgataac atgac					25

<210> SEQ ID NO 11
<211> LENGTH: 25
<212> TYPE: DNA
<213> ORGANISM: Artificial Sequence
<220> FEATURE:
<223> OTHER INFORMATION: Primer sequence

<400> SEQUENCE: 11
acaacttcta attagtgtta atgac					25

<210> SEQ ID NO 12
<211> LENGTH: 22
<212> TYPE: DNA
<213> ORGANISM: Artificial Sequence
<220> FEATURE:
<223> OTHER INFORMATION: Primer sequence

<400> SEQUENCE: 12
aaggccgggc gcggtgactt ac					22

<210> SEQ ID NO 13
<211> LENGTH: 23
<212> TYPE: DNA
<213> ORGANISM: Artificial Sequence
<220> FEATURE:
<223> OTHER INFORMATION: Primer sequence

<400> SEQUENCE: 13
ctctgggcca tgttgctggt tac					23

<210> SEQ ID NO 14
<211> LENGTH: 24
<212> TYPE: DNA
<213> ORGANISM: Artificial Sequence
<220> FEATURE:
<223> OTHER INFORMATION: Primer sequence

<400> SEQUENCE: 14
caactgtcac acaggccaaa acag					24

<210> SEQ ID NO 15
<211> LENGTH: 23
<212> TYPE: DNA
<213> ORGANISM: Artificial Sequence
<220> FEATURE:
<223> OTHER INFORMATION: Primer sequence

<400> SEQUENCE: 15
ccagaagtgg agggaggtag cac					23

<210> SEQ ID NO 16
<211> LENGTH: 25
<212> TYPE: DNA
<213> ORGANISM: Artificial Sequence
<220> FEATURE:
<223> OTHER INFORMATION: Primer sequence

<400> SEQUENCE: 16
gctgtcatag gtgtccttga ggctc					25

<210> SEQ ID NO 17

```
<211> LENGTH: 23
<212> TYPE: DNA
<213> ORGANISM: Artificial Sequence
<220> FEATURE:
<223> OTHER INFORMATION: Primer sequence

<400> SEQUENCE: 17
caaagtgaga ctccgtctgc tgc                                                23

<210> SEQ ID NO 18
<211> LENGTH: 27
<212> TYPE: DNA
<213> ORGANISM: Artificial Sequence
<220> FEATURE:
<223> OTHER INFORMATION: Primer sequence

<400> SEQUENCE: 18
ggcaaaggcg ccattctcct gggtaca                                            27

<210> SEQ ID NO 19
<211> LENGTH: 27
<212> TYPE: DNA
<213> ORGANISM: Artificial Sequence
<220> FEATURE:
<223> OTHER INFORMATION: Primer sequence

<400> SEQUENCE: 19
gccagtcaga aatgtttat tgagctc                                             27

<210> SEQ ID NO 20
<211> LENGTH: 23
<212> TYPE: DNA
<213> ORGANISM: Artificial Sequence
<220> FEATURE:
<223> OTHER INFORMATION: Primer sequence

<400> SEQUENCE: 20
actgacacag gtgacagcat ctg                                                23

<210> SEQ ID NO 21
<211> LENGTH: 23
<212> TYPE: DNA
<213> ORGANISM: Artificial Sequence
<220> FEATURE:
<223> OTHER INFORMATION: Primer sequence

<400> SEQUENCE: 21
gtccagtcgg tacatgtctt cac                                                23

<210> SEQ ID NO 22
<211> LENGTH: 18
<212> TYPE: DNA
<213> ORGANISM: Artificial Sequence
<220> FEATURE:
<223> OTHER INFORMATION: Primer sequence

<400> SEQUENCE: 22
cctggcaccc agcacaat                                                      18

<210> SEQ ID NO 23
<211> LENGTH: 19
<212> TYPE: DNA
<213> ORGANISM: Artificial Sequence
<220> FEATURE:
<223> OTHER INFORMATION: Primer sequence

<400> SEQUENCE: 23
```

```
gggccggact cgtcatact                                                  19

<210> SEQ ID NO 24
<211> LENGTH: 21
<212> TYPE: DNA
<213> ORGANISM: Artificial Sequence
<220> FEATURE:
<223> OTHER INFORMATION: Guide sequence

<400> SEQUENCE: 24
cccagtgagt acgatggcca g                                               21

<210> SEQ ID NO 25
<211> LENGTH: 21
<212> TYPE: DNA
<213> ORGANISM: Artificial Sequence
<220> FEATURE:
<223> OTHER INFORMATION: Guide sequence

<400> SEQUENCE: 25
ttagtgatat tgttccgtgg g                                               21

<210> SEQ ID NO 26
<211> LENGTH: 21
<212> TYPE: DNA
<213> ORGANISM: Artificial Sequence
<220> FEATURE:
<223> OTHER INFORMATION: Guide sequence

<400> SEQUENCE: 26
tcatggcctt tccccttctc a                                               21

<210> SEQ ID NO 27
<211> LENGTH: 21
<212> TYPE: DNA
<213> ORGANISM: Artificial Sequence
<220> FEATURE:
<223> OTHER INFORMATION: Guide sequence

<400> SEQUENCE: 27
gtcacttgca gtctgattaa g                                               21

<210> SEQ ID NO 28
<211> LENGTH: 21
<212> TYPE: DNA
<213> ORGANISM: Artificial Sequence
<220> FEATURE:
<223> OTHER INFORMATION: Guide sequence 'FOP1'

<400> SEQUENCE: 28
aaaaggtgag gtcacgaggc c                                               21

<210> SEQ ID NO 29
<211> LENGTH: 57
<212> TYPE: DNA
<213> ORGANISM: Homo sapiens

<400> SEQUENCE: 29
tttttttttt tcgagacgga gtttcgctct tgttgcccag gctggagtgc aatggca        57

<210> SEQ ID NO 30
<211> LENGTH: 298
<212> TYPE: DNA
<213> ORGANISM: Homo sapiens
```

<400> SEQUENCE: 30

```
ttcttttttt ttttcgagac ggagtttcgc tcttgttgtg caggctggag tgcaatggcg      60
agatctcagc tcactgcaac ctctgcctac cggattcaag tgattctcct gcctcagcct     120
cccgagtatc tgggattaca ggcgtgtgcc accatgccca gctaattttg tattttagt      180 agagatggga tttctccatg ttagtcaggc tggtcttgaa ctcctgacct caggtgatct     240
gcctgccttg gcctcccaaa gtgctgggat tacaggcgtg agccactgtg cccggcct      298
```

<210> SEQ ID NO 31
<211> LENGTH: 295
<212> TYPE: DNA
<213> ORGANISM: Homo sapiens

<400> SEQUENCE: 31

```
tttttttttt ttttggagac ggagtttcgc tcttgttgcc caggctggag tgcaatggca      60
tgatctcggc tcaccgcaac ctccgcctcc cagattcaag caattctcct atctcagcct     120
cccaagtagc tgggattaca ggcatgtgcc accgcgccca gctaattttg tattttagt      180 agagatgggg tttctccatg ttgaggctgg tctcgaactc ctgacctcag gtgatctgcc     240
caccttcgcc tcccaaagtg ctgggattac aggcgtaagt caccgcgccc ggcct          295
```

<210> SEQ ID NO 32
<211> LENGTH: 560
<212> TYPE: DNA
<213> ORGANISM: Homo sapiens

<400> SEQUENCE: 32

```
ggcctgctct atggcgtccc tgtgagcctc aaggagtgct tcacctacaa gggccaggac      60
tccacgctgg gcttgagcct gaatgaaggg gtgccggcgg agtgcgacag cgtagtggtg     120
catgtgctga agctgcaggg tgccgtgccc ttcgtgcaca ccaatgttcc acagtccatg     180
ttcagctatg actgcagtaa ccccctcttt ggccagaccg tgaacccatg gaagtcctcc     240
aaaagcccag ggggctcctc aggggggtgaa ggggccctca tcgggtctgg aggctccccc    300
ctgggcttag gcactgatat cggaggcagc atccgcttcc cctcctcctt ctgcggcatc     360
tgcggcctca gcccacagg gaaccgcctc agcaagagtg gcctgaaggg ctgtgtctat      420
ggacaggagg cagtgcgtct ctccgtgggc cccatggccc gggacgtgga gagcctggca    480
ctgtgcctgc gagccctgct gtgcgaggac atgttccgct tggaccccac tgtgcctccc    540
ttgcccttca gagaagaggt                                                560
```

<210> SEQ ID NO 33
<211> LENGTH: 561
<212> TYPE: DNA
<213> ORGANISM: Homo sapiens

<400> SEQUENCE: 33

```
ggccttctct atggggtccc catgagcctc aaggacacct atgacagcat gggccatgac      60
tgtgcatgcc gcctggccta gttcctggag aagcctgcga ccaaggacgg ggtcattatg     120
aaagtgctca aggcccaagg agccatcccc tttgttaaga ccaacatccc actgacgctg     180
ctcagctttg aatgcggcaa ctcccatcta tggccagatg ttgagcccac tgaacttaaa    240
gaagacatgt gggggctcct caggggtgta ggggctctgc tggcagaaag ggggtccatc    300
ctaggcatgg gtactgacac aggtgacagc atctgcatac cagccagctt ctgtggtgtt   360
tatggcctct ggaccacagg ttcccgcctc agctacactg gaattgcctc tgccatcaag   420
```

```
gggaaaaaaa tcggtgacca cggtggctgg ccccatggcc caggacgtgg agagcctggc    480
gctgtgcctg caagccctgc tgagtgaaga catgtaccga ctggaccccca ctgtgctcca    540 gatgcccttt agggaggagg t                                              561
```

<210> SEQ ID NO 34
<211> LENGTH: 221
<212> TYPE: DNA
<213> ORGANISM: Homo sapiens

<400> SEQUENCE: 34

```
ctgtacaact gcctggactt ccctgcaggg gtggtgcctg tcaccacggt gactgctgag     60
gacgaggccc agatggaaca ttacaggggc tactttgggg atatctggga caagatgctg    120
cagaagggca tgaagaagag tgtggggctg ccggtggccg tgcagtgtgt ggctctgccc    180
tggcaagaag agttgtgtct gcggttcatg cgggaggtgg a                       221
```

<210> SEQ ID NO 35
<211> LENGTH: 221
<212> TYPE: DNA
<213> ORGANISM: Homo sapiens

<400> SEQUENCE: 35

```
ctgtacaacc tcctggactt ccccgcgggc gtggtgcctg tcactatcgt gacactacag     60
gacgaggagg aactggcctt ctacaagggg tgctacggag atagttctga caaaaatttc    120
tcagaggcgg taagaggatc cgtcggactt ctggtgactg tgcagtgcat tgctttgcca    180
tgggaagagg agctgtgtct ccggttcatg aaggaggtgg a                       221
```

<210> SEQ ID NO 36
<211> LENGTH: 166
<212> TYPE: PRT
<213> ORGANISM: Homo sapiens

<400> SEQUENCE: 36

```
Met Leu Ser Pro Val Cys Phe Leu Pro Leu Leu Asp Thr Ser Cys Phe
1               5                   10                  15

Gly Phe Leu Ala Ile Trp Ser His Ser Leu Thr Pro Lys Lys Leu Trp
            20                  25                  30

Glu Gln His Thr Ala Val Glu Glu Tyr Glu Gln Glu Phe Ile Ala Lys
        35                  40                  45

Trp Arg Ser Leu Asp Leu Asp Val Leu Leu Val Pro Val Leu Gly Ser
    50                  55                  60

Ala Phe Tyr Ile Gly Ser Ser Leu Ala Ser Glu Ser Gln Ser Tyr
65                  70                  75                  80

Val Thr Leu Tyr Asn Leu Leu Asp Phe Pro Ala Gly Val Val Pro Val
                85                  90                  95

Thr Ile Val Thr Leu Gln Asp Glu Glu Glu Leu Ala Phe Tyr Lys Gly
            100                 105                 110

Cys Tyr Gly Asp Ser Ser Asp Lys Asn Phe Ser Glu Ala Val Arg Gly
        115                 120                 125

Ser Val Gly Leu Leu Val Thr Val Gln Cys Ile Ala Leu Pro Trp Glu
    130                 135                 140

Glu Glu Leu Cys Leu Arg Phe Met Lys Glu Val Asp Thr Leu Val Lys
145                 150                 155                 160

Asn Gln Arg Gly Pro Lys
                165
```

<210> SEQ ID NO 37
<211> LENGTH: 139
<212> TYPE: PRT
<213> ORGANISM: Homo sapiens

<400> SEQUENCE: 37

Ser Arg Ser Ala Gly Lys Leu Trp Glu Leu Gln His Glu Ile Glu Val
1               5                   10                  15

Tyr Arg Lys Thr Val Ile Ala Gln Trp Arg Ala Leu Asp Leu Asp Val
                20                  25                  30

Val Leu Thr Pro Met Leu Ala Pro Ala Leu Asp Leu Asn Ala Pro Gly
            35                  40                  45

Arg Ala Thr Gly Ala Val Ser Tyr Thr Met Leu Tyr Asn Cys Leu Asp
        50                  55                  60

Phe Pro Ala Gly Val Val Pro Val Thr Thr Val Thr Ala Glu Asp Glu
65                  70                  75                  80

Ala Gln Met Glu His Tyr Arg Gly Tyr Phe Gly Asp Ile Trp Asp Lys
                85                  90                  95

Met Leu Gln Lys Gly Met Lys Lys Ser Val Gly Leu Pro Val Ala Val
            100                 105                 110

Gln Cys Val Ala Leu Pro Trp Gln Glu Glu Leu Cys Leu Arg Phe Met
        115                 120                 125

Arg Glu Val Glu Arg Leu Met Thr Pro Glu Lys
    130                 135

<210> SEQ ID NO 38
<211> LENGTH: 139
<212> TYPE: PRT
<213> ORGANISM: Homo sapiens

<400> SEQUENCE: 38

Ser Leu Thr Pro Lys Lys Leu Trp Glu Gln His Thr Ala Val Glu Glu
1               5                   10                  15

Tyr Glu Gln Glu Phe Ile Ala Lys Trp Arg Ser Leu Asp Leu Asp Val
                20                  25                  30

Leu Leu Val Pro Val Leu Gly Ser Ala Phe Tyr Ile Gly Ser Ser Ser
            35                  40                  45

Leu Ala Ser Glu Ser Gln Ser Tyr Val Thr Leu Tyr Asn Leu Leu Asp
        50                  55                  60

Phe Pro Ala Gly Val Val Pro Val Thr Ile Val Thr Leu Gln Asp Glu
65                  70                  75                  80

Glu Glu Leu Ala Phe Tyr Lys Gly Cys Tyr Gly Asp Ser Ser Asp Lys
                85                  90                  95

Asn Phe Ser Glu Ala Val Arg Gly Ser Val Gly Leu Leu Val Thr Val
            100                 105                 110

Gln Cys Ile Ala Leu Pro Trp Glu Glu Glu Leu Cys Leu Arg Phe Met
        115                 120                 125

Lys Glu Val Asp Thr Leu Val Lys Asn Gln Arg
    130                 135

<210> SEQ ID NO 39
<211> LENGTH: 29582
<212> TYPE: DNA
<213> ORGANISM: Homo sapiens

<400> SEQUENCE: 39

```
tctcctgcct cagcctccca agtagctggg actacaggtg cctgccacca tgcccagcta    60 attttttatat ttttagtaga gatggggttt cactgtgtta gctaggatgg tctcgatctc   120
ctgaccttgt gatccatctg ccttggcctc ccaaagtgct gggattacag gtgtgagcca   180
cctcacccgg cctactttga caatcttttt aaaagtgtcc ttgtagactg cactggaagc   240
aagccctatt aggcattcga tttgcccagt ttttcccttt tccagagcct ccaaagtcca   300
cttgcctgag ggccatgact aaagtggtgg cctcttttt atcctgtttg tcccattcca   360
cctgctcctc ctgatcttta ttataaaaaa ccaaggtttc caagttcaat agggtttcta   420
agttttgctc caggcctaag gcggactttt gaagtttttt tctaatgtct gcagctgact   480
gagtgataaa cttattcttc aagattagtt ggccttcaat agagttaggt gacagagagg   540
tatgctttct caatgcctcc cttagtctct ccagaaaggc agtaggattt tcttcctttc   600
cctgtattat agtggacatc attgaataat tcataggttt cttcctagtt ttccttagtc   660
cttctagcac gcaagttagc aaatgtctgc tgcaccaatc tccatgttct gattctgtgt   720
cccagtgagg gtctacactg ggaactgcct gctggcctgt ggggaatcgt tctttcctct   780
gttgtcatct tgtcattgac ctgactgaga taccagagat caccaaactc tcgggctgca   840
gttatggcag cacttctctc atttgggttt agtgtctgat ttagcaataa cattatatct   900
ttccatgtca gatcaaagga ttgtcctaac ccttggaaaa catcaatata gccatcaggg   960
ttatctgaga atttacctag gcctatttta atttgcttta agtctgagag agaaaaaggt  1020
acatgcactc tggctgggcc gaattctcct cctcccattg cttggagagg ggcataattg  1080
gggaatatta gcactctttg gttcattgtt taccccttttg tctatctcct tttggacgtt  1140
tgggttgaag gggggtcctc attagttggg gaaggagtcg gggggacacc agggtaggga  1200
ggtagactct agggcttcct gtaggacata aatcacactt tttacataat tgcgagttgt  1260
ctcttaatga aaagaaagtt tgtacatatg gcacttcatt ccatttgcct tcttctctac  1320
aaaagaggtc tcactgtaag atggtgttat aatttatatt tccctcagga ggccaggttt  1380
ctcccccttg aagaggatat catggccagg tggtactgca gaagaatata agtcatttct  1440
ttcttagcgt ctgagggtca aattggtccc aaatctccag aatacatctt aggggcgttt  1500
ttgccttgtg gggaacgttt cccattgctt tggaggtccc ttcgtggtcg ccaaatgtta  1560 ctgggggtc cttgctccca gagctcccaa gatggtggcg ggccgcttcc aagatggtgg  1620
caagcctggt gttctctgac ctgggggttct tggcctcacg aattccaagg aatggaatct  1680
tgggccatgc ggtgagtttt atagctctat tagaagccgt gggtcatgga agagaactgt  1740
ggaacccagt gactagtgtt cagcttgatt aggatgaacc tgggcactta gccgtgcagg  1800
aacaatggca aacctttagc ctgattggga gcggcaatgg gcgcctcgct ggatcaggag  1860
cacagtagac accctgccgg atccagaggg atggaagtcg gcggcgggtc tgcgatggca  1920
gcaaacagca gtggatgtcg agcgaaagct cagctccagc catagcaaac acggaccaga  1980
agagagtgca gttgcaagat ttaatagagt gaaaacagag ctcccataca aagggagggg  2040
acccaaagag ggtagccatt ttttcacttt ttttttttaa cttttgttga aaacatttta  2100
agtttggaat tcaactatt ctttgctatt aataagacct cattcagtcc atattaactt  2160
agaattggta tagatgggtc cttcctgatt ctgtaagtgc tttaaggctt ggctgagtgc  2220
aaacagctct cacatttgaa caggccaatt attaggcaat tttcctaact ctgcttctac  2280 aagagttttcc ttatcactta ctgaatacccc attgtgtctt tttccctcaa ttacccagga  2340
ggaaccatct atcatcctgt cctgaaggga gttcttccta ggtctggtcg gaccttttgta  2400
```

```
tggtaattaa ttaagattta gatcccatgt taggaaacct gctgggttaa gggaattttc    2460
agtggttaat attaaatcat ttttttctaa cagaacagcc tcatacttta aggttcttga    2520
gtcagtaagc tacctttttt ttttttttgac ttaggatagt tctgacctga tgaggtgtgc   2580
tcacaatgag gtttcctcta aaagttgttt ttctactttc ttctgttagc aaagcagttg    2640
ctgctacaga ttgaatgcat ttgggccatc tgccggttac tgggttaagg agttttgatt    2700
agggaggtta cggttgtca gtggcctcag tgcttttggg ctacatcctt gtttacactg     2760
acaacaaggt ggtattggag tgttataggg tcatggagaa gaccttcaat tatcaattac    2820
aggttttgaa tttatcctg gcttttaaag gaatagggta cactgttttc tctttactac     2880
ttctatctct ctttctctct ctctctcttt gactctctct ctctttccct gtctctgact    2940
ccctctctct ctctcttttt cttttgagac agagtctagc tctatcaccc aggctggagt    3000
gcagtggcgc gatctcggct cactgcaagc tccgcctccc aggttcacgc cattctcctg    3060
cctcagcctc ctgagtagct gggactacag gcgcccgcca ccacgcctgg ctaatttttt    3120 tgtatttta gtagagatgg ggtttcacgg tgttagccag gatggtcttg atctcctgac    3180
ctcgtgatcc accggccttg gcctcccaaa gtgctgggat tacaggcatg agccaccacg    3240
cctggcttct gtctttctgt ctctttctct ctctgcctct ctttctctct ctttgcctct    3300
ctctttctct ccaacttcct ctcccagttt ctctttcctc tctgctggtc tttccctgcc    3360
tctgccagct gcttatgctg ctgttctccc ctctccttcc ccttcccta gggaagggac     3420 cgtcaggagt gcagctactt tttcttcccc gagaagaaag gaaggggaa ttctgaatat     3480 ttttcttact accggaggtt gtgtgaggt ttttgatccc ctgaaatttg tggaaggctc     3540
aacacctcaa accaggggt atcttgcctt gcctgacctg gaaggctcaa ccccctcaaac    3600 caggggtgt tttgccttgc tgccctggaa ggctcaatcc ctcaaactag gaggtgtctt     3660
gccttgcttc cctggaaggt tgacctgttt cctcccttc ccctctgaa ggtcctttgc      3720 acacttccca ctcgtgttgt cctctctggc tgctccccca agggagaatt aggccccct    3780 cagcattggc attccagtag aaatcccacc gcaggatcct ccctaagcca tatgaggtag    3840
ctacggaaac gtggagagga cccactcact ccgtccagca gtaggacttg tcatcatcca    3900
cacgaacaac accacaggta gggttgtttg tgatcattca cgcacacaca catttagccc    3960
tccagaattt gaccaccaag gaagtacctt accggctccc tcggcttctt cctttgtctg    4020
tgcacagagt tgtctctgca gtgtgtgagg atgctttacc ctaggttgcc tgctggtttc    4080
ttttcacatt gctgagagct caggttattt cttgcactgg gtgagtcctg atttctcacc    4140
cctgaggcca tcacaagagg gtggggcata cctcctcagg agagagaacc agagactgcc    4200
cctgaagggg aatgtaatca cgagcaagcc cccaaattgt tataaataaa gtttccccc    4260 agtgccgcaa aagaaatagc actcgaatat aaaattttct ttttttttctt ctcagcaagg   4320 caatttactt ctatagaagg gtgcgccctc acagacggag caaaggtgag cgcacacctg    4380
gacaagggag gggaaggtgg ttcttatgcc tgacccacgt gattcctgat gctgtgtcct    4440
tcccctgttg gctagggtta gacctatagg ctaaactaat tccgattggc taatttaaag    4500
acagtgaggg ggtgagtggt ttggcgggaa aaatggttac cgcagagcag gaaatcggaa    4560
tgaaccacgg tgaagaatga gtgagggagg agcaggtaat cgaaaaatgt tgctttatga    4620
ggaagttaag tttaaaagta gaaggcaaag aattgaagat actgacatat tgattctttt    4680
aagataaatt tagaactcat atctaacagc tggcatgtct ggcatgggc tccggctggg    4740
```

```
gcgcagtctt cagcatttgg ggctctgggg tgcaggggc  agaggacggc cggggctgtg   4800
gtgcccaacc ggtgctaaac tcaagcttgg gaggtcgccc acgagaaaca gtcgcccttc   4860
cccacccgcc tgctcggctt ggcggggagc gggatgtcgc tgggggcgat gccaggcggg   4920
ccgcctctga tagcctctag gctctggcgc gcttccccgc ccctcccgcg caggcgggcg   4980
tgggatcccg gctgatccag tccgggtttt gcggcggagc gggcgggctg cgcgtgcggc   5040
ggcttcaact gtcgcggtag gcagcagcag gctgaaggga tcatggtgca gtacgagctg   5100
tgggccgcgc tgcctggcgc ctccggggtc gccctggcct gctgcttcgt ggcggcggcc   5160
gtggccctgc gctggtccgg gcgccggacg gcgcggggcg cggtggtccg ggcgcgacag   5220
aggcagcgag cgggcctgga gaacatggac agggcggcgc agcgcttccg gctccaggtg   5280
actgccggag cgtagtggga tgggcgcggc ctgagggtac tcgcagcggc actttcagcc   5340
gccggacccg ccgagggaca ggggatgggg cgggcagagc agatgtgtaa ctctccagaa   5400
tctctccttg ccctaagata ttccgcactt tctgagccag gtagagcacg ggggaagaaa   5460
ggaaacggta gtgtcaaggc aggtggtgga aggcctttcc ctcactgggt caaagaggag   5520
ttttgctttg tgccaaagaa tctcacgatt gctgcctatt ggaatgcgaa aacgcaagcg   5580
tgacaaccag tgggatgcca ggggttgagg actttggaat cgcagagtgt aatggccaag   5640
gggatctgga gagcttagag ttttgttttt tgtttttttt tgttttgttt tgagacggag   5700
tctcgctctg actcccaggc aagagtgcag tggtgcgatc tcggctcact gcaacctccg   5760
cctcccgggt gcaagcgatt cttgctgcct cagcatcccc agtagctggg attacagggg   5820
cccgccacta cgcctggcta ttttttgcat ttttagtaga gactgggttt caccatgttg   5880
gccaggctga tctcaaacgc ctgacctcag ttgatacacc tgcctcggcc tcccaaagtg   5940
ctgggcgtga gccaccgcgc ctggctgagt tcaagcttct tgatttgtgc atttggatcc   6000
taagagggag ccagaaagaa acctgccaag tgcacaggga gatcttggca aagccaggct   6060
agaagggaag tctctctggc tcctgctgtg gtgtccaacc cctggcaagc cctttccatg   6120
agcaggttta gttccagccc tccgtgggtg gtctgtcaac aagcttttct ccctgcgctg   6180
cctttggatc acctcagtat gtgggtttgg aggcgtggaa gggcctggct gagggtttgg   6240
aagatgtggc ttgaagaggg gcttttcctc tgggtgtgtg aaacactgac cccagttaaa   6300
gccttcttat gtgctgagag agggagggct tgctgtatct gtgggacctg acaggtggga   6360
aggctttaca ggttgggaac cgcaggactc aggagggtgt gcctgggtgg gagacagaaa   6420
gagtcacaga aaattgtgtt cagcagatgt tccgcaagtg attttgagt tggggcagag   6480 ctggaactag aacctaggtg cccgctgcac tctgcagcca cactttcgtg gagaggaaca   6540
ggagagagat atgaggaagg caccttgcat gccagcccag ggtgtagccc tgcatgttga   6600
agggggccag ccctccaca  cctgtgggta tttctcctca ggtgggacaa gagactgaga   6660
aaagaaataa gacacagaga caaagtatag agaaagaaca gtgggcccag gggaccaccg   6720
ctcagtatag ggaggacccg cgccagcact ggtctctgag ttccgtcagt atttattgat   6780
cactatctct accatctcgg tgagggggat gtggcaggac tatagggtaa tggtggggaa   6840
agggtcaaca ggaaaacatg tgagcaaagg actctgtgtc ataagtttaa ggaaaggtgc   6900
tgtgccttga tgtgtatgta ggccagattt atgtttgact ttatacaagc atctcagtgc   6960
agtaaacaac agtattgtca ccagcatgtc tcacctccag ccataaggtg gttttctcct   7020
atctcagtaa atagaacgta ggatcgggtt ttacactgac acattccatt cccagggacg   7080
agcaggagat agatgccttc ctcttatctc aactgcaaag aggccttcct ctttcactga   7140
```

```
tcctcctcag cacagaccct ttacgggtat cgggctgagg tatggtcagg tctttcccct    7200
cccacaaggc cgtatctcag gctgtctcag tggggagaaa ccttggagaa tacccaggct    7260
ttcttgggca gaggtgcctg cagccttccg cagtgcattg tgcccctggg tactcaagac    7320
gggagaatgg cgatgacttt ttgccaagca tactgcctgc aaacacattt ttaacaaagc    7380
acatcctgca cagccctaat taaaccttga gtcaacacag cacatgtttc tgcgagcata    7440
gggttggggc taggtttaca gattaccagc atctcaaggc agaagaattt ctcttagtac    7500
agaacaaaat ggaatttctt atgtctactt ctttttacat agacacagta acagtctgat    7560
ctctcttttc cccacacatg tgttgcggtt ttggctggct gtaatgtatg aatttactcc    7620
aaaccatccc tggggccaag atatctcata tttatttagt aagataaaaa atatatctgg    7680
ttccagcctc cactccaccaa gctggctgaa aagtccacca tcagtcagtt tttagggttt    7740
cttccttcca gagtgagagg gccctggtgg tcaacccaaa ttggccatct ccctacaca     7800 agcacaggtt cttcactgtc tagttgccct ctctggctgg gcgctggagg tcctccttag    7860
agatcctcct gtttatccct ggctctgtgc agccagctga gttctgccag ctccaagagc    7920
agcgtgggca gcactagcag ggatctgctc acagctcttg cctgcagaac tcccctcctg    7980
gttgcaagga atccacctgg ctggcagggg tgtgggatgg tagcaggatg ggtcttcctg    8040
cacttcggct ccaaacagca gcatctatat ggttttcctc tggagcaact gctcttcatt    8100 attttttacga acagattatt ccaggacaga agttttggct ctgaaagctt ggctctttca    8160
ggaggagaag cgggaaatta cctttcaggt ttccagtgat tgtggttttg agtaatcagc    8220
aaaggggtgg ggtcctgatt gacaatagct ttgtaggctt tgcgggggag taggattttt    8280
ttttggtttt tgttattttt gttttttgtt tttgagacgg agtcttgctc tgtcgcccag    8340
gctggagtgc aatggtgcga tctcggctta ctgcaacctc tgcctcccag gttcaagcga    8400
ttctcctgcc tcagcctccc gagtagctgg gattacaggc gcctgccacc atgcctggct    8460
aatttttgca ttttagtag agacggggct tcaccatgtt ggccatggct ggcctcgacc    8520
tcccgacctc aggtgatccg cccgcctcgg cctcccaaag tgctgggatt ataggcatga    8580
gccaccgcgc ctggccaatg cctggctaat ttctgtagtt ttagtataaa cggtttcgtc    8640
atgttggcca ggctagtctt gaactctttt tttttttttt tttttgagat gaagtctcac    8700
tttgttgccc cagctggagt gcactggtgc aatctcggct cactgcaacc tccacctccc    8760
gggttcaagc aattctcctg cctcagcctc ctagtagct ggggttacag gtgcctgcca     8820
ccatgcccgc taatttttg tatttttag tagagatggg atttcaccat cttggccagg      8880
ctggtcttga actcctgacc tcaggtgatc cccctgcctt ggcttcccaa agtgttggga    8940
taacaggtgt gagccacctc acccggccag gacgtgggga ttttagctga acccagccca    9000
ggcttgggaa cagctctttc ccccgcctct cctcccttct gcctacaact cctaaggcac    9060
ccttctgttt ggctctggag tccttgaatg atgggcaggt aggatctgtg actgtctggg    9120
caacctttct tctggggctc ttagcccagc cctgaatcac aaggggggcac ctgagataag   9180 cagggctcca gcaggccctg ggagaacaca gcgatttgta gtaaagctcc tgtctgatag    9240
attctggaca aagcgatttg gcaaccaaga ttcttttttt tttttgagtc agagtcttgc    9300
tctgttgccc aggctggagt gtagtggctc aatcttggct cactgcaacc tccgcctccc    9360
gggttcaagt gattctcctg cctcagcctc ctggagtagc taggactaca ggtgcctgcc    9420
accacatcca gctaattttt gcattttggg tagagacagg gtttcgccat gttggccagg    9480
```

| | |
|---|---|
| ctggtctcga actcctgacc tcaggtgatc cgcctgcctc ggcctcccaa agtgctggga | 9540 |
| ttacaggtgt gagccaccac tcccggattc ttggctgtgt ccaaggagga cacagctgga | 9600 |
| tgaaggggta cctaaacacc ttctgaattt tcacaaaata gttcacctct ctctaaactc | 9660 |
| ttgagcaaat ctagagaaaa atgtgttttct ggtaattctg ttgacgcttc acccattttt | 9720 |
| tcccaccctg cccctgaat aagttttgat atcttttcta gaccgaagag aaggaccacc | 9780 |
| atcaatagaa tagtatagct gggagagaca tcacagaaca cctatttatg cccttatgcc | 9840 |
| tttgtacatg cagttttgtt ttaccctgaa tggttttttcc tacatctctt acaacccgct | 9900 |
| tatcaatccc actggcattg tggttcagaa ggagaaaaca aaacagatgg aggaggggca | 9960 |
| atgcctccta agtgattggt agagtatccc tctcttgaaa aattgtgcat gcaggtggcc | 10020 |
| acaggtttag atgttacctg tatactatac ttccctgcat tctccgcaaa atcaggtttc | 10080 |
| cgcatgttca ctgattggtc ttctggaggt gcagacttac tttggtgtct aggagaaaat | 10140 |
| gtctcagctg cctgacacta gttgaagatt taaaaatagc tgttagcagc tgtgtcatta | 10200 |
| actgtcaaca ggcaagaaca taggaaagaa tgaaaatgtg tgctgagcgt ggaggggagc | 10260 |
| acattgctag ctgctagctg ccgtgcacag gcactctgtg ggcgccttgt agcgaggtcg | 10320 |
| ggggagttgg tgaccggact gtcaggtggc agttattcca gggtggtgaa tgctctgctg | 10380 |
| atttcgatgt ccttctccat actcttaggc atttttttaaa atacaatgaa cctgtattta | 10440 |
| tataatgaaa acaaaaataa agcaaaattt gattttcatt gtgagatggg aaaggcaaga | 10500 |
| tgcagtactg tgtgtatagt atgattcctt tgtgcaaaaa agaatatata tagacaactg | 10560 |
| ttgacatggt gggttttca taaatatttt cttttcctgt aagagtacac cagaaactgt | 10620 |
| taattatagt tttcctttat agaggaggga ctgtgcaagg agaaccaggg gtggagggaa | 10680 |
| tgctcacttt tcattttgta tacctttaaa gaatatatca agaggattat ctagtgtgtt | 10740 |
| tggggagaag tcttgaaccc attttttctt ctttgtagct ccttgtgtta gaaaaaaaat | 10800 |
| ccaaagtaag tactctatca gttcaatgaa ttcaggaaag tgctcctgac actgaggaca | 10860 |
| tcagggggca gaggctgtgg catgtgctcg agagggcag gcgccaggct ctgggtgtg | 10920 |
| gggggtggga gggggcagtg gtgcctgggt ggggagaggt gcacatgagt ctgagaggac | 10980 |
| cacagcttgg aagcacctcc tggaatatgc tctggagcct gtggtgtgat gagatgggga | 11040 |
| ttttaagggg agaggcaagg ccaggttggg ttttgcactg tctggcccta gtggaaagtg | 11100 |
| tgggttggag gtgcaggacc tgggcagggc agcagttggg tggccgcgtg tgacctagga | 11160 |
| gacaaggatg agtctgaggc ccggtgaggg ccttggtaga ggggatggag aggtgaccat | 11220 |
| ttttcagagc tacttagctt ggtgactgga tgcaggtggt ggtgggaagg aggagccaga | 11280 |
| aagcacctg tttcatttcc tgaacacctg gatggatggc ggggcctccc ctgagtacag | 11340 |
| ggtacaggat acataaggag gagctggtca aaagtcgggc aggtgatgag cttagaggaa | 11400 |
| ggacagggaa ggtggacagg tgacaggaat agcccagtga gctggtttgg gctccattgc | 11460 |
| ctcgggctgg gtaggggatc tgggggatgt gggatgagtg gagagcctgg agtcagaggt | 11520 |
| gcttagggga ggagtggaag ccagggtagg ggaggagggt aagaggggag gggaggaggg | 11580 |
| gaagggtaga ggggagaagg ggaagcaagg ggaggtgagg aagggaaggg gagaagggaa | 11640 |
| aggaagggga ggggaggaag ggaagggaag ggtagagggg aggagggga agcaagggga | 11700 |
| gggaggaag ggaagggtag aggggaggga gggaagcca gggagggga ggagggaaag | 11760 |
| ggtagagggg aggaggaaa ccaggggagg ggaggagggg aaatttgggga gggaagaggg | 11820 |
| ggaagtgggg aggggaggag ggggaagcag gccaggggag gaggggagt aggggaggg | 11880 |

```
gagtagggggg attagggggga ggggaggagt agaagcaggg ttggaggggt gggaggaatg    11940
gaagcaggag gaggggaagc cttctcccag aatcagagag ggaagagaag gtacccagag    12000
ctctgtctct ccccacatct ggcatcttct tatccttcaa atcacagctg aaatgtggtt    12060
tcttcagata ggcagccttt aagaactgga acactcactg tgagggtctg cggcttcatt    12120
cttgaagtca gtgagaccaa gaacccacca attccggaca cagaatgaat gtgtaaaccc    12180
ttccttttgg gtgtggcctt cagtcacaga cccagcctcc caagatgggg tcttcttgtt    12240
tttgcccttc cctgctagag gttggcaacc ccctgagtag tgttcagagc tgctctgtgg    12300
gtgtggggat ggcatggggt caggtgcagg cagatggctg gtgggcaaga aggcacctct    12360
ctctcagcct cagtttatct gtgcaatggg aatggcagta agacttaatc aaaacatgga    12420
tgacatcagc gtggtgttgg cacacagaag gcagccactg ctggtgtata tttgtagtgg    12480
tttaatcatc agtctggagc taggcacagt agcatgtgcc tgtagttcca gctactcggg    12540
aggctgaagt gggaggatca cttgagccca ggagttcaag tctagcctgg gcaacacggc    12600
cagacactgt ctctaaggaa aaaaaaaacc tacttgggca ggtcggctcg ctgggcaccc    12660
cttcaacaag cttctggagg agacagagct gcattctcta gggatggcaa gggcctgccc    12720
aggctgggcc atgtcagagc tgctggggca tgggccactg gtgtctgctg caggcccatg    12780
agacttcggc gagtagggga ctgatccgag tttgttcccc acagaaccca gacctggact    12840
cagaggcgct gctagccctg cccctgcctc agctggtgca gaagttacac agtagagagc    12900
tggcccctga ggccgtgctc ttcacctatg tgggaaaggt aaggccagcc aaggccagcc    12960
cctccctggg aaaggtaagg ccagccaagg ccagcccctc cctttcccct ccctctgtcc    13020
gcacaggctg tggggaaaac ctggcctgga gttagtcctg ctgggggcca tggtgggacc    13080
tacagtgcca gggactgcca gggagggaag gagccagagc gtgtgcgtgt gtgtatgtat    13140
gtgtgtatga gacactgagc atgctgtctt agctagtaac ctggctttta gcccagactt    13200
ccctctccct cctgcctcca ccccattggg caacaagtct ggtctgttcc cttctttttt    13260
tttgagatgg agtttcgctc ttgttgttca ggctggagtg caatggcaca atcttggcgc    13320
actgcaacct ccacctcctg ggttcaagca attctcctgc ctcagcctcc caagtagctg    13380
ggattacagg catgcaccac tacacccggc taatgaaaag aaaaaaaatt ttttttttt    13440 ttttgagatg gagtctcgct ctgttgccca ggctggaatg cagtggcatg atcttggctc    13500
actgcagcct ccacctcctg ggttcaagtg attcttctgc ctcagcctcc tgagtagctg    13560
ggagtacagg cacctgctaa cacacccagc taattttgt atttttagta gagatgggat    13620
tttaccatgt tggtcaggct ggtctggaac tcctgacctc aagtgatcca cccgcctcgg    13680
tctcccaaag tgctggggtt acagctgtga gccactgcag ctggccccca actaattttt    13740
tgtatttagt agagacgggg tttcaccatg ttgatcaggc tggtctcaaa ctcctgacct    13800
caggtgatcc acccgcctcg gccttccaaa gtgctaggat tacaggcgtg agccaccatg    13860
cccgaccccg tcttttttt tgagatggga gtcttgctct gtcgcccagg ctggagtgca    13920
gtggcatgat cttggctcac tacaacctcc acctcccggg ttcaagtgat tctcatacct    13980
cagcctcccg agtagctggg attatagaca tgcaccccca tgcttggcta atttttgtat    14040
ttttatttgg ccgggctggt ctggaactcc caacctcagg tgatcctctg aaagtgctgg    14100
gattacaggc gtgagccacc gcgcctggcc tgttctcttc ttttacccag ccctctcctg    14160
tctccatccc cttttggccac cctggcccgc caccaccatc tcccgccatg cccaagcacc    14220
```

```
agcctcctgg tcaggtgccc tcttgtgtcc ccagctcttc aggccatctc ttgtactcct   14280
cctctgtgtg tggcatcacc tctggccaag gccttctgga gcttgggtgt cagcagctct   14340
gcactggctt gggtggggct cctttacctg gaaggctgtt tccctcttct ttgcccctgt   14400
ccgtgccacg ggctcccctg ctgagccttc ggggctcag agcaggaggc accgtcttcc   14460
attcgccacc tgaggtaggg tttcctcttc caggcctact ctcattctaa tagcacattt   14520
ctcatcacag tgtcaggctt gtcttctcta tctctttccc atgggggtc tttgtggaca   14580
gagcttgtct catttgtctt tgaaccttag tgctcaacat gttgcatttc acgtaataaa   14640
tgctcaagaa atatgtttga aagaaaggg agggagggag gaaagaagga gacaaattgt   14700
gctttgagtg tggcctgcat gatttcttga aagggtgtgg gacagtgagt gtgaccccta   14760
ggcaggtgaa cttgtctggg tgcagtgtat gtgacaatgc tgtgggggct gcagctgagg   14820
aagcgagcgc atgctgggct ggtgtcactg agagggggca cgtacatagt ctcagcagat   14880
ggtcttgctt cttccctgtc aatgtccctg aaaggctcct gcccttccta gttaatctag   14940
tctatctggt tagattagcc ttctctgttc ctgcctcggg taccccgggg acagattttg   15000
cacatgcctg aatatggcaa cacagcccac cctgtttccc ccagatactc cccaggagca   15060
ggaatattta ctgaaagctg catctcactc tgccctcacc tttccttctg taggaccctg   15120
tgtggtgagg tttgagcatt ctaggcagat ttccactatt agcatgttct tccctttttgt   15180
caagctccta ctccacatgg cttgattatc aaattcaaga tttcctgggt aaggggaggc   15240
ttgactgggc tacatgtggg gaaggcgtgg ggttgaggag agactgctgg gctccgggag   15300
gcaggagtct ggtctagtcc tgctctgtgg ttgcccttca gtgtgaccag tgatggggcg   15360
ctgcccctgt ctggtttctg tctgcctcac tggcagagat gtggcttggg ggaggtgagg   15420
gagtggccag tggtcatctt cctcccagct cacccctac ctgggggggca cctgaggcca   15480
gtatcttgct cccttgagtg tcccggttgt gccctggtcc tggttgaagg ccagagacag   15540
ccaggatgag gcctgggcca aatgtcccta gtgaggcaga tgctgagccc taggtcatcc   15600
tctgtgcccc aggctctggg ccatgttgct ggttacccct ctccctgggt atactttaaa   15660
aggccagttc tacatgatgt atatttcacc acaatttctt aaaaaggcca gcctcctttt   15720
atcttatgtc tacttccct tcctcaggcc tgggaagtga acaaagggac caactgtgtg   15780
acctcctatc tggctgactg tgagactcag ctgtctcagg ccccaaggca gggcctgctc   15840
tatggcgtcc ctgtgagcct caaggagtgc ttcacctaca aggtatgctc tgcctcagcg   15900
ccaggcctcc atcgtcccct catccctgc cagcctgctc tgcatcttgg gtcattttgg   15960
gcccttagag gaggtatcag gtccagaggc cttccgaggg gacactggta tacctgtttt   16020
ggcctgtgtg acagttgttg gagtggaccc ttggctgccc acgggccctg actcactccc   16080
ttctggtgcc catccctcct cccagggcca ggactccacg ctgggcttga gcctgaatga   16140
aggggtgccg gcggagtgcg acagcgtagt ggtgcatgtg ctgaagctgc agggtgccgt   16200
gcccttcgtg cacaccaatg ttccacagtc catgttcagg ttgggtcttg gggtggggcg   16260
gggcggggca ggggcaccgg tcccagcatg gcacgggctg acccattctt ggctcctcca   16320
gctatgactg cagtaacccc ctctttggcc agaccgtgaa cccatggaag tcctccaaaa   16380
gcccagggg ctcctcaggg ggtgaagggg ccctcatcgg gtctggaggc tcccccctgg   16440
gcttaggcac tgatatcgga ggcagcatcc gcttcccctc ctccttctgc ggcatctgcg   16500
gcctcaagcc cacagggaac cgcctcaggt aaggtgggtg gagggcgctt ctgggcccct   16560
cgctgtgtga ccttggccta gcttccaacc tctctgggct ccaggcgggg attcggtctc   16620
```

```
cggggttttg ctgggaggaa gcattacagt accactggcc gggcgtgggt cctagtttcc   16680
aaagcggtga gtgttcagag ctgctctgtg ggtgtgggga tggcggcggg tggccatttc   16740
ctgtttccag catcttatgt ttcttatcca gcaagagtgg cctgaagggc tgtgtctatg   16800
gacaggaggc aggtgaggtc cgtggtgctc tcagtgcccc gaggagggtg ggggtcggcc   16860
tgacccgctt ccgcccgtgc ttctcaggtg gcagggcagt gtctggcccc caggctgctc   16920
taggtctggg ttcctcgctc cttgtctgct tacctccctc acctctctgc cccacagtgc   16980
gtctctccgt gggcccatg gcccgggacg tggagagcct ggcactgtgc ctgcgagccc   17040
tgctgtgtga ggacatgttc cgcttggacc ccactgtgcc tcccttgccc ttcagagaag   17100
aggtgagcag ggctgggtgg gcatgaatgt ggaccgctga acccagacag ccaccccagg   17160
ccttgtgggc aggccttgga gccctgtct cctgagaacc gtcccccagg cctctgaggc   17220
cagggcgggt tgctcctcca cagacggcca ccagatggag cccttgcctg catttggaaa   17280
tcctcaggct ttttttttt ttcctttct ttctttcttt tttttttttt tttgagact   17340 gagtatcgct ctgtccctca ggctggagtg cagtggcgcg atctcggctc actgcaagct   17400 ccgcctccg ggttcacgcc attctcctgg gttcacgcca ttctcctgcc tcagcctccc   17460
gagtagctgg gactacaggc gcccggcacc acgcccggct aattttttt gtattttttag   17520 tagtagagac ggggtttcac cgtgttatcc aggatggtct ggatctcctg acctcgtgat   17580
ccgcccgcct cggcctccca agtgctggg attacaggct tgagttaccg cgccggccgg   17640
aaatccacag gctttcaaag gtgcccagcc tcagctgctg gcaccaggga tgcaggaatc   17700
atttcccagc ctgctgacct tcagcaaaca gcagccttc taacagtatt cctgtccaca   17760
ttttgggagc agcacgccac gctgcctgca gaccccagct catgtagcct gttcctgcca   17820
gacttgctgc tacgtgagcc agggtctgca agcagcgtgg tgtgctgctc cccaaaatac   17880
caccacagca gcctgttgct gagacaggct gggcttgttg cttctgtgg cgaggcagca   17940 ctgtcttgca aagccttagg atcatctcag agggcaggaa gggtggggag atctgctgag   18000
attttgaagt ctggtttaag gtggatcttt caacatgggg gttggttaag attggtttaa   18060
gttggttaag attggttaag atccttaatc cccatgttaa ggattggtgg gcacagcagg   18120
gtgtggattt tgaggcgaga ggtgtcaacc gatgcttcct gttgaagagt tggaatgaat   18180
cggaaggtta tttgtgttat gtgtgttatt tggaggaggt gggggagtgg ccagtggtca   18240
tcttcctccc agctcatccc ctactgcggg gcatctgaga ccagtatttt gctctcttga   18300
gtgttctggt tgtgctctgg tcctggtact ctctctctct ctgtctctgt gtgcgttggg   18360
gttgaaggcc agaaacagcc aggttgaggc tggggccaga tgtccccagt gaggcaggtg   18420
ctgggcccta ggtcatcctc tgtgcccact ccaacagagt gcaggagctg taaagttaga   18480
ttggtgcaga cagaggaaga gtgaagtcac gttaatgtag acagtaagct gtgtgacgta   18540
agccccgttt ctcagcagtc cagcgattgt ctatcttgta cagacctctt gccctcgccc   18600
cagccaaggt tgccttggaa aggctgaggg tttgtggacg ggaaggagag tgggccttgg   18660
tgtttcttgg gagtggggca gcagggcaga tctgggctgg gtagggtgaa ctcccccctcc   18720 ccaggcagag ggagatattc taaccgaacc cacggggata ggcagccgtg aagtccttcc   18780
tcggaggaga ggaggagatg aggtccctgt ctggaagtct ggaacagttt atcatgagag   18840
ccaggacagg tggtggagag cctcagctca gaagacagga tgcctgcatt ccagacctgt   18900
cttgtcactc tgcattgggt agctttgggc aagtcccagt cccacctaat ctccctattg   18960
```

```
agacctcaag cctcagtttc ctcatatgac cagtaggaat ccttatcctt gctctgccca    19020
cctgagtcac tgtgaaggtg ttttatgaaa gggtcagatg cagaagggc tggcctcgct    19080 gactgcagcc tcgcagctgt gtctggggct gagtagtttc tctgatctct aggggtcctg    19140 cctaggttg tcttctcctg acctgcccct gtccctgtg ttttccctcc aggtctacac     19200
cagctctcag cccctgcgtg tggggtacta tgagactgac aactatacca tgccctcccc    19260
ggccatgagg cgggccgtgc tggagaccaa acagagcctt gaggctgcgg ggcacacggt    19320
atgactgcag ggtcctggaa gtactggcat ctcctcccct cacgggaagc cttcctggta    19380
cccatggcta ctccatccct ggcatcctgg cactctgacg atgttgtcgt cggggtgaac    19440
tgtgaccctg tgggacaagt atatagaggg ctgatcaaga gtattggagt gagtgattga    19500
tggagaactt tagccctgtg ctgtgtgatg tgtgagcact gcatgtgggg aggctcttca    19560
gctctaaaca gtggtgcaca gctgtccaga ggctcccagg gccagtgggt tttggtctgg    19620
tcattacaca acttatgtg tggctccaga cttctctcat gctgtgcatt ccacagtgag     19680
ttttcatggg tcagtaaggc tgcctttgta gctctagtga gagctatctt gtgggcaggg    19740
ttggtccaat ccatcctcag ggccgcccag acagcatggg gatcatgaag ccagttgtta    19800
ggtcaggagg ccttacaccc ctcaatccct gcagctggtt cccttcttgc caagcaacat    19860
accccatgct ctggagaccc tgtcaacagg tgggctcttc agtgatggtg gccacaccttt   19920 cctacagaac ttgtgagtga tagtgggctt tgggtcttg gtgggatcag acaagtaggc     19980
agacctgggg gagcagcagg gtgtggtgat gcctggatgg gccttagctg aatccaacaa    20040
aggcctgagc actctgggca gggacctcgc tgtccctcca gctgggcaca ttgagcctgg    20100
agatcccttg ccagggtgcc agcccgaggg gaggctgggt tgagtatctg tggcctaccc    20160
ctgatctgag cttgttgtga ggtaggaggt gggcaggagg ttgcctctct gtttgggaag    20220
gatttgggcc aagggcagga tccaggcagg agggtggggg tttggacttg atgctgtgac    20280
tccaggctct gtctgacttg agccaagtct tcttttttgag caggacctca gctttctctc    20340
ctgtaaagtg ggtgggttgg accagactcc ctttaaggga cttttgcagag ctcattttta    20400 gagaagttcg ttcctctggg atgcttctag tcattaaagg tgtcagggc agagaacagg     20460 cctgcaaagg tgcctcctgg tgacatacct ctgctggatg gactggaacc cttcagaaca    20520
cagtccccct tcctccactt cactgatgga gaacttggcc ctgcagcctg gagcttggcc    20580
ctgcagcttc actcagtcaa gggcccagcc tgtcatgttc ctttccttcc cctagcagcc    20640
aagtgtggtc caggcttcag tggaaggggt cactcctcac tctggccctg gaatgagtc     20700 cccaggatca gctgcctgag acctttccct gagatcttga gccagagata gcctcagagc    20760
cctgcttcat gggcagccca ccctcgattt ccccacctgt gcctccaggc tgtacctccc    20820
taaggggagg taccctcagg gaggcctcat cagggagatg ttgccctcag ttcttagagc    20880
tctgagctgg gtttgctgga gagggatacc ctgagtcctg ccttggggag ctcccgtgga    20940
tgtgggttgc agcccaggca tcccaaagga tcagcagaaa caaacggcat gtttggaagg    21000
agggagctga gtctggtgag gaggaggtgg acaggatccc tgcatagaga atgggattgc    21060
tgtgggccgg gcgagcaagc tggaaggat gtggggatgg gagtgcctgg accgagcatt     21120
ttgtttccca gcaaaggtga tttcgtggac ccctgcctgg gggacctggt ctcaattctg    21180
aagcttcccc aatggcttaa aggactgctg gccttcctgg tgaagcctct ggtgagggca    21240
caaggagtga aggggctagg atggctgggg gggaacctag ggcctcctat cgcatgatcc    21300
cccatggcct ccctcagcct ctcttggttt gggcaggcat ggcctcctct tctctccagt    21360
```

```
ccccacccag actgctctcc tcctctgtcc cctgcgatct tcagccaacc cgcatgctga   21420
aaggggtgcc gacctgggcc ctgggggagg gcatggaggg aggggtcccc agtggcttgg   21480
cctgaagaag gttgacgtct gccgtggccc agagctgagt caccgaccct gcgtctgtcc   21540
tgtgcagctg ccaaggctgt cagctttcct cagcaacatg aagtctcggt aagggttctt   21600
ctgtgtctag ctgccggccc ctgcctgtcc tgatccgagt ctgggtctgg gtagtttctg   21660
acaggaaagg acttgaggga agtagcctct gaggctggaa gtgcccagg  cagggggca    21720 acctttgtgg ccttcagatg ggactttgaa gttgtcttgg caaggtccag ttctggctgg   21780
agagcaaagg cctgaggggg acaagaggat ggggagttg  gaggggagga ggttgacctg   21840 gctgggcat  gagtggaaag gaccaggaag tgggggttgg cctgggccaa gggtggggca   21900
cccgggagag atgccactgt tagagatctg agctgacctg agctgcgcca ggccctactt   21960
gccccttagt ggctggggct ggaaaagcag ggcgtaaacc tccctgtttc atgccctgac   22020
gtcccatgga ctcactcctt cccttaccac caggcttcag gactggcagc agctatggcc   22080
tctcccgtgt cctgagggta gcgaggaatc gggcctgggc tagtcctggc tctgctgtgg   22140
agtcaccaag tgccagcctg tgcccctctg gggcctgatt ttctcatcca gacagtaggg   22200
gtttgaactt ccctctcaga gctcccatgg ggttgtgaag ggtccacgga ggggtgagat   22260
ctagagggtt ggcagtaggg gtctgatgtt gctgatctcc gtggctgtga ccatcatggc   22320
tggtgaccac actccttctg cccagttcgg ctggaaaact ctgggaactg cagcacgaga   22380
tcgaggtgag gccagagcct ctggattgga gcagggtggt ggggggaggg tggagttgga   22440
cagggtaccc gctagcagtg tctcgtggcc actgccccca tggggctcct agactggcct   22500
gtcatccccc ttccactccc tggaccacca cttgggccca gctctctgac ccttacttgc   22560
ctagatgccc atcctttgag gctgggtcag ccccaggctc ctgtcctggc cgccttttg    22620 cccctctgga gctgccttg tgtggctccg cctcagcggg aagaggtgta tccacaattc    22680
attctggagg cagaacgact gatgccctct gagaggcagc actgcctgcc cggaggacct   22740
gtgtcccact gtggctctgt tcagatccag gggcaggtgc tggggccaga gccaccccag   22800
ccacagtccc tgagttaaag agcctggggt gggctaggtc tgagtgcttt cacctggtgt   22860
gttgtgtcct ccgcaggtgt accgcaaaac cgtgattgcc cagtggaggg cgctggacct   22920
ggatgtggtg ctgaccccca tgctggcccc tgctctggac ttgaatgccc caggcagggc   22980
cacaggtgag gcccgacacc ctgcctgtcc cttctgtgaa tctggccatg tgccctgcag   23040
ggctgcgagg aaatggaaga agagccctct ggaggaccc  tgccctctcg ggcccacag    23100 tctggctgac tggagacatg gcagtcatgt gggttgccct ggcagggatt gattttcctg   23160
tcatcagcac tattcaagtt ggggatcttg agttacagaa tctagtttgg ggaggtgatg   23220
gtttgaagtc caggtgggat ttagataaat caagaaaata ggggccaggg cggtggctca   23280
cacctataat ccgagcactt tgggaggctg aggctgagg  atcacttgag cccaggagct   23340
caagagcagt ccaggcaaca tagtgaggct cctgttgcta caaaaaatag aaaaattagc   23400
tgggtgtggt tgcatgttcc tgtagtcctg gctactcggg gggctgaggc aggaggattg   23460
cttgagccca ggaggtcaag gctgcagtga gttatgatca caccactgca ctccagcctg   23520
ggtgacagag tgagactgtc tcaaaaaaag gaaaaggaaa agaaaacagg aacagcattc   23580
ccagtggaga aagtacatgg gcaaaggcat ggggcaaaca tcagtgggtt gtccagcccg   23640
gccctgaaat ctgaattcct gggctttgtc actcagacct cagtcctggg agagagcctt   23700
```

```
tctctggctg tagacacagg gtgccatttc atatgaggtt tgactcaggc ccggagttgg    23760
cactgaagat tctcagggcc tgctgcagct gcctgtaatg tgttccaggg gccgtcagct    23820
acactatgct gtacaactgc ctggacttcc ctgcaggggt ggtgcctgtc accacggtga    23880
ctgctgagga cgaggcccag atggaacatt cagggggcta ctttgggat atctgggaca     23940 agatgctgca gaaggtgagg actgacctgc ccctcaactg gactcactcc ccaccctgac    24000
tctggccgct gtggaggaaa cagtaccagc actgcgggtt tgccagcctt tcttaagcaa    24060
gacctgaagg actatggcct ggccctacgt tgtggcctct ctctagctgg gtgcttcctg    24120
ggcctggggg tggggagtcc tgccttgcta accctatcct gatgcctgta tccctatag     24180 ggcatgaaga agagtgtggg gctgccggtg gccgtgcagt gtgtggctct gccctggcaa    24240
gaagagttgt gtctgcggtt catgcgggag gtggagcgac tgatgacccc tgaaaagcag    24300
tcatcctgat ggctctggct ccagaggacc tgagactcac actctctgca gcccagccta    24360
gtcagggcac agctgccctg ctgccacagc aaggaaatgt cctgcatggg gcagaggctt    24420
ccgtgtcctc tcccccaacc ccctgcaaga agcgccgact ccctgagtct ggacctccat    24480
ccctgctctg gtccctctc ttcgtcctga tccctccacc cccatgtggc agcccatggg     24540
tatgacatag gccaaggccc aactaacagt caagaaacag ctcctcgtct gtgtggtttc    24600
tgggcgtcat cgtgagggtg gggtttggag cctgttgaga gcagggctgg cttgactgtg    24660
catacccagg ctccagccat gccagtctcc tgctccacaa cctcccctgg tgcccatcac    24720
ccacaggagg ggtgcaggct tgtatccccc agcacttcgg ccgtgcccct cctctctcac    24780
ctacactaag ccctgctctg ctggacactg cccttggtct ccttccttct tctgcttctt    24840
tccctgccta gaaagctctt tctgttcctc tgctttctat cctttgagac ctgactcaga    24900
tccttctctc tccaggacac ctttcctcct ccctctgggc cctggagtat atgggctatt    24960
tcttcccagt ctgccctgtg tggtgggcat tggtgggtgt gtctgcctgc cttagcacac    25020 tggcttttcct tgacgcagg gaacccattg ccacatctct gtcttctgtg ccagcacgg    25080 cagcaggga agcactgagt tgggttgcag agagtccgaa gtgctggccc tgagctgctg    25140
ctgtttggga gaggagccca tgggcctggg gaggccggca tgagacaagg tgacctggta    25200
gagtgtgctc tcagggctgg ccaaggcctg gattgccctg ggaaggtttc ctgaaggagg    25260
tggacgtgtg ttgagtctag aagttttcca gagactgagc tagggggttga ggacatctca    25320 gagagaaggg acagtatgcc caaagatcag ggtgggtttg ctaaatggca ggcatgttga    25380
atgggcacag gggaagcaga gatataggtg aggacagatc aaggtggact tgggcagcca    25440
ggtcaggaac ttgagttctg tctcaaggac agtgggactc tggaaagatc atagctcggc    25500
ctgaggacta gactcgtggg gcaaaacctg tagaagggta aagaagctgc tccatgatcc    25560
ctaatttggg gagagggggcc taaagcctga accttggccc aggggtaaag aggggcccctt   25620 tgggaattga caggatggag gtgagctgtc tcagctcgtc tgctatccac ctcttactgg    25680
actatgtcac ctggctggta gaaaggtggc atctgtagcc gacctagga gtttccttct     25740 tttttttttt ttttagcag agtttcgctc ttgttgctca ggctggtgtg caatggtgtg     25800
atctcggctc actgcaactc cgcctcctgg gttcaagcaa ttttccacct cttgggttca    25860
agtgattctc ctgcctcagc ctcctgagca gctgggatta caggcatgcg ccaccatgcc    25920
cggctaattt tgtatttta gtagagacgg ggtttctcca tgttggtcag actggtcttg     25980
aactcccgac ctcaggtgat ccgcccacct cggcctccca aagtgctggg attacaggtg    26040
aaagccacca tgcccggctg accctaggag tttcttaacc ccattagccc agttgctttg    26100
```

```
ctcttccctg gccccagccc taattctcct gctggctgga gatgtttcag agcctgagcc   26160
ctctaggtag ggcaggtcca cggctcctac ctgtctgtct cagattcttt ctagaagagt   26220
tgccttccca agacttcctt ctccaccctg gttttcatac tcctccagaa gtgctttgcc   26280
ctccaggttg ccacacccat tggcgcctgc accatctccc agtgccatcc ctgcctctgt   26340
ggggccattt tcagggcaga ggtgaggtcc caacctacat ggggacaccc agattgggac   26400
atctaggtag atgctgcact tgccctgat ttcttgtaac cactgctgta attttgcctt    26460
tttcataaaa ccactaccat ctgcccagc ttcctcctcc tgccccattt ctctctttca    26520
gttaccgata tctttgtgcc ttcagacacg aggctgcaga gtggaggtgc cttcactcgt   26580
tcattgattc agcccttgga gcctcagcat ggccatgtcc agacctcagc tgacctgagt   26640
caagcctggg cttctgggga cgtggacatt gacacaaaca catctgttcc tcctgtgatt   26700
agggctgggg gacaggatag acaaggggtc aaatgctgcc aaggggaggg ggaagtggtc   26760
actgaggcta gtacatggcc actgtgtttc atctccacca ccatgctcta gtccaagcca   26820
cctccctcat ctggacgctg cagtgacttc ccttctgggc tccctgcttt caaccctggc   26880
tgccctctaa tccattctcc acacagagct ggaatgatct tttaaaagta taaatcaggc   26940
taggcgcagt ggctcatgcc tgtaatcctc gcactttggg aggctgaggc gggtggatca   27000
ccgaggtcag gagctccaga ctagcctggc caacatggcg aaaccctgtc tctactaaaa   27060
gtacaaaaag tcttgacagg catggtggcg tgcatctgta gtcccagcta ctgaggaggc   27120 ttgaacgtg gctccaatgt caccttccct gctcacccat ttataaaacg gcctccttta    27180 tttcttttc ttttttttgag acggagtcta gttctgttgc caggctggag tgcagtggcg   27240
cgatctcagc tcactgcaac ctccaccctcc tgggttcaag caattctctt gcctcagcct   27300
cctgaatagc tgggattata ggcaagcgac accacgccca ggtagttttt tttttttttt   27360
tgagatagag tcttgctctg ttgcccaggc tggagtgcag tggcgcgatc ttggctcgct   27420
gcaacctccc tctgcctccc gggttcaagc gattctattg cctcagcctc ctgagtagat   27480
tgaattacag gcacgcgcca ccatgcccaa gctaattttt gtattttag tagagacagg    27540 gtttcaccat gtcaaccagg atggtcttga tctccttacc tcgtgatctg cccgcctcgg   27600
cctctcaaag tgctgggatt acaggtatga gccaccacgc ccggccttgg tttcttgatt   27660
atctcaagct gggccctgct tcagagcttt catgttagct cttctctctg cttggaacac   27720
gcagctccaa tgtcaccttc cctgctcacc catttataaa atggcctccc ttgttactct   27780
cttttctttt ttcttttttt cttttttttct gagacggagt cttgctctgt tacccaggct   27840
ggagtgcagt ggcatgattt tggcttactg caacctctgc ctcccggatt caaccaattc   27900
tcctgcccca gcctcccaag tagctgggat tacaggtgtc tgccaccata tcagcgaat   27960 ttttgtattt ttagttggga cggggtttca acatgttggt ctggctggtc ttgagcttgt   28020
gatctgcctg cctgggcctc ccaaagtgct gggattacag gggtaagcca ctgcacccga   28080
gcccttgttt ctttctttct tttttttttt tttgttttt tttgacagag tctcactctg    28140
tcgcccacgc tggagtgcag tggcacaatt tcagctcact gcaacctccg cctcctgggt   28200
tcaagcggtt ctcctgcctc agcctcctga gtagctggta ttacaggcgt gcgccaccac   28260
gcccagctaa ttttttgtatt ttagtagaga tggggtttca ccatgttggt caggctggcc   28320
tcgaactcct gacctcatga tctgcctgcc tgggccttac aggcatgagc caccacgccc   28380
tgccccttgt tactttctaa taggttaccc tttgttcttt tttttttttt ttttttttatt   28440
```

-continued

```
aagacggagt tttgctcttg ttgcccaggt tggagtgtaa tggcaggatc ttggctcact    28500
gcaaactctg cctcctgggt tcaagcaatt ctcctgcctc agcctcccaa gtagctggga    28560
ttacaggcat gcgccaccat gcccagctaa ttttgtattt ttagtagaga cagggtttct    28620
ccatgttggt caggctggtc ttgaactccc gacctcaggt gatccaccct cctgggcctc    28680
ccaaagtgct gggattacag gtgtgagcca cctcgcctgg ccacccttttg ttctttgtag    28740 cattatcact ctctgagctc tttgatgttt ttttgtctcc tccactaaac cataagcttc    28800
ctgagagctg tgctttgtct tgttcatcac ttgttcttgg cttagaggat ggtgctccac    28860
aaattctggg atgataaagt gtggctgtgt gaggggccaa ggcactgtgc tgggtgctgg    28920
cagtgacaaa tgaggcagcc ctggcccctg tcctcgtgga gctcacattc tggagggatt    28980
tgttgaatga acagaagggg gacagagagt tgtgctaatg aagacctcta aatatttaat    29040
gtctggagtg ataacatgac ttttgatccg gaaaaaggg gaaagggaat tctagaccac    29100
atttactgag tacctactat gagccatcta ctttctgggc acttcacagt catgccattt    29160
aatcctctgt gaaccctatg atgggcattt ttgccccct tttacagaaa gtttacgtat    29220
cttgcccagg gtcccacagc tagaagttgg gggcttggaa ccgaaagcta ggccagtctg    29280
tcagcaactg catgaggtct ttctgttgat gccaagcccc agtgagtacg atggccagaa    29340
gagtgagagc acaaatcagc ctcctcctca tacctctctg accaccagtg tgctggtggc    29400
tactgcctgt tttcatggcc tttcccctc tcaccgggtc cactgccaca gcttctttt    29460 tttttcgag acggagtttc gctcttgttg tgcaggctgg agtgcaatgg cgagatctca    29520
gctcactgca acctctgcct accggattca agtgattctc ctgcctcagc ctcccgagta    29580
tc                                                                  29582
```

<210> SEQ ID NO 40
<211> LENGTH: 579
<212> TYPE: PRT
<213> ORGANISM: Homo sapiens

<400> SEQUENCE: 40

```
Met Val Gln Tyr Glu Leu Trp Ala Ala Leu Pro Gly Ala Ser Gly Val
1               5                   10                  15

Ala Leu Ala Cys Cys Phe Val Ala Ala Val Ala Leu Arg Trp Ser
            20                  25                  30

Gly Arg Arg Thr Ala Arg Gly Ala Val Arg Ala Arg Gln Arg Gln
        35                  40                  45

Arg Ala Gly Leu Glu Asn Met Asp Arg Ala Ala Gln Arg Phe Arg Leu
    50                  55                  60

Gln Asn Pro Asp Leu Asp Ser Glu Ala Leu Leu Ala Leu Pro Leu Pro
65                  70                  75                  80

Gln Leu Val Gln Lys Leu His Ser Arg Glu Leu Ala Pro Glu Ala Val
                85                  90                  95

Leu Phe Thr Tyr Val Gly Lys Ala Trp Glu Val Asn Lys Gly Thr Asn
            100                 105                 110

Cys Val Thr Ser Tyr Leu Ala Asp Cys Glu Thr Gln Leu Ser Gln Ala
        115                 120                 125

Pro Arg Gln Gly Leu Leu Tyr Gly Val Pro Val Ser Leu Lys Glu Cys
    130                 135                 140

Phe Thr Tyr Lys Gly Gln Asp Ser Thr Leu Gly Leu Ser Leu Asn Glu
145                 150                 155                 160

Gly Val Pro Ala Glu Cys Asp Ser Val Val Val His Val Leu Lys Leu
```

-continued

```
              165                 170                 175
Gln Gly Ala Val Pro Phe Val His Thr Asn Val Pro Gln Ser Met Phe
            180                 185                 190
Ser Tyr Asp Cys Ser Asn Pro Leu Phe Gly Gln Thr Val Asn Pro Trp
            195                 200                 205
Lys Ser Lys Ser Pro Gly Ser Ser Gly Gly Glu Gly Ala Leu
210                 215                 220
Ile Gly Ser Gly Ser Pro Leu Gly Leu Gly Thr Asp Ile Gly Gly
225                 230                 235                 240
Ser Ile Arg Phe Pro Ser Ser Phe Cys Gly Ile Cys Gly Leu Lys Pro
            245                 250                 255
Thr Gly Asn Arg Leu Ser Lys Ser Gly Leu Lys Gly Cys Val Tyr Gly
            260                 265                 270
Gln Glu Ala Val Arg Leu Ser Val Gly Pro Met Ala Arg Asp Val Glu
            275                 280                 285
Ser Leu Ala Leu Cys Leu Arg Ala Leu Leu Cys Glu Asp Met Phe Arg
            290                 295                 300
Leu Asp Pro Thr Val Pro Pro Leu Pro Phe Arg Glu Glu Val Tyr Thr
305                 310                 315                 320
Ser Ser Gln Pro Leu Arg Val Gly Tyr Tyr Glu Thr Asp Asn Tyr Thr
            325                 330                 335
Met Pro Ser Pro Ala Met Arg Arg Ala Val Leu Glu Thr Lys Gln Ser
            340                 345                 350
Leu Glu Ala Ala Gly His Thr Leu Val Pro Phe Leu Pro Ser Asn Ile
            355                 360                 365
Pro His Ala Leu Glu Thr Leu Ser Thr Gly Gly Leu Phe Ser Asp Gly
            370                 375                 380
Gly His Thr Phe Leu Gln Asn Phe Lys Gly Asp Phe Val Asp Pro Cys
385                 390                 395                 400
Leu Gly Asp Leu Val Ser Ile Leu Lys Leu Pro Gln Trp Leu Lys Gly
            405                 410                 415
Leu Leu Ala Phe Leu Val Lys Pro Leu Leu Pro Arg Leu Ser Ala Phe
            420                 425                 430
Leu Ser Asn Met Lys Ser Arg Ser Ala Gly Lys Leu Trp Glu Leu Gln
            435                 440                 445
His Glu Ile Glu Val Tyr Arg Lys Thr Val Ile Ala Gln Trp Arg Ala
            450                 455                 460
Leu Asp Leu Asp Val Val Leu Thr Pro Met Leu Ala Pro Ala Leu Asp
465                 470                 475                 480
Leu Asn Ala Pro Gly Arg Ala Thr Gly Ala Val Ser Tyr Thr Met Leu
            485                 490                 495
Tyr Asn Cys Leu Asp Phe Pro Ala Gly Val Val Pro Val Thr Thr Val
            500                 505                 510
Thr Ala Glu Asp Glu Ala Gln Met Glu His Tyr Arg Gly Tyr Phe Gly
            515                 520                 525
Asp Ile Trp Asp Lys Met Leu Gln Lys Gly Met Lys Lys Ser Val Gly
            530                 535                 540
Leu Pro Val Ala Val Gln Cys Val Ala Leu Pro Trp Gln Glu Glu Leu
545                 550                 555                 560
Cys Leu Arg Phe Met Arg Glu Val Glu Arg Leu Met Thr Pro Glu Lys
            565                 570                 575
Gln Ser Ser
```

```
<210> SEQ ID NO 41
<211> LENGTH: 579
<212> TYPE: PRT
<213> ORGANISM: Homo sapiens

<400> SEQUENCE: 41

Met Val Gln Tyr Glu Leu Trp Ala Ala Leu Pro Gly Ala Ser Gly Val
1               5                   10                  15

Ala Leu Ala Cys Cys Phe Val Ala Ala Val Ala Leu Arg Trp Ser
            20                  25                  30

Gly Arg Arg Thr Ala Arg Gly Ala Val Val Arg Ala Gln Arg Gln
            35                  40                  45

Arg Ala Gly Leu Glu Asn Met Asp Arg Ala Ala Gln Arg Phe Arg Leu
    50                  55                  60

Gln Asn Pro Asp Leu Asp Ser Glu Ala Leu Leu Ala Leu Pro Leu Pro
65                  70                  75                  80

Gln Leu Val Gln Lys Leu His Ser Arg Glu Leu Ala Pro Glu Ala Val
                85                  90                  95

Leu Phe Thr Tyr Val Gly Lys Ala Trp Glu Val Asn Lys Gly Thr Asn
            100                 105                 110

Cys Val Thr Ser Tyr Leu Ala Asp Cys Glu Thr Gln Leu Ser Gln Ala
            115                 120                 125

Thr Arg Gln Gly Leu Leu Tyr Gly Val Pro Val Ser Leu Lys Glu Cys
    130                 135                 140

Phe Thr Tyr Lys Gly Gln Asp Ser Thr Leu Gly Leu Ser Leu Asn Glu
145                 150                 155                 160

Gly Val Pro Ala Glu Cys Asp Ser Val Val His Val Leu Lys Leu
                165                 170                 175

Gln Gly Ala Val Pro Phe Val His Thr Asn Val Pro Gln Ser Met Phe
            180                 185                 190

Ser Tyr Asp Cys Ser Asn Pro Leu Phe Gly Gln Thr Val Asn Pro Trp
            195                 200                 205

Lys Ser Ser Lys Ser Pro Gly Gly Ser Ser Gly Glu Gly Ala Leu
210                 215                 220

Ile Gly Ser Gly Gly Ser Pro Leu Gly Leu Gly Thr Asp Ile Gly Gly
225                 230                 235                 240

Ser Ile Arg Phe Pro Ser Ser Phe Cys Gly Ile Cys Gly Leu Lys Pro
            245                 250                 255

Thr Gly Asn Arg Leu Ser Lys Ser Gly Leu Lys Gly Cys Val Tyr Gly
            260                 265                 270

Gln Glu Ala Val Arg Leu Ser Val Gly Pro Met Ala Arg Asp Val Glu
    275                 280                 285

Ser Leu Ala Leu Cys Leu Arg Ala Leu Leu Cys Glu Asp Met Phe Arg
290                 295                 300

Leu Asp Pro Thr Val Pro Pro Leu Pro Phe Arg Glu Glu Val Tyr Thr
305                 310                 315                 320

Ser Ser Gln Pro Leu Arg Val Gly Tyr Tyr Glu Thr Asp Asn Tyr Thr
                325                 330                 335

Met Pro Ser Pro Ala Met Arg Arg Ala Val Leu Glu Thr Lys Gln Ser
            340                 345                 350

Leu Glu Ala Ala Gly His Thr Leu Val Pro Phe Leu Pro Ser Asn Ile
            355                 360                 365

Pro His Ala Leu Glu Thr Leu Ser Thr Gly Gly Leu Phe Ser Asp Gly
    370                 375                 380
```

```
Gly His Thr Phe Leu Gln Asn Phe Lys Gly Asp Phe Val Asp Pro Cys
385                 390                 395                 400

Leu Gly Asp Leu Val Ser Ile Leu Lys Leu Pro Gln Trp Leu Lys Gly
                405                 410                 415

Leu Leu Ala Phe Leu Val Lys Pro Leu Leu Pro Arg Leu Ser Ala Phe
            420                 425                 430

Leu Ser Asn Met Lys Ser Arg Ser Ala Gly Lys Leu Trp Glu Leu Gln
            435                 440                 445

His Glu Ile Glu Val Tyr Arg Lys Thr Val Ile Ala Gln Trp Arg Ala
        450                 455                 460

Leu Asp Leu Asp Val Val Leu Thr Pro Met Leu Ala Pro Ala Leu Asp
465                 470                 475                 480

Leu Asn Ala Pro Gly Arg Ala Thr Gly Ala Val Ser Tyr Thr Met Leu
                485                 490                 495

Tyr Asn Cys Leu Asp Phe Pro Ala Gly Val Val Pro Val Thr Thr Val
            500                 505                 510

Thr Ala Glu Asp Glu Ala Gln Met Glu His Tyr Arg Gly Tyr Phe Gly
        515                 520                 525

Asp Ile Trp Asp Lys Met Leu Gln Lys Gly Met Lys Lys Ser Val Gly
530                 535                 540

Leu Pro Val Ala Val Gln Cys Val Ala Leu Pro Trp Gln Glu Glu Leu
545                 550                 555                 560

Cys Leu Arg Phe Met Arg Glu Val Glu Arg Leu Met Thr Pro Glu Lys
                565                 570                 575

Gln Ser Ser
```

GENE THERAPY OF THE FAAH PSEUDOGENE

CROSS-REFERENCES TO RELATED APPLICATIONS

This application is a National Stage of International Application No. PCT/GB/2019/050368, filed Feb. 12, 2019, which claims priority to Great Britain Application Number 1802326.7, filed Feb. 13, 2018, the disclosures of which are incorporated herein by reference in their entirety.

FIELD OF THE INVENTION

The present invention relates to analgesic treatments to reduce pain.

BACKGROUND TO THE INVENTION

Fatty-acid amide hydrolase (FAAH) is the major catabolic enzyme for a range of bioactive lipids, including the N-acyl ethanolamines (such as anandamide (AEA), palmitoylethanolamide (PEA) and oleoylethanolamine (OEA)) and N-acyltaurines.[1, 2] Anandamide, an endogenous ligand for cannabinoid receptors (i.e. an endocannabinoid), has been shown to have roles in nociception, fear extinction memory, anxiety and depression.[3, 4] Faah knockout mice have significantly elevated brain tissue levels of anandamide and display an analgesic phenotype in response to acute thermal stimuli and show reduced pain in formalin and carrageenan inflammatory models.[5, 6]

The human FAAH gene contains a commonly carried hypomorphic SNP (C385A; rs324420) that significantly reduces the activity of the FAAH enzyme.[7] Genetic association studies have investigated the link between this, and other FAAH SNPs, and pain sensitivity.[8-10] Notably, homozygous carriers of the hypomorphic SNP in a cohort of women undergoing breast cancer surgery were shown to have significantly lower cold pain sensitivity and less need for postoperative analgesia.[8] Furthermore, a mouse knockin model of the human SNP showed that both the mouse and human SNP carriers display enhanced fear-extinction learning and decreased anxiety-linked behaviours.[11]

Although FAAH is therefore an attractive drug target for treating pain, as well as anxiety and depression, recent clinical trials with FAAH inhibitors have however proven unsuccessful.[12, 13] The present invention describes routes to inhibiting FAAH function using gene therapy which are expected to have none of the side effect problems of small molecule FAAH antagonists.

SUMMARY OF THE INVENTION

The inventors have discovered a link between a microdeletion in a fatty-acid amide hydrolase pseudogene (FAAH-OUT) and an individual's ability to feel pain. In particular, through studying an individual (PFS) with a hypoalgesic phenotype, the inventors identified a microdeletion in FAAH-OUT in the individual that is absent from individuals with a normal pain phenotype. The microdeletion disrupts normal expression of the full-length FAAH-OUT transcript (e.g. results in lower or higher FAAH-OUT expression) with a consequent diminished FAAH function, and increased levels of endogenous analgesic molecules such as anandamide. It is also possible to directly disrupt the FAAH gene using gene therapy.

The invention provides a method of analgesic treatment to reduce pain, comprising administering an effective amount of an inhibitor of fatty-acid amide hydrolase pseudogene (FAAH-OUT) to an individual suffering from pain.

The invention also provides an inhibitor of FAAH-OUT for use in a method of treating pain, the method comprising administering an effective amount of said inhibitor to a subject.

The invention further provides a method of analgesic treatment to reduce pain, comprising administering an effective amount of an inhibitor of fatty-acid amide hydrolase gene (FAAH) to an individual suffering from pain, wherein the inhibitor is a single-stranded or double-stranded DNA or RNA molecule directed against FAAH.

The invention also provides an inhibitor of FAAH for use in a method of treating pain, the method comprising administering an effective amount of said inhibitor to a subject.

BRIEF DESCRIPTION OF THE FIGURES

FIG. 1: (A) Genomic map showing FAAH, FAAH-OUT and microdeletion in PFS. Human chromosome 1 showing the gene footprints of FAAH and FAAH-OUT. Exons are denoted by black boxes and direction of transcription shown by arrows. FAAH SNP rs324420 maps to exon 3 (shown by asterisk). The 8,131 bp microdeletion detected in PFS is shown and is flanked by Alu repeat sequences (grey boxes). The promoter region and exons 1 and 2 of FAAH-OUT map to the deleted sequence. (B) Real-time RT-qPCR showing expression profile of FAAH-OUT in human tissues. FAAH-OUT is expressed in a wide range of human tissues, notably in dorsal root ganglia (DRG) and several brain regions. Expression is shown relative to beta actin.

FIG. 7: Comparison of FAAH and FAAH-OUT cDNA sequences. (A) Alignment between FAAH and FAAH-OUT exonic sequences identify an 800 bp region with ~70% nucleotide identity. The high sequence homology means that the genes potentially share microRNA seed sites, with 2 examples shown in bold and underlined text (miR-125a-5p/125b-5p/351/670/4319; CAGGGG and miR-128/128ab; CTGTGC), as predicted by miRcode. (B) Most likely peptide generated from FAAH-OUT cDNA, as predicted by ATG$^{pr}$. (C) The putative FAAH-OUT protein shares 69% homology (50% identity) over a 139 amino acid segment of the FAAH enzyme.

FIG. 8: Real-time RT-qPCR in patient PFS fibroblast cell line and 4 unrelated female fibroblast controls. (A) Relative FAAH expression to β-actin. FAAH expression was significantly reduced in PFS fibroblasts compared to four control cell lines. Data were normalized with the mean FAAH level of control fibroblast cells taken as 100% (n=4, control fibroblast cells). (B) Relative BDNF expression to β-actin. BDNF expression was significantly increased in PFS fibroblasts compared to four control cell lines. The average expression level of BDNF in four control fibroblast lines was normalized with the BDNF expression level in the PFS fibroblast sample taken as 100% (n=4, control fibroblast cells). P values were generated by t-test, $p<0.01$, *$p<0.001$. Error bars=SEM FIG. 9: Gene editing in HEK293 cells. (A) Microdeletion in FAAH-OUT induced by transiently transfecting SaCas9 plasmids (HMa and HMb) each bearing 2 guide sequences that flank the microdeletion identified in patient PFS. Genomic DNA was used as template to PCR-amplify edited DNA from HMa transfected cells (~463 bp) and from HMb transfected cells (~598 bp). No corresponding edited fragment was amplified from cells transfected with a vector containing no guide sequences. (B) RT-qPCR analysis of FAAH mRNA levels following transient transfection with HMa or HMb. The microdeletion in FAAH-OUT results in a significant reduction in FAAH expression. P values were generated by t-test, $p<0.01$, *$p<0.001$. Error bars=SEM

BRIEF DESCRIPTION OF THE SEQUENCES

SEQ ID NO: 1 is the cDNA sequence of wild-type human FAAH that does not contain the hypomorphic rs324420 SNP.

SEQ ID NO: 2 is the cDNA sequence of human FAAH that contains the hypomorphic SNP rs324420 (C385A).

SEQ ID NO: 3 is the cDNA sequence of wild-type human FAAH-OUT

SEQ ID NO: 4 is cDNA sequence of human FAAH-OUT comprising the microdeletion.

SEQ ID NO: 5 is the genomic DNA sequence of wild-type human FAAH-OUT

SEQ ID NO: 6 is the genomic DNA sequence of FAAH-OUT comprising the microdeletion.

SEQ ID NO: 7 is the genomic DNA sequence corresponding to the microdeletion.

SEQ ID NOs: 8 to 23 are primer sequences.

SEQ ID NOs: 24 to 28 are guide sequences.

Figure 6:
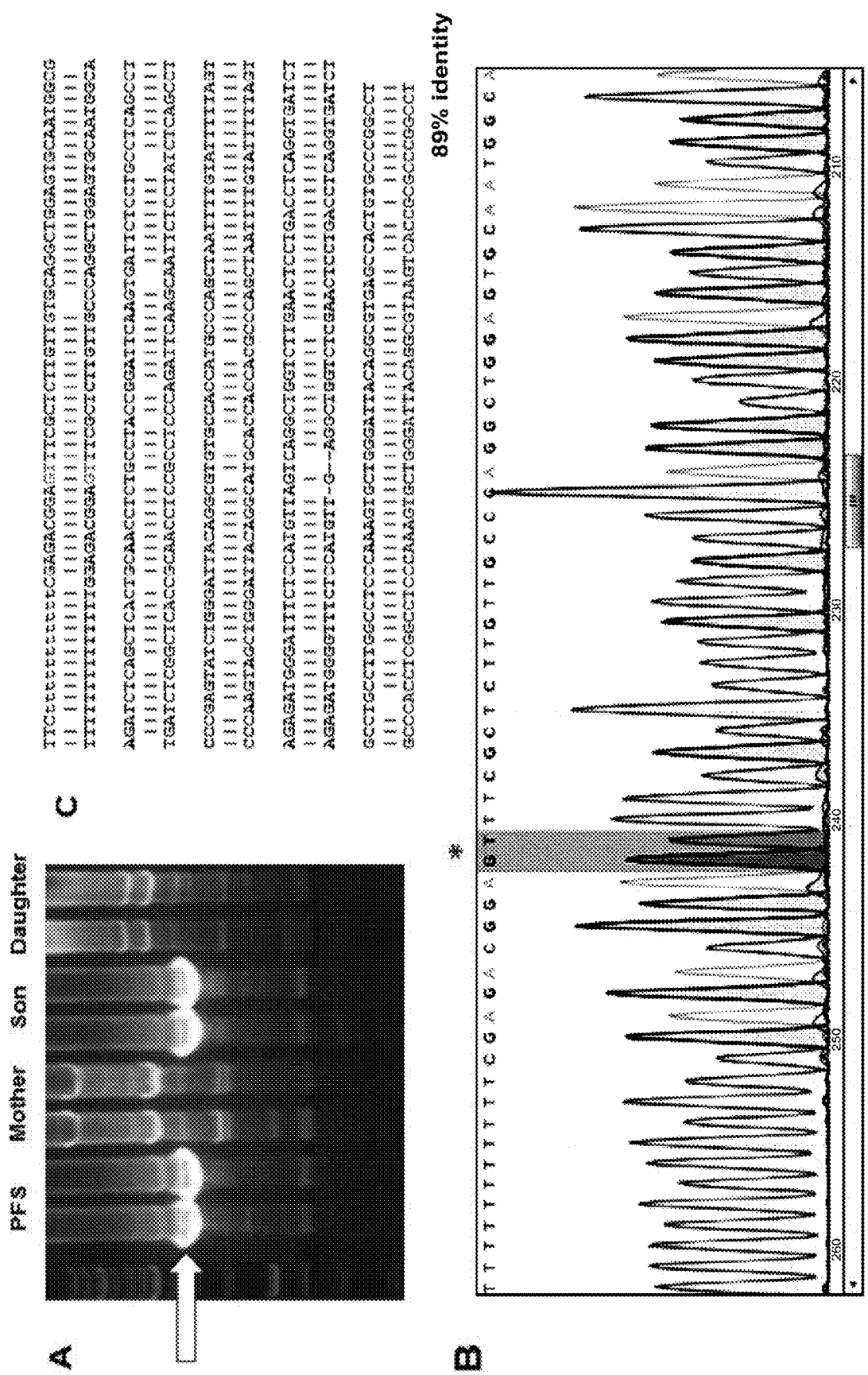
FIG. 6: Validating microdeletion in PFS. (A) PCR primers located outside of the microdeleted region amplified a 2,259 bp region from PFS and her son (i.e. the allele containing the microdeletion), as indicated by the white arrow. The wild-type allele product from the same reaction is 10,390 bp (beyond the capability of the DNA polymerase). A 1 kb ladder is in lane 1. (B) Sanger sequencing of the mutant allele identified the microdeletion breakpoint (the 8,131 bp deleted sequence on the wild-type allele is normally located at the asterisk between the highlighted bases). (C) AluSp sequences (human genome build 38/human; chr1:46418719-46419015 and chr1:46426839-46427143) flank the microdeleted region. Alignment of these sequences shows 89% identity over 298 bp, likely predisposing the region to a genomic rearrangement.

SEQ ID NOs: 29 to 38 correspond to the sequences from FIGS. 6 and 7.

SEQ ID NO: 39 is the genomic DNA sequence of wild-type human FAAH, including 5 kb either side of FAAH.

SEQ ID NO: 40 is the amino acid sequence of wild-type human FAAH that does not contain the hypomorphic rs324420 SNP.

SEQ ID NO: 41 is the amino acid sequence of human FAAH that contains the hypomorphic SNP rs324420.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting. All publications, patents and patent applications cited herein, whether supra or infra, are hereby incorporated by reference in their entirety.

As used in this specification and the appended claims, the singular forms "a", "an", and "the" include plural referents unless the content clearly dictates otherwise. Thus, for example, reference to "a peptide" includes "peptides", and the like.

Fatty-Acid Amide Hydrolase Pseudogene (FAAH-OUT)

Fatty-acid amide hydrolase pseudogene (FAAH-OUT) may also be referred to herein as FAAHP1 or FAAHP. FAAH-OUT is expressed in fetal and adult brain and in dorsal root ganglia tissue. FAAH-OUT may also be expressed in other parts of the nervous system, such as in the spinal cord. Wildtype FAAH-OUT has a genomic DNA sequence of SEQ ID NO: 5. Sequence alignments show that there is nucleotide identity of about 70% within an 800 bp region between FAAH and FAAH-OUT. The footprint of FAAH-OUT gene in genomic DNA is 26960 bp. FAAH-OUT transcript (cDNA) is 2845 nucleotides. The FAAH-OUT protein may be about 166 amino acids in length. FAAH-OUT may function as a long non-coding RNA. FAAH-OUT may include a microdeletion. Typically, the microdeletion is around 8 kb in length. For example, using Sanger sequencing, the microdeletion in genomic DNA may be around 8,131 bp in length. The microdeletion is located around 4.7 kb downstream of the FAAH 3' UTR. The microdeletion removes the promoter and first two exons of FAAH-OUT. In some instances, a regulatory element or an enhancer element of FAAH is located within the microdeletion. The disruption of FAAH-OUT by the microdeletion therefore affects expression of FAAH.

In some instances, FAAH-OUT may be targeted in the treatments described herein.

Fatty-Acid Amide Hydrolase (FAAH) and a SNP Located within FAAH Gene

Fatty-acid amide hydrolase (FAAH) is a member of the serine hydrolase family of enzymes and is the major catabolic enzyme for a range of bioactive lipids, including the N-acyl ethanolamines (e.g. anandamide (AEA), palmitoylethanolamide (PEA) and oleoylethanolamine (OEA)) and N-acyltaurines. FAAH knockout mice have significantly elevated brain tissue levels of anandamide and display an analgesic phenotype. The human FAAH gene contains a commonly carried hypomorphic SNP (C385A; rs324420) that significantly reduces the activity of the FAAH enzyme.

Methods of Treatment/Medical Uses

Analgesic Treatment

The present invention relates to a method of analgesic treatment to reduce pain using gene therapy. The method comprises administering an effective amount of an inhibitor of FAAH-OUT expression to an individual suffering from pain. The present invention also relates to an inhibitor of FAAH-OUT for use in a method of treating pain, the method comprising administering an effective amount of said inhibitor to a subject. The present invention also relates to the use of an inhibitor of FAAH-OUT expression in the manufacture of a medicament for treating pain. The method also comprises administering an effective amount of an inhibitor of FAAH expression to an individual suffering from pain, wherein the inhibitor is a single-stranded or double-stranded DNA or RNA molecule directed against FAAH. The present invention also relates to an inhibitor of FAAH for use in a method of treating pain, the method comprising administering an effective amount of said inhibitor to a subject, where the inhibitor is a single-stranded or double-stranded DNA or RNA molecule directed against FAAH. The present invention also relates to the use of an inhibitor of FAAH expression in the manufacture of a medicament for treating pain.

The method may be for treating pain. In the case of treatment, the patient typically feels pain or has undergone a procedure that is known to be painful. As used herein, the term "treatment" includes any of following: the prevention of pain; a reduction or prevention of the development or progression of pain; and the reduction or elimination of existing pain.

Therapy and prevention includes, but is not limited to preventing, alleviating, reducing, curing or at least partially arresting symptoms and/or complications resulting from or associated with pain. When provided therapeutically, the therapy is typically provided at or shortly after the onset of pain. Such therapeutic administration is typically to prevent or ameliorate pain progression or to reduce the severity of pain. When provided prophylactically, the treatment is typically provided before the onset of pain. Such prophylactic administration is typically to prevent or delay the onset of pain.

Many different types of pain can be treated or prevented, as can pain originating from many different sources. The pain may be acute (e.g. post-operative pain) or chronic (e.g. painful conditions such as rheumatoid arthritis, peripheral neuropathy, idiopathic pain, cancer). The pain may be nociceptive pain, neuropathic pain or inflammatory pain. Nociceptive pain is the normal response to noxious insult or injury of tissues such as skin, muscles, visceral organs, joints, tendons, or bones. For instance, nociceptive pain may be somatic (e.g. musculoskeletal, cutaneous) or visceral. Neuropathic pain is caused by damage or disease affecting the somatosensory nervous system. Neuropathic pain may involve peripheral sensitisation or central sensitisation. It may lead to sensory abnormalities, such as numbness or hypersensitivity (hyperalgesia or allodynia). Examples of neuropathic pain include but are not limited to Carpal tunnel syndrome, central pain syndrome, degenerative disc disease, diabetic neuropathy, phantom limb pain, postherpetic neuralgia (shingles), pudendal neuralgia, sciatica and trigeminal neuralgia. Neuropathic pain may also be caused by Guillain-Barre syndrome, cancer, multiple sclerosis, kidney disorders, alcoholism, HIV, nerve damage from spinal cord injury, post-mastectomy pain (PMPS), postoperative hernia repair pain, phantom limb pain (post-amputation) and other types of post-surgical pain. Inflammatory pain is caused by activation and sensitisation of the nociceptive pathway by mediators released at a site of tissue inflammation, which alters the activity of ion channels within affected sensory fibres. Inflammatory pain is typically caused by osteoarthritis, rheumatoid arthritis, Crohn's disease or fibromyalgia.

Treatment or prevention of pain is understood to be effective if pain is either reduced or eliminated. Reduction or elimination of pain can be measured by any suitable technique known in the art, for example via the techniques known as the McGill pain questionnaire or McGill pain index. The McGill Questionnaire consists primarily of three major classes of world descriptors-sensory, affective and evaluative, which are used by patients to specify pain experience. The three major measures are the pain rating index, the number of words chosen and the present pain intensity based on a 1-5 intensity scale.

General

An individual to be treated by the administration of a substance (i.e. inhibitor) may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is preferred.

Specific routes, dosages and methods of administration of the therapeutic agents described herein may be routinely determined by the medical practitioner. These are discussed in more detail below.

The measurement of the levels of chemicals having roles in nociception can be carried out by analysing blood samples or tissue samples. Such chemicals may include, but are not limited to N-acyl ethanolamines (e.g. anandamide (AEA), palmitoylethanolamide (PEA) and oleoylethanolamine (OEA)) and N-acyltaurines. As an example, significant increases in blood tissue levels of AEA are observed in a subject having an analgesic phenotype.

Exemplary assays for measuring pain-related chemicals are also described in the Examples.

Other Treatments

The methods of the present invention may also be used to treat anxiety, depression or post-traumatic stress disorder (PTSD), to reduce fear levels and for rapid wound healing.

FAAH-OUT Inhibitors

A FAAH-OUT inhibitor is any compound, agent or substance that can reduce the effect of FAAH-OUT or suppress FAAH-OUT expression. The suppression is preferably selective for FAAH-OUT over FAAH. Such inhibitors include but are not limited to oligonucleotides, antibodies, small molecules. A particularly preferred agent are oligonucleotides. For example, siRNA or shRNA knockdown may be employed, or antisense oligonucleotides and the Crispr/Cas9 system may be employed for reducing the effect of or suppressing FAAH-OUT. CRISPR interference (CRISPRi) may also be employed, for instance using a catalytically dead/inactive Cas9 (e.g. dCas9) optionally via an effector (e.g. repressor) domain such as a KRAB domain. In some embodiments, the inhibitor modifies the DNA sequence encoding FAAH-OUT. In some instances, the modification is made by gene editing. In some instances, the inhibitor targets FAAH-OUT but affects expression of FAAH. For instance, the inhibitor may disrupt or lead to the removal of a regulatory element or an enhancer element of FAAH that is located in FAAH-OUT.

A FAAH-OUT inhibitor may target a sequence encoding the FAAH-OUT gene having SEQ ID NO: 5 or an expression product of the FAAH-OUT gene. An expression product of the FAAH-OUT gene may be RNA or protein. The sequence encoding the FAAH-OUT gene may be a sequence having at least 60%, at least 65%, at least 70%, at least 75%, at least 80%, at least 85%, at least 90%, at least 95%, at least 98% or at least 99% identity to the sequence of SEQ ID NO: 5. The identity level is preferably at least 85% or higher. Identity relative to the sequence of SEQ ID NO: 5 can be measured over a region of at least 1000 bp, at least 2000 bp, at least 3000 bp, at least 4000 bp, at least 5000 bp, at least 6000 bp, at least 7000 bp, at least 8000 bp, at least 9000 bp, at least 10000 bp, at least 11000 bp or more contiguous nucleotides the sequence shown in SEQ ID NO: 5, or more preferably over the full length of SEQ ID NO: 5.

Oligonucleotides

The present invention provides oligonucleotides that are able to suppress or reduce the effect of FAAH-OUT. Such oligonucleotides directed against FAAH-OUT are inhibitors of FAAH-OUT according to the present invention. As noted above, oligonucleotides may alternatively be used to suppress FAAH or FAAH.

The terms "oligonucleotide", "nucleic acid molecule" and "polynucleotide" are used interchangeably herein and refer to a polymeric form of nucleotides of any length, either deoxyribonucleotides or ribonucleotides, or analogs thereof. In the context of this invention, the term "oligonucleotide" refers to an oligomer of nucleotide or nucleoside monomers consisting of naturally-occurring bases, sugars and inter-sugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

The oligonucleotides described herein can be single-stranded DNA or RNA, double-stranded DNA or RNA, DNA-RNA hybrids, or chimeric DNA-RNA structures. Examples of double-stranded RNA include, e.g., siRNA, short hairpin RNA (shRNA) and other RNAi agents such as pre-miRNA. Single-stranded oligonucleotides include, e.g., antisense oligonucleotides, ribozymes, mature miRNA, and triplex-forming oligonucleotides.

Using known techniques and based on a knowledge of the sequence of FAAH-OUT or FAAH, double-stranded RNA (dsRNA) molecules can be designed to suppress FAAH-OUT or FAAH expression by sequence homology-based targeting of its RNA transcript. Such dsRNAs will typically be siRNAs, usually in a stem-loop ("hairpin") configuration, or micro-RNAs (miRNAs). The sequence of such dsRNAs will comprise a portion that corresponds with that of a portion of the mRNA transcript of FAAH-OUT or FAAH. This portion will usually be 100% complementary to the target portion within the allele comprising the dominant mutation but lower levels of complementarity (e.g. 60% or more, 65% or more, 70% or more, 75% or more, 80% or more, 85% or more, 90% or more, or 95% or more) may also be used.

In some instances, the total length of the oligonucleotide may be up to 100, 90, 80, 70, 60, 50, 40, 30 or 20 nucleotides. In others, the total length may be 29, 28, 27, 26, 25, 24, 23, 22, 21, 20, 19, 18, 17, 16, 15, 14, 13, 12, 11 or 10 nucleotides.

Using known techniques and based on a knowledge of the sequence of the FAAH-OUT (e.g. based on the nucleotide sequences of SEQ ID NO: 5) or FAAH (encoded by SEQ ID NO: 1, 2 or 39), a single-stranded antisense oligonucleotide (AON) can be designed to suppress FAAH-OUT or FAAH by sequence homology-based targeting of its RNA transcript. The sequence of such AONs will comprise a portion that corresponds with that of a portion of the mRNA transcript or FAAH-OUT or FAAH. This portion will usually be 100% complementary to the target portion within the allele but lower levels of complementarity (e.g. 60% or more, 65% or more, 70% or more, 75% or more, 80% or more, 85% or more, 90% or more or 95% or more) may also be used. The AON may act by binding to pre-mRNA or mRNA via Watson-Crick base pairing and induces gene suppression by different mechanisms such as through RNase H-mediated mRNA degradation. The AON may have a base sequence that is complementary to the mRNA of FAAH-OUT or FAAH. They are prone to rapid degradation by intracellular endonucleases and exonucleases.

The AONs may be gapmers or altimers. A gapmer is a chimeric AON that contains a central block of DNA molecules and is flanked by blocks of 2'-O modified ribooligonucleotides or other artificially modified ribooligonucleotide monomers that protect the internal block from nuclease degradation. The oligonucleotides contain DNA bases, wherein some or all of the DNA bases have a phosphorothioated backbone. For example, none, 5 or more, 10 or more, 15 or more, 20 or more, 25 or more, or all of the DNA bases have a phosphorothioated backbone. DNA that contain phosphorothioated backbones provide an increased resistance to nucleases compared to unmodified DNA.

In one embodiment, the oligonucleotide for use in the invention comprises modifications to help enhance its properties. Hence, the oligonucleotide may be modified by the substitution of at least one nucleotide with at least one modified nucleotide, ideally so that the in vivo and in vitro stability of the oligonucleotide is enhanced as compared to a corresponding unmodified oligonucleotide. The modified nucleotide may, for instance, be a sugar-modified nucleotide or a nucleobase-modified nucleotide. In some instances, two, three, four, five, six or seven modified nucleotides may be included, or at least that number, in others eight, nine, ten, eleven or twelve such modifications, or at least that number, may be included, in other cases, fifteen, twenty, twenty-one, twenty-two, twenty three, twenty-four, twenty-five or at least such numbers may be modified. In still others all of the nucleotides may be modified, or all but one, two, three, four or five nucleotides.

In some instances, the modified nucleotide is a 2'-deoxy ribonucleotide. In certain instances, the 2'-deoxy ribonucleotide is 2'-deoxy guanosine or 2'-deoxy adenosine. In other instances, the modified nucleotide is a 2'-O-methylguanosine, 2'-O-methyl (e.g., 2'-O-methylcytidine, 2'-O-methylpseudouridine, 2'-O-methyluridine, 2'-O-methyladenosine, 2'-O-methyl) ribonucleotide. In some cases, the modified nucleotide is selected from a 2'-amino, 2'-thio and 2'-fluoro modified ribonucleotide. In a further instances, the modified nucleotide is selected from the group consisting of 2'-fluoro-cytidine, 2'-fluoro-uridine, 2'-fluoro-guanosine, 2'-fluoro-adenosine, 2'-amino-cytidine, 2'-amino-uridine, 2'-amino-adenosine, 2'-amino-guanosine, 2'-amino-butyryl-pyrene-uridine and 2'-amino-adenosine. In an additional instances, the modified nucleotide is selected from 5-iodo-uridine, ribo-thymidine, 5-bromo-uridine, 2-aminopurine, 5-methyl-cytidine, 5-fluoro-cytidine, and 5-fluoro-uridine, 2,6-di-aminopurine, 4-thio-uridine, and 5-amino-allyl-uridine.

In some instances, the modified nucleotide includes: derivatization of the 5 position, for instance being selected from 5-(2-amino) propyl uridine, 5-bromo uridine, 5-propyne uridine, 5-propenyl uridine; derivatization of the 6 position, for instance 6-(2-amino)propyl uridine; derivatization of the 8-position for adenosine and/or guanosines, for instance 8-bromo guanosine, 8-chloro guanosine, or 8-fluoroguanosine, Nucleotide analogs which may be employed include deaza nucleotides, e.g., 7-deaza-adenosine; O- and N-modified (for instance alkylated, such as N6-methyl adenosine) nucleotides; and other heterocyclically modified nucleotide analogs. Examples of modifications to the sugar portion of the nucleotides which may be employed include the 2' OH-group being replaced by a group selected from H, OR, R, F, Cl, Br, I, SH, SR, NH2, NHR, NR2, COOR, or OR, wherein R is substituted or unsubstituted C1-C6 alkyl, alkenyl, alkynyl, aryl and so on. The phosphate group of the nucleotide may also be modified, such as by substituting one or more of the oxygens of the phosphate group with sulphur (for instance by employing phosphorothioates). Modifications may decrease the rate of hydrolysis of polynucleotides comprising the modified bases, for example by inhibiting degradation by exonucleases. In one preferred instance, the oligonucleotide is resistant to ribonucleases. Oligonucleotides which may be employed include those with modifications to promote such resistance, for instance an oligonucleotide of the invention may have preferably been modified with a 2'-O-methyl group (e.g., 2'-O-methylcytidine, 2'-O-methylpseudouridine, 2'-O-methylguanosine, 2'-O-methyluridine, 2'-O-methyladenosine, 2'-O-methyl) and additionally comprise a phosphorothioate backbone.

In some instances, oligonucleotides for use in the invention comprise oligonucleotides that contain phosphorothioate and 2'-O-methyl (e.g., 2'-O-methylcytidine, 2'-O-methylpseudouridine, 2'-O-methylguanosine, 2'-O-methyluridine, 2'-O-methyladenosine, 2'-O-methyl) modification. Other forms of oligonucleotide modifications may be employed, for example, locked nucleic acids (oligonucleotides comprising at least one 2'-C,4'-C-oxy-methylene-linked bicyclic ribonucleotide monomer). In some instances the modified nucleotide employed may be 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluraci 1, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In some instances, the modified oligonucleotide may include modifications to the phosphate backbone such as methyl phosphonates, methyl phosphonothioates, phosphoromorpholidates, phosphoropiperazidates and phosphoramidates. In one example, every other one of the internucleotide bridging phosphate residues may be modified as described. In another non-limiting example, such oligonucleotides are oligonucleotides wherein at least one, or all, of the nucleotides contain a 2' loweralkyl moiety (e.g., C1-C4, linear or branched, saturated or unsaturated alkyl, such as methyl, ethyl, ethenyl, propyl, 1-propenyl, 2-propenyl, and isopropyl).

In one embodiment, the oligonucleotide for use in the invention is a small interfering RNA (siRNA). An siRNA acts by activating the RNAi-induced suppression complex (also known as the RISC complex). The siRNA molecules can be unmodified or modified and are capable of suppressing (i.e. partially or completely preventing) expression of FAAH-OUT (e.g. having SEQ ID NO: 36) or FAAH protein (e.g. having SEQ ID NOs: 40 or 41). The siRNA may prevent expression of FAAH-OUT or FAAH. The siRNA may prevent expression of mRNA encoding FAAH-OUT or FAAH protein. The siRNA may prevent translation of an mRNA encoding FAAH-OUT or FAAH protein. The siRNA may reduce or prevent FAAH-OUT or FAAH protein expression by affecting the post translational modification of FAAH-OUT or FAAH protein. An siRNA is typically about 5 to 60 nucleotides in length, about 5 to 55 nucleotides in length, about 5 to 50 nucleotides in length, about 5 to 45 nucleotides in length, about 5 to 40 nucleotides in length, about 5 to 35 nucleotides in length, about 5 to 30 nucleotides in length, about 5 to 25 nucleotides in length, about 5 to 20 nucleotides in length, about 5 to 15 nucleotides in length, or about 5 to 10 nucleotides in length.

In some embodiments, the modified siRNA contains at least one 2'O-Me purine or pyrimidine nucleotide such as a 2'O-Me-guanosine, 2'O-Me-uridine, 2'O-Me-adenosine, and/or 2'O-Me-cytosine nucleotide. The modified nucleotides can be present in one strand (i.e., sense or antisense) or both strands of the siRNA. The siRNA sequences may have overhangs or blunt ends.

The modified siRNA may comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides.

Suitable siRNA sequences can be identified using any means known in the art. Typically, the methods described in Elbashir et al., *Nature*, 411:494-498 (2001) and Elbashir et al., *EMBO* 1, 20:6877-6888 (2001) are combined with rational design rules set forth in Reynolds et al., *Nature Biotech.*, 22(3):326-330 (2004).

Preferably, siRNA are chemically synthesized. The oligonucleotides that comprise the siRNA molecules of the invention can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). The synthesis of oligonucleotides makes use of common nucleic acid protecting and coupling groups, such as dimethoxytrityl at the 5'-end and phosphoramidites at the 3'-end. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

In one embodiment, the oligonucleotide for use in the invention is a guide RNA comprising a guide RNA sequence and a tracr RNA. The guide RNA sequence is capable of hybridizing to a target sequence in the DNA of an allele. The tracr RNA is coupled to the guide RNA sequence. The guide RNA hybridises to the site of the allele carrying a dominant mutation and targets a CRISPR-Cas enzyme to said site. In some embodiments, the guide sequence is between 10-30, or between 15-25, or between 15-20 nucleotides in length. Preferably the CRISPR-Cas enzyme is a Type II CRISPR enzyme, for example Cas-9. The enzyme complexes with the guide RNA. In one embodiment, the complex is targeted to the DNA sequence of FAAH-OUT or FAAH and will bind by hybridization. In another embodiment, the complex is targeted to the DNA sequence of the regulatory region, e.g. the promoter, of FAAH-OUT or FAAH. In another embodiment, the complex is targeted to the DNA sequence of the first two exons of FAAH-OUT or FAAH. In some embodiments, any region of FAAH-OUT or FAAH may be targeted which leads to deletion of FAAH-OUT or FAAH and/or disruption of its function. In one embodiment, the enzyme is active and acts as an endonuclease to cleave the DNA either via activation of the non-homologous end-joining or homologous DNA repair pathway, resulting in a blunt end cut or a nick. A repair template sequence can be supplied and be introduced into the allele by homologous recombination, thereby replacing the sequence that it targeted, such as a mutation in the DNA of an allele. In another embodiment, the enzyme is targeted to the DNA of FAAH-OUT or FAAH but the enzyme comprises one or more mutations that reduce or eliminate its endonuclease activity such that it does not edit FAAH-OUT or FAAH but does prevent or reduce its transcription. In another embodiment, the enzyme can be engineered such that it is fused to a transcriptional repressor to reduce or disable its endonuclease function. The enzyme will be able to bind the guide RNA and be targeted to the DNA sequence, but no cleavage of the DNA takes place. FAAH-OUT or FAAH may be suppressed, for example, by the shutting down of the promoter or blockage of RNA polymerase. In another embodiment, the transcription repressor may be bound to the tracr sequence. Functional domains can be attached to the tracr sequence by incorporating protein-binding RNA aptamer sequences, as described in Konermann et al (Genome-scale transcriptional activation by an engineered CRISPR-Cas9 complex, Nature, 517, 583-588, 2015). The transcription repressor-tracr sequence complex may be used to target other moieties to a precise gene location as desired.

Other gene editing methods well known in the art may be employed in the invention. Such methods include but are not limited to zinc finger nuclease gene editing methods, recombinant adeno-associated virus (rAAV) genome editing methods, non-Cas9 CRISPR systems using Cpf1 for gene editing, and methods using transposons. Exemplary nucleases used in these methods include but are not limited to zinc finger nucleases (ZFN), meganucleases and transcription activator-like effector-based nucleases (TALEN).

An oligonucleotide for use in the invention may be conjugated with a peptide or receptor. To assist with delivery of the oligonucleotide, the peptide may for example be a cell penetrating peptide. This technique is described in, for example, WO2009/147368, WO2013/030569, WO2012/150960 and WO2004/097017. The oligonucleotides may also be conjugated to a carrier or encapsulated within a liposome.

The oligonucleotides for use in the invention may be complementary to a region of the RNA transcript from FAAH-OUT or FAAH. In one instance, the oligonucleotide will be complementary to 10, 11, 12, 13, 14, 15, 16, 17, 18, 19, 20, 21, 22, 23, 24, 25, 26, 27, 28, 29, or 30 nucleotides of that sequence, preferably complementary to 13-25 or 16-21 nucleotides of that sequence.

In one instance, the oligonucleotide is at least 10, 11, 12, 13, 14, 15, 16, 17, 18, 19, 20, 21, 22, 23, 24, 25, 26 or 27 nucleotides in length, preferably at least 19, 20, 21, 22, 23, 24, 25 or 26 nucleotides in length, for example 13-25 or 16-21 nucleotides in length. In one embodiment, the oligonucleotide is between 10 and 35 nucleotides in length, for example, 10, 11, 12, 13, 14, 15, 16, 17, 18, 19, 20, 21, 22, 23, 24, 25, 26, 27, 28, 29, 30, 31, 32, 33, 34, 35 nucleotides in length. In one embodiment, the oligonucleotide is between 18 and 30 nucleotides in length, for example, 18, 19, 20, 21, 22, 23, 24, 25, 26, 27, 28, 29 30 nucleotides in length. It may be that the region of the oligonucleotide capable of hybridisation to is that length, or at least that length, but there are also additional nucleotides at the 5' and/or 3' ends of the oligonucleotide, though in other instances the overall length of the oligonucleotide is that number of nucleotides.

In general, oligonucleotide sequences which are perfectly complementary to a portion of the target RNA may preferably be employed. In some instances though sequence variations that might be expected due to genetic mutation, strain polymorphism, or evolutionary divergence may be present. For example, oligonucleotide sequences with insertions, deletions, and single point mutations relative to the target sequence may also be effective for inhibition. Greater than 70% sequence identity (or complementarity), e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the oligonucleotide sequence and the target RNA, e.g., target pre-mRNA, is preferred.

Sequence identity, including determination of sequence complementarity for nucleic acid sequences, may be determined by sequence comparison and alignment algorithms known in the field. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions*100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The oligonucleotide for use in the invention may also hybridise to a site within the FAAH-OUT or FAAH that may be a site with a polymorphism, such as a Single Nucleotide Polymorphism (SNP), microsatellite polymorphism, insertion polymorphism and deletion polymorphism. Preferably the polymorphism is a SNP. Such polymorphisms may be identified by genotyping the subject and sequencing the mutant allele present in their genome, or they may be known or suspected to be present a priori. Targeting an oligonucleotide to such a mutation in the allele will suppress the allele and effect treatment of pain, even if the mutation targeted is non-causative of the disease. Further, both the causative mutation and one or more non-causative ones can be targeted with different oligonucleotides.

Suppression of the expression of an allele can be measured by any suitable technique known in the art. For example, reverse transcription, Sanger sequencing and quantitative real-time PCR is a frequently used technique. The oligonucleotides of the invention can suppress the expression of the allele by any amount, preferably up to 95%, 90%, 85%, 80%, 75%, 70%, 65%, 60%, 55%, 50%, 45%, 40%, 30%, 20% or 10%.

Oligonucleotide Delivery

The oligonucleotides for use in the present invention may be introduced into cells using any suitable method. For instance transfection, electroporation, fusion, liposomes, extracellular vesicles (e.g. exosomes or microvesicles), colloidal polymeric particles, dendrimers and viral and non-viral vectors as well as other means known in the art may be used to deliver the oligonucleotide sequences to cells.

In some instances, the oligonucleotide is delivered using methods involving liposome-mediated uptake. Lipofectins and cytofectins are lipid-based positive ions that bind to negatively charged nucleic acid and form a complex that can ferry the nucleic acid across a cell membrane and may be employed. In one instance a lipofectin is used in the delivery of the oligonucleotide, particularly Lipofectamine 2000. In one instance the oligonucleotide may be delivered using a jetPRIME® reagent. For example, the oligonucleotide may be delivered to cells in vitro using a method involving jetPRIME® reagent. In some instances, no transfection reagents may be required and oligonucleotide may be taken up by target cells directly via gymnosis.

In one embodiment, the oligonucleotides may be delivered using a composition comprising a dendrimer. Dendrimers are nano-sized, radially symmetric molecules with well-defined, homogeneous, and monodisperse structure that has a typically symmetric core, an inner shell, and an outer shell (Madaan et al. (2014) J Pharm Bioallied Sci. 2014 July-September; 6(3): 139-150). Any dendrimer may be suitable for delivery of oligonucleotides. The dendrimer for use with the oligonucleotides may comprise of consist of polyamidoamine (PAMAM), a poly(propylene imine) (PPI, poly-L-lysine, melamine, poly(etherhydroxylamine) (PEHAM), poly(esteramine) (PEA) and/or polyglycerol. Delivery may be direct to the subject, or for instance to cells or tissues, for instance with the cells or tissues subsequently being reintroduced. Oligonucleotides may be directly introduced into a target cell or introduced extracellular into a cavity, interstitial space, into the circulation of a subject, introduced orally, or may be solution containing the RNA using methods for introducing nucleic acid into cells in vivo.

The oligonucleotides may be delivered by any suitable route of administration. In some instances, administration may be systemic, in others it may be localised. For instance, the oligonucleotides may be administered by direct injection at a tissue site or infusion into a body fluid. Vascular or extravascular circulation, the blood or lymph system, and the cerebrospinal fluid are examples of locations where the RNA may be introduced.

The oligonucleotide may be, for instance, delivered to the nervous system of a subject by any suitable method. For example, injection and in particular intravenous injection of the oligonucleotide reagents of the invention can be used for delivery to peripheral neurons via diffusive and/or active means. Alternatively, the oligonucleotides can be modified to promote crossing of the blood-brain-barrier (BBB) to achieve delivery of said reagents to neuronal cells of the central nervous system (CNS). In certain instances, the oligonucleotides can be delivered by transdermal methods. The oligonucleotide may also be delivered via an implantable device.

Physical methods of introducing an oligonucleotide include injection of a solution containing the oligonucleotide, bombardment by particles covered by the oligonucleotide, soaking the cell or organism in a solution of the oligonucleotide, or electroporation of cell membranes in the presence of the oligonucleotide. A viral vector packaged into a viral particle can be used to achieve efficient introduction of the oligonucleotide into a cell and transcription of oligonucleotide encoded by the expression construct. Other methods known in the art for introducing nucleic acids to cells may be used, such as lipid-mediated carrier transport, chemical-mediated transport, such as calcium phosphate, and the like. The oligonucleotide may be introduced along with components that perform one or more of the following activities: enhance uptake of the oligonucleotide of the invention by a cell, inhibit annealing of single strands of oligonucleotide of the invention, stabilise single strands of oligonucleotide, prevent degradation of the oligonucleotide or otherwise increase inhibition of the target gene.

The oligonucleotides may be modified so that they target specific cells, for instance by binding to receptors found on a particular cell type. The oligonucleotides may be delivered to cells using a vector.

This is also described further in the "Administration route, formulations and dosages" section below.

Vectors

A vector that can be used in the invention may be of any type, for example it may be a plasmid vector or a minicircle DNA.

Typically, vectors that can be used in the invention are viral vectors. The viral vector may for example be based on the herpes simplex virus, adenovirus or lentivirus. The viral vector may be an adeno-associated virus (AAV) vector or a derivative thereof. The viral vector derivative may be a chimeric, shuffled or capsid modified derivative. The viral vector may comprise an AAV genome from a naturally derived serotype, isolate or clade of AAV. The serotype may for example be AAV2, AAV5, AAV8 or AAV9. Preferably, the serotype may be AAV9.

The efficacy of gene therapy is, in general, dependent upon adequate and efficient delivery of the donated DNA. This process is usually mediated by viral vectors. Adeno-associated viruses (AAV), a member of the parvovirus family, are commonly used in gene therapy. Wild-type AAV, containing viral genes, insert their genomic material into the chromosome of the host cell. The AAV single-stranded DNA genome comprises two inverted terminal repeats (ITRs) and two open reading frames, containing structural (cap) and packaging (rep) genes.

For therapeutic purposes, the only sequences required in cis, in addition to the therapeutic gene, are the ITRs. The AAV virus is therefore modified: the viral genes are removed from the genome, producing recombinant AAV (rAAV). This contains only the therapeutic gene, the two ITRs. The removal of the viral genes renders rAAV incapable of actively inserting its genome into the host cell DNA. Instead, the rAAV genomes fuse via the ITRs, forming circular, episomal structures, or insert into pre-existing chromosomal breaks. For viral production, the structural and packaging genes, now removed from the rAAV, are supplied in trans, in the form of a helper plasmid. AAV is a particularly attractive vector as it is generally non-pathogenic; the majority people have been infected with this virus during their life with no adverse effects.

rAAV transduces cells via serotype specific receptor-mediated endocytosis. A major factor influencing the kinetics of rAAV transgene expression is the rate of virus particle uncoating within the endosome. This, in turn, depends upon the type of capsid enclosing the genetic material (Ibid.). After uncoating the linear single-stranded rAAV genome is stabilised by forming a double-stranded molecule via de novo synthesis of a complementary strand. The use of self-complementary DNA may bypass this stage by producing double-stranded transgene DNA. Natkunarajah et al (2008) found that self-complementary AAV2/8 gene expression was of faster onset and higher amplitude, compared to single-stranded AAV2/8. Thus, by circumventing the time lag associated with second-strand synthesis, gene expression levels are increased, when compared to transgene expression from standard single-stranded constructs. Subsequent studies investigating the effect of self-complementary DNA in other AAV pseudotypes (e.g. AAV2/5) have produced similar results. One caveat to this technique is that, as AAV has a packaging capacity of approximately 4.8 kb, the self-complementary recombinant genome must be appropriately sized (i.e. 2.3 kb or less).

An AAV genome is a polynucleotide sequence which encodes functions needed for production of an AAV viral particle. These functions include those operating in the replication and packaging cycle for AAV in a host cell, including encapsidation of the AAV genome into an AAV viral particle. Naturally occurring AAV viruses are replication-deficient and rely on the provision of helper functions in trans for completion of a replication and packaging cycle. Accordingly and with the additional removal of the AAV rep and cap genes, the AAV genome of the vector of the invention is replication-deficient.

The AAV genome may be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype or isolate or clade of AAV. As is known to the skilled person, AAV viruses occurring in nature may be classified according to various biological systems.

Commonly, AAV viruses are referred to in terms of their serotype. A serotype corresponds to a variant subspecies of AAV which owing to its profile of expression of capsid surface antigens has a distinctive reactivity which can be used to distinguish it from other variant subspecies. Typically, a virus having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10 and AAV11, also recombinant serotypes, such as Rec2 and Rec3, recently identified from primate brain. In vectors used in the invention, the genome may be derived from any AAV serotype. The capsid may also be derived from any AAV serotype. The genome and the capsid may be derived from the same serotype or different serotypes. Reviews of AAV serotypes may be found in Choi et al (*Curr Gene Ther.* 2005; 5(3); 299-310) and Wu et al (*Molecular Therapy.* 2006; 14(3), 316-327).

The AAV serotype determines the tissue specificity of infection (or tropism) of an AAV virus. Accordingly, preferred AAV serotypes for use in AAV viruses administered to patients in accordance with the invention are those which have natural tropism for or a high efficiency of infection of brain tissue or dorsal root ganglia tissue.

Effects of Inhibitor Administration

Administration of an inhibitor may lead to an increase in the level of N-acyl ethanolamines and N-acyl taurines in the individual. For instance, the administration of an inhibitor leads to an increase in the levels of anandamide (AEA), palmitoylethanolamide (PEA) and/or oleoylethanolamine (OEA). The administration of an inhibitor may also lead to an increase in N-acyl-taurines e.g. N-tetracosanoyl-taurine [NAT(24:0)] and N-eicosanoyl-taurine [NAT(20:0)].

Combination Therapies

An inhibitor may be used in combination with one or more other therapies or agents intended to treat or ameliorate pain in the same individual. The therapies or agents may be administered simultaneously, in a combined or separate form, to an individual. The therapies or agents may be administered separately or sequentially to an individual as part of the same therapeutic regimen.

Exemplary agents include, but are not limited to, non-steroidal anti-inflammatory drugs (NSAIDS) such as ibuprofen, aspirin, naproxen, fenoprofen, flurbiprofen, ketoprofen, oxaprozin, diclofenac sodium, etodolac, indomethacin, ketorolac, sulindac, tolmetin, meclofenamate, mefenamic acid, nabumetone, piroxicam, COX-2 inhibitors such as celecoxib, opioids such as morphine, codeine, oxycodone, hydrocodone, dihydromorphine, pethidine, fentanyl, oxymorphone, methadone, cannabinoids. Anaesthetics, anticonvulsants, antidepressants, neuromodulators, pain-relief injections and psychological therapy, for example, and any other therapy or pain management, may also be used.

Administration Routes, Formulations and Dosages

Specific routes, dosages and methods of administration of the substance (including inhibitors of FAAH-OUT or FAAH expression) for use in the invention may be routinely determined by the medical practitioner. Typically, a therapeutically effective amount of the substance is administered to the patient. A therapeutically effective amount of the substance is an amount effective to reduce pain in the context of analgesic treatment. A therapeutically effective amount of the substance is administered. The dose may be determined according to various parameters, especially according to the compound used; the age, weight and condition of the patient to be treated; the route of administration; and the required regimen. Again, a physician will be able to determine the required route of administration and dosage for any particular patient.

The substance can be administered to the patient by any suitable means. The substance can be administered by enteral or parenteral routes such as via oral (e.g. inhalation), buccal, anal, pulmonary, intravenous, intra-arterial, intramuscular, intraosseous, intraspinal, intracranial, intraperitoneal, intradermal, subcutaneous, intrathecal, intra-articular, topical or other appropriate administration routes. Intrathecal administration is particularly preferred.

The substance may be administered in a variety of dosage forms. It may be administered orally (e.g. as tablets, troches, lozenges, aqueous or oily suspensions, dispersible powders or granules), parenterally, subcutaneously, intravenously, intramuscularly, intraosseously, intrasternally, intraspinally, intracranially, transdermally or by infusion techniques. The substance may also be administered as a suppository. A physician will be able to determine the required route of administration for each particular patient.

The inhibitor, e.g. oligonucleotide, siRNA, vector or isolated cell can be formulated for use with a pharmaceutically acceptable carrier or diluent and this may be carried out using routine methods in the pharmaceutical art. The pharmaceutical carrier or diluent may be, for example, an isotonic solution. Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

Solid oral forms may for example contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions. For suppositories, traditional binders and carriers may include, for example, polyalkylene glycols or triglycerides; such suppositories may be formed from mixtures containing the active ingredient in the range of 0.5% to 10%, preferably 1% to 2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Pharmaceutical compositions suitable for delivery by needleless injection, for example, transdermally, may also be used.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the substance in the patient and the duration of treatment desired.

The skilled person and particularly an appropriate physician will be able to identify an appropriate dosage, for instance taking factors such as age, sex, weight, conditions of the patient to be treated, the severity of the disease and the frequency and route of administration and so on into account.

The substance may be an oligonucleotide. Preferably, such oligonucleotides are provided in the form of an expression vector, which may be expressed in the cells of the patient to be treated. This is also described in the section above, "Oligonucleotide delivery", and the sections below. The oligonucleotides may be naked nucleotide sequences or be in combination with cationic lipids, polymers or targeting systems. The oligonucleotides may be delivered by any available technique, such as those described above. For example, the oligonucleotides may be introduced by needle injection, preferably intradermally, subcutaneously or intramuscularly. Alternatively, the oligonucleotides may be delivered directly across the skin using an oligonucleotide delivery device such as particle-mediated gene delivery. The oligonucleotide may be administered topically to the skin, or to mucosal surfaces for example by intranasal, oral, intravaginal or intrarectal administration. A preferred delivery method is intrathecal administration of an AAV vector.

Uptake of oligonucleotide constructs may be enhanced by several known transfection techniques, for example those including the use of transfection agents. Examples of these agents includes cationic agents, for example, calcium phosphate and DEAE-Dextran and lipofectants, for example, lipofectam and transfectam.

Pharmaceutical compositions may comprise one or more inhibitors, oligonucleotides, siRNAs, vectors, or isolated cells as described. Pharmaceutical compositions may comprise additional active ingredients as well one or more inhibitors, oligonucleotides, siRNAs, vectors, or isolated cells as described. They may also comprise additional therapeutic or prophylactic agents. The additional therapeutic agents or prophylactic agents may be useful for treating or preventing pain.

Administration may be, for instance, by inhalation. Systemic administration may be, for instance, by transmucosal or transdermal means. Transmucosal administration can be accomplished through the use of nasal sprays or suppositories. For transdermal administration, the oligonucleotides may be, for instance, formulated into a transdermal patches or plasters, ointments, salves, gels, or creams. The oligonucleotides may be, for instance, prepared in the form of suppositories or retention enemas. In some instances, the oligonucleotides may be formulated with carriers that protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid.

In one embodiment, the pharmaceutical compositions may be formulated in unit dosage forms. In some embodiments the compositions may be formulated in ampoules. The pharmaceutical compositions may be included in a container, pack, or dispenser together with instructions for administration.

The dosage of the oligonucleotide administered will depend upon the particular method being carried out, and when it is being administered to a subject, the nature of disease, the condition of the subject, the particular formulation, and the route of administration. Examples of intracellular concentrations of the oligonucleotide include those in the range from about 0.005 to 50 µM, or more preferably 0.02 to 5 µM. For administration to a subject such as a human, a daily dosage ranging from about 0.001 to 50 mg/kg, preferably 0.01 to 10 mg/kg, and more preferably from 0.1 to 5 mg/kg may be employed. The skilled person and particularly an appropriate physician will be able to identify an appropriate dosage, for instance taking factors such as age, sex, weight and so on into account.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The invention is illustrated by the following Example:

Example 1

Methods
German DFNS Protocol for Quantitative Sensory Testing (QST)

QST was performed following informed consent on the dorsum of the foot and the hand according to the German neuropathic pain network (DFNS) protocol by a DFNS trained experimenter.[15] This protocol includes 13 parameters which are designed to detect both gain and loss of function and is summarised below:

Thermal Stimuli:
Temperature testing was conducted using a TSA-2001-II (Medoc, Israel) with a thermode of contact area 9 $cm^2$. Thresholds were obtained using ramped stimuli (1° C./s) from 32° C. (centre of neutral range) until terminated by subject-control or automated cut-off temperatures whereby the temperature would return to baseline temperature. Thermode temperature was held at 32° C. during 10 s inter-stimulus intervals. Sequentially, cooling and warming detection thresholds (CDT, WDT) were assessed. The presence of paradoxical heat sensations (PHS) was investigated by alternating warming and cooling which were also used to determine thermal sensory limen (TSL). Cold and heat pain thresholds (CPT, HPT) were then measured. Tests were performed in triplicate and mean data used for comparison. All subjects were unaware of the timing of initiation of temperature increase and inter-stimuli intervals.

Mechanical Stimuli:
Mechanical detection threshold (MDT) was assessed using a standardized set of identically round-tipped von Frey hairs (Optihair$_2$-Set, Marstock, Nervtest, Germany) of twofold incremental bending forces within the range 0.25-512 mN. MDT was calculated as a geometric mean of five thresholds ascertained using sequential ascending and descending applications of the hairs by a 'method of limits'. Assessment of vibration sense (VS) was performed with a Rydel-Seiffer graded tuning fork (64 Hz, 8/8 scale) that was placed over the processus styloideus ulnae or malleolus internus and left there until the subject could not feel vibration any more and was performed three times. Mechanical pain threshold (MPT) were ascertained using a set of seven mechanical probes which exert fixed intensities of 8, 16, 32, 64, 128, 256, 512 mN with a blunt contact area of 0.2 mm diameter. Stimuli were applied in ascending sequence at a rate of 2 s on, 2 s off until a stimulus was perceived as sharp and subsequent descending until no longer reported as such. Threshold was calculated as the geometric mean of five of these series. Wind up ratio (WUR) is a perceptual model of temporal spinal wind up was generated from the perceived intensity of painfulness from a single application of 256 mN pinprick compared to 10 repetitions of the same stimulus applied at a rate of 1/second within a 1 cm$^2$ area. Pain intensity was reported using a numerical rating scale (NRS) where 0 represents no pain and 100, maximal imaginable pain. The process was repeated five times and WUR calculated by dividing the mean pain report following the ten applications, by the mean intensity reported from single stimuli. Mechanical pain sensitivity (MPS) was assessed using the same set of seven weighted pinprick stimuli to obtain a stimulus-response function for pinprick-evoked pain (the strongest pinprick force was about eight times the mean mechanical pain threshold). Subjects were asked to give a pain rating for each stimulus on a '0-100' numerical rating scale ('0' indicating "no pain", and '100' indicating "most intense pain imaginable"). This test was designed to detect pinprick hyperalgesia. Dynamic mechanical allodynia (DMA) was assessed as part of this test using a cotton wisp, a cotton wool tip and a standardised brush (Somedic Sweden) exerting a force of 200-400 mN. Pressure pain threshold (PPT) was assessed at the thenar eminence and instep using a pressure gauge devise (FDN 200, Wagner instruments, USA) with a probe area of 1 cm$^2$. Pressure pain threshold was determined using three series of ascending stimulus intensities at an increasing ramp of 50 KPa/s.

The findings for each parameter are compared with a control Caucasian population by means of Z-scores. The Z-score represents the result of a raw score minus the mean of the population and this is further divided by the standard deviation of the population. Z scores above or below ±2 standard deviations represent hyper-/hyposensitivity and hyper-/hypo-algesia. In the cases when upper limits allowed by the ethics committee for pain testing were reached, the cut-off value expressed is equivalent to the maximum stimulation before it causes any tissue damage (0° to 52° C. for temperature, 512 mN for mechanical pain, 10 Kg for pressure pain).

Skin Biopsy

A punch skin biopsy was taken from 10 cm above the lateral malleolus of the leg of the proband and fixed overnight with 2% periodate-lysine-paraformadelhyde and preserved in sucrose before blocked and processed into 50 μM sections. Nerve fibres were stained using rabbit anti-PGP (protein gene product) 9.5 Ab (1:2000; Ultraclone Ltd, Yarmouth, Isle of Wight, UK) and Cy3 anti-rabbit (1:500; Jackson Immunoresearch, West Grove, PA, USA). By means of a Zeiss LSM 710 confocal microscope, z-stacks (2 μm intervals), maximum intensity projections were generated with a Plan-Apochromat objective at 20× magnification (Carl Zeiss MicroImaging GmbH, Jena, Germany). Analysis was performed as per published guidelines.[16] PGP 9.5-positive nerve fibres crossing the dermal-epidermal junction were counted and IENFD counts are given in number of fibres per millimetres of skin.

Whole Exome Sequencing

For enrichment of exons and flanking intronic sequences we used the Agilent Human SureSelect V5 kit with UTRs. We performed 100 bp paired-end runs on a Genome Analyzer HiSeq 2000 system (Illumina) generating sequences of 5.2 (PFS), 5.3 (son), 5.4 (mother) and 5.6 (daughter) Gb. This amount of data resulted in the following percentages of targets being covered at greater than or equal to 10×: 95.7 (PFS), 96 (son), 96 (mother) and 96.2 (daughter). Sequence alignment and variant calling was performed against the reference human genome assembly (hg19) by using the Burrows-Wheeler Aligner[17] and the Genome Analysis Toolkit.[18, 19] Format conversion and indexing were performed with the Picard software. Single nucleotide variants and small insertions and deletions were checked against established databases (1000 Genomes Project and dbSNP v.142). Variants were further checked using the ExAC browser, db SNP v.150 and in our in-house database of sequencing data for other diseases (n>2000). The protein coding effects of variants was predicted using SIFT, Polyphen2 and M-CAP. Splicing changes were analysed using the NNSPLICE Splice Site Predictor. Novel variants were verified by Sanger sequencing and checked to see how they segregated within the family (primers available on request).

Genomic Copy Number Analyses

Genomic DNA isolated from a peripheral blood sample from PFS was used for the Cytoscan HD Copy Array (Affymetrix) and run by AROS according to the manufacturer's conditions. Data was analysed using Chromosome Analysis Suite (Affymetrix) software and novel genomic variants identified by comparison to the Database of Genomic Variants (DGV).

Deletion Breakpoint Cloning

A range of primers were designed that were predicted to flank the microdeletion identified in the Cytoscan HD Copy Array. A 2,259 bp product was amplified from PFS and the son using LA Taq DNA Polymerase (Clontech) and the primers 5'CCACCAGTGTGCTGGTGGCTAC (SEQ ID NO: 8) and 5'AGCCTCTGGGGCACTTTGACTC (SEQ ID NO: 9) (FIG. 6A). Primers closer to the deletion breakpoints were then designed and used to amplify a 1349 bp product using KAPA HiFi DNA Polymerase and the primers 5'TTAATGTCTGGAGTGATAACATGAC (SEQ ID NO: 10) and 5'ACAACTTCTAATTAGTGTTAATGAC (SEQ ID NO: 11). Sanger sequencing of the gel purified PCR product (Qiagen) using primers 5' TTAATGTCTGGAGTGATAA-CATGAC (SEQ ID NO: 10) and 5' AAGGCCGGGCGCGGTGACTTAC (SEQ ID NO: 12) enabled identification of the microdeletion breakpoints (FIG. 6B).

PCR Amplification and Sanger Sequencing of SNP Rs324420

Genomic DNA was used as template to amplify a 424 bp product from the region containing SNP rs324420 using primers 5' CTCTGGGCCATGTTGCTGGTTAC (SEQ ID NO: 13) and 5' CAACTGTCACACAGGCCAAAACAG (SEQ ID NO: 14). Purified PCR products were Sanger sequenced by standard methods.

Cloning FAAH-OUT

Partial expressed sequence tags (ESTs) were identified downstream of the microdeletion that in Refseq were assembled into a 1267 bp sequence (NR_045483) and annotated as 'fatty acid amide hydrolase pseudogene (FAAHP1) non-coding RNA'. To identify further 5'exons, the FAAHP1 locus from a variety of species was searched using the UCSC genome browser. This led to the identification of EST CN788775 in the cow genome. The nucleotide sequence of this EST was compared to the human genome using the Blat tool and consensus splice donor and acceptor sites identified within the human genomic DNA sequence. Human adult brain total RNA was reverse transcribed into cDNA using oligo d(T) and the Superscript III first-strand synthesis system (Invitrogen). A forward primer mapping to the most 5' predicted exon (5' CCAGAAGTG-GAGGGAGGTAGCAC (SEQ ID NO: 15) and a reverse primer in a downstream predicted exon (5' GCTGTCAT-AGGTGTCCTTGAGGCTC (SEQ ID NO: 16) were designed and used to amplify a product from human adult brain cDNA. Sanger sequencing confirmed the amplicon to be novel human exons mapping 5' to FAAHP1. Next, 5'RACE was carried out using whole human brain Marathon-Ready cDNA (Clontech) using reverse primer (5' CAAAGTGAGACTCCGTCTGCTGC (SEQ ID NO: 17) according to the manufacturer's conditions. The generated amplicon was cloned into the pCR-Blunt II-TOPO (Thermofisher) and sequenced using M13 forward and reverse primers. A forward primer (5' GGCAAAGGCGCCAT-TCTCCTGGGTACA (SEQ ID NO: 18) was then designed at the most 5' end of the newly identified transcript and a reverse primer (5'GCCAGTCAGAAAATGTTTATT-GAGCTC (SEQ ID NO: 19) in the most 3' exon of NR_045483. Human cerebral cortex cDNA was used as template to amplify a 2845 bp product, which was subsequently cloned into pCR-Blunt II-TOPO and fully sequenced. The insert of the sequenced clone (CC2) has been submitted to GenBank under accession number KU950306 and we name the gene FAAH-OUT Real-Time qPCR Analysis in Human Tissues One μg of total RNA derived from a range of human tissues (Clontech) was reverse transcribed using oligo d(T) and Superscript III first-strand synthesis system (Invitrogen) according to the manufacturer's conditions. Real time PCR was carried out using the Universal SYBR Green Supermix protocol (Bio-Rad) and the following primers: FAAH-OUT, 214 bp (5' ACTGACACAGGTGACAGCATCTG (SEQ ID NO: 20) and 5' GTCCAGTCGGTACATGTCTTCAC (SEQ ID NO: 21); and Actin (ACTB), 144 bp (5' CCTGGCACCCAGCACAAT (SEQ ID NO: 22) and 5' GGGCCGGACTCGTCATACT (SEQ ID NO: 23). These assays were performed on the BioRad CXF Connect™ real-time thermal cycler. FAAH-OUT expression was compared with that of Actin measured on the same sample in parallel on the same plate, giving a CT difference (ΔCT) for ACTB minus the test gene. Mean and standard error were performed on the ΔCT data and converted to relative expression levels (2" ΔCT).

RNAscope in Adult Human Dorsal Root Ganglia Tissue

RNAscope fluorescent in situ hybridization was performed with the RNAscope® Multiplex Fluorescent V2 Kit according to the manufacturer's experimental protocol for formalin-fixed paraffin-embedded (FFPE) samples. The fluorochromes used to detect target RNA molecules were Opa1520 (green) and Opa1650 (red) by PerkinElmer at 1:1000 dilution. The specific RNAscope® probes for FAAH (#534291-C2) and FAAH-OUT (#534301-C3) RNAs were designed and synthesized by ACD company (BioTechne). DAPI staining was used to stain nuclei. Images were collected using Zeiss LSM-880 microscope with Airscan using 4× averaging, exported as uncompressed TIF files and finalised using Adobe Lightroom 7 photoshop.

Assessment of Plasma Endocannabinoids (EC)

Levels of AEA, PEA, OEA and 2-AG were measured by mass spectrometry from blood samples taken from PFS and 4 unrelated normal controls. Study participants were PFS (index patient, female, post-menopausal (aged 69), FAAH-OUT microdeletion and A/C for rs324420); control A (female, post-menopausal (aged 50), CC for rs324420); control B (male, aged 57, CC for rs324420); control C (female, post-menopausal (aged 50), AC for rs324420) and control D (male, aged 49, AC for rs324420). Study participants were free of all medications for at least four weeks. Whole blood, anticoagulated with EDTA, was obtained between 8-9 AM following overnight fasting through venipuncture of a forearm vein. Ex vivo blood was settled on ice for <20 mins and centrifuged at 4° C. and plasma stored at −80° C. until assayed. Assay of plasma levels of endocannabinoids N-arachidonoylethanolamide (AEA) and 2-arachidonoylglycerol (2-AG) was performed using a previously published method.[20] In brief, 500 ul of plasma was directly pipetted into 2 ml of acetonitrile, to which the internal standards [$^2$H$_8$]-AEA (5 pmol) and [$^2$H$_8$]-2-AG (5 nmol) (Cayman Chemicals, Ann Arbor, MI) had already been added. All samples were sonicated and stored at −20° C. overnight to precipitate proteins. The following morning all samples were centrifuged at 1500×g for 4 minutes, after which the supernatant was transferred to a new vial and centrifuged again under the same parameters. The supernatant from this second centrifugation was then transferred to a clean borosilicate glass tube and dried down under nitrogen gas. All samples were then resuspended in 200 ul of acetonitrile and stored at −80° C. until analysis. AEA and 2-AG were quantified using liquid chromatography and tandem mass spectrometry (LC-MS/MS) as described previously[20] and all values were normalized to concentration per ml plasma.

Fibroblast Cell Lines and Microarray Analyses

Primary fibroblasts were extracted from a skin biopsy from patient PFS and 4 unrelated female controls (A, D, E and F) and passaged in DMEM containing 20% foetal bovine serum. RNA was isolated using TRIzol Reagent (Life Technologies) and Purelink RNA micro kit (Thermo Fisher) according to the manufacturer's instructions. Microarray analyses were carried out using the Clarion D human transcriptome array (Applied Biosystems) and WT plus kit. Differential gene expression analysis of transcriptome array data was performed using the Transcriptome Analysis Console (TAC Ver 4.0, Thermo Fisher).

CRISPR/Cas9 Plasmids

Plasmids 61591[21] and 106219[22] (Addgene) were modified for the gene editing (SaCas9) and transcriptional repression (dSaCas9-KRAB) CRISPR experiments. For gene editing plasmid 61591, the CMV promoter was replaced with a shorter promoter sequence derived from the housekeeping Eefla1 gene and the bGH polyadenylation sequence was replaced with a shorter synthetic polyadenylation sequence. gBlocks gene fragments (IDT) were designed to contain a U6 promoter, guide sequence and modified guide scaffold[23] with the design enabling two guide cassettes to be inserted into one plasmid by In-Fusion cloning (Takara). Guide sequences were designed to flank the microdeletion observed in patient PFS. Plasmid HMa contained guides CCCAGTGAGTACGATGGCCAG (SEQ ID NO: 24) and TTAGTGATATTGTTCCGTGGG (SEQ ID NO: 25). Plasmid HMb contained guides TCATGGCCTTTCCCCTTCTCA (SEQ ID NO: 26) and GTCACTTGCAGTCTGATTAAG (SEQ II) NO: 27). The 'empty vector' control contained Eefla1-promoter driven SaCas9 but no guide sequences. For the transcriptional repression CRISPRi experiments the AgeI-EcoRI fragment from plasmid 106219 containing the dSaCas9-KRAB sequence was used to replace the SaCas9 sequence from plasmid 61591, to give a CMV driven dSaCas9-KRAB Next a gBlocks gene fragment (IDT) was designed to contain a synthetic poly(A) sequence, U6 promoter, guide sequence and modified guide scaffold[23]. This sequence was cloned into the EcoRI-NotI sites of the modified plasmid 61591 using In-Fusion cloning (Takara). The guide sequence 'FOP1' (AAAAGGTGAGGTCACGAGGCC (SEQ ID NO: 28)) was located within a DNase hypersensitivity site approximately 323 by upstream of the FAAH-OUT transcriptional start site. The 'empty vector' control contained the CMV driven dSaCas9-KRAB but no guide sequence.

Transfection of CRISPR/Cas9 Plasmids into HEK293 Cells

Lipofectamine 3000 (Invitrogen) was employed as a DNA carrier for transfection into human embryonic kidney 293 cells (ECACC) according to the manufacturer's procedures. The HEK293 cells were cultured in Dulbecco's modified Eagle's medium (Life Technologies, Inc.) with 10% fetal bovine serum (Hyclone). Lipofectamine 3000 was diluted into Opti-MEM I Reduced Serum Medium (Life Technologies, Inc.). 5 μg of plasmid DNA was first diluted into Opti-MEM and 10 μl of P3000 reagent was added to the mixture. The DNA-liposome complex was prepared by adding diluted DNA into diluted Lipofectamine (ratio 1:1) and incubating the mixture at room temperature for 30 min. DNA-liposome mixture was added to 70% confluent HEK293 cells. After 24 hours of incubation at 37° C., media was removed and the transfection steps were repeated. The cells were incubated at 37° C. in a 5% $CO_2$ incubator with 92-95% humidity for another 24 hours. To extract total RNA from cultured cells, medium was first aspirated off and cells were rinsed with ice cold PBS. 1 ml of Trizol® was added directly to the cells and it was incubated for 5 minutes at room temperature. Cell lysate was passed through a pipet up and down several times. RNA was extracted using Pure-Link™ RNA Micro Scale Kit (Invitrogen) according to the manufacturer's procedures. Genomic DNA was isolated using the DNeasy Blood and Tissue kit (Qiagen) and used as template to confirm gene editing. Primers 5'TTAATGTCTG-GAGTGATAACATGAC (SEQ ID NO: 10) and 5'ACAACTTCTAATTAGTGTTAATGAC (SEQ ID NO: 11) were used to amplify a ~463 bp band from HMa transfected cells and a ~598 bp band from HMb transfected cells. The size of the microdeletion induced by plasmids HMa and HMb was ~9017 bp and ~8882 bp respectively.

Taqman Real-Time PCR

Primary fibroblast and HER cell RNA (5 μg) (from the CRISPR/Cas9 experiments) was reverse transcribed using oligo d(T) and Superscript III first-strand synthesis system (Invitrogen) according to the manufacturer's conditions. Taqman real-time PCR was carried out using the following probes: FAAH (Hs01038660_m1), BDNF (Hs03805848_m1) and Actin (Hs01060665_g1). FAAH or BDNF expression was compared with that of Actin measured on the same sample in parallel on the same plate, giving a CT difference ($\Delta CT$) for ACTB minus the test gene. Mean and standard error were performed on the $\Delta CT$ data and converted to relative expression levels ($2^{\Delta CT}$).

Results

Case Report

A 66-year-old Caucasian female (herein called PFS) presented to Raigmore Hospital in Inverness, Scotland for orthopaedic surgery, specifically a trapeziectomy with LRTI and EPL realignment following a diagnosis of bilateral pantrapezial osteoarthritis. PFS had a significant deformity and deterioration in the use of the right thumb, but which she reported as painless. The pre-assessment note classed her as ASA I (American Society Anesthesiologist grading) but highlighted that she had a history of vomiting after intake of Morphine. For the surgery she was given general anaesthesia along with an ultrasound guided axillary nerve block. Intra-operatively [between 1530-1630 hours] she received Fentanyl 50 mcg iv, Propofol 200 mg iv, Ondansetron 4 mg iv and 20 ml of 0.25% 1-bupivacaine in the axillary nerve block. Post-operatively, her pain intensity score was recorded as 0/10 on the nursing early warning chart (NEWS) consistently till the next day when she was discharged home after the surgery. The only post-operative analgesic she received during her hospital stay was intravenous Paracetamol 1 gm iv in the post anaesthesia care unit [1705 hours] on the day of her surgery. She was also administered Cyclizine 50 mg iv [1655 hours] and Cyclizine 50 mg iv at 1705 hours. PFS did not, extraordinarily, require post-operative pain killers for this known painful surgery (trapeziectomy), and at the bedside was observed to show no pain from pinching or from peripheral iv cannula manipulation, which led to further investigations.

PFS had previously been diagnosed with osteoarthritis of the hip which she reported as painless, which was not consistent with the severe degree of joint degeneration. At 65 years-of-age she received a hip replacement and was administered only two tablets of Paracetamol 1 gram orally on post-operative day 1 and 2. PFS reports that she was encouraged to take the Paracetamol but that she did not ask for any pain killers. She was also administered a single dose of Morphine (MST Morphine Sulphate 10 mg) on the post-operative evening. This caused severe nausea and vomiting for 2 days. Post-operatively, her pain intensity scores were recorded as 0/10 throughout except for one score of 1/10 at 2200 hours on the post-operative evening. Her past surgical history is notable for multiple varicose vein and dental procedures. PFS states that she has never required analgesia following any of these interventions.

PFS reports a long standing history of painless injuries where she did not use analgesics (e.g. suturing of a cut ear, fractured left wrist). Throughout her life she has had numerous episodes where she has burned and cut herself without any pain being elicited. She often smells the burning flesh before noticing any burning injury and that is the only alerting situation to the injury. She notes these wounds heal very quickly and often leave little or no residual scar. Mosquito bites cause her inflammation (redness and swelling) and nettle stings are noted as pleasant and not painful.

Menstruation began at 11 years-of-age with periods being uncomfortable, causing her bloating, and a general feeling of unpleasantness. She did not complain about pain during her two childbirths at 29 and 42 years of age (although remembers receiving gas analgesia). She recalls labour as causing her a sensation of pressure, felt unpleasant, but not painful. She required stitches for a tear but no painkillers were required.

PFS lives with her husband and has been a teacher before she retired. She has a daughter and son from her previous marriage. Her family history is unremarkable for neuropathy or painful conditions. Her mother and daughter appear to perceive pain normally. Her father (now deceased) had little requirement for pain killers. Her son also reports of having some degree of pain insensitivity but not to the same extent as his mother. He does not feel pain from donating blood or from cuts or bruises and frequently scalds his mouth with hot drinks and food and not realising until skin starts to peel off. He reports never having the need to take pain killers.

PFS is not taking any medication at present and is fit and active. She is awaiting a trapeziectomy in her other hand. She has no other medical conditions apart from arthritis. PFS has a very talkative and happy, non-anxious, disposition with an ever-optimistic outlook. She reports of long-standing memory lapses (e.g. frequently forgetting words mid-sentence and placement of keys). She reports of never panicking, not even in dangerous situations, such as in a recent road traffic accident.

Figure 4:
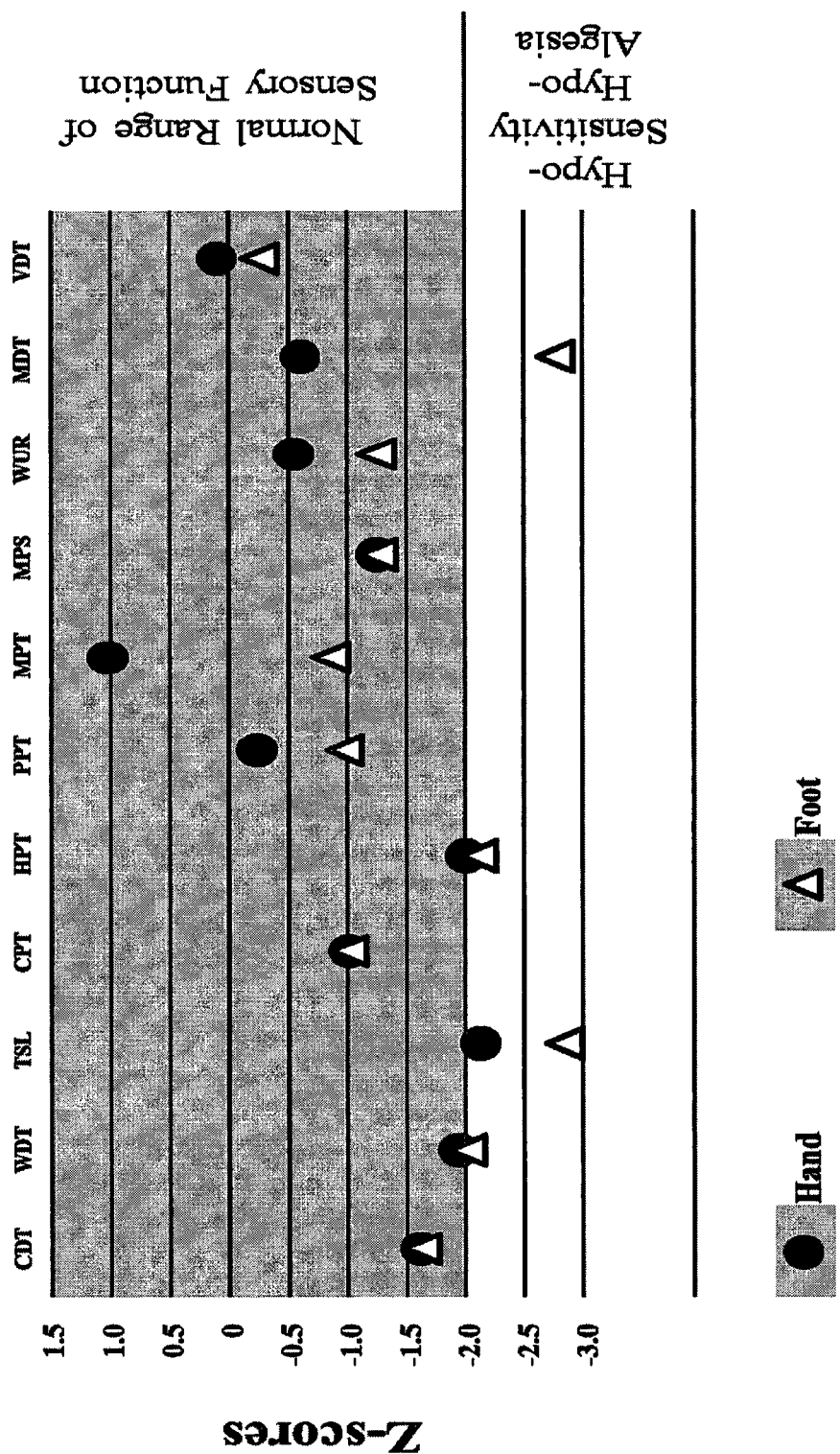
FIG. 4: Quantitative sensory testing in patient PFS. Quantitative Sensory Testing (QST) was performed according to the protocol of the German Research Network on Neuropathic Pain. QST is a measurement of sensory perception to a given stimulus. This test can show abnormalities in sensory function but does not localize abnormalities to specific structures of the nervous system. Comparisons of evaluated sites are done against a Caucasian control population for each one of the evaluated sites. Gain of sensory function is presented as a z score >2, and loss of sensory function as <2. Control Site: hand, Test site: foot. The test revealed pathological hyposensitivity in the warm detection thresholds and thermal sensory limen for both hand and foot and some hyposensitivity in the foot for thermal pain thresholds. Mechanical detection thresholds were abnormal in the foot. There was no evidence of paradoxical heat sensations and/or dynamic mechanical allodynia. CDT, cold detection thresholds; WDT, warm detection thresholds; TSL, thermal sensory limen; CPT, cold pain thresholds; HPT, heat pain thresholds; PPT, pressure pain thresholds; MPT, mechanical pain thresholds; MPS, mechanical pain sensitivity; WUR, wind up ratio; MDT, mechanical detection thresholds; VDT, vibration detection thresholds; DMA, dynamic mechanical allodynia; PHS, paradoxical heat sensations.

Following the painless trapeziectomy surgery, at 67 years-of-age, PFS was referred to and further investigated by pain genetics teams from University College London and the University of Oxford. Ethical approval was granted from both Institutions and written consent taken. On clinical examination there were multiple scars around the arms and on the back of hands. Blood pressure was 105/75 mmHg lying with no postural drop. Examination of the cranial nerves was normal and there was no muscle weakness or significant motor abnormalities in the limbs. All deep tendon reflexes were preserved. In the upper limbs light touch, joint position sense and vibration were preserved distally, but temperature sensation was lost to the wrists bilaterally and pin prick sensation was impaired to the shoulder (i.e. it was felt as a touch but did not elicit the sharp pricking painful sensation). In the lower limbs touch, joint position sense and vibration were also preserved distally. Temperature sensation was lost to the base of the toes and pinprick sensation was lost to the knees. Quantitative sensory testing (FIG. 4) demonstrated hyposensitivity to noxious heat both in the hands and the feet. A skin biopsy showed a normal intra-epidermal nerve fibre density.

Additional Clinical Information

PFS was born in 1947 and reports of no problems with walking or speech and other developmental milestones were achieved without issues. Education was unremarkable and has completed primary school teacher training and has a diploma in special needs education. She has no problems smelling and can tell the difference between coffee, orange, perfume, mint and she enjoys spices and different flavours. PFS has never smoked tobacco and very occasionally consumes alcohol. She has been a vegetarian for 38 years and a vegan for 11 years and there is no clinical history of vitamin deficiencies. Of note, her dental surgeon observed, most unusually, that her saliva dissolves the fixative for a temporary denture after just 90 mins.

Upon examination at 67 years-of-age her height was 170 cm and weight was 63 kg. The intra epidermal nerve fibre density from the distal leg (10 cm above the lateral malleolus) was 5.8 f/mm and within normal range for age and gender.[24] Nerve conduction tests demonstrated normal motor and sensory conduction parameters. She refers to a burning sensation in her toes due to the hallux valgus which is accompanied by tingling and pins and needles which she describes as being "pleasant". Sweating is normal in warm conditions.

Genetic Tests

Figure 5:
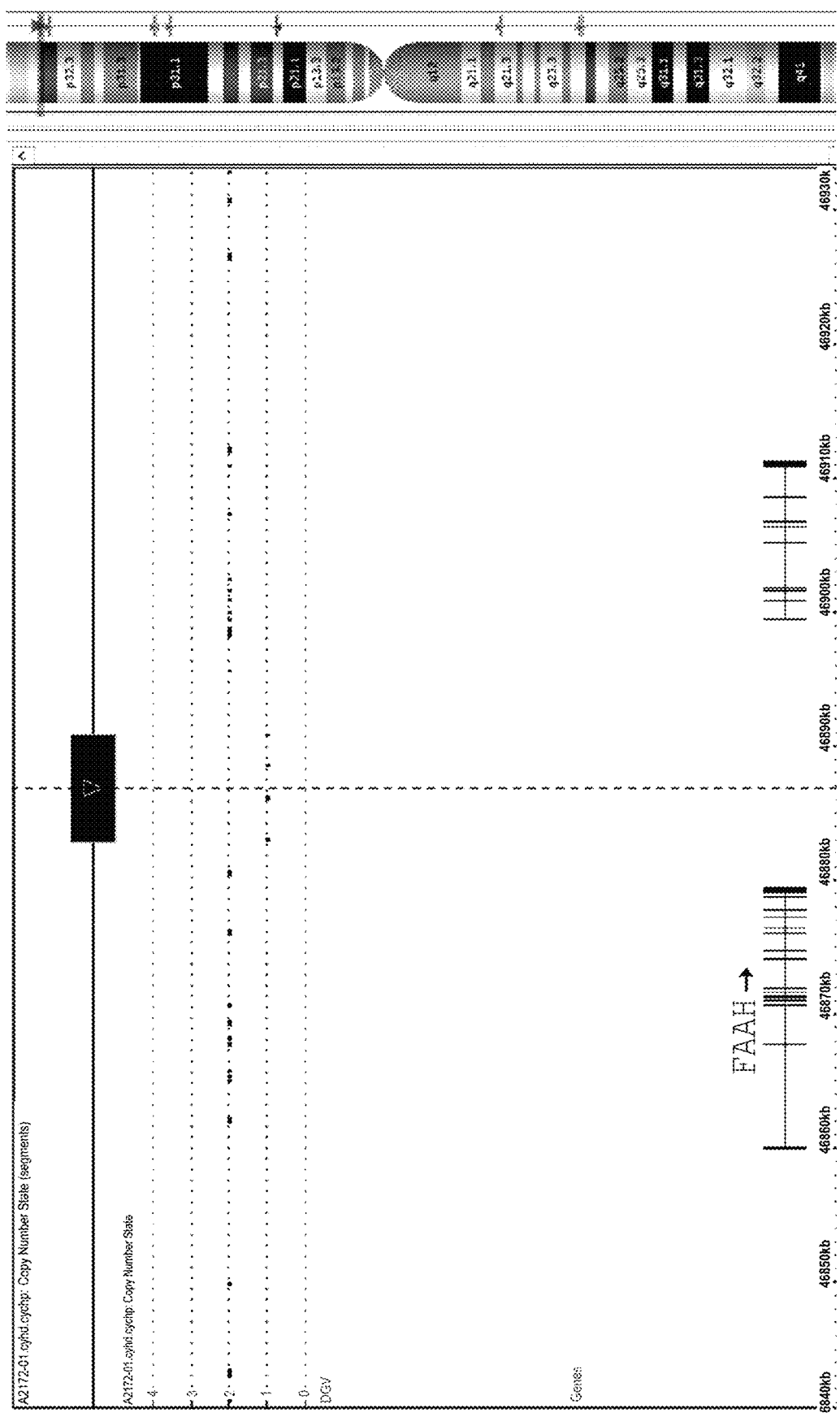
FIG. 5: Identification of microdeletion using the Cytoscan HD array. Chromosome Analysis Suite (Affymetrix) screenshot showing the heterozygous ~8 kb microdeletion identified on chromosome 1 in PFS. Eight consecutive probes (denoted by spots along the −1 dotted line) show a −1 allele copy number and span chromosome 1p33:46,882,936-46,890,857 (build hg19). At the time of analysis, this microdeletion (filled rectangle) was not annotated in the Database of Genomic Variants (see empty track in Database of genomic variants (DGV) in figure. A similar deletion has subsequently been reported in 1 out of 5008 alleles in phase 3 of the 1000 Genomes Project (this individual, HG10353, is homozygous WT for FAAH SNP rs324420). The microdeletion is located ~4.7 kb downstream of the FAAH 3'UTR. Non-annotated exons are shown next to the FAAH gene at the bottom of the figure. We subsequently extended this novel gene footprint into the microdeletion region using 5'RACE.

Genomic DNA was isolated from peripheral blood samples donated from PFS, her two children and her mother. Exome sequencing was performed for all 4 members to identify a pathogenic mutation for this novel disorder. Given the partial phenotype in the son we predicted a dominant inheritance pattern with variable expressivity. We also considered that PFS may be presenting with a full phenotype due to the inheritance of an additional loss of function allele. Given the previously undescribed phenotype, we searched for novel variants in PFS's exome which were absent in her unaffected mother and daughter, but inherited by her son. Following filtering of variants we identified 4 candidate mutations in PFS and her son: MACF1 (NM_012090: c.C14416T:p.L4806F); USP24 (NM_015306:c.G6490A: p.V2164M); KIAA1107 (NM_015237:c.A3359G: p.N1120S) and NSD1 (NM_022455:c.C6703T:p.H2235Y). The variants in USP24, KIAA1107 and NSD1 are annotated as benign by the Polyphen2 (HumVar) tool. The MACF1 variant is annotated as 'probably damaging' and is a neural gene. However, we considered this microtubule-actin cross-linking factor to be a low priority candidate following an analysis of known gene functions in relation to pain.[25] Instead, we broadened our genetic analyses and searched for cytogenetic copy number changes using the Cytoscan HD Array (Affymetrix). This analysis identified an ~8 kb heterozygous microdeletion in PFS on chromosome 1 (FIG. 5) that began ~4.7 kb downstream from the 3' end of FAAH (FIG. 1A). One Colombian male (HG01353) out of 5008 alleles screened in the 1000 genomes project also carries a similar-sized microdeletion, but is homozygous wild-type for FAAH SNP rs324420.

Validating Microdeletion and Cloning of FAAH-OUT

To confirm the existence of the microdeletion, PCR primers flanking the predicted deleted region were designed and used to amplify the mutant PFS allele (FIG. 6A). The deletion breakpoints were identified by Sanger sequencing (FIG. 6B) which showed the size of the microdeletion to be 8,131 bp. AluSp repeat sequences (FIGS. 1 and 6C) flank the microdeletion and are likely to predispose this region to genomic rearrangements. PCR analysis (FIG. 6A) showed the partially affected son inherits the microdeletion, but it is not present in the genomes of the unaffected mother and daughter. Furthermore, Sanger sequencing showed PFS to be heterozygous for the FAAH hypomorphic SNP (rs324420) (Table 1).

TABLE 1

Genotype summary
The proband (PFS) carries both the FAAH-OUT microdeletion and the hypomorphic FAAH SNP and displays a full hypoalgesic phenotype. Her son carries the FAAH-OUT microdeletion and presents a partial hypoalgesic phenotype. Neither the unaffected mother nor daughter carry the microdeletion and have no pain-sensing deficits.

|  | Hypoalgesic phenotype | FAAH-OUT microdeletion | FAAH hypomorphic SNP (rs324420) |
|---|---|---|---|
| PFS | Full | Het | Het |
| Mother | Normal | WT | Het |
| Son | Partial | Het | WT |
| Daughter | Normal | WT | Het |

Figure 2:
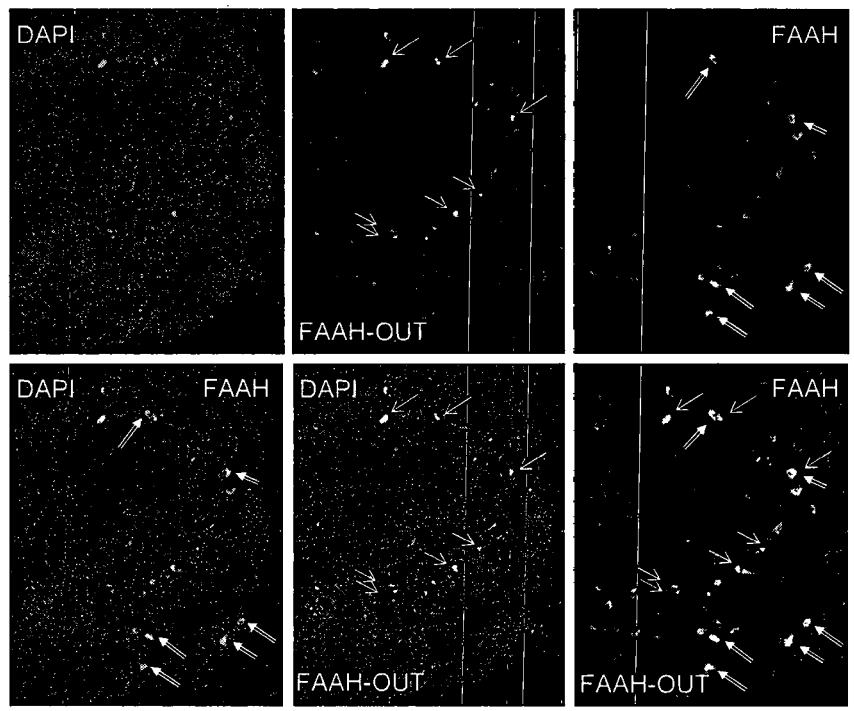
FIG. 2: FAAH and FAAH-OUT RNA localise differently in human DRG sections. FAAH and FAAH-OUT RNA expression as detected by fluorescent in situ hybridization of RNA (RNAscope® Technology). 5 µm thick FFPE fixed human DRG sections were analysed with probes against FAAH and FAAH-OUT. DAPI staining was used as a control for cell nuclei. Examples of FAAH-OUT (single-tail arrows) and FAAH expression (double-tail arrows) are shown. (A) Overall image of human DRG node shows that FAAH RNA is readily detected in cytoplasm of neurons whereas FAAH-OUT RNA is localised to nuclei. (B) and (C) show areas B and C respectively, which are outlined in the main view (A) to provide a closer view on FAAH and FAAH-OUT expressing neurons.

Given the extraordinary phenotype in PFS and the vicinity of the microdeletion to FAAH, we investigated how the microdeletion could be pathogenic. Interestingly, partial human expressed sequence tags (ESTs) were identified downstream of the microdeletion that were annotated as an FAAH pseudogene, FAAHP1 (herein called FAAH-OUT), and further analyses using the cow genome identified potential further conserved 5' exons. Using RT-PCR and 5'RACE we cloned a full-length transcript with robust expression in adult brain. Like FAAH, this 2.845 kb FAAH-OUT sequence is expressed in fetal and adult brain and in dorsal root ganglia tissue (FIG. 1B). RNAscope analyses in adult human dorsal root ganglia sections show that the FAAH-OUT transcript predominantly localises to the nucleus, which is consistent with a potential role of the RNA regulating the expression of FAAH (FIG. 2). Sequence alignments show ~70% nucleotide identity within an 800 bp region between FAAH and FAAH-OUT (FIG. 7A). Open reading frame and Kozak consensus analyses ($ATG^{Pr}$) indicate that the most likely predicted FAAH-OUT peptide contains 166 amino acids (FIG. 7B) and shares 69% similarity to a region of FAAH (FIG. 7C), although FAAH-OUT is potentially more likely to function as a long non-coding RNA.[26, 37]

Figure 3:
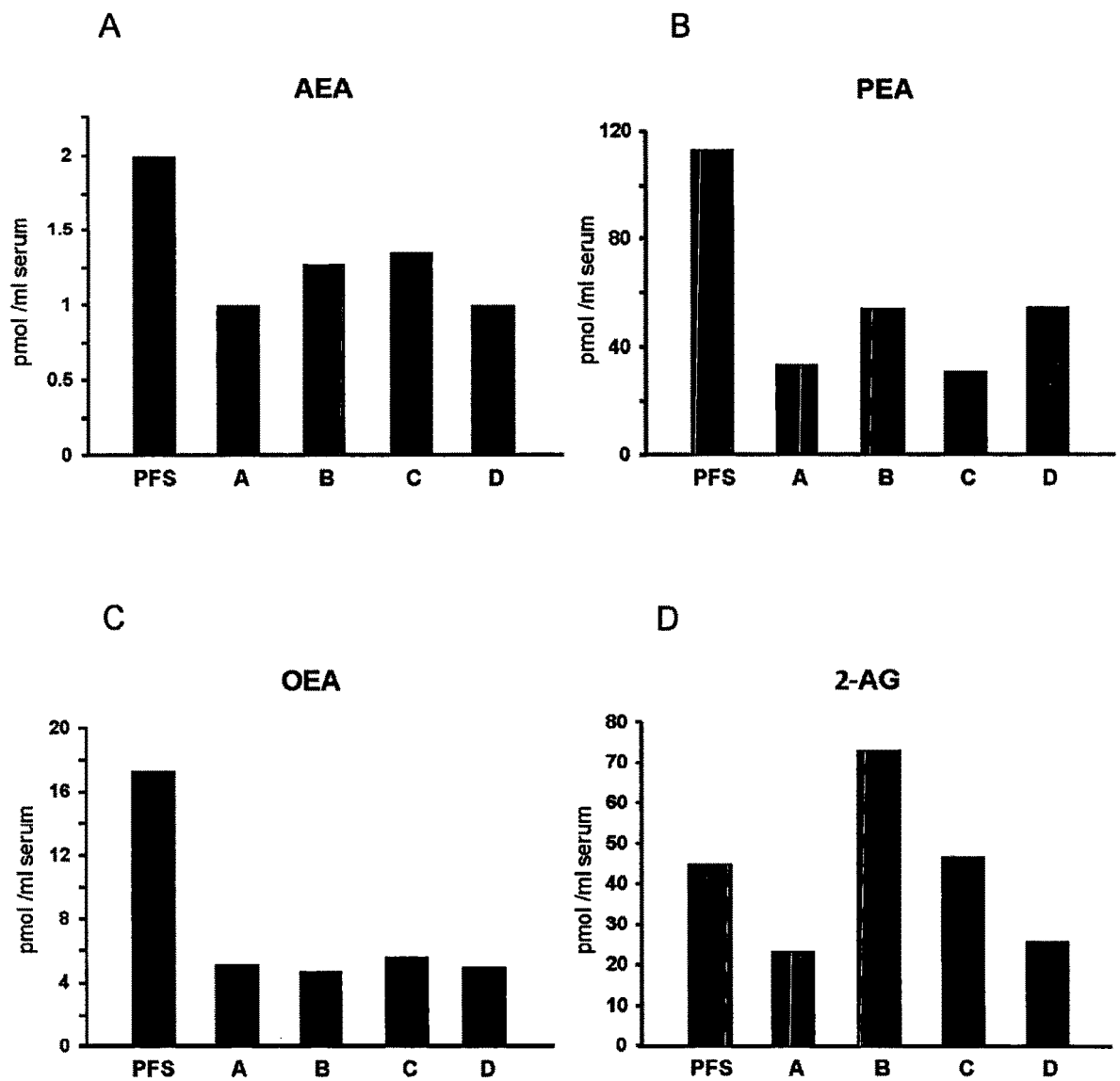
FIG. 3: Circulating AEA, PEA and OEA levels are significantly increased in PFS. Levels of AEA, PEA, OEA and 2-AG were measured by mass spectrometry from blood samples taken from PFS and 4 unrelated normal controls. AEA, PEA and OEA are substrates for FAAH; 2-AG is not. Controls A and B are homozygous WT for the hypomorphic SNP, controls C and D are heterozygous carriers. Average values for the 4 controls are AEA (1.15 pmol/ml), PEA (43.4 pmol/ml), OEA (5.06 pmol/ml) and 2-AG (42.2 pmol/ml), which is consistent with previous data using a similar measurement protocol.[14] Average values for PFS (2 readings) were AEA (1.99 pmol/ml), PEA (113.07 pmol/ml), OEA (17.26 pmol/ml) and 2-AG (45 pmol/ml).

To determine the effects of carrying both the microdeletion in FAAH-OUT and the hypomorphic FAAH SNP, we measured circulating fatty acid amide levels from blood samples from PFS and compared them to four control individuals, 2 of which were heterozygous carriers of the SNP. Strikingly, AEA levels were increased by 70% and circulating levels of OEA and PEA were approximately tripled compared to controls (FIG. 3). The levels of 2-AG, another endocannabinoid but not a substrate for FAAH, were largely unaltered. These results are consistent with FAAH showing a significant loss of function in the patient.

BDNF is Upregulated in Patient Fibroblasts

To further investigate the downstream effects of carrying the FAAH-OUT microdeletion and hypomorphic FAAH SNP, we isolated fibroblasts from a skin biopsy from patient PFS and 4 unrelated female normal controls. Real-time qPCR showed a ~64% reduction in FAAH transcript in the patient fibroblast cell line compared to controls (FIG. 8A). Furthermore, microarray analyses showed that brain-derived neurotrophic factor (BDNF) was significantly upregulated in the patient fibroblasts compared to controls, which was verified by real-time qPCR (FIG. 8B). An upregulation of BDNF is consistent with previous data showing that inhibition of FAAH results in elevated anandamide and BDNF levels and has been linked to an antidepressant-like effect in a rat model of subchronic mild stress.[27]

Gene Editing in HEK293 Cells

Figure 10:
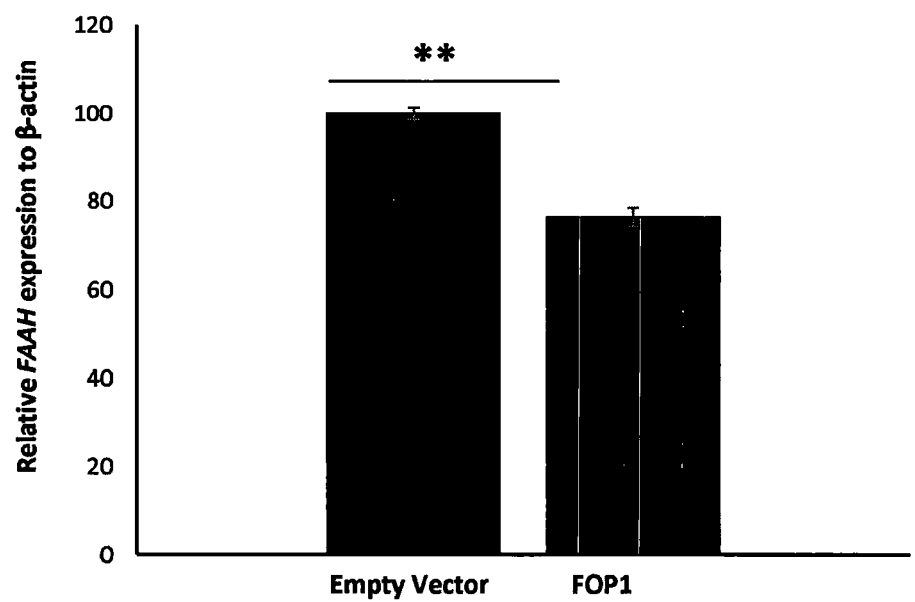
FIG. 10: CRISPRi in HEK293 cells. dSaCas9-KRAB directed to the promoter of FAAH-OUT by guide 'FOP1' results in a significant reduction in FAAH expression. P values were generated by t-test, **$p<0.01$. Error bars=SEM

Next, we used gene editing with CRISPR/Cas9 to introduce a similar sized microdeletion in HEK293 cells to the one identified in patient PFS. Transfection of SaCas9 plasmids 'HMa' and 'HMb' (bearing different guide-pairs that flank the microdeletion) resulted in gene editing and generation of a microdeletion in the HEK293 cells (FIG. 9A). Real-time qPCR showed that following transient transfection, the level of FAAH transcript was significantly reduced for both plasmids HMa and HMb compared to transfection with a control vector, indicating that the microdeletion directly affects FAAH expression (FIG. 9B). We then searched for DNase hypersensitivity sites upstream of the FAAH-OUT gene and designed a guide sequence 'FOP1' within the promoter region of FAAH-OUT. Transient transfection of this CRISPRi plasmid bearing dSaCas9-KRAB and guide FOP1 resulted in a ~25% reduction in FAAH expression (FIG. 10). Taken together, this data indicates that expression of the full-length FAAH-OUT transcript in cis is needed for normal expression of FAAH, and is a potential gene therapy route to inhibit normal FAAH function.

Discussion

The endocannabinoid system is an important physiological system that performs a wide array of homeostatic functions and is important for pain perception.[28] FAAH is a critical enzyme for the breakdown of a range of bioactive lipids (including the endocannabinoid AEA and related fatty-acid amides and N-acyl-taurines) with diverse physiological roles. Mouse modelling of FAAH loss of function mutations and pharmacological inhibition studies have shown a range of phenotypes including hypoalgesia, accelerated skin wound healing, enhanced fear-extinction memory, reduced anxiety and short term memory deficits.[6, 11, 29-32] Furthermore, human hypomorphic FAAH SNPs are associated with a reduced need for post-operative analgesia, increased postoperative nausea and vomiting induced by opioids and decreased anxiety-linked behaviours.[8, 11, 14, 33-35]

Here we report a new human genetic disorder in a patient with hypoalgesia, altered fear and memory symptoms and a non-anxious disposition. This disorder is due to the co-inheritance of a microdeletion in a novel pseudogene and a known FAAH hypomorphic SNP. The microdeletion is flanked by repeat sequences which likely predispose the region to genomic rearrangements, as seen in other genomic disorders.[36] Consequently there is likely to be additional similar individuals in the general population. The likelihood that this disorder has been under-reported is highlighted by the fact that PFS was diagnosed at 66-years-of-age, despite a recurrent history of painless injuries. Lipid profiling in peripheral blood samples showed significant increases in AEA, OEA and PEA in PFS, which could be further exaggerated in the brain and DRG. Further work is needed to understand which fatty-acid amide is the major contributor to the patient phenotype.

The microdeletion removes the promoter and first two exons of FAAH-OUT but how this disrupts the function of FAAH is still to be exactly elucidated. One hypothesis is that the FAAH-OUT transcript normally functions as a decoy for microRNAs due to the high sequence homology and protects FAAH mRNA from degradation (FIG. 6A).[26] Alternatively, FAAH-OUT may have an epigenetic role in regulating FAAH transcription, or the deletion removes a critical transcriptional regulatory element.[36, 37] The RNAscope experiments in adult human dorsal root ganglia suggest a nuclear function for FAAH-OUT. The gene editing and CRISPRi experiments in HEK293 cells indicate that transcription of full-length FAAH-OUT in cis is needed for normal FAAH expression.

This patient provides new insights into the role of the endocannabinoid system in analgesia and more specifically on the FAAH genomic locus and highlights the importance of the adjacent, previously uncharacterised FAAH-OUT gene to pain sensation. Given the previous failure of FAAH-inhibitor analgesic drug trials, these results have significance as they may provide a new route to developing FAAH-related analgesia through targeting of FAAH-OUT.

REFERENCES

1. Deutsch D G, Chin S A. Enzymatic synthesis and degradation of anandamide, a cannabinoid receptor agonist. Biochem Pharmacol 1993; 46:791-6.
2. Cravatt B F, Giang D K, Mayfield S P, Boger D L, Lerner R A, Gilula N B. Molecular characterization of an enzyme that degrades neuromodulatory fatty-acid amides. Nature 1996; 384:83-7.
3. Woodhams S G, Sagar D R, Burston J J, Chapman V. The role of the endocannabinoid system in pain. Handb Exp Pharmacol 2015; 227:119-43.
4. Mechoulam R, Parker L A. The endocannabinoid system and the brain. Annu Rev Psychol 2013; 64:21-47.
5. Cravatt B F, Demarest K, Patricelli M P, et al. Supersensitivity to anandamide and enhanced endogenous cannabinoid signaling in mice lacking fatty acid amide hydrolase. Proc Natl Acad Sci USA 2001; 98:9371-6.
6. Lichtman A H, Shelton C C, Advani T, Cravatt B F. Mice lacking fatty acid amide hydrolase exhibit a cannabinoid receptor-mediated phenotypic hypoalgesia. Pain 2004; 109:319-27.
7. Chiang K P, Gerber A L, Sipe J C, Cravatt B F. Reduced cellular expression and activity of the P129T mutant of human fatty acid amide hydrolase: evidence for a link between defects in the endocannabinoid system and problem drug use. Hum Mol Genet 2004; 13:2113-9.
8. Cajanus K, Holmstrom E J, Wessman M, Anttila V, Kaunisto M A, Kalso E. Effect of endocannabinoid degradation on pain: role of FAAH polymorphisms in experimental and postoperative pain in women treated for breast cancer. Pain 2016; 157:361-9.
9. Kim H, Mittal D P, Iadarola M J, Dionne R A. Genetic predictors for acute experimental cold and heat pain sensitivity in humans. J Med Genet 2006; 43:e40.
10. Greenbaum L, Tegeder I, Barhum Y, Melamed E, Roditi Y, Djaldetti R. Contribution of genetic variants to pain susceptibility in Parkinson disease. Eur J Pain 2012; 16:1243-50.
11. Dincheva I, Drysdale A T, Hartley C A, et al. FAAH genetic variation enhances fronto-amygdala function in mouse and human. Nat Commun 2015; 6:6395.
12. Huggins J P, Smart T S, Langman S, Taylor L, Young T. An efficient randomised, placebo-controlled clinical trial with the irreversible fatty acid amide hydrolase-1 inhibitor PF-04457845, which modulates endocannabinoids but fails to induce effective analgesia in patients with pain due to osteoarthritis of the knee. Pain 2012; 153:1837-46.
13. van Esbroeck A C M, Janssen A P A, Cognetta A B, 3rd, et al. Activity-based protein profiling reveals off-target proteins of the FAAH inhibitor BIA 10-2474. Science 2017; 356:1084-7.
14. Spagnolo P A, Ramchandani V A, Schwandt M L, et al. FAAH Gene Variation Moderates Stress Response and Symptom Severity in Patients with Posttraumatic Stress Disorder and Comorbid Alcohol Dependence. Alcohol Clin Exp Res 2016; 40:2426-34.
15. Rolke R, Baron R, Maier C, et al. Quantitative sensory testing in the German Research Network on Neuropathic Pain (DFNS): standardized protocol and reference values. Pain 2006; 123:231-43.
16. Lauria G, Hsieh S T, Johansson O, et al. European Federation of Neurological Societies/Peripheral Nerve Society Guideline on the use of skin biopsy in the diagnosis of small fiber neuropathy. Report of a joint task force of the European Federation of Neurological Societies and the Peripheral Nerve Society. Eur J Neurol 2010; 17:903-12, e44-9.
17. Li H, Durbin R. Fast and accurate short read alignment with Burrows-Wheeler transform. Bioinformatics 2009; 25:1754-60.
18. DePristo M A, Banks E, Poplin R, et al. A framework for variation discovery and genotyping using next-generation DNA sequencing data. Nat Genet 2011; 43:491-8.
19. McKenna A, Hanna M, Banks E, et al. The Genome Analysis Toolkit: a MapReduce framework for analyzing next-generation DNA sequencing data. Genome Res 2010; 20:1297-303.
20. Qi M, Morena M, Vecchiarelli H A, Hill M N, Schriemer D C. A robust capillary liquid chromatography/tandem mass spectrometry method for quantitation of neuromodulatory endocannabinoids. Rapid Commun Mass Spectrom 2015; 29:1889-97.
21. Ran F A, Cong L, Yan W X, et al. In vivo genome editing using Staphylococcus aureus Cas9. Nature 2015; 520:186-91.
22. Thakore P I, Kwon J B, Nelson C E, et al. RNA-guided transcriptional silencing in vivo with S. aureus CRISPR-Cas9 repressors. Nat Commun 2018; 9:1674.
23. Tabebordbar M, Zhu K, Cheng J K W, et al. In vivo gene editing in dystrophic mouse muscle and muscle stem cells. Science 2016; 351:407-11.
24. Bakkers M, Merkies I S, Lauria G, et al. Intraepidermal nerve fiber density and its application in sarcoidosis. Neurology 2009; 73:1142-8.
25. Moffat J J, Ka M, Jung E M, Smith A L, Kim W Y. The role of MACF1 in nervous system development and maintenance. Semin Cell Dev Biol 2017; 69:9-17.
26. Ebert M S, Sharp P A. Emerging roles for natural microRNA sponges. Curr Biol 2010; 20:R858-61.
27. Vinod K Y, Xie S, Psychoyos D, Hungund B L, Cooper T B, Tejani-Butt S M. Dysfunction in fatty acid amide hydrolase is associated with depressive-like behavior in Wistar Kyoto rats. PLoS One 2012; 7:e36743.
28. Aizpurua-Olaizola O, Elezgarai I, Rico-Barrio I, Zarandona I, Etxebarria N, Usobiaga A. Targeting the endocannabinoid system: future therapeutic strategies. Drug Discov Today 2017; 22:105-10.
29. Sasso O, Pontis S, Armirotti A, et al. Endogenous N-acyl taurines regulate skin wound healing. Proc Natl Acad Sci USA 2016; 113:E4397-406.
30. Goonawardena A V, Sesay J, Sexton C A, Riedel G, Hampson R E. Pharmacological elevation of anandamide impairs short-term memory by altering the neurophysiology in the hippocampus. Neuropharmacology 2011; 61:1016-25.
31. Clapper J R, Moreno-Sanz G, Russo R, et al. Anandamide suppresses pain initiation through a peripheral endocannabinoid mechanism. Nat Neurosci 2010; 13:1265-70.
32. Kathuria S, Gaetani S, Fegley D, et al. Modulation of anxiety through blockade of anandamide hydrolysis. Nat Med 2003; 9:76-81.
33. Sadhasivam S, Zhang X, Chidambaran V, et al. Novel associations between FAAH genetic variants and postoperative central opioid-related adverse effects. Pharmacogenomics J 2015; 15:436-42.
34. Hariri A R, Gorka A, Hyde L W, et al. Divergent effects of genetic variation in endocannabinoid signaling on human threat- and reward-related brain function. Biol Psychiatry 2009; 66:9-16.
35. Gunduz-Cinar O, MacPherson K P, Cinar R, et al. Convergent translational evidence of a role for anandamide in amygdala-mediated fear extinction, threat processing and stress-reactivity. Mol Psychiatry 2013; 18:813-23.
36. Harel T, Lupski J R. Genomic disorders 20 years on—mechanisms for clinical manifestations. Clin Genet 2017.
37. Elling R, Robinson E K, Shapleigh B, et al. Genetic Models Reveal cis and trans Immune-Regulatory Activities for lincRNA-Cox2. Cell Rep 2018; 25:1511-24 e6.

Sequences

SEQ ID NO: 1-cDNA sequence of wild-type human FAAH (without hypomorphic rs324420 SNP)
TCCGGGTTTTGCGGCGGAGCGGGCGGGCTGCGCGTGCGGCGGCTTCAACTGTCGCGGTAGGCAGCAGCAGGCTGAA
GGGATCATGGTGCAGTACGAGCTGTGGGCCGCGCTGCCTGGCGCCTCCGGGGTCGCCCTGGCCTGCTGCTTCGTGG
CGGCGGCCGTGGCCCTGCGCTGGTCCGGGCGCCGGACGGCGCGGGGCGCGGTGGTCCGGGCGCGACAGAGGCAGCG
AGCGGGCCTGGAGAACATGGACAGGGCGGCGCAGCGCTTCCGGCTCCAGAACCCAGACCTGGACTCAGAGGCGCTG
CTAGCCCTGCCCCTGCCTCAGCTGGTGCAGAAGTTACACAGTAGAGAGCTGGCCCCTGAGGCCGTGCTCTTCACCT
ATGTGGGAAAGGCCTGGGAAGTGAACAAAGGGACCAACTGTGTGACCTCCTATCTGGCTGACTGTGAGACTCAGCT
GTCTCAGGCCCCAAGGCAGGGCCTGCTCTATGGCGTCCCTGTGAGCCTCAAGGAGTGCTTCACCTACAAGGGCCAG
GACTCCACGCTGGGCTTGAGCCTGAATGAAGGGGTGCCGGCGGAGTGCGACAGCGTAGTGGTGCATGTGCTGAAGC
TGCAGGGTGCCGTGCCCTTCGTGCACACCAATGTTCCACAGTCCATGTTCAGCTATGACTGCAGTAACCCCCTCTT
TGGCCAGACCGTGAACCCATGGAAGTCCTCCAAAAGCCCAGGGGGCTCCTCAGGGGGTGAAGGGGCCCTCATCGGG
TCTGGAGGCTCCCCCCTGGGCTTAGGCACTGATATCGGAGGCAGCATCCGCTTCCCCTCCTCCTTCTGCGGCATCT
GCGGCCTCAAGCCCACAGGGAACCGCTCAGCAAGAGTGGCCTGAAGGGCTGTGTCTATGGACAGGAGGCAGTGCG
TCTCTCCGTGGGCCCCATGGCCCGGGACGTGGAGAGCCTGGCACTGTGCCTGCGAGCCCTGCTGTGCGAGGACATG
TTCCGCTTGGACCCCACTGTGCCTCCCTTGCCCTTCAGAGAAGAGGTCTACACCAGCTCTCAGCCCCTGCGTGTGG
GGTACTATGAGACTGACAACTATACCATGCCCTCCCCGGCCATGAGGCGGGCCGTGCTGGAGACCAAACAGAGCCT
TGAGGCTGCGGGGCACACGCTGGTTCCCTTCTTGCCAAGCAACATACCCCATGCTCTGGAGACCCTGTCAACAGGT
GGGCTCTTCAGTGATGGTGGCCACACCTTCCTACAGAACTTCAAAGGTGATTTCGTGGACCCCTGCCTGGGGGACC
TGGTCTCAATTCTGAAGCTTCCCCAATGGCTTAAAGGACTGCTGGCCTTCCTGGTGAAGCCTCTGCTGCCAAGGCT
GTCAGCTTTCCTCAGCAACATGAAGTCTCGTTCGGCTGGAAAACTCTGGGAACTGCAGCACGAGATCGAGGTGTAC
CGCAAAACCGTGATTGCCCAGTGGAGGGCGCTGGACCTGGATGTGGTGCTGACCCCCATGCTGGCCCCTGCTCTGG
ACTTGAATGCCCCAGGCAGGGCCACAGGGGCCGTCAGCTACACTATGCTGTACAACTGCCTGGACTTCCCTGCAGG
GGTGGTGCCTGTCACCACGGTGACTGCTGAGGACGAGGCCCAGATGGAACATTACAGGGGCTACTTTGGGGATATC
TGGGACAAGATGCTGCAGAAGGGCATGAAGAAGAGTGTGGGGCTGCCGGTGGCCGTGCAGTGTGTGGCTCTGCCCT
GGCAAGAAGAGTTGTGTCTGCGGTTCATGCGGGAGGTGGAGCGACTGATGACCCCTGAAAAGCAGTCATCCTGATG
GCTCTGGCTCCAGAGGACCTGAGACTCACACTCTCTGCAGCCCAGCCTAGTCAGGGCACAGCTGCCCTGCTGCCAC
AGCAAGGAAATGTCCTGCATGGGGCAGAGGCTTCCGTGTCCTCTCCCCCAACCCCCTGCAAGAAGCGCCGACTCCC
TGAGTCTGGACCTCCATCCCTGCTCTGGTCCCCTCTCTTCGTCCTGATCCCTCCACCCCCATGTGGCAGCCCATGG
GTATGACATAGGCCAAGGCCCAACTAACAGTCAAGAAACAGCTAAAAAAAAAA SEQ ID NO: 2-cDNA sequence of human FAAH with hypomorphic SNP rs324420
(C385A) (bold and underlined)
TCCGGGTTTTGCGGCGGAGCGGGCGGGCTGCGCGTGCGGCGGCTTCAACTGTCGCGGTAGGCAGCAGCAGGCTGAA
GGGATCATGGTGCAGTACGAGCTGTGGGCCGCGCTGCCTGGCGCCTCCGGGGTCGCCCTGGCCTGCTGCTTCGTGG
CGGCGGCCGTGGCCCTGCGCTGGTCCGGGCGCCGGACGGCGCGGGGCGCGGTGGTCCGGGCGCGACAGAGGCAGCG
AGCGGGCCTGGAGAACATGGACAGGGCGGCGCAGCGCTTCCGGCTCCAGAACCCAGACCTGGACTCAGAGGCGCTG
CTAGCCCTGCCCCTGCCTCAGCTGGTGCAGAAGTTACACAGTAGAGAGCTGGCCCCTGAGGCCGTGCTCTTCACCT
ATGTGGGAAAGGCCTGGGAAGTGAACAAAGGGACCAACTGTGTGACCTCCTATCTGGCTGACTGTGAGACTCAGCT
GTCTCAGGCCaCAAGGCAGGGCCTGCTCTATGGCGTCCCTGTGAGCCTCAAGGAGTGCTTCACCTACAAGGGCCAG
GACTCCACGCTGGGCTTGAGCCTGAATGAAGGGGTGCCGGCGGAGTGCGACAGCGTAGTGGTGCATGTGCTGAAGC
TGCAGGGTGCCGTGCCCTTCGTGCACACCAATGTTCCACAGTCCATGTTCAGCTATGACTGCAGTAACCCCCTCTT
TGGCCAGACCGTGAACCCATGGAAGTCCTCCAAAAGCCCAGGGGGCTCCTCAGGGGGTGAAGGGGCCCTCATCGGG
TCTGGAGGCTCCCCCCTGGGCTTAGGCACTGATATCGGAGGCAGCATCCGCTTCCCCTCCTCCTTCTGCGGCATCT
GCGGCCTCAAGCCCACAGGGAACCGCTCAGCAAGAGTGGCCTGAAGGGCTGTGTCTATGGACAGGAGGCAGTGCG
TCTCTCCGTGGGCCCCATGGCCCGGGACGTGGAGAGCCTGGCACTGTGCCTGCGAGCCCTGCTGTGCGAGGACATG
TTCCGCTTGGACCCCACTGTGCCTCCCTTGCCCTTCAGAAGAGGTCTACACCAGCTCTCAGCCCCTGCGTGTGG
GGTACTATGAGACTGACAACTATACCATGCCCTCCCCGGCCATGAGGCGGGCCGTGCTGGAGACCAAACAGAGCCT
TGAGGCTGCGGGGCACACGCTGGTTCCCTTCTTGCCAAGCAACATACCCCATGCTCTGGAGACCCTGTCAACAGGT
GGGCTCTTCAGTGATGGTGGCCACACCTTCCTACAGAACTTCAAAGGTGATTTCGTGGACCCCTGCCTGGGGGACC
TGGTCTCAATTCTGAAGCTTCCCCAATGGCTTAAAGGACTGCTGGCCTTCCTGGTGAAGCCTCTGCTGCCAAGGCT
GTCAGCTTTCCTCAGCAACATGAAGTCTCGTTCGGCTGGAAAACTCTGGGAACTGCAGCACGAGATCGAGGTGTAC
CGCAAAACCGTGATTGCCCAGTGGAGGGCGCTGGACCTGGATGTGGTGCTGACCCCCATGCTGGCCCCTGCTCTGG
ACTTGAATGCCCCAGGCAGGGCCACAGGGGCCGTCAGCTACACTATGCTGTACAACTGCCTGGACTTCCCTGCAGG
GGTGGTGCCTGTCACCACGGTGACTGCTGAGGACGAGGCCCAGATGGAACATTACAGGGGCTACTTTGGGGATATC
TGGGACAAGATGCTGCAGAAGGGCATGAAGAAGAGTGTGGGGCTGCCGGTGGCCGTGCAGTGTGTGGCTCTGCCCT
GGCAAGAAGAGTTGTGTCTGCGGTTCATGCGGGAGGTGGAGCGACTGATGACCCCTGAAAAGCAGTCATCCTGATG
GCTCTGGCTCCAGAGGACCTGAGACTCACACTCTCTGCAGCCCAGCCTAGTCAGGGCACAGCTGCCCTGCTGCCAC
AGCAAGGAAATGTCCTGCATGGGGCAGAGGCTTCCGTGTCCTCTCCCCCAACCCCCTGCAAGAAGCGCCGACTCCC
TGAGTCTGGACCTCCATCCCTGCTCTGGTCCCCTCTCTTCGTCCTGATCCCTCCACCCCCATGTGGCAGCCCATGG
GTATGACATAGGCCAAGGCCCAACTAACAGTCAAGAAACAGCTAAAAAAAAAA SEQ ID NO: 3-cDNA sequence of wild-type human FAAH-OUT
ggcaaaggcg ccattctcct gggtacagtg acttgcagtc tcagtgatga ccattgagat ggagactgga
tggaggcccc tgaggagagc agaatggttc ccacatcagg gccctctgc accactttc cagtctcctc
atgtcttctc tgttcctcgt ctgggaagtc atctccctta ccccacaac tccctccac cagcagggag
agtcaataga ctggggaggc tggaaccccca gatcagagtc atggccttgc tttggagtca agggggaagc
ccagctgggc gggctggtct catgtcctgg catcatctcc cctggggtgg atgcctgatg agccctgccc
gctcctccag gtgttctttc ctttcctctc ttcctgtccc ccagaacctc cactctaggc aaacatggcc
tgttcagttc cacctccatg cgtctgctta tgcggaacaa aggagctttg ggagaatcct gaaggcaatg
ggaaccccag gagcaacccc atccataact cctgagggtt ggagtaggga atctgagggg tgggatctga
gaggtaggat gggtgggagt aggatgtgac agaggtgagg tcagctgccc agctgcaggc ttgggcccct
cttcaggctc gcctgctaaa gcctcttcct ctgcatggcc cgggagatag gggttttgtc gccaggaagt
gggg taagaactag gaggaggttg atcactgcca cacccaggcc ccgagatgtg cgtgggtgcc
ctggcagcat cgctgacaaa tactcctgag gaaacagcag ctggattcac acaggtcgtg caatacctaa
ggtggcttgg ctgtttgact ccctgatgat gctacttctg ctggccctgc tgggggctgg cctactgggg
gcttccctgc tcacctcgtg gcatgctcca gcccggaaca agatcccag ggcccagaag tggagggagg
tagcactgca gaagatggag gacctggccc agtgactccg gcagcagacg gagtctcact ttgttgccca
ggctggagtg cagtggcctg atctcagctc cctgcaacct ccacctcccg agttgaagca attctcttgc

```
ctcagcctcc agagtagctg ggattacagg agccagatct ggaccccaag ccaatcctgg agctgcccct
ggcagagctg gcccagcagc ttcggaccga agagctgagt ctggagagca tcctctgtag ctacttaaag
caggcactga aggtgcacca ggaggtgaac tgcctgatgg atttcctggg ggaatgtgag gaggaactgc
aggcattaaa gaagcttaag aagagtgaga gaggccttct ctatgggstc cccatgagcc tcaaggacac
ctatgacagc atgggccatg actgtgcatg ccgcctggcc tagttcctgg agaagcctgc gaccaaggac
ggggtcatta tgaaagtgct caaggcccaa ggagccatcc cctttgttaa gaccaacatc ccactgacgc
tgctcagctt tgaatgcggc aactcccatc tatggccaga tgttgagccc actgaactta aagaagacat
gtgggggctc ctcagggggt gagggggtct gctggcagaa aggggggtcca tcctaggcat gggtactgac
acaggtgaca gcatctgcat accagccagc ttctgtggtg tttatggcct ctggaccaca ggttcccgcc
tcagctacac tggaattgcc tctgccatca aggggaaaaa aatcggtgac cacggtggct ggcccatgg
cccaggacgt ggagagcctg gcgctgtgcc tgcaagccct gctgagtgaa gacatgtacc gactggaccc
cactgtgctc cagatgccct ttagggagga ggtgaagacc cccttccca ccccaggctg cagtgagtga
gaagcccaca tgctcagtcc agtttgtttc cttccctgc tggacaccag ctgctttggc ttcttggcta
tctggagcca tagcttgaca cccaagaaac tgtgggaaca gcacacagca gtggaggaat atgagcaaga
gttcatagcc aagtggaggt ccctggacct ggatgtgctg ctggtgccag ttctgggctc tgccttctat
ataggctctt cctccctagc atcagaaagt cagtcttatg tgaccctgta caacctcctg gactttcccg
cgggcgtggt gcctgtcact atcgtgacac tacaggacga ggaggaactg gccttctaca aggggtgcta
cggagatagt tctgacaaaa atttctcaga ggcggtaaga ggatccgtcg gacttctggt gactgtgcag
tgcattgctt tgccatggga agaggagctg tgtctccggt tcatgaagga ggtggacacc ttggtcaaga
atcagagggg gcccaagtga taggctcctg gaatggagta acagctcatg aaacacgggg ctggttgtgg
tggctcatac ttgtaatccc agcagttcag gaggcagagg ctggcagatc gcttgaggcc acgagtttga
gaccaacctg ggcaacatag tgagaccctg cttctaaagc attttcttgg tgttactcct gtagatcctc
acccaagtgt gctcctgatg ccccttcctt ctcatgaata ccatgtccac cttatgtctc ctccttctgg
aaccccacca ggttccttt ctttgttggt ccctctgtgt gggtgctcaa tattcctcag atgggcccag
gatggggagc agggtgagga gctcaataaa cattttctga ctggc SEQ ID NO: 4-cDNA sequence of human FAAH-OUT comprising the microdeletion
g agccagatct ggaccccaag ccaatcctgg agctgcccct ggcagagctg gcccagcagc
ttcggaccga agagctgagt ctggagagca tcctctgtag ctacttaaag caggcactga aggtgcacca
ggaggtgaac tgcctgatgg atttcctggg ggaatgtgag gaggaactgc aggcattaaa gaagcttaag
aagagtgaga gaggccttct ctatgggstc cccatgagcc tcaaggacac ctatgacagc atgggccatg
actgtgcatg ccgcctggcc tagttcctgg agaagcctgc gaccaaggac ggggtcatta tgaaagtgct
caaggcccaa ggagccatcc cctttgttaa gaccaacatc ccactgacgc tgctcagctt tgaatgcggc
aactcccatc tatggccaga tgttgagccc actgaactta aagaagacat gtgggggctc ctcagggggt
gagggggtct gctggcagaa aggggggtcca tcctaggcat gggtactgac acaggtgaca gcatctgcat
accagccagc ttctgtggtg tttatggcct ctggaccaca ggttcccgcc tcagctacac tggaattgcc
tctgccatca aggggaaaaa aatcggtgac cacggtggct ggcccatgg cccaggacgt ggagagcctg
gcgctgtgcc tgcaagccct gctgagtgaa gacatgtacc gactggaccc cactgtgctc cagatgccct
ttagggagga ggtgaagacc cccttccca ccccaggctg cagtgagtga gaagcccaca tgctcagtcc
agtttgtttc cttccctgc tggacaccag ctgctttggc ttcttggcta tctggagcca tagcttgaca
cccaagaaac tgtgggaaca gcacacagca gtggaggaat atgagcaaga gttcatagcc aagtggaggt
ccctggacct ggatgtgctg ctggtgccag ttctgggctc tgccttctat ataggctctt cctccctagc
atcagaaagt cagtcttatg tgaccctgta caacctcctg gactttcccg cgggcgtggt gcctgtcact
atcgtgacac tacaggacga ggaggaactg gccttctaca aggggtgcta cggagatagt tctgacaaaa
atttctcaga ggcggtaaga ggatccgtcg gacttctggt gactgtgcag tgcattgctt tgccatggga
agaggagctg tgtctccggt tcatgaagga ggtggacacc ttggtcaaga atcagagggg gcccaagtga
taggctcctg gaatggagta acagctcatg aaacacgggg ctggttgtgg tggctcatac ttgtaatccc
agcagttcag gaggcagagg ctggcagatc gcttgaggcc acgagtttga gaccaacctg ggcaacatag
tgagaccctg cttctaaagc attttcttgg tgttactcct gtagatcctc acccaagtgt gctcctgatg
ccccttcctt ctcatgaata ccatgtccac cttatgtctc ctccttctgg aaccccacca ggttccttt
ctttgttggt ccctctgtgt gggtgctcaa tattcctcag atgggcccag gatggggagc agggtgagga
gctcaataaa cattttctga ctggc SEQ ID NO: 5-genomic DNA sequence of wild-type human FAAH-OUT
TTTCGCTCTTGTTGTGCAGGCTGGAGTGCAATGGCGAGATCTCAGCTCACTGCAACCTCTGCCTACCGGATTCAAG
TGATTCTCCTGCCTCAGCCTCCCGAGTATCTGGGATTACAGGCGTGTGCCACCATGCCCAGCTAATTTTGTATTTT
TAGTAGAGATGGGATTTCTCCATGTTAGTCAGGCTGGTCTTGAACTCCTGACCTCAGGTGATCTGCCTGCCTTGGC
CTCCCAAAGTGCTGGGATTACAGGCGTGAGCCACTGTGCCCGGCCTGCCACAGCTTTTTGCCTCGCTTCCCTGGGC
TCCAGACTGGACATCTCCAACAATCTTTCACATGGCAGTTAGGCAATCTCATGCTTAAAATCTTTGGACTCACTTG
TGCCAAGTCCAGAAGCCTTGTTATGACCTGCAAGGCCATGATTAACCTGACCCTGCAGCTGGCCCCTGCGGCCTCA
TCTCCTGCCCTTCCTCAGTGCTCACAGCCCGGCCACGTGGCCTGCAGGTAATGTTCAGAACACCGAGTGATCTCCC
GCCTCCACGCCCTTTGCTCTTGGTGCTTGCTGTGCCTGGAGTGTTGTTCCTGGGGTCTCCACCTAAAGACCACCTA
CTCGTCCAAGGTGAGGGCAATTGCTCTTCCAACTCTGTCAGGCGTGTGTTGAAAGAGCTTCTTTGTGCTTCTGCACG
TGGTCAAAAGCAAGGTCTGTGTATTAATAGAACCCAACATCTGTTAGGCTGTGGAGTTGAATACCCATTATCTCAT
TTGGAAAGTGGGCATTACTATTTCCATTTAAAAAATTTATTTATTTATTTATTTTTTGAGACAGAGTCTCTCTCTG
TCGCCCAGGCTGGAGTTCAATGGCACGATCTTGGCTCACTGCAACCTCTGTCTCTGGGTTCAAGTGATTCTCCTGC
CTCAGCCTCCCAAGTAGCTGGGATTACAGGCGCCTGCCACTGTGCCCGGCTATGTTTTGTATTTGTAGTAGAGATG
GGGTTTCACCACGTTGGCCAGGCTGGTTTCGAACTCCCGACCTCAGGTGGTCCACCTGCCTTGGCCAAAGTGCTGG
GATTACAGGCGTGAGCCACTGCGCCTGGCCTTTTTTCTTTTCTTTTTCTTTGAGATGGCGTCTTCCTCTGCCACCC
AGGCTGGAGTGCAGTGGTGCGATCTCAGCTCACTGCAGCCTCCGCCTCCTGGCTTCAAGCGATTTTCCTGCCTCAG
ACTCCCGAGTATAGCTGGGACTCCAGGCGCCTGCCACCATGCCTGGCTATGTTTTGTATTTTGTAGTAGAGATGGG
TTTCACTATGTTGGCCAGGCTGGTCCTCAACTCCTGATCTCAAGTGATCCGCCCGCCTTGGCCTCCCAAAGTGCTG
AGATTACAGGTGTGAGCTACCGTGTCTGGCCCTATTATTTCCATTTTATACATAAGGAAACTGAAGTTCAGAGGGG
ATTGCTGACTTGTTGAAGGCTGATCATTATGGGTTACAGAGAAGACTTGAAACCCACACGCTCAACTCTAAACTTA
CTGTGACTTCCTCATTTGTACAATCATCACAAGAACATGCATTCAACATTCTTCGGACACCAGCCTCTGTGCTAGG
CGACCACAACACTTTGAAGACAGAAGCAGTCCTGTGTACTGTGCACCTCTGCCAATATCTGTTTACAGGAGATAGC
TGCCATGTCCCTGTCCACCCTCCCTTTTCTCTCCTGGCGATTGCGATATTGGAGTTTTAGGACACAGCCAGAGCAC
```

-continued

| Sequences |
|---|
| TTGTCATTTGTTCCTGTTGGACACCATTTTTAGGATTATCCCAAGAGCTCTGGCTGTTTCTGCTCTTCCTCCCAAC |
| ATGTGCTTATCCACAAATCTGAGCACTGGACCTCTGCAACTTCATCCAAGTCACCCATAAACCTATGGATCACAGC |
| AGACCAAGGAAAGGGCGTGACCTACACCCTTAACAGACAGACACATAACCGAGTTTTGAGCTTCCCAGCCAGATGT |
| ATCTTTAGTTCACATTTCTCTGGCTGGGCTTAGCTGGGCCCTCCCAAGTTTCCTACACATAGATTTGGGGTGGCGG |
| CCCTGGGCACCTCAGGAAGGTGAAGCCACTTGGGATCGGGCTGTGTATGCTCAGCACCCAGCATGGTGCCTGGTAC |
| TCAGTGGGTACCCAGAGAAGGCTTGTTGAATGGAGCAATGGGTGACTTGTTATTAGGGAACCCATTTTGGTCCATT |
| CTGATTACTTCCTCTTCTCACCTCCAATAGGGAATTTTCCAATCAGTCCCTGACCCTTTGCTCCTTTCACATTTAT |
| TGTATCTACCTCCATGATCTTTTTTTTTTTTTTTTGAGATGGAGTCTTGCACTGTTGCCCAGGCTGGAGTGCAA |
| TGGCAGGATCTCGGCTTACTGCAACCTCTGCCTCCTGGGTTCAAGCGATTTTCCTGCCTCAGCCTCCGGAGTAGCT |
| GGGATTATAGGCGCCTGCCACCACGCCCAGCTAATTTTTTGTATTTATAGTAGAGATGGGGTTTCACTATGTTGGC |
| TAGGCTGGTCTCGAACTCTTGACCTCAGGCAATCCACCTGCCTCAGCCTCCCAAAATGCTAGGAGCCATGATCTTG |
| ATTAGTGCCCATGAGGACAAATAATTCCCAGTCTACATTCAACCTATAGCTTTCTCCTGGTCTGTAGATCCTCATC |
| TATCCACTTCTCTCATCCTCTTAACTCCTTCATCTCTCTCAGGCTGTTGAAAGAGCTTCTTTGTGCTTCTGCACTT |
| GGTAGAAAGCAGGGACTGTGTCTTAATAGAATCCAACATCCGTTAGGCTGTGGAGTTGAACCCATTATCTCCTTTG |
| TAAAATGGGCTTATTATTTCCATTTCATATATAAGGAAACTGAAATTCAGAGAGGGTTGCTCTCTGAACAACAATG |
| GAGGGTTGCTCCCTCCATTCATCCTCCCATCCATGCAATAAAAATATTGAATTCTTCCCACAGTATGTTCAGGGTA |
| ACCAATCAGAAATAGTCCCTGCCTGAATGGAGCTTCCATTCTACCAGGAAACAGACATCAAATGTAGAATTACACA |
| GAAACACTCGTTAGAAGTGCAATCAAGCAGAAGCCCTGGGTATTATGAGAATAAACCACGTGGGATCTGATCCAGC |
| CTGAGATGTGTGTATGTGTGTGTCAGGGAATGCTTCCTGGAGGAAGTAACATTGAAGCTGAAAACTGCATTGTCAC |
| CTGAGCCAAGGAATGAGTGTGTTTCAAGGAGGGTGAAGCTGACAACTCTAAATGCTGCTGATTTACTCTTGAGGAG |
| ATCACTGGGATGATATAGGCACAAGCCAGACTTTGTTGGGTGGGGGAGTGAGTGAAAGGTGAAGAAGTAAAGGCAG |
| CCCGTGTAGAAAACTGGAAAAGTTCAGGAAGCGGACAAAAGACGTGGTAGTAGTTAGGGAGGGTGTAAATCTGAGG |
| GAATCATCCCTCATCCCCCAAGATAGGAGAGACTTAGCATGTTAAATGCTGCTAGGAAAGAGCTAGCAGCAACGCA |
| CAGAGGGGGAAGTCAAGGTAGGAATGGAGGGCTCAACCTGCCATCATTTCTTCACTGAAGAGATACCATTGAACA |
| CATACCATGTGCCAGGTGTTTTGAAAAAGGCTGACAAGGTCTATGCTCCCCCAACCCCCCAGCTAATTTTTTTGCA |
| TTTTCTGTAGAGATGGGGTCTTGCCGTGTTGTCCAGGTTGAGCTCAAACTCCTGAGCTCAATTGATCCGCCCAAAG |
| TGCTGGGATTACAGGCGTGAGCCACTGTGCCTGGCCTCGTCTGTGCTTTTACGGAGCTTATTTTCTAGGGAGGGAG |
| GCAGGAGGTGAGTTACAGATCAACAAGAAAACTTCAGCTAATGATAAGTGTAATGATGAGATAAAATGAGGTATGT |
| GGTAACGGAAGGGTGTAACCCAGGAAAAGGTGAGGTCACGAGGCCTAGAGTGCTGTGCCGTGGGATGTGGTGCGGG |
| TGACAAGTGGCCTGGGGAGCTGAAGATATGGGGGAGAGCTGGAGTTCATGAAGGTGGAGTGGGGGCTATGGAAGA |
| AAATGGTCAGAAAAGAGGCAGAAGGACAGAGGAGGGCTGGTCTGGAGGCCCCAGGGAGATGACAGAGTGTTACAGA |
| GTGGGCAACTTCAGGGTCACCCTTAGTCAACTGCTGACCTCGCATCTGTTCCTTTAGACCCTCGGGTACTCAGACT |
| CAACATTACCAACCATGAATTCAGTTCCTTCCCACCCTAACCTGCTGCTGCCCTGGCTTCCTGGTCTGGAGGGCAA |
| AGGCGCCATTCTCCTGGGTACAGTGACTTGCAGTCTCAGTCGATGACCATTGAGATGGAGACTGGATGGAGGCCCT |
| GAGGAGAGCAGAATGGTTCCCACATCAGGGCCCCTCTGCACCACTTTTCCAGTCTCCTCATGTCTTCTCTGTTCCT |
| CGTCTGGGAAGTCATCTCCCTTACCCCCACAACTCCCCTCCACCAGCAGGGAGAGTCAATAGACTGGGGAGGCTGG |
| AACCCCGGATCAGAGTCATGGCCTTGCTTTGGAGTCAAGGGGGAAGCCCAGCTGGGCGGGCTGGTCTCATGTCCTG |
| GCATCATCTCCCCTGGGGTGGATGCCTGATGAGCCCTGCCCGCTCCTCCAGGTGTTCTTTCCTTCCTCTCTTCCT |
| GTCCCCCAGAACCTCCACTCTAGGCAAACATGGCCTGTTCAGTTCCACCTCCATGCGTCTGCTTATGCGGAACAAA |
| GGAGCTTTGGGAGAATCCTGAAGGCAATGGGAACCCCAGGAGCAACCCCATCCATAACTCCTGAGGGTTGGAGTAG |
| GGAATCTGAGGGGTGGGATCTGAGAGGTAGGATGGGTGGGAGTAGGATGTGACAGAGGTGAGGTCAGCTGCCCAGC |
| TGCAGGCTTGGGCCCTTCTTCAGGCTCGCCTGCTAAAGCCTCTTCCTCTGCATGGCCCGGGAGATAGGGGTTTTGT |
| CGCCAGGAAGTCCAGATGGGGTAAGAACTAGGAGGAGGTTGATCACTGCCACACCCAGGGCCCGAGATGTGCGTGG |
| GTGCCCTGGCAGCATCGCTGACAAATACTCCTGAGGAAACAGCAGCTGGATTCACACAGGTCGTGCAATACCTAAG |
| GTGGCTTGGCTGTTTGACTCCCTGATGATGCTACTTCTGCTGGGGCTGCTGGGGGCTGGCCTACTGGGGGCTTCCC |
| TGCTCACCTCGTGGCATGCTCCAGCCCGGAACAAGATCCCCAGGGCCCAGAAGTGGAGGGAGGTAGCACTGCAGAA |
| GATGGAGGACCTGGCCCAGTGACTCCGGCAGCAGGTGAGTCGACACGGGTCCCGGAGGCCCCAGCCACAGGGGC |
| CTTGGCCCTCAATCCCAACAGGAGGACTACACCTCAGGATGCCCCTCCCGTCCATGACCCCAGCCCCCGCAGACAC |
| AGGGAGCAGGTGGGCACTTCCCCACCCCCAGTTCTCCCCCCATGCCAGGCTCTGTGTGTGGTTGTCAGTTCTCCTCC |
| ATCCCCGGCCTTTGAGACCCTGGAGATTGGGGGCAGTGTATTCTTTCTCTGTTCTCCCAGCACTTGGCACGTGGCT |
| CAGTAACATGGGAGGTGCCCACTTAGGGTATTTGCGAAATAAGATAAACTGATGGAGGCCATTGGAGGAGGGAGG |
| CTCGATCTCTTTTAGCCCCTGAGCACTCCAAAATCCCCCAAGACAGGAACCCTAGTCTACCTGTCCCCTCCTACCT |
| CCACCCCATTCAGCTCTGAAAACACTTGCTGAGCCCTGATAAGTGCAGAGCATGGGGGCTGGGATGGGGTCTCC |
| CAGGAAGCTGCAGGTCTTCAGAGGCAGCTTTGGCAACTCGGAGTGGGGGTATTTCACTGGGATAGCCTCTGTGGCT |
| GGCTGGGCTGAGACTGGCAGGCGAAGTGGCTGAGCCATAGATGTATCAGCAAAGCCTGCCCCAGGTGGCAGAGAGA |
| AGGGCGGGAAGGAGGGACATGGAGACAAACATAGACTGAGCCTGGGATTTGCTGTGTGGCCTGGAGGATGTGACAA |
| CCCGTCTCTGGGCTTGACTCCCCAGCTGTCTGAGGGGGGATGGGCTCATGGTCTCTCGGGGTCTCCAGCTTTGG |
| TTGATGATGGTGGACTCAGTCGGGAGCCCGAGGTAGGGCTGGGGCTAGTGCCTGAGGTGCTGTTCCCATGCTT |
| TGGAGTTCCTGAGTGTCCTCTGCTGTCCCCTGGATGGTGATTGATGCCCCAATGGGCAGCTTCTCTGTCTGAGTT |
| GCTGCAGTTGCTGAGTATGTGTATTAATATTAATTAGGGCTAATTAGTTGGATAAATCAATCTGCCCCCAGAGAGC |
| AGCTGCCCCTCCCTGGTTGATGAGGAGGAAGTCTGGGCTAATGGGTTGCAGTGGTGAATGGGCATGATGGAGGCGT |
| CCTGTGTGCGTGTGGAGGCCCCATCTGTGTGCGGTGGTGGGTATAGCTTCCTTTACTGCGGACGAGGGCCTGCTTT |
| CTTGTGCCTCCTGCTGGCATTTCATTGTGTTGTGGTTGGTTGTGTGTCTGGTCTGGCTGTGTGGTTATGTGCCTGG |
| CTGGGTGTGCATGTGTTGGGTTATTGGTTGGAGTGTGTACATCTAGCTATGTGTGGCTGGTGTGGGTCTGAATGTC |
| TGGTAGAGAGTGTTTGTGTGTGGTTGTGTGTCTGATGTGTGGGGCAGCTGGTTTGGTATGTGTCTGGGCATCTGG |
| TTGGTGAACATGTGGATGTCTGGGCTGTTGGGCTGGGGACCTGGAGGGTATATGTCTGGATGGCTGGAGGAGTG |
| GAAGAGGGTTTTGGGGTGAGGTCACTCATGGTGTCTCCAGCCTCCCATTGTGGTTTCAGGCTTCTTGGCTCTCAGCA |
| CCTTGCTGTCTCCCAACAAGCTATACAGGTCTGTCCTGGGCACCTTCTCAGTCATGTCACCCTCTCTCTGCCAGT |
| GACAACCTCGAGACCTCAGGTGTCCACCTTTATGTCCCGGGGAGGTGCAAGGCTGGGACACAGGTCAAACCCTCAC |
| AGGCTCAGCAAACAAATTCAATTCTGCTGAGTTTAGTAAAATTTCCCAGGGAATTTCTCCAGGTCTTGCCCTGTGC |
| TGAGCTCTGGGGACACATTCATTATAAAGATGAATCTGACCCCTGACTCACACTTGTGCTAAAAATGTTCCCAACC |
| TGGGAGGGGCGTGGTGGAGATAGAGCTGTGCAGACTATGCAGGGCAGCAGCACGGCAGAGTGTGGTGAGGCCAGAT |
| GCCCACAGAACTGGTGACTTGGCAGGAGGGTGGCTGGTCTGTCTGGAGAGGATCATGTTGGGAGGGCTCCCCAGAC |
| GGGTGGTGAGTGAGCTGAACCTCATGGCACCTGTAGGACTTTTCTGAAAGGAGAAACGAGAAAGGCAGTACCAGGG |
| AGGGAGAAGCCCCAGATGAGGCAGTGTTTCTGTAGAACGTATAGAAAATAATATTCCTAGGACCCATTGGGTAAAT |
| GGACCAGCTGCTCATGGCTGGAACTGCTCAAGCTACTCATGGCCAGGAAGCTCTGCTCACCTCAGGCAGAGCCTGG |
| CCACCTTGAGAGTTGACGGTTTTTATGATACTAAACATTTAACCACCACATTGGAATTTTTTTTTTTTTCAGACGG |

-continued

| Sequences |
|---|
| AGTCTCACTTTGTTGCCCAGGCTGGAGTGCAGTGGCCTGATCTCAGCTCCCTGCAACCTCCACCTCCCGAGTTGAA |
| GCAATTCTCTTGCCTCAGCCTCCAGAGTAGCTGGGATTACAGGCAAGTCCCACCAAGCCCAACTAATTTTTGTATT |
| TTTCGTAGACATGGGGTTTCACCATGTTGGCCAGGATGGTCTTGATCTCTTGACCTCGTGATCCTCCCACCTTGGC |
| CTCCCAAAGTGCTGGGATTACAGGCGTGAGCCACCGTGCCCGGCCATAAATATTAATAATACATTGATTCACTAAA |
| AACTTTAAATTACATTTTTTTTGTTTTTCAAACTAGGCTGGAGGCAGCACCCTGAGTACAGAGAAGGCTGGATGTC |
| CGTGGGGCTGTGGGATGGAGCTGGAGGGAAGGGTTAGCTCCAAACTAAATTACATATTAAAAAGTGATATAACTTG |
| AGGCTCAATTTTTCATCAAATTATTCAAATAATTTGTTGATTTTTAGCTTTTTTTTTTTTTTTGGAGACGGAGT |
| TTCGCTCTTGTTGCCCAGGCTGGAGTGCAATGGCATGATCTCGGCTCACCGCAACCTCCGCCTCCCAGATTCAAGC |
| AATTCTCCTATCTCAGCCTCCCAAGTAGCTGGGATTACAGGCATGCACCACCACGCCCAGCTAATTTTGTATTTTT |
| AGTAGAGATGGGGTTTCTCCATGTTGAGGCTGGTCTCGAACTCCTGACCTCAGGTGATCTGCCCACCTCGGCCTCC |
| CAAAGTGCTGGGATTACAGGCGTAAGTCACCGCGCCCGGCCTTTTTTCTCTTTCTTTTTTTTTTTTTTGAGACAGA |
| GTTTTGCTCTTGTTGCTCATGCTGGAGTGCAATGGCGCAATCTTGGCTCACTGCAATCTCCGCCTCCCGGGTTCAA |
| GTGATTCTCCTGCCTCAGCCTCCTAGGTAGCTGGGATTACAGGCGCTCACCACCATGCCCGGCTAAATTTTTTTTT |
| TTTTGGATTTTGAGTAGAAACGGGGTTTCACCATGTTAGTCTCGAACTCCTGACCACAGGTGATCCGCCCGCTTTG |
| GCCTCCCAAAGTGCTGGGATTACAGATGCTCGCCACTGCGCCTGGCTAATTTGTTGATTTTTAGAATTTGTTGTGA |
| GGATCCTGTGATGTGGCTATCATCTTTTGAAAGTTGTCCCTGTCTTTCAAAGCGCTCCTGATACATTGGAGTCATT |
| AGGTCACTTGCAGTCTGATTAAGGAGAGTCTTTCTCTTAACGTTAGTGATATTGTTCCGTGGGTGGAGTCCTCTCT |
| CAGCTTTTGCTGAACCAGTAGCAATTACACTCACAATTTTCTAGCTTTTTCTAATACAGTGTTAGATTTCATGTAGT |
| TAAGCATCTCTGTTGTCAATTAAGTAATAAACATTGTTATTAGAATGTCATTAACACTAATTAGAAGTTGTCTAGC |
| ATGGCAGCTAAGAGTGTGGCTTCTGTTGTTGGGCTGGCTGTTTGAATCCTGACTCTTGACACTTTTTATTTTGTTT |
| GATTTTATCATTTTACATTGTCTTGAACTCCTGGCCTCAAGCAATCCTTCCCACCTCAGACTCCCAAAGTGCTAGCA |
| TTACAGGCGTGAGCCACCAAACCCAGCAAACACTTACACTTAAATGACTACTCTGTATCTTAACTTCTTCATCTCT |
| ACAATGGTATGATGATTGTAATGATAGCACTCAAACAAGTTAATAAATGTTTACAGTGGTGCCTGGTACACAGCAA |
| ACACCATACAGATGCTCCTCGACTTACCGTGGGGCTTCATCCTGATAAACATCATCCTAAATTGAAAATATTGTAAG |
| TTGAAAATGCACTTAATACATACAACCCACCCAACATCATAGCTTAGCCTAGCCTTTTTGAAACATGCTCAGAACA |
| CTTACATTAGCCCACGGTTGGGCAAAATCACCTGGCAACACAGTACCCTGTAGAGGATTCACTGTTTCCCTTGTGA |
| TTTTGTGGCTGACTGGGAGCTAGTCTTGCTGGCACTGTCCAGTATCGAGAATCAAGAGAGTATCTTACTGCTTTTT |
| TTTTTTTTTTCTTTTTTTTGAGACGGAGTCTGGCTCTGTCTCCCAGGCTGGAGTGCAGTGGCGCAGTCTCAGCTC |
| ACTGCAACCTCTGCCTCCCAGGTTCAAGAGATTCTCCTGCCTCATCCTCCCGAGTAGCTGGGATTACAGGTGTGCG |
| CCACCACGCCCGGCTAACTTTGTATTTTTAGTAGAGACAGGGTTTTGCCATGTTGGCCAGGCTGGTCTTGAACTC |
| CTGACCTCAGGTGATCCCCCCACCTTGGCCTCCCAAAGTGCTGGAATTACAGGCGTGAGCAAACGTGCCCGGCCTT |
| TTACTGCTTTCCGATGAATGTATATCAATCGCTTTTGCGCTACCGTAAAGTCAAAGATTGTAAGTTGAACCATGGT |
| AAGTTGGGACTGTCTGTACAAGTGATAGTTCTCACTTTAGGAATGAAGCTACTGTTGTTGTCCATGGTGAGTGGGT |
| ATTTTGGGTGAGCAGAATATGTTCTATTAGATGGATGTGACATTCTGTCCTCCCAGGTCCCTGGAGCGCCTGCTGT |
| GGTCTCAGCAGCCACCTGCAGAGGTCACATTAGCCACTCCCCAACCCCTGCCCTTGCCTGCTCTTCCCACCTCTCC |
| CCAAGCTCCCTGAGAGTCAAAGTGCCCCAGAGGCTGCCATTCCCACAAATGCCTCCACAAGGACAGCTGCAGGGGA |
| AGGCTAGCCTCAGGGGCCCAGAGGGACACATTGGGCACTTGCCCATGGGGTGCCACCAGGGGTGTTGTCTCTCCAG |
| GTAGAAATATAGAAATGGGGGCTGGTGTGCAGCTGCTGATGTCTCTGGGGTGCGTCTGGGGACCTGTGAGTGCAGG |
| GAGGTCCCTGGCGGGGCCCGCTAGGGCTCCTTAGGGTTGGAGGGCGCAGGGCAAGGGATGAACCCAGGCTGGCCCT |
| CCACAGTCCCTATGCCTAGAGGGTCCCTGCTGGGCTGAGCATTAACTTTACTTGCTGGACTGTGTAGAGAGGGTGG |
| AGTCCTGGGGAGGGGCTAGGACAACTAGGGTGGTGGGGGGTGCCCAGCAGAGCAGCTTTTTGCCCAAGTGACTCAGA |
| AATGTTTCAGTAGTTTAGCCACTGGCATGGCTGTGGTGGTGCATCCTGGCTGAATGCTAGCCCTGTCCAAGGGATC |
| TGTGTCTGGACCCTCCTGAGAGTCCCTGTGGCACACCAGCTGGGGAGCTCTGAGCTGAGGCACAGCAAGGAAAGGG |
| ACTGGACAGTGTGGCTGGAGCAGCATGCATGGGAGAGGCTGAGAGAGACAGGCCCACTGGACCCAAGCAGGGAAAG |
| ACCCTGGTCCAGTGCCTGGCACCCTTAAAAAGCCTCCCTTCCACAAGATGCCCCAAGGACCAGGAGAGGGTAGTGGT |
| TAAGGTATGGACGGCCTGGGTTTAAGCCCAGGCTCCCCTGTCCTCTGACCTTGGGCAAGAGAGTTAGTCTCTCCGG |
| GTCTCAGTTGCCTTCACTGGGGAAATGGAAACAGTAATAACAGCACTTAGCCAAGGGTTTTTGTGAGGATTTAATG |
| AAACGGTGCAGTAAAGGGCTTGAGAGGGTTTCCAGCCCCACAGTGATACTCTGAATACTTGGTCAATGGGAATTGT |
| GTACATCGAAGCAAGAACCCATGTTACACATTTACAGTGAAGGCTTTGCAAGTGGTGCTGGTGAGAATGGTGCTGC |
| AATGTTATCCTGAGGGCTACTGGGACCTATTTTCAGAGTGGGCCTTATAAGATCTTAAAAGGATTGCCCAGGCTGC |
| AGTGAAGAGGCTGAGTTGGAGGAGTGGAGGCCAAGCCGTGGAGGCCAAGCCAAGGAGGCCAGTGAGGAGGCCAATG |
| AGCCAACAGAGAGAGGTCCTTAGGCAGGCAAGAGGCCTGAGGGTCCGAGGTGGGAGATACGAAGGAGTAGAACCAC |
| CTGCAGGCAGTGTGTGCAGTTAAGAATGTGGTCACTGGTGTTGACTGCCTGGCTCTGCCCACTTACTGGC |
| TGTGTATCCTCGGGCAAAGAGGAGGAGGTCTCTGTGCCTCAGTGTTGTCTTCTGCTGTGAAATGAGAAACGATGT |
| GACCTACCTCTTAGGGTTGTTACAATTAAAAATTGTAAATTTTTAATTTACAATTTTCTTGGAGACAGGGTCTCAT |
| GTCATCCAGGCTGGAATGCAGCAGTGAGATCATAGCTCACTGCAGCCTCAAACTCCTGGCTTCAAGAAATCCTCCC |
| ACCTCGGCCTTCCAAAATTCATTATAGGCAATGACTGATTATATGCAAAGTGTCTGGAATAGGGCCTGGCACTATT |
| AAGTGTTAGAACACATCCTAGTGTGATTATGTTAGCTAGTGTAACTATTATCAGAACTTGGGTGTGAGGGAGGACC |
| TAGGATGATTCTGAGGTTTGTTGCTTTGGTGACATGCATGTCATCAATTGGGAATTTCAAGAAGAACAGATTTGGC |
| TGAAAGAAGGTGAGTCCTGGGGAGTCTGTGTATATGTGGGTAGGTAAAGGGGTCTGAGTCCTGGCGGAAGAGAGGC |
| CTAGGTTAGAGAAACAGGTGGCCTGCTTATCCTTGGGGTGCACCTGGCTGCCGAGGTCACCCATGGAGAGTGGGCA |
| GGCAGGGAGAGAAAAGGTCATGCCCTGAGGAACACCAACATTTCAGGCAACTGAGAAGGAGCCACCTGAGGGTGGG |
| AGGAGGCCAGCAGAGTTGGGGGCATAGAGAGCTTTGGGAGGGAGAGTGTCAGACGCTGCTGAGGAGAGTGAGATGA |
| AGACTAACCCGAATCCATAAGATTTAGTAACCGAGAAGTCTTGATGCCCTTGGTGAGAAGGGGCCCAGTGCAGAGG |
| GGAGGACAGATGTCAGACTGGTTGCTTTGAGGAATGAAAGAAGACAGACTGGAGCCAGGGGATCCTAACCTCCAAG |
| GGAAATTTATTTGTCTCCACCTTCCCCCACCTCCAGGACCCAAGAAAAAGCCCACTTCTTGCCCAACCCATACTCCAG |
| CTTGGAGGCATCGGGGTCTTAACCAGAGCTGAGGGGGGCAAGAGGAAGAGAACTTTGCCTTCCTGAGTGCCTGCTG |
| TGTGCTAGACCTTTGTCATGTCACACTTGCCCAGGGCGGCAGTCCTGAGGGCCTGGTATCAGACCTCCCCTCATAT |
| CCTGAAGGACGGGGCTCAGAGCAGTTGAGGGGCTGACTCAGGATGGACTCCTAGTCCTTCCCTCTCTGAGGAGACC |
| TAGGCCATGGGAGGAGCAGAGAACCACCTCCAGTTACCCAGCTGACCAAGGGCGCGGCCAAGATGGTGCTAACTCT |
| CTTGCCACCCATGCTGGACTCCTGCCTCCCTAAAGTCAGCTCAGCAGGGGAGGAACTGGGTAGGGAGGAGAGGTGG |
| GATGCCTGGGATGCCCCTGAAGGCCAGCCACCCAGGGCTGAACTTCACTTCCATAACCTCCAGTCTCATGATGTCA |
| CATGTGGAGTCACCCCCACTCCAGTTGTGACCCTTCTGAAGAGCAGCATGAAGGGGCAGGCCCTTCTCCACGCCAG |
| GCCCTGGGCTGGCCACTGGGGCAGAGGCAGAGGAGAACATCGTGCCCTTGGAGGGTTTTCATGACAACCTGGAGA |
| CACAACAGATGTTTTAGTGCTAAGCATGAGTGCCGGAACATGTACCGAGAGACATGGGCGTGTGTGCAGCTGTGC |
| ATAGGGGAGTCTGGGGTGTGATGTGGAGTGTGTGGGAGTGGGCCTTAGCGGGTCCATCTTGGATATCTGCCTACTC |
| CATCTCATTTCTGCAGGAGCCAGATCTGGACCCCAAGCCAATCCTGGAGCTGCCCCTGGCAGAGCTGGCCCAGCAG |

-continued

| Sequences |
|---|
| CTTCGGACCGAAGAGCTGAGTCTGGAGAGCATCCTCTGTAGCTACTTAAAGCAGGTGGTGGCCAGGGCACAGGATC |
| CAAGCCCGGGGCTCTGGGCTGGAGTGGGGGATGTCACTTGTCATTGTTTACTCAGAGGAGCTGAGGGGCAGGTGT |
| AACTCTGCCACTGACTTGGGAGGTGGCACATGCCACAGTTACCTCAGGGTGGCAGGAGGGGCTGGGGCAACCGAGT |
| GCCCTGCTTTGGTCCTGGCCTCACCTGGGGCTGTTGTCTGCTGTCTTCACTGTTGTGCAGGCACTGAAGGTGCACC |
| AGGAGGTGAACTGCCTGATGGATTTCCTGGGGGAATGTGAGGAGGAACTGCAGGCATTAAAGAAGCTTAAGAAGAG |
| TGAGAGAGGCCTTCTCTATGGGGTCCCCATGAGCCTCAAGGACACCTATGACAGCATGGTGAGCCTGGGGTGTACA |
| TGCACACGAATGTGCATATGCACGCTTGTGCCACCAGCCTGGAGCTTGGTGTGTGACACTGGGGGGCTCAGTGTGT |
| GACAATGGGTGAGTCATTTAAAACTGCACAGCTACGAAGCGGCAAACTGAGGTTTATACCCAGAATTTGGGTTCCA |
| AACCCCAAATTCTCAGCCACCCACACTCTTTTGCCATCCGTGAAGTGCTGCGCTTGTGTCCCCAGGGGTGTGAGAGT |
| GTGTGTGAGGGGGGTGGAATGGGGCTGAAAATCAGCCAGCTGGCTGGTTCCACCCTGACCCCCATGGCTGGAGGCA |
| ATGTTCCTTCCCTGCAGGGCCATGACTGTGCATGCCGCCTGGCCTAGTTCCTGGAGAAGCCTGCGACCAAGGACGG |
| GGTCATTATGAAAGTGCTCAAGGCCCAAGGAGCCATCCCCTTTGTTAAGACCAACATCCCACTGACGCTGCTCAGG |
| TCTCTGAAGCGGGCTAGCTGGGGTCGGGGGCTGGGCTAAGCCCAGGGCTGAAACAGCTCTTTGAAGTCCTGATTCA |
| GGGCAGAGGGTGAGGAGGGGGCTAGTCATACAGACTTCAAAGACCAGGGTTCTTGGGCCAGCCCCTTCTGTCCCCG |
| GGGCTGAGTTTCTTTATCACAGAACATGTGGATGGACTCCACAGTCTGTAAGGGCCCTTCGGGCTCCAAGGTTCTG |
| TAAAGCTACACTCTTTTTCTATCCCAGTTTCTCTCTCAAATTGTTCTATTTCTACCCAGGCTTCTCTCTTTGATTG |
| TTCTCCCCATCGCTTATTCTCTCCCTTCTCTACTCAGCCTGTAGTGCATCTGTGTTTCGTGAGGAACATGTTCTCA |
| GTTCTGATGGCAGAGCTGTGGGCTCTTTGGTCCTGATATTAGGAGTCATGGCTGGTGTCTGATCTTGGTCTTTCTT |
| GCAGCAGCAGCCCCTCACCCCAGCTGGAAGGGAGCCCAGGAAGCCTCAGCCTTAGGGAGGAGCTCATGGAGCCCAG |
| GAAGCCCTGGGGTTGACTCTGGAGGGTGGTTGGCCCCCATATGGGGAGAGGTTGCCGAGTGAGGCTTTCACCCTC |
| AGCTCATTTTCTTCTGCTTCCCTTAGCTTTGAATGCGGCAACTCCCATCTATGCCAGATGTTGAGCCCACTGAAC |
| TTAAAGAAGACATGTGGGGGCTCCTCAGGGGGTGAGGGGCTCTGCTGGCAGAAAGGGGTCCATCCTAGGCATGGG |
| TACTGACACAGGTGACAGCATCTGCATACCAGCCAGCTTCTGTGGTGTTTATGGCCTCTGGACCACAGGTTCCCGC |
| CTCAGGTACTCATTGATGGTGGTGGGGTGGGCTCGGACCTGCCTAAGGGAACTAGAGGGTGGGGAAGTAGAGG |
| GGTCTGCTCCTCCCATCAACTTTCATCTACCCAACTCAGTACTAGGGGAAGTGGGTAGGAGGGCTTCAAATAACTC |
| CTGCAGTAGCCATGCTAAACATACCATATTTTTCCAGGTGGCAGTAGAATAGACCTTCCACTCATTAACTCATCAG |
| CTCATTAATTCATTAATCTATACAGCTATCCATCCACATACCCTTCTCTTACTCATCAATCTGTCCATGTATCTA |
| TCTGTCCTTCATCCATTCAATCACCCACATGGTCATCATCTCAGCTCTATCCATCCATCAATCAATTTTACCATTCATC |
| CACTATTTATTTAAAAGATTTCTATTGACTATTTACTGTGTCAGACACAACAGCTCCTTGGGTACTAGCTACTTGG |
| GTTACTTCGGTGAACAAAAGAGACAAATATCTCAGCCCTTGAAAAACTTACACATACTCTTCCTTCCAACCATTTA |
| TCCATCCATCTTTCCATCCATCCATTTGTGTATCCATCCATCAATCCACATTTGTATCTCTCCATCCATCCATCCA |
| TCCATCCATCCATCCATCCATCCATCCATCCATCCGTTCATGTATATGCATGCATGCATCCACCCATCTCT |
| CAACCCCTCTCTGTGTACCCACACCATGGCCCCTATTCTGGGGACATAGACCACTCTTGGACCCAGCCCCTGCCCC |
| TGCTGTGCTCTTAGACACACAAATGAGTTAGTCAGAAAGTGATCAGGTCTGTAAGAGAGGGTCAAAGCTTACAAGA |
| GGAAGCTGACATTTTCTTTAACAGAGATTTATTAAAAGCTTATACTCTTGACTTTCAGAGGCAGGGCAAGGGAAGG |
| GAAGGATTCCTGGAGGAGGCAGCATTTGAGCGTGGTTTTGAGGGCCAGACATGCCAAGATGATGTGGCGTCTAGAA |
| GGCTGTAAGATTGTTTGTAAGCGGCTGACTTTGCCTGCAGCAATATGCACGTGTGGAAGGGCTAGAAGGGGAAGCC |
| ATGGAGAGTTAGAGTCTTGAAAAGCAGTCAAAGAGATCAGACTATGCTGTGGGCAGCAGAGGGTCAGGGAATGTTG |
| AAGCAGCTCCTATTTTTGTGGGCTGCGCCCTGGGGGAGCACATCGCCTGGGTGCTCAAGCCTCCTAGCACCCAGGC |
| CCCTCCCTTCACATGCTGAGCTGGGCTCTGGGTCGGAATGTTTTGCAGCTACACTGGAATTGCCTCTGCCATCAAG |
| GGGAAAAAAATCGGGTAAGTCCTGGTCTGTGCCTGTGGCCACCCCATTTAAAGATGAAACTGCCAGTCTTTCTCCC |
| AAGGACATTTTGCTCAGCTCATATCTCCAGACAGATCAGCCCCACAGATGATGACTGAGAGGGCAGACTGCATGGT |
| TCCCACCTGGCCTCCCCTTGTCCAGTGACTCTTGGCCCTCTGAGAAGGGCTTTTGTCCTGCTATCTAGCTTTAATC |
| TCTTCCTTCGTCCTGACCATGACCCTGGAACCCACCCTCTGAGGCCAGGCAGTTGGGATCCCCAGGGCACAACAAA |
| TGAGAGGTGCTTGCTGGGCGCAGTGGCTCATGCCTGTAATCCCAGCACTTTGGGAGGCTGAGGTGGGCGATCATTT |
| GAGGTCAGGAATTCGAGACCAGCCTGGCCAACATGGTGAAACCCCGTCTCTACTAGAAATACAAAAATTAGCCAGG |
| TGTGGTGGCGGGCACCTGTAATTCCAGCTACTGGGGAGGCTGAGGCAGGAGAATCACTTGAACCCGGGAGGTGGAG |
| GTTGTAGTAAGCAGAGATGGTGCCACTGCACTCCAGCCTGGGTGACAGAGAAAAACTTCGTCTCAAAAACCAACAA |
| ACAAAAAACAAAACACAACAAGCAAACAAAACGAGAGGTGCCTGCCTCTCTCCCCTCCTCTTTGTGCAGTGACCAC |
| GGTGGCTGGCCCCATGGCCCAGGACGTGGAGAGCCTGGCGCTGTGCCTGCAAGCCCTGCTGAGTGAAGACATGTAC |
| CGACTGGACCCCACTGTGCTCCAGATGCCCTTTAGGGAGGAGGTAAGCCAGGTGGGAGAGCAGACCTGGGGGTTTC |
| CTTGCCCCCCACCATCATTCCTCCCTGACCTGTCTGCCATCCTTACCTTCCCAGGTGAAGACCCCCTTTCCCACCCC |
| AGGCTGCAGTGAGTGAGAAGCCCACATGCTCAGTCCAGTTTGTTTCCTTCCCCTGCTGGACACCAGCTGCTTTGGC |
| TTCTTGGCTATCTGGAGCCATAGCTTGTAAGTGCCCCCAAAGAGGGCCTCCAGTGCCATATACCCAACCCATGCAG |
| TTAGAATACTCAGCAAGTGTGGTTGAGAGGGTGTGGCATCAGTTAAGCTGGGTTTTTAACCCTCTAGGTAACCCT |
| GGCCAAGTCACATCTCTTCTTTCAGCCTTAGCCTCCCCATCAATACAATAAAGAGGTTAGGCTGGGAGATTACTCC |
| ACACCCTTCTGTCTACAGCAGCCTTCATTTATTCGTTAATTCATTCAACAACATTTGCTTGTACCAGTTGTGTGCC |
| AGGCTCTGCGTGTCTCATCCTAACACTCTATAGAGTGAGCAGTGCTCCTCCCATTTACAGCTGGGGAGACTGAGGG |
| GAAGTGAAATGACTTGCCTAAGATCATGTAGTTAGTAACTGGAGAGCTGGCTTTGAACCCAGCCCTATCTAACTG |
| CAGAACCCTCTCCATAGGGCAGTTTCTGTCTACGTCCCGGCAATGTCTGTTCCTCGGATTCCCTACACCCCTCCTA |
| GCATTATCAACCTGAGATCATTGTATATCATCCATGATTTGCCCCTACAAACATGTGTTGTGACGGGTGAGGGG |
| CGGCTGCCTTTCTGGCAGCACCCCACTTCCCAGGACTAGGGGCCCTCCATCTCAGACCCTGGTCTGGGTATTTGTC |
| CCTATAGATCTCCAGCCTCATATTCTCCTAACATTTCTTTAGCTTAAAGATATTTGAGTCTATGCATGACTTACTC |
| ACCTGCCCACCCACTCAACTCCAACCATCCATTCACCCACTCACCCACATATGCATTCAACCCTCTGCCCACCCAA |
| CTACCCACCATCTCATACATACATCCACCCACCCACCCAGGAGTCTGTCTACCATCTATCTACTATCCACCCCATC |
| TGCCCAACCACCCATCTCATCCATTTCTCTTTCCTCCAGGGGTTTCCGCAGAGCACACTAGAGCCTGGAGAGTATAT |
| AGGGGAGGCTCCCAGGGGGTCTTGGGGTGTCCACATGGATTCCCCCCTTTGTGAGGACAGCTGTAGACCAAGGCCCT |
| GCCCTTAAAGTCTGGCTCCTGGATAGAGTGGGGCCACCTTGTCCCCAGCACAATCTCTCCTCCGAGCTCCATCCAG |
| CCCCTTGTGCCCCTAGGTTTACACCAGTAACCGGCCCCTTCGAATTGGCTACTATGAATCAGATGGTTACATCCAG |
| CCATCCCCTAGCATGGCCAGGGCTGTGCAGCTCACCTCCTGGCTGCTCCAGGATGCTTGACACCAGGTAGTCTCAC |
| CTGGTCTCGGGTGAGAGAGTCTGGGCCAGTGCGAGGATGCTGGGCGGGGCCATCCTTGGAGACAAAGGTGGCTA |
| CATCTGCGTTTGAGGTGCTGAGATAACTGTGTTCCCCCTATGCTTCCTGGAAGAGCTGATGGGATGGAGGTGGGG |
| ATAGGGTGAGCCCTACCCTAGAAGGAAGGCATTAAGCTTTTGTGCTTCCTCCTTCGGTGGTGGAGATTCAGGGACT |
| CACTCCTATAATTCCTTCAGCTTGGGTCTCTGTTGCCTCCATCAAGTGGCCGTAAGGAGCTTTCTGTCTCCAAAAT |
| CCCTACCTTAGCCCTACCCCAAACTCCCCTGCCCCAGTGGCTTGTCCTGGCCTCACTTCCCCTTTGAGATTCTAC |
| CATGTGATCTTGGGCTAGCCTTTTAACCTCTCTGGGCTTGTTTTCTACCCAATGCGGTGGCTGTGAAGATTAAATG |
| TGGTTCCATAGATAAAGCACTTGGCACGCTGGCTGGATCACAGTGAAGCATGAAGGAAATGAGGGCTGCTCTCGTT |

-continued

| Sequences |
|---|
| CTGTTCTGTCACATCTGTGTGTGAGGGTGAGGGAGTGGGGTGGCAGGAGAGCAACCAGTGACACAGGCCTCCCATG |
| CCATGCTGAGGCGCTGAGGTGGACGGAGATGCACGAGATGATGTGGCATCCTTCTTGAAATCTTGGGGGATGCAGA |
| GACAGAGAACCAGGCAGGGTCGGGAAGCTCCAGACACTGACTCTGCCTCTGCCTCCCCAGGTTATCCCCTTCTCC |
| ATCCCCCAGGCAGAATACGCCATCAAAGACTTGTACACGGGGGGATGTTTACTGATGGAGGGGCCACTCTTCTAGA |
| GAAGCTATACGTTATCTGCTGGGACTCAGGGGTGGGGCATGGTGGAAACAAGGTAGGGGAGTGGGCTGGAGCCAAC |
| CTGAGTCCCAGGAGGGAAACTGGGGGCCTGGGCTGGGGTGCCTCTGCCTAATAGTGTGACCTTATGCCGCAAACCA |
| CACACTGGGCCTGTCTTTTAGGATGCACCTGTTCCGGGGGTGGGGCAGAAGTACATCTTTGGGTTTGGCCTCCTTCT |
| TGTCTACGGCGTGGAAGTTGGGTGGCTGTGGGGGCAGGCCACTGGCTAAGGGCTGTGACTTACCCATCTGCGACTG |
| GTTCCTCAGAGAGGGGGACATTGTGGATCCCAGCATAAAGGGCATGGTCAACCAGCTCTGCCTGCCAGACCCCTTC |
| AAATGTTTCTTGGCCTGGATCCCAAAGTACATAGTAAGTGCAGGCCCTAGTCAGGGAGGGCTTTGGAAGGGCAGGG |
| AGCACAGGGAGTAGGAGGGGCTCAGAAAGCAGAGGGAGCTCACAGAAGGAGTGGAAGTGGGGTCAGGAGGAGGAT |
| GAGGCCCAGAGAATGGTGGTAGCTCAGAGAGGGGTTCAAAATGGGGAAGAAGAATGAAGGGCTGGGTGCACAGTGG |
| CTCATGTATGTAATCCCAGCACTTTGGGAGGCCAAGGTAGGAAGATCACTTGAGCCCAGGAGTCTGAGACCAGCCT |
| GGGCAACATAGTGAGACTCCATTCTCTAAAAAGAATGGAAAAAAAAATAGCTGGGCATGGTGGTGCATGCCTGTGG |
| TCCCAGCTACTCAGGAGGCTGAGGTGGGAGTATCACTTGAGCCCAGAAGATCAAGGCTGCAGTGAGCTGAGATTAT |
| GCACTGCACTCCAGCTTGGGTGACAAGTAAGACTCTGACTCAAAAAAAATAAAAAAAAATTAATTAAAACAAATAA |
| TGAAAGAAGGGGATGGGGCTAAAAGAGTAGGGTGCTCACAGAGAGGGGAGGGGGTTTCAGAGAGGAGGCTCAGAAA |
| GGGGGAAGGGCATTTGGAGGGCTACAGGGCCAGTGTGAGCTCAGGGCTTGGTGAAGTGGTGTAGGCTTGTTGAGGA |
| TCGGAGGGTTCCACGTCAGTGCGTTGAGCAATGCTACCCTTCTTGGACCCCCTCCTGGGCAGGCTGACTGTTTCCC |
| TGTGGGTTCTGAAGTTGGACTCCCCCTCTCAGCCCCCCTCTAGGATCCCCAAACTAGCCAGCATCTTGAAGAGATT |
| CGTGGAGTGGGGTGAGTCTCCCTAGGGCCAGCTCTTGCTCCAATGGTTGTCCATGGGATGGTGGGAATTGAGGAGG |
| GGCATGAGGCTAGAGCTGGTATCCACTAAGGGGGGATCTATTTAGATTTCGGACTCTAATTAGGGTTTTAGGATCA |
| TGCCTGACATTAGCTTAGATTGAGACTTTTGATTGGTGTTGGGACTTTATTTGGAGTTAAGATCTGAATTAAGGCC |
| GGGTGTGGTGGCTCATGCCTGTAATCCCAGCACTTTGGGAGGCTGAGCGGGGAGGATCACTTGAGGCCAGGGGTTC |
| AAGACCAGCCAGGACAACATGATGAAACCCTGTCCCTACTAAAAATACAAAAATCAGCGGGTGTGGTGGTATGTGT |
| CTTTATCCCAGCTACTCGGGAGGCTGAGGCACGAGAATCACTTGAACCCAGGAGGTGGAGCTTGCAGTGGGCCAAG |
| ATGGTGCCACTGCACTCTAGCCTGGGTGATAGAGATAGACTCTGTCTCAAGGGAAAAAAAAATCTGAATTAAGGCT |
| AGGTTGAGGTAAAATTTGGGACTGAAGTTGAGATTAGGTTTTATTTGGGGATGGGCTTAAGACTGAGCTGAGGGTT |
| GGAGTTGGTTTGAGTTGGGGTTGGTGGGGCGAAGATAGATTTGGAAGAGGGTTGGGACTGAGGCTGGAGTTGGGGT |
| GGGGCTAGAGTTAGGGTTAGAGATGAGGTTGGGAGAGGCTGGTATGGGCTTGGGTTTGCTGTTGGGCTTGGCCTGG |
| TGGGGTTGGCATGAAGATGCTGGGCAGAATTGGGCTGGAGTGGACTGAGGGCTAACTGGGTGCCTCACAGATTAGG |
| GTAAGGAGCCTGTGGCCTTTGAGGCAGCCCATGAGTTCCTGTGACTGGTGGAATGGGGGGTAGATTGACCAGAGGA |
| TGTGTGCTCTTGGGGACCTTGAGCAGGCAAGATGTCTTGGCCAGGGGACAAGACACGGGGTCACTCCCAGCCCATC |
| AGCTGATTTGCAGCGTGCACTGAGGCCTTGGTTGTCATGTCCCCATTTGTATAAAAGGGTTCCCTCCCATGCTGAC |
| CTTTGAACTTGTCAGAGTCTTCCTCATTCTTTCAGGACACCCAAGAAACTGTGGGAACAGCACACAGCAGTGGAGG |
| TAATGCCTGTCTGGGAAGACCTTGAGGGGCTGCTGGAGCTGGGGCTGCAGACACCTGGGTAGTGCCCTGAGTGGTC |
| AGAGTTATGAACTGGCCTGCAGAGAAGGCCCAGCTGGACCTGGGTGGGGGGGCTTGGTGACCTCAGAAGTTATTCT |
| AGTCCATCTCCCTAGAGCATTGTCCCCAAATCCTTGTGACCTGAAATTCAGCTTCCCATCCCTTCACCTCTGTCCC |
| TGGGAAGATCCTGAACCTCCACAGGTATCTCAGGCTGAAGCTTATAGCCTGAGACTTCCTCCTGGTGTGCAACTCA |
| GTGCTGCCTGGCAGCATCTGACCTTGCTCTGGCAAACAGTAACCCCTGCCTTCCTACCCCTCCCATCCCTCACTGTC |
| CCTGCAGGAATATGAGCAAGAGTTCATAGCCAAGTGGAGGTCCCTGGACCTGGATGTGCTGCTGGTGCCAGTTCTG |
| GGCTCTGCCTTCTATATAGGCTCTTCCTCCCTAGCATCAGGTGAGAGCACACTGGGTCTTGGTGGGGTTGAGATTG |
| GGAGTCCGGGACTCCTGAGTCCTGCCCCAGCTTCTGTGATCTTGCCCTCTATCTCCATTAACTTTTTAAAAATATT |
| TCTTAAATTGAGATAAAAGTCAGATAACACAAACTTACCATTTTAAAGTGTACAATTAAGTGGTTTTTAATATTTC |
| AAAATGTCTGCAACCACCACCATTATCTAATGTCTGAACATTTCTGTTACCCTGAAAGGAAAACTTGTACCTGTT |
| AGCAATTTCCATTCACTTTAAAAATGAACTTTATGGAAGTATAATTTACATGCAATAAAATTCACCGATTTTAAGT |
| ATAATTTGATGAATTTTGACAAATGTATACTGTTGTATAACCACCACTATAATCAGAAATACAGAACAGAATATAT |
| TTTTAGATTTTACAGATACATGTTCCATCACCCCCAAATTTCCCTCATGTCTCTGCAGTTCACTCTATCCCTAACC |
| CCAGTAACCACTGATCTGCTTTCTGTCACCATAGTTTTGCCTTTTCTAGAATTTCATACAAATGGAATCAAAGGGT |
| ATGAAGCTTTTGTGTTTGGCTTCTTCCACCTAGCACATCCATTTACTGTTTTTTTTTTTTTTTTTTTTTTTTTT |
| TTTTTTTTTGAGACAGAGTCTTGCTCTGTCACCCAGGCTGGAGCGCAGTGGCATGATCTCAGCTCACTGCAACCTC |
| CTCTGCCTCCTGATTTCAAGCAATTCTCCTGCCTCAGCCTCCCAAGTAGCTGGAATTACAGGTGTGTGCCACCACG |
| TCCAGCTAATCTTTGCATTTTTAGTAGAGACGGGGTTGCGCCATGTTGGCTAGGCTGGTCTCAAACTCCTAACCTC |
| AGGTGATCCACCCACCTCAGCCTCCCAAAGTCCTGGCATTACAGGCGTGAGCCACTGTGCCCAGCCCATCCATTTA |
| CTCTTAACATGCCCTCTGCTGCCCTACTTCAAAAGGGGTCTTCAGCCCAGCCTGTCAAAACATGGGCTCAGGACA |
| GGGTAATATCTGGGCCATCCCTGGGTCCCATGCACAGGTACTGGTCTCAAAGGTGCTACCCAAGGCAGGATAAAAC |
| TCAGTTCCAAACCTGAGCCTGGACTCCTCTCCCCTGACCTTAAGAACATGTCCTCCTGGGTCCCCGACTGTGGCC |
| AGCCAAAGGCTCATCCCACGCCTGACTCTCCCTGCACACATGTGGCTGCTGCAGAAGAGCTGTCCTTTCAACTCCA |
| GGTGGCGCTGTACACCCTTACTATCTTGAAGTCCGGTACACAGGAGGGCGTGGGCTGAATCCTCTGCCATCCACTA |
| GCTGTGTAGCCTTAGAAAAGGCTAATCCTGCCCCTAATCCTGCCACCTCGATTTCCTCACTTGTACACAGTCAATA |
| GTAATCCACACCTCACAGAGTGGAGAGGATTCAAGGGATCAGCAATGTGATGAGGCCAGCAGCACAGTGCCTGGCACTG |
| AGTGAGGCTTCTGCAATGCAGATTCCGTCCTTCCCTCCACCCTGGGGAGAGCATGAGGCCATTGTCAAGATGACCC |
| CTGACACAAATTGGCTAGTCCGAGCCCAGAGCGCTGAAGTTCCAGAAGGACCGGGAGGGGGCGCCCACCCACATT |
| CTTCCCCACCTGAGTCTGCGCTGACGATTTCCTGGGCTTATCTGGATCTTCCTGCAGAAAGTCAGTCTTATGTGAC |
| CCTGTACAACCTCCTGGACTTTCCCGCGGGCGTGGTGCCTGTCACTATCGTGACACTACAGGACGAGGAGGAACTG |
| GCCTTCTACAAGGGGTGCTACGGAGATAGTTCTGACAAAAATTTCAGAGAGTCAGTTTCCTTCTCCAGACTGTCTC |
| CCGGAGCGGGGACAAACCAGGGCTGGTTCTCTCCGGGTTGGGGCCCCTGACGGTAGTGGTGGAGAGAGTAGGGCGG |
| GACTGGTCATTCCTGGTGTTCACCCTTTGGCACTTATGCTAGTTTCACCCCAACCCTGAGGACACATCATTTGACC |
| TCCTTGTCAGCCCCATCCATGTCAGGGGAGAAAACTTTGCAAAACCAGTGGTTTTCTTTGTATTTCTTCTGCCTCC |
| TCCTCCTCCCCCTCCCCTCCCCTCTTCCTCCTTCTCCTCCTCCTCTTCCTCCTCCTCCTCCTCTTCTCCCCCTCCT |
| TCTTCTTTTCTTCTTCCTCCTCCTCCTCCTCCTCCTCCTCCTCCCCCTCCTCCTTCCTCCCCTCTCCTTCCTCTTC |
| CCTTTTCCTTCCTTCTCCTTCTCCTTCTTCCTCCTTTTCCTTCTCCTTCTTTTTTGAGACAGAGTCTT |
| GCTCTATCGCCCAGGCTGGAGTGCAGTGGCACGATCTCGGCTCACTGCAACCTCTGCCTCCTGGGTTCAAGTGATT |
| CTCCTGCCTCAGCCTCCCAAGTAGCTGGGATTACAGGCACCTGCCACCACGCCCGGCTAATTTTTTTTTTTTTTTTT |
| TGAGATGGAATCTCACTCTTTTGCCCAGGCTGATGTGCAGTGGTGCAATCTCAGCTCACTGCAACCTCCACATCCT |
| GAGTTTGAGCCATCCTCCTGCCTCTCAGCCTCCCAAGTAGCTGGGACTACAGGCATGCACCACCATGCTCGGCTAA |
| TTTTTGTAATTTTAGTAGAGACACGGTTTCACCATGTTGGTCAGGCTGGTCTCAAACTCCTGGCCTCAAGTGATCT |

| Sequences |
|---|
| GCCTGCCTCGGCCTCCCAATGTGCTGGGATTACAGGTGTGAGCCATTGCGCCCGGCCTTCTTTGCATTGCTGTAGG
TAAAAATGATCTCAGAGGCAGGGAGGGCAGAGCAGGGCAAAAGCCGCTGGTTATGAGCTTACTGTGTATCTGCTCT
GGATATGACCTCTCTTGGGACCTCTGTTTCTTCACCAGGAAATGGGAATAAAAACATCTACTTTGTAGGGTTGTG
CTAAAGGTTAATTAATTTGAAAAAGTGAATGAAGCAATTTGCATAAGGTCTTGTGTGTAGGAAGTGTTCGATAAAT
ACTATGATTAGTAAGTCAGAGTGGTTTCATAAAAGAAAATATTACCAAATATTTAACTGCAGGGTCTAAAATAACA
CACCTGACTTTGGTGAGAGAGAGAAGGAGAGAGAGGAAGAGAAAGAGGCCGACTCTGAAACATATGCACGTATCTG
AGTCAGACATTAAGTAACTTACTTTTTCTGGAAATTGATTTTAGTGCTAGAGTTACCCAGTGGAACTGCTGACCTG
AATTCTGAGAAAATAACAATAATGACACTATCTCATGTGTCTTGAGCACTTACTCTGTTCCAGGAGCTGTTTAAAA
GTGCCGTGTATAAATATTAAATCATTAAATTCAATAACTCTCCTGTGAGGTTTTTTAAATGAGGAAAATGGAGGCA
CAGACAGATTAAGGGACTGGGCCAAAGCCACACAGCCAATTGAAGTGGAGGAGCTAGGACTTGAAACAGGTGATCT
GACTCCAGAGACAAAGGCAAATAAAGCCTCAAATGATATCATCACAAAGCAAAGAAAACAGGTTTGAATTCCTACA
AGGACGTTTGGATTTCGTGGCAGGGACTCAGGCTTAGCCCCCATGTTCCTGGGCCTGTTTTGGGCCAAGGCAATGC
TTTCACTGTGGAAGGGTAACCAGGCTCTGGATCAGGGATTAGCATGCTCTTCTTTCTCTTGCTTGAACATTGAGTG
GATGCTCGGCTTTCTCTTTCGTCATTATAATCAGCATTCTGCACAGGGAGCAAGTTTTACATGTTAACCCTGAAGA
ACTATGGGCAATAAAATCAGAACAGTCTTTTCAGGTTTCACTGAGAGCTGAGGAAGCCTGGAATTCTGAGATCTAG
GTCATTTTTACCTTAATATAGATTGGGAAAGGGATGTTTGGACTAAAGCATACCTAGACCAACCGTTGGTACGGAG
GCCCAGAATAGCATGGGTGATGAACAGAGCCAGGCAAGGGGCCTGTGAAGCAGGCTCTGAGTTCCCGACCTTCTCT
ACTGGCAGGCGGTAAGAGGATCCGTCGGAGTTCTGGTGACTGTGCAGTGCATTGCTTTGCCATGGGAAGAGGAGCT
GTGTCTCCGGTTCATGAAGGAGGTGGACACCTTGGTCAAGAATCAGAGGGGGCCCAAGTGATAGGCTCCTGGAATG
GAGTAACAGCTCATGAAACACGGGGCTGGTTGTGGTGGCTCATACTTGTAATCCTGCACGTTCAGGAGGCAGAGGC
TGGCAGATCGCTTGAGGCCACGAGTTTGAGACCAACCTGGGCAACATAGTGAGACCCTGCTTCTAAAGCATTTTCT
TGGTGTTACTCCTGTAGATCCTCACCCAAGTGTGCTCCTGATGCCCCTTCCTTCTCATGAATACCATGTCCACCTT
ATGTCTCCTCCTTCTGGAACCCCACCAGGTTCCTTTTCTTTGTTGGTCCCTCTGTGTGGGTGCTCAATATTCCTCA
GATGGGCCCAGGATGGGAGCAGGGTGAGGAGCTCAATAAACATTTTCTGACTGGC SEQ ID NO: 6-genomic DNA sequence of FAAH-OUT comprising the microdeletion
TTTCGCTCTTGTTGCCCAGGCTGGAGTGCAATGGCATGATCTCGGCTCACCGCAACCTCCGCCTCCCAGATTCAAG
CAATTCTCCTATCTCAGCCTCCCAAGTAGCTGGGATTACAGGCATGCACCACCACGCCCAGCTAATTTTGTATTTT
TAGTAGAGATGGGGTTTCTCCATGTTGAGGCTGGTCTCGAACTCCTGACCTCAGGTGATCTGCCCACCTCGGCCTC
CCAAAGTGCTGGGATTACAGGCGTAAGTCACCGCGCCCGGCCTTTTTTCTCTTTCTTTTTTTTTTTTTGAGACAG
AGTTTTGCTCTTGTTGCTCATGCTGGAGTGCAATGGCGCAATCTTGGCTCACTGCAATCTCCGCCTCCCGGGTTCA
AGTGATTCTCCTGCCTCAGCCTCCTAGGTAGCTGGGATTACAGGCGCTCACCACCATGCCCGGCTAAATTTTTTTT
TTTTTGGATTTTGAGTAGAAACGGGGTTTCACCATGTTAGTCTCGAACTCCTGACCACAGGTGATCCGCCCGCTTT
GGCCTCCCAAAGTGCTGGGATTACAGATGCTCGCCACTGCGCCTGGCTAATTTGTTGATTTTTAGAATTTGTTGTG
AGGATCCTGTGATGTGGCTATCATCTTTTGAAAGTTGTCCCTGTCTTTCAAAGCGCTCCTGATACATTGGAGTCAT
TAGGTCACTTGCAGTCTGATTAAGGAGAGTCTTTCTCTTAACGTTAGTGATATTGTTCCGTGGGTGGAGTCCTCTC
TCAGCTTTTGCTGAACCAGTAGCAATTACACTCACAATTTTCTAGCTTTTCTAATACAGTGTTAGATTTCATGTAG
TTAAGCATCTCTGTTGTCAATTAAGTAATAAACATTGTTATTAGAATGTCATTAACACTAATTAGAAGTTGTCTAG
CATGGCAGCTAAGAGTGTGGCTTCTGTTGTTGGGCTGGCTGTTTGAATCCTGACTCTTGACACTTTTTATTTTGTT
TGATTTTATCATTTTACATTGTCTTGAACTCCTGGCCTCCAAGCAATCCTCCCACCTCAGACTCCCAAAGTGCTAGC
ATTACAGGCGTGAGCCACCAAACCCAGCAAACACTTACACTTAAATGACTACTCTGTATCTTAACTTCTTCATCTC
TACAATGGTATGATGATTGTAATGATAGCACTCAAACAAGTTAATAAATGTTTACAGTGGTGCCTGGTACACAGCA
AACACCATACAGATGCTCCTCGACTTACCGTGGGGCTTCATCCTGATAAACTCATCCTAAATTGAAAATATTGTAA
GTTGAAAATGCACTTAATACATACAACCCACCCAACATCATAGCTTAGCCTAGCCTTTTTGAAACATGCTCAGAAC
ACTTACATTAGCCCACGGTTGGGCAAAATCACCTGGCAACACAGTATCACCTGTAGAGGATTCACTGTTTCCCTTGTG
ATTTTGTGGCTGACTGGGAGCTAGTCTTGCTGGCACTGTCCAGTATCGAGAATCAAGAGAGTATCTTACTGCTTTT
TTTTTTTTTTTTTCTTTTTTTTGAGACGGAGTCTGGCTCTGTCTCCCAGGCTGGAGTGCAGTGGCGCAGTCTCAGCT
CACTGCAACCTCTGCCTCCCAGGTTCAAGAGATTCTCCTGCCTCATCCTCCCGAGTAGCTGGGATTACAGGTGTGC
GCCACCACGCCCGGCTAACTTTTGTATTTTTAGTAGAGACAGGGTTTTGCCATGTTGGCCAGGCTGGTCTTGAACT
CCTGACCTCAGGTGATCCCCCCACCTTGGCCTCCCAAAGTGCTGGAATTACAGGCGTGAGCAAACGTGCCCGGCCT
TTTACTGCTTTCCGATGAATGTATATCAATCGCTTTTGCGCTACCGTAAAGTCAAAGATTGTAAGTTGAACCATGG
\TAAGTTGGGACTGTCTGTACAAGTGATAGTTCTCACTTTAGGAATGAAGCTACTGTTGTTGTCCATGGTGAGTGG
GTATTTTGGGTGAGCAGAATATGTCTATTAGATGGATGTGACATTCTCTCTGAGGTCCTGGAGCGCCTGCT
GTGGTCTCAGCAGCCACCTGCAGAGGTCACATTAGCCACTCCCCAACCCCTGCCCTTGCCTGCTCTTCCCACCTCT
CCCCAAGCTCCCTGAGAGTCAAAGTGCCCCAGAGGCTGCCATTCCCACAAATGGCCATGCAAGGACAGCTGCAGGG
GAAGGCTAGCCTCAGGGGCCCAGAGGGACACATTGGGCACTTGCCCATGGGGTGCCACCAGGGGTGTTGTCTCTCC
AGGTAGAAATATAGAAATGGGGGCTGGTGTGCAGCTGCTGATGTCTCTGGGGTGCGTCTGGGGACCTGTGAGTGCA
GGGAGGTCCCTGGCGGGGCCCGCTAGGGCTCCTTAGGGTTGGAGGGCGCAGGGCAAGGGATGAACCCAGGCTGGCC
CTCCACAGTCCCTATGCCTAGAGGGTCCCTGCTGGGCTGAGCATTAACTTTACTTGCTGGACTGTGTAGAGAGGGT
GGAGTCCTGGGGAGGGCTAGGACAACTAGGGTGGTGGGGGGTGCCCAGCAGAGCAGCTTTTTGCCAAGTGACTCA
GAAATGTTTCAGTAGTTTAGCCACTGGCATGGCTGTGGGTGGTGCATCCTGGCTGAATGCTAGCCCTGTCCAGGGA
TCTGTGTCTGGACCCTCCTGAGAGTCCCTGTGGCACACCAGCTGGGGAGCTCTGAGCTGAGGCACAGCAAGGAAAG
GGACTGGACAGTGTGGCTGGAGCAGCATGCATGGGAGAGGCTGAGAGAGACAGGCCCACTGGACCCAAGCAGGGAA
AGACCCTGGTCCAGTGCCTGGCACCTTAAAAAGCCTCCCTTCCACAAGATGCCCAAGAGCCAGGAGAGGGTAGTG
GTTAAGGTATGGACGGCCTGGGTTTAAGCCCAGGCTCCCCTGTCCTCTGACCTTGGGCAAGAGAGTTAGTCTCTCC
GGGTCTCAGTTGCCTTCACTGGGGAAATGGAAACAGTAATAACAGCACTTAGCCAAGGGTTTTTGTGAGGATTTAA
TGAAACGGTGCAGTAAAGGGCTTGAGAGGGTTTCCAGCCCCACAGTGATACTCTGAATACTTGGTCAATGGGAATT
GTGTACATCGAAGCAAGAACCCATGTTACACATTTACAGTGAAGGCTTTGCAAGTGGTGCTGGTGAGAATGGTGCT
GCAATGTTATCCTGAGGGCTACTGGGACCTATTTTCAGAGTGGGCCTTATAAGATCTTAAAAGGATTGCCCAGGCT
GCAGTGAAGAGGCTGAGTTGGAGGAGTGGAGGCCAAGCCGTGGAGGCCAAGCCAAGGAGGCCAGTGAGGAGGCCAA
TGAGCCAACAGAGAGAGGTCCTTAGGCAGGCAAGAGGCCTGAGGGTCCGAGGTGGGAGATACGAAGGAGTAGAACC
ACCTGCAGGCAGTGTGTGCAGTTAAGAATGTGGTCACTGGTGTTGGACTGCCTGGGTCCAGCTCTGCCACTTACTG
GCTGTGTATCCTCGGGCAAAGAGGAGGAGGTCTCTGTGCCTCAGTGTTGTCTTCTGCTGTGAAATGAGAAACGAT
GTGACCTACCTCTTAGGGTTGTTACAATTAAAAATTGTAAATTTTTAATTTACAATTTTCTTGGAGACAGGGTCTC
ATGTCATCCAGGCTGGAATGCAGCAGTGAGATCATAGCTCACTGCAGCCTCAAACTCCTGGCTTCAAGAAATCCTC
CCACCTCGGCCTTCCAAAATTCATTATAGGCAATGACTGATTATATGCAAAGTGTCTGGAATAGGGCCTGGCACTA
TTAAGTGTTAGAACACATCCTAGTGTGATTATGTTAGCTAGTGTAACTATTATCAGAACTTGGGTGTGAGGGAGGA |

| Sequences |
|---|
| CCTAGGATGATTCTGAGGTTTGTTGCTTTGGTGACATGCATGTCATCAATTGGGAATTTCAAGAAGAACAGATTTG
GCTGAAAGAAGGTGAGTCCTGGGGAGTCTGTGTATATGTGGGTAGGTAAAGGGGTCTGAGTCCTGGCGGAAGAGAG
GCCTAGGTTAGAGAAACAGGTGGCCTGCTTATCCTTGGGGTGCACCTGGCTGCCGAGGTCACCCATGGAGAGTGGG
CAGGCAGGGAGAGAAAAGGTCATGCCCTGAGGAACACCAACATTTCAGGCAACTGAGAAGGAGCCACCTGAGGGTG
GGAGGAGGCCAGCAGAGTTGGGGGCATAGAGAGCTTTGGGAGGGAGAGTGTCAGACGCTGCTGAGGAGAGTGAGAT
GAAGACTAACCCGAATCCATAAGATTTAGTAACCGAGAAGTCTTGATGCCCTTGGTGAGAAGGGGCCCAGTGCAGA
GGGGAGGACAGATGTCAGACTGGTTGCTTTGAGGAATGAAAGAAGACAGACTGGAGCCAGGGGATCCTAACCTCCA
AGGGAAATTTATTTGTCTCCACCTTCCCCCACCTCCAGGACCAAGAAAAGCCCACTTCTTGCCCAACCCATACTCC
AGCTTGGAGGCATCGGGGTCTTAACCAGAGCTGAGGGGGGCAAGAGGAAGAGAACTTTGCCTTCCTGAGTGCCTGC
TGTGTGCTAGACCTTTGTCATGTCACACTTGCCCAGGGCGGCAGTCCTGAGGGCCTGGTATCAGACCTCCCCTCAT
ATCCTGAAGGACGGGGCTCAGAGCAGTTGAGGGGCTGACTCAGGATGGACTCCTAGTCCTTCCCTCTCTGAGGAGA
CCTAGGCCATGGGAGGAGCAGAGAACCACCTCCAGTTACCCAGCTGACCAAGGGCGCGGCCAAGATGGTGCTAACT
CTCTTGCCACCCATGCTGGACTCCTGCCTCCCTAAAGTCAGCTCAGCAGGGGGAGGACTGGGTAGGGAGGAGAGGT
GGGATGCCTGGGATGCCCCTGAAGGCCAGCCACCCAGGGCTGAACTTCACTTCCATAACCTCCAGTCTCATGATGT
CACATGTGGAGTCACCCCCACTCCAGTTGTGACCCTTCTGAAGAGCAGCATGAAGGGGCAGGCCCTTCTCCACGCC
AGGCCCTGGGCTGGCCACTGGGGGCAGAGGCAGAGGAGAACATCGTGCCCTTGGAGGGTTTTCATGACAACCTGGA
GACACAACAGATGTTTTTAGTGCTAAGCATGAGTGCCGGAACATGTACCGAGAGACATGGGCGTGTGTGCAGCTGT
GCATAGGGGAGTCTGGGGTGTGATGTGGAGTGTGTGGGAGTGGGCCTTAGCGGGTCCATCTTGGATATCTGCCTAC
TCCATCTCATTTCTGCAGGAGCCAGATCTGGACCCCAAGCCAATCCTGGAGCTGCCCCTGGCAGAGCTGGCCCAGC
AGCTTCGGACCGAAGAGCTGAGTCTGGAGAGCATCCTCTGTAGCTACTTAAAGCAGGTGGTGGCCAGGGCACAGGA
TCCAAGCCCGGGGCTCTGGGCTGGAGTGGGGGATGTCACTTGTCATTGTTTTACTCAGAGGAGCTGAGGGGCAGGT
GTAACTCTGCCACTGACTTGGGAGGTGGCACATGCCACAGTTACCTCAGGGTGGCAGGAGGGGCTGGGGCAACCGA
GTGCCCTGCTTTGGTCCTGGCCTCACCTGGGGCTGTTGTCTGCTGTCTTCACTGTTGTGCAGGCACTGAAGGTGCA
CCAGGAGGTGAACTGCCTGATGGATTTCCTGGGGGAATGTGAGGAGGACTGCAGGCATTAAAGAAGCTTAAGAAG
AGTGAGAGAGGCCTTCTCTATGGGGTCCCCATGAGCCTCAAGGACACCTATGACATGGTGAGCCTGGGGTGTA
CATGCACACGAATGTGCATATGCACGCTTGTGCCACCAGCCTGGAGCTTGGTGTGTGACACTGGGGGCTCAGTGT
GTGACAATGGGTGAGTCATTTAAAACTGCACAGCTACGAAGCGGCAAACTGAGGTTTATACCCAGAATTTGGGTTC
CAAACCCCAAATTCTCAGCCACCACACTCTTTTGCCATCCGTGAAGTGCTGCGCTTGTGTCCCCAGGGGTGTGAGA
GTGTGTGTGAGGGGGGTGGAATGGGGCTGAAAATCAGCCAGCTGGCTGGTTCCACCCTGACCCCCATGGCTGGAGG
CAATGTTCCTTCCCTGCAGGGCCATGACTGTGCATGCCGCCTGGCCTAGTTCCTGGAGAAGCCTGCGACCAAGGAC
GGGGTCATTATGAAAGTGCTCAAGGCCCAAGGAGCCATCCCCTTTGTTAAGACCAACATCCCACTGACGCTGCTCA
GGTCTCTGAAGCGGGCTAGCTGGGGTCGGGGGCTGGGCTAAGCCCAGGGCTGAAACAGCTCTTTGAAGTCCTGATT
CAGGGCAGAGGGTGAGGAGGGGGCTAGTCATACAGACTTCAAAGACCAGGGTTCTTGGGCAGCCCCTTCTGTCCC
CGGGGCTGAGTTTCTTTATCACAGAACATGTGGATGGACTCCACAGTCTGTAAGGGCCCTTCGGGCTCCAAGGTTC
TGTAAAGCTACACTCTTTTTCTATCCCAGTTTCTCTCTCAAATTGTTCTATTTCTACCCAGGCTTCTCTCTTTGAT
TGTTCTCCCCATCGCTTATTCTCTCCCTTCTCTACTCAGCCTGTAGTGCATCTGTGTTTCGTGAGGAACATGTTCT
CAGTTCTGATGGCAGAGCTGTGGGCTCTTTGGTCCTGATATTAGGAGTCATGGCTGGTGTCGATCTTGGTCTTTC
TTGCAGCAGCAGCCCCTCACCCCAGCTGGAAGGGAGCCCAGGAAGCCTCAGCCTTAGGGAGGAGCTCATGGAGCCC
AGGAAGCCCTGGGGTTGACTCTGGAGGGTGGTTGGCCCCCATATGGGGAGAGGTCTGCCGAGTGAGGCTTTCACCC
TCAGCTCCATTTTCTTCTGCTTCCCTTAGCTTTGAATGCGGCAACTCCCATCCTATGGCCAGATGTTGAGCCCACTGA
ACTTAAAGAAGACATGTGGGGGCTCCTCAGGGGGTGAGGGGCTCTGCTGGCAGAAAGGGGGTCCATCCTAGGCATG
GGTACTGACACAGGTGACAGCATCTGCATACCAGCCAGCTTCTGTGGTGTTTATGGCCTCTGGACCACAGGTTCCC
GCCTCAGGTACTCATTGATGGTGGTGGTGGGGTGGGCTCGGACCTGCCTAAGGGAACTAGAGGGTGGGAAGTAGA
GGGGTCTGCTCCTCCCATCAACTTTCATCTACCCAACTCAGTACTAGGGGAAGTGGGTAGGAGGGCTTCAAATAAC
TCCTGCAGTAGCCATGCTAAACATACCATATTTTTCCAGGTGCAGTAGAATAGACCTTCCACTCATTAACTCATC
AGCTCATTAATTCATTAATCTATACAGCTATCCATCCACATACCCCTTCTCTTACTCATCAATCTGTCCATGTATC
TATCTGTCCTTCATCCATTCAATCACCCACATGGTCATCATCTCAGTCTCTATCCATCAATCAATTTTACCATTCA
TCCACTATTTATTTAAAGATTTCTATTGACTATTTACTGTGTCAGACACAACAGCTCCTTGGGTACTAGCTACTT
GGGTTACTTCGGTGAACAAAAGAGACAAATATCTCAGCCCTTGAAAAACTTACACATACTCTTCCTTCCAACCATT
TATCCATCCATCTTTCCATCCATCCATTTGTGTATCCATCCATCAATCCACATTTGTATCTCTCCATCCATCCATC
CATCCATCCATCCATCCATCCATCCATCCATCCATCCATCGTTCATCGTATATGCATGCATCCACCCATCT
CTCAACCCCTCTCTGTGTACCCACACCATGGCCCCTATTCTGGGGACATAGACCACTCTTGGACCCAGCCCCTGCC
CCTGCTGTGCTCTTAGACACACAAATGAGTTAGTCAGAAAGTGATCAGGTCTGTAAGAGAGGGTCAAAGCTTACAA
GAGGAAGCTGACATTTTCTTTAACAGAGATTTATTAAAAGCTTATACTCTTGACTTTCAGAGGCAGGGCAAGGGAA
GGGAAGGATTCCTGGAGGAGGCAGCATTTGAGCGTGGTTTTGAGGGCCAGACATGCCAAGATGATGTGGCGTCTAG
AAGGCTGTAAGATTGTTTGTAAGCGGCTGACTTTGCCTGCAGCAATATGCACGTGTGGAAGGGCTAGAAGGGGAAG
CCATGGAGAGTTAGAGTCTTGAAAAGCAGTCAAAGAGATCAGACTATGCTGTGGGCAGCAGAGGGTCAGGGAATGT
TGAAGCAGCTCCTATTTTTGTGGGCTGCGCCCTGGGGGAGCACATCGCCTGGGTGCTCAAGCCTCCTAGCACCCAG
GCCCCTCCCTTCACATGCTGAGCTGGGCTCTGGGTCGGAATGTTTTGCAGCTACACTGGAATTGCCTCTGCCATCA
AGGGGAAAAAAATCGGGTAAGTCCTGGTCTGTGCCTGTGGCCACCCCATTTAAAGATGAAACTGCCAGTCTTTCTC
CCAAGGACATTTTGCTCAGCTCATATCTCCAGACAGATCAGCCCCACAGATGATGACTGAGAGGGGCAGACTGCATG
GTTCCCACCTGGCCTCCCCCTTGTCCAGTGACTCTTGGCCCTCTGAGAAGGGCTTTTGTCCTGCTATCTAGCTTTAA
TCTCTTCCTTCGTCCTGACCATGACCCTGGAACCCACCCTCTGAGGCCAGGCAGTTGGGATCCCAGGGCACAACA
AATGAGAGGTGCTTGCTGGGCGCAGTGGCTCATGCCTGTAATCCCAGCACTTTGGGAGGCTGAGGTGGGCGATCAC
TTGAGGTCAGGAATTCGAGACCAGCCTGGCCAACATGGTGAAACCCCGTCTCTACTAGAAATACAAAAATTAGCCA
GGTGTGGTGGCGGGCACCTGTAATTCCAGCTACTGGGGAGGCTGAGGCAGGAGAATCACTTGAACCCGGGAGGTGG
AGGTTGTAGTAAGCAGAGATGGTGCCACTGCACTCCAGCCTGGGTGACAGAGAAAAACTTCGTCTCAAAAACCAAC
AAACAAAAAACAAAACACAACAAGCAAACAAAACGAGAGGTGCCTGCCTCTCTCCCCTCCTCTTTGTGCAGTGACC
ACGGTGGCTGGCCCCATGGCCCAGGACGTGGAGAGCCTGGCGCTGTGCCTGCAAGCCCTGCTGAGTGAAGACATGT
ACCGACTGGACCCCACTGTGCTCCAGATGCCCTTAGGGAGGAGGTAAGCCAGGTGGGAGAGCAGACCTGGGGGTT
TCCTTGCCCCCCACCATCATTCCTCCCTGACCTGTCTGCCATCTTTACCTTCCCAGGTGAAGACCCCCTTTCCCACC
CCAGGCTGCAGTGAGTGAGAAGCCCACATGCTCAGTCCAGTTTGTTTCCTTCCCCTGCTGGACACCAGCTGCTTTG
GCTTCTTGGCTATCTGGAGCCATAGCTTGTAAGTGCCCCAAAGAGGGCCTCCAGTGCCATATACCCAACCCATGC
AGTTAGAATACTCAGCAAGTGTGGTTGAGAGGGTGTGGCATCCAGTTAAGCTGGGTTTTTAACCCTCTAGGTAACC
CTGGCCAAGTCACATCTCTTCTTTCAGCCTTAGCCTCCCCATCAATACAATAAAGAGGTTAGGCTGGGAGATTACT
CCACACCCTTCTGTCTACAGCAGCCTTCATTTATTCGTTAATTCATTCAACAACATTTGCTTGTACCAGTTGTGTG
CCAGGCTCTGCGTGTCTCATCCTAACACTCTATAGAGTGAGCAGTGCTCCTCCCATTTACAGCTGGGGAGACTGAG |

| Sequences |
| --- |
| GGGAAGTGAAATGACTTGCCTAAGATCATGTAGTTAGTAACTGGCAGAGCTGGCTTTGAACCCAGCCCTATCTAAC |
| TGCAGAACCCTCTCCATAGGGCAGTTTCTGTCTACGTCCCGGCAATGTCTGTTCCTCGGATTCCCTACACCCCTCC |
| TAGCATTATCAACCTGAGATCATTGTATATCATCCATGATTTGCCCCTACAAACATGTTGTGTGACGGGTGAGG |
| GGCGGCTGCCTTTCTGGCAGCACCCCACTTCCCAGGACTAGGGGCCCTCCATCTCAGACCCTGGTCTGGGTATTTG |
| TCCCTATAGATCTCCAGCCTCATATTCTCCTAACATTTCTTTAGCTTAAAGATATTTGAGTCTATGCATGACTTAC |
| TCACCTGCCCACCCACTCAACTCCAACCATCCATTCACCCACTCACCCACATATGCATTCAACCCTCTGCCCACCC |
| AACTACCCACCATCTCATACATACATCCACCCACCCACCCAGGAGTCTGTCTACCATCTATCTACTATCCACCCCA |
| TCTGCCCAACCACCCATCTCATCCATTTCTCTTTCCTCCAGGGGTTTCCGCAGAGCACCTAGAGCCTGGAGAGTAT |
| ATAGGGAGGCTCCCAGGGGGTCTTGGGGTGTCCACATGGATTCCCCCTTTGTGAGGACAGCTGTAGACCAAGGCC |
| CTGCCCTTAAAGTCTGGCTCCTGGATAGAGTGGGGCCACCTTGTCCCCAGCACAATCTCTCCTCCGAGCTCCATCC |
| AGCCCCTTGTGCCCCTAGGTTTACACCAGTAACCGGCCCCTTCGAATTGGCTACTATGAATCAGATGGTTACATCC |
| AGCCATCCCCTAGCATGGCCAGGGCTGTGCAGCTCACCTCCTGGCTGCTCCAGGATGCTTGACACCAGGTAGTCTC |
| ACCTGGTCCTGGGTGAGAGAGAGTCTGGGCCAGTGCGAGGATGCTGGGCGGGGCCATCCTTGGAGACAAAGGTGGC |
| TACATCTGCGTTTGAGGTGCTGAGATAACTGTGTTCCCCCTATGCTTCCTGGAGAAGACTGATGGGATGGAGGTGG |
| GGATAGGGTGAGCCCTACCCTAGAAGGAAGGCATTAAGCTTTTGTGCTTCCTCCTTCGGTGGTGGAGATTCAGGGA |
| CTCACTCCTATAATTCCTTCAGCTTGGGTCTCTGTTGCCTCCCATCAAGTGGCCGTAAGGAGCTTTCTGTCTCCAAA |
| ATCCCTACCTTAGCCCTACCCCAAACTCCCCTGCCCCCAGTGGCTTGTCCTGGCCTCACTTCCCCTTTGAGATTCT |
| ACCATGTGATCTTGGGCTAGCCTTTTAACCTCTCTGGGCTTGTTTTCTACCCAATGCGGTGGCTGTGAAGATTAAA |
| TGTGGTTCCATAGATAAAGCACTTGGCACGCTGGCTGGATCACAGTGAAGCATGAAGGAAATGAGGGCTGCTCTCG |
| TTCTGTTCTGTCACATCTGTGTGTGAGGGTGAGGGAGTGGGGTGGCAGGAGGACAACCAGTGACACAGGCCTCCCA |
| TGCCATGCTGAGGCGCTGAGGTGGACGGAGATGCACGAGATGATGTGGCATCCTTCTTGAAATCTTGGGGGATGCA |
| GAGACAGAGAACCAGGCAGGGTCGGGGAAGCTCCAGACACTGACTCTGCCTCTGCCTCCCCAGGTTATCCCCTTCT |
| CCATCCCCCAGGCAGAATACGCCATCAAAGACTTGTACACGGGGGGATGTTTACTGATGGAGGGGCCACTCTTCTA |
| GAGAAGCTATACGTTATCTGCTGGGACTCAGGGGTGGGGCATGGTGGAAACAAGGTAGGGGAGTGGGCTGGAGCCA |
| ACCTGAGTCCCAGGAGGGAAACTGGGGGCCTGGGCTGGGGTGCCTCTGCCTAATAGTGTGACCTTATGCCGCAAAC |
| CACACACTGGGCCTGTCTTTAGGATGCACCTGTTCCGGGGGTGGGGCAGAAGTACATCTTTGGGTTTGGCCTCCTT |
| CTTGTCTACGGCGTGGAAGTTGGGTGGCTGTGGGGGCAGGCCACTGGCTAAGGGCTGTGACTTACCCATCTGCGAC |
| TGGTTCCTCAGAGAGGGGGACATTGTGGATCCCAGCATAAAGGGCATGGTCAACCAGCTCTGCCTGCCAGACCCCT |
| TCAAATGTTTCTTGGCCTGGATCCCAAAGTACATAGTAAGTGCAGGCCCTAGTCAGGGAGGGCTTTGGAAGGGCAG |
| GGAGCACAGGGAGTAGGAGGGGCTCAGAAAGCAGAGGGAGCTCACAGAAGGAGTGGAAGTGGGGTCAGAGAGGAGG |
| ATGAGGCCCAGAGAATGGTGGTAGCTCAGAGAGGGGTTCAAAATGGGGAAGAAGAATGAAGGGCTGGGTGCACAGT |
| GGCTCATGTATGTAATCCCAGCACTTTGGGAGGCCAAGGTAGGAAGATCACTTGAGCCCAGGAGTCTGAGACCAGC |
| CTGGGCAACATAGTGAGACTCCATTCTCTAAAAAGAATGGAAAAAAAAATAGCTGGGCATGGTGGTGCATGCCTGT |
| GGTCCCAGCTACTCAGGAGGCTGAGGTGGGAGTATCACTTGAGCCCAGAAGATCAAGGCTGCAGTGAGCTGAGATT |
| ATGCACTGCACTCCAGCTTGGGTGACAAGTAAGACTCTGACTCAAAAAAAATAAAAAAAAATTAATTAAAACAAAT |
| AATGAAAGAAGGGAGTGGGCTAAAAGAGTAGGGTGCTCACAGAGAGGGGAGGGGGTTTCAGAGAGGAGGCTCAGA |
| AAGGGGGAAGGGCATTTGGAGGGCTACAGGGCCAGTGTGAGCTCAGGGCTTGGTGAAGTGGTAGGCTTGTTGAG |
| GATCGGAGGGTTCCACGTCAGTGCGTTGAGCAATGCTACCCTTCTTGGACCCCCTCCTGGGCAGGCTGACTGTTTC |
| CCTGTGGGTTCTGAAGTTGGACTCCCCCTCTCAGCCCCCCTCTAGGATCCCCAAACTAGCCAGCATCTTGAAGAGA |
| TTCGTGGAGTGGGGTGAGTCTCCCTAGGGCCAGCTCTTGCTCCAATGGTTGTCCATGGGATGGTGGGAATTGAGGA |
| GGGGCATGAGGCTAGAGCTGGTATCCACTAAGGGGGGATCTATTTAGATTTTCGGACTCTAATTAGGGTTTTAGGAT |
| CATGCCTGACATTAGCTTAGATTGAGACTTTTGATTGGTGTTGGGACTTTATTTGGAGTTAAGATCTGAATTAAGG |
| CCGGGTGTGGTGGCTCATGCCTGTAATCCCAGCACTTTGGGAGGCTGAGCGGGGAGGATCACTTGAGGCAGGGGT |
| TCAAGACCAGCCAGGACAACATGATGAAACCCTGTCCCTACTAAAAATACAAAAATCAGCGGGTGTGGTGGTATGT |
| GTCTTTATCCCAGCTACTCGGGAGGCTGAGGCACGAGAATCACTTGAACCCAGGAGGTGGAGCTTGCAGTGGGCCA |
| AGATGGTGCCACTGCACTCTAGCCTGGGTGATAGAGATAGACTCTGTCTCAAGGGAAAAAAAAAATCTGAATTAAGG |
| CTAGGTTGAGGTAAAATTTGGGACTGAAGTTGAGATTAGGTTTTATTTGGGGATGGGCTTAAGACTGAGGCTGGGG |
| TTGGAGTTGGTTTGAGTTGGGGTTGGTGGGGCGAAGATAGATTTGGAAGAGGGTTGGGACTGAGGCTGGAGTTGGG |
| GTGGGGCTAGAGTTAGGGTTAGAGATGAGGTTGGGAGAGGCTGGTATGGGCTTGGGTTTGCTGTTGGGCTTGGCCT |
| GGTGGGGTTGGCATGAAGATGCTGGGCAGAATTGGGCTGGAGTGGACTGAGGGCTAACTGGGTGCCTCACAGATTA |
| GGGTAAGGAGCCTGTGCCTTTGAGGCAGCCCATGAGTTCCTGTGACTGGTGGAATGGGGGTAGATTGACCAGAG |
| GATGTGTGCTCTTGGGGACCTTGAGCAGGCAAGATGTCTTGGCCAGGGGACAAGACACGGGGTCACTCCCAGCCCA |
| TCAGCTCGATTTGCAGCGTGCACTGAGGCCTTGGTTGTCATGTCCCCATTTGTATAAAAGGGTTCCCTCCCATGCTG |
| ACCTTTGAACTTGTCAGAGTCTTCCTCATTCTTTCAGGACACCCAAGAAACTGTGGGAACAGCACACAGCAGTGGA |
| GGTAATGCCTGTCTGGGAAGACCTTGAGGGGCTGCTGGAGCTGGGGCTGCAGACACCTGGGTAGTGCCCTGAGTGG |
| TCAGAGTTATGAACTGGCCTGCAGAGAAGGCCCAGCTGGACCTGGGTGGGGGGGCTTGGTGACCTCAGAAGTTATT |
| CTAGTCCATCTCCCTAGAGCATTGTCCCCAAATCCTTGTGACCTGAAATTCAGCTTCCCATCCCTTCACCTCTGTC |
| CCTGGGAAGATCCTGAACCTCCACAGGTATCTCAGGCTGAAGCTTATAGCCTGAGACTTTCCTCCTGGTGTGCAACT |
| CAGTGCTGCCTGGCAGCATCTGACCTTGTCTGGCAAACAGTAACCCCTGCCTTCCTACCCCTCCCATCCCTCACTG |
| TCCCTGCAGGAATATGAGCAAGAGTTCATAGCCAAGTGGAGGTCCCTGGACCTGGATGTGCTGCTGGTGCCAGTTC |
| TGGGCTCTGCCTTCTATATAGGCTCTTCCTCCCTAGCATCAGGTGAGAGCACACTGGGTCTTGGTGGGGTTGAGAT |
| TGGGAGTCCGGGACTCCTGAGTCCTGCCCCAGCTTCTGTGATCTTGCCCTCTATCTCCATTAACTTTTTAAAAATA |
| TTTCTTAAATTGAGATAAAAGTCAGATAACACAAACTTACCATTTTAAAGTGTACAATTAAGTGGTTTTTAATATT |
| TCAAAATGTCGTGCAACCACCACCATTATCTAATGTCTGAACATTTCTGTTACCCTGAAAGGAAAACTTGTACCTG |
| TTAGCAATTTCCATTCACTTTAAAAATGAACTTTATGGAAGTATAATTTACATGCAATAAAATTCACCGATTTTAA |
| GTATAATTTGATGAATTTTGACAAATGTATACTGTTGTATAACCACCACTATAATCAGAAATACAGAACAGAATAT |
| ATTTTTAGATTTTACAGATACATGTTCCATCACCCCCAAATTTCCCTCATGTCTCTGCAGTTCACTCTATCCCTAA |
| CCCCAGTAACCACTGATCTGCTTTCTGTCACCCATAGTTTTGCCTTTTCTAGAATTTCATACAAATGGAATCAAAGG |
| GTATGAAGCTTTTGTGTTTGGCTTCTTCCACCTAGCACATCCATTTACTGTTTTTTTTTTTTTTTTTTTTTTTTTT |
| TTTTTTTTTGAGACAGAGTCTTGCTCTGTCACCCAGGCTGGAGCGCAGTGGCATGATCTCAGCTCACTGCAACC |
| TCCTCTGCCTCCTGATTTCAAGCAATTCTCCTGCCTCAGCCTCCCAAGTAGCTGGAATTACAGGTGTGTGCCACCA |
| CGTCCAGCTAATCTTTGCATTTTTAGTAGAGACGGGGTTGCGCCATGTTGGCTAGGCTGGTCTCAAACTCCTAACC |
| TCAGGTGATCCACCCACCTCAGCCTCCCAAAGTCCTGGCATTACAGGCGTGAGCCACTGTGCCCAGCCCATCCATT |
| TACTCTTAACATGCCCTCTGCTGCCCTACTTCAAAAGGGGTCTTCAGCCCAGCCTGTCCAAAACATGGGCTCAGGA |
| CAGGGTAATATCTGGGCCATCCCTGGGTCCCATGCACAGGTACTGGTCTCAAAGGTGCTACCCAAGGCAGGATAAA |
| ACTCAGTTCCAAACCTGAGCCTGGACTCCTCTCCCTGACCTTAAGAACATGTCCTCCTGGGTCCCCGACTGTGG |
| CCAGCCAAAGGCTCATCCCACGCCTGACTCTCCCTGCACACATGTGGCTGCTGCAGAAGAGCTGTCCTTTCAACTC |

```
CAGGTGGCGCTGTACACCCTTACTATCTTGAAGTCCGGTACACAGGAGGGCGTGGGCTGAATCCTCTGCCATCCAC
TAGCTGTGTAGCCTTAGAAAAGGCTAATCCTGCCCCTAATCCTGCCACCTCGATTTCCTCACTTGTACACAGTCAA
TAGTAATCCACACCTCACAGAGTGGAGAGGATTCAAGGGATCAGCAATGTGATGAGGCCAGCACAGTGCCTGGCAC
TGAGTGAGGCTTCTGCAATGCAGATTCCGTCCTTCCCTCCACCCTGGGGAGAGCATGAGGCCATTGTCAAGATGAC
CCCTGACACAAATTGGCTAGTCCGAGCCCAGAGCGCTGAAGTTCCCAGAAGGACCGGGAGGGGGCGCCCACCCACA
TTCTTCCCCACCTGAGTCTGCGCTGACGATTTCCTGGGCTTATCTGGATCTTCCTGCAGAAAGTCAGTCTTATGTG
ACCCTGTACAACCTCCTGGACTTTCCCGCGGGCGTGGTGCCTGTCACTATCGTGACACTACAGGACGAGGAGGAAC
TGGCCTTCTACAAGGGGTGCTACGGAGATAGTTCTGACAAAAATTTCTCAGAGGTCAGTTTCCTTCTCCGAGCCTC
TCCCGGAGCGGGACAAACCAGGGCTGGTTCTCTCCGGGTTGGGGCCCCTGACGGTAGTGGTGGAGAGAGTAGGGC
GGGACTGGTCATTCCTGGTGTTCACCCTTTGGCACTTATGCTAGTTTCACCCCAACCCTGAGGACACATCATTTGA
CCTCCTTGTCAGCCCCATCCATGTCAGGGGAGAAAACTTTGCAAAACCAGTGGTTTTCTTTGTATTTCTTCTGCCT
CCTCCTCCTCCCCCTCCCCCTCCCCCTCTTCCTCCTTCTCCTCCTCCTCTTCCTCCTCCTCCTCCTTCTCCCCCTC
CTTCTTCTTTTTCTTCTTCTCCTCCTCCTCCTCCTCCTCCTCTTCTCCCCCTCCTTCTCCTTCTCCTTCTTC
CTCCTTTTCCTTCTCCTTCTCCTTCTCCTTCTTCCTCCTTTTCCTTCTCCTTCTCCTTCTTTTTGAGACAGAGTC
TTGCTCTATCGCCCAGGCTGGAGTGCAGTGGCACGATCTCGGCTCACTGCAACCTCTGCCTCCTGGGTTCAAGTGA
TTCTCCTGCCTCAGCCTCCCAAGTAGCTGGGATTACAGGCACCTGCCACCACGCCCGGCTAATTTTTTTTTTTTT
TTTGAGATGGAATCTCACTCTTTTGCCCAGGCTGATGTGCAGTGGTGCAATCTCAGCTCACTGCAACCTCCACATC
CTGAGTTTGAGCCATCCTCCTGCCTCTCAGCCTCCCAAGTAGCTGGGACTACAGGCATGCACCACCATGCTCGGCT
AATTTTTGTAATTTTAGTAGAGACACGGTTTCACCATGTTGGTCAGGCTGGTCTCAAACTCCTGGCCTCAAGTGAT
CTGCCTGCCTCGGCCTCCCAATGTGCTGGGATTACAGGTGTGAGCCATTGCGCCCGGCCTTCTTTGCATTGCTGTA
GGTAAAAATGATCTCAGAGGCAGGGAGGGCAGAGCAGGGCAAAAGCCGCTGGTTATGAGCTTACTGTGTATCTGCT
CTGGATATGACCTCTCTTGGGACCTCTGTTTCTTCACCAGGAAAATGGGAATAAAACATCTACTTTGTAGGGTTG
TGCTAAAGGTTAATTAATTTGAAAAAGTGAATGAAGCAATTTGCATAAGGTCTTGTGTGTAGGAAGTGTTCGATAA
ATACTATGATTAGTAAGTCAGAGTGGTTTCATAAAAGAAAATATTTAACTGCAGGGTCTAAAATAA
CACACCTGACTTTGGTGAGAGAGAGAAGGAGAGAGAGGAAGAGAAAGAGGCCGACTCTGAAACATATGCACGTATC
TGAGTCAGACATTAAGTAACTTACTTTTTCTGGAAATTGATTTTAGTGCTAGAGTTACCCAGTGGAACTGCTGACC
TGAATTCTGAGAAAATAACAATAATGACACTATCTCATGTGTCTTGAGCACTTACTCTGTTCCAGGAGCTGTTTAA
AAGTGCCGTGTATAAATATTAAATCATTAAATTCAATAACTCTGTGAGGTTTTTAAATGAGGAAAATGGAGG
CACAGACAGATTAAGGGACTGGGCCAAAGCCACACAGCCAATTGAAGTGGAGGAGCTAGGACTTGAAACAGGTGAT
CTGACTCCAGAGACAAAGGCAAATAAAGCCTCAAATGATATCATCACAAAGCAAAGAAAACAGGTTTGAATTCCTA
CAAGGACGTTTGGATTTCGTGGCAGGGACTCAGGCTTAGCCCCCATGTTCCTGGGCCTGTTTTGGGCCAAGGCAAT
GCTTTCACTGTGGAAGGGTAACCAGGCTCTGGATCAGGGATTAGCATGCTCTTCTTTCTCTTGCTTGAACATTGAG
TGGATGCTCGGCTTTCTCTTTCGTCATTATAATCAGCATTCTGCACAGGGAGCAAGTTTTACATGTTAACCCTGAA
GAACTATGGGCAATAAAATCAGAACAGTCTTTTCAGGTTTCACTGAGAGCTGAGGAAGCCTGGAATTCTGAGATCT
AGGTCATTTTTACCTTAATATAGATTGGGAAAGGGATGTTTGGACTAAAGCATACCTAGACCAACCGTTGGTACGG
AGGCCCAGAATAGCATGGGTGATGAACAGAGCCAGGCAAGGGGCCTGTGAAGCAGGCTTCTGAGTTCCCGACCTTCT
CTACTGGCAGGCGGTAAGAGGATCCGTCGGAGTTCTGGTGACTGTGCAGTGCATTGCTTTGCCATGGGAAGAGGAG
CTGTGTCTCCGGTTCATGAAGGAGGTGGACACCTTGGTCAAGAATCAGAGGGGGCCCAAGTGATAGGCTCCTGGAA
TGGAGTAACAGCTCATGAAACACGGGCTGGTTGTGGTGGCTCATACTTGTAATCCCAGCAGTTCAGGAGGCAGAG
GCTGGCAGATCGCTTGAGGCCACGAGTTTGAGACCAACCTGGGCAACATAGTGAGACCCTGCTTCTAAAGCATTTT
CTTGGTGTTACTCCTGTAGATCCTCACCCAAGTGTGCTCCTGATGCCCCTTCCTTCTCATGAATACCATGTCCACC
TTATGTCTCCTCCTTCTGGAACCCCACCAGGTTCCTTTTCTTTGTTGGTCCCTCTGTGTGGGTGCTCAATATTCCT
CAGATGGGCCCAGGATGGGGAGCAGGGTGAGGAGCTCAATAAACATTTTCTGACTGGC
```

SEQ ID NO: 7-genomic DNA sequence corresponding to the microdeletion
```
TTTCGCTCTTGTTGTGCAGGCTGGAGTGCAATGGCGAGATCTCAGCTCACTGCAACCTCTGCCTACCGGATTCAAG
TGATTCTCCTGCCTCAGCCTCCCGAGTATCTGGGATTACAGGCGTGTGCCACCATGCCCAGCTAATTTTGTATTTT
TAGTAGAGATGGGATTTCTCCATGTTAGTCAGGCTGGTCTTGAACTCCTGACCTCAGGTGATCTGCCTGCCTTGGC
CTCCAAAGTGCTGGGATTACAGGCGTGAGCCACTGTGCCCGGCCTGCCACAGCTTTTGCCTCGCTTCCCTGGGC
TCCAGACTGGACATCTCCAACAATCTTTCACATGGCAGTTAGGCAATCTCATGCTTAAAATCTTTGGACTCACTTG
TGCCAAGTCCAGAAGCCTTGTTATGACCTGCAAGGCCATGATTAACCTGACCCTGCAGCTGGCCCCTGCGGCCTCA
TCTCCTGCCCTTCCTCAGTGCTCACAGCCCGGCCACGTGGCCTGCAGGTAATGTTCAGAACACCGAGTGATCTCCC
GCCTCCACGCCCTTTGCTCTTGGTGCTTGCTGTGCCTGGAGTGTTGTTCCTGGGGTCTCCACCTAAAGACCACCTA
CTCGTCCAAGGTGAGGGCAATTGCTCTTCCAACTCTGTCAGGCTGTGTTGAAAGAGCTTCTTTGTGCTTCTGCACG
TGGTCAAAAGCAAGGTCTGTGTATTAATAGAACCCAACATCTGTTAGGCTGTGGAGTTGAATACCCATTATCTCAT
TTGGAAAGTGGGCATTACTATTTCCATTTAAAAAATTTATTTATTTATTTTTTTGAGACAGAGTCTCTCTCTG
TCGCCCAGGCTGGAGTTCAATGGCACGATCTTGGCTCACTGCAACCTCTGCCTCCCGGGTTCAAGTGATTCTCCTGC
CTCAGCCTCCCAAGTAGCTGGGATTACAGGCGCCTGCCACTGTGCCCGGCTATGTTTTGTATTTGTAGTAGAGATG
GGGTTTCACCACGTTGGCCAGGCTGGTTTCGAACTCCCGACCTCAGGTGGTCCACCTGCCTTGGCCAAAGTGCTGG
GATTACAGGCGTGAGCCACTGCGCCTGGCCTTTTTCTTTCTTTTCTTTGAGATGGCGTCTTCCTCTGCCACCC
AGGCTGGAGTGCAGTGGTGCGATCTCAGCTCACTGCAGCCTCCGCCTCCTGGGTTCAAGCGATTTTCCTGCTCAG
ACTCCCGAGTATAGCTGGGACTCCAGGCGCCTGCCACCATGCTCGGCTATGTTTTGTATTTGTGGTAGAGATGGGG
TTTCACTATGTTGGCCAGGCTGGTCCTCAACTCCTGATCTCAAGTGATCCGCCCGCCTTGGCCTCCCAAAGTGCTG
AGATTACAGGTGTGAGCTACCGTGTCGGCCCTATTATTTCCATTTTATACATAAGGAAACTGAAGTTCAGAGGGG
ATTGCTGACTTGTTGAAGGCTGATCATTATGGGTTACAGAGAAGACTTGAAACCCACACGCTCAACTCTAAACTTA
CTGTGACTTCCTCATTTGTACAATCATCACAAGAACATGCATTCAACATTCTTCGGACACCAGCCTCTGTGCTAGG
CGACCACAACACTTTGAAGACAGAAGCAGTCCTGTGTACTGTGCACCTCTGCCAATATCTGTTTACAGGAGATAGC
TGCCATGTCCCTGTCCACCCTCCCTTTTCTCTCCTGGCGATTGCGATATTGGAGTTTTAGGACACAGCCAGAGCAC
TTGTCATTTGTTCCTGTTGGACACCATTTTTAGGATTATCCCAAGAGCTCTGGCTGTTTCTGCTCTTCCTCCCAAC
ATGTGCTTATCCACAAATCTGAGCACTGGACCTCTGCAACTTCATCCAAGTCACCCATAAACCTATGGATCACAGC
AGACCAAGGAAAGGGCGTGACCTACACCCTTAACAGACAGACACATAACCGAGTTTTGAGCTTCCCAGCCAGATGT
ATCTTTAGTTCACATTTCTCTGGCTGGGCTTAGCTGGGCCCTCCCAAGTTTCCTACACATAGATTTGGGGTGGCGG
CCCTGGGCACCTCAGGAAGGTGAAGCCACTTGGGATCGGGCTGTGTATGCTCAGCACCCAGCATGGTGCCTGGTAC
TCAGTGGGTACCCAGAGAAGGCTTGTTGAATGGAGCAATGGGTGACTTGTTATTAGGGAACCCATTTTGGTCCATT
CTGATTACTTCCTCTTCTCACCTCCAATAGGGAATTTTCAATCAGTCCCTGACCCTTTGCTCCTTTTCACATTTAT
TGTATCTACCTCCATGATCTTTTTTTTTTTTTTTGAGATGGAGTCTTGCACTGTTGCCCAGGCTGGAGTGCAA
TGGCAGGATCTCGGCTTACTGCAACCTCTGCCTCCTGGGTTCAAGCGATTTTCCTGCCTCAGCCTCCGGAGTAGCT
```

-continued

| Sequences |
|---|
| GGGATTATAGGCGCCTGCCACCACGCCCAGCTAATTTTTTGTATTTATAGTAGAGATGGGGTTTCACTATGTTGGC |
| TAGGCTGGTCTCGAACTCTTGACCTCAGGCAATCCACCTGCCTCAGCCTCCCAAAATGCTAGGAGCCATGATCTTG |
| ATTAGTGCCCATGAGGACAAATAATTCCCAGTCTACATTCAACCTATAGCTTTCTCCTGGTCTGTAGATCCTCATC |
| TATCCACTTCTCTCATCCTCTTAACTCCTTCATCTCTCTCAGGCTGTTGAAAGAGCTTCTTTGTGCTTCTGCACTT |
| GGTAGAAAGCAGGGACTGTGTCTTAATAGAATCCAACATCCGTTAGGCTGTGGAGTTGAACCCATTATCTCCTTTG |
| TAAAATGGGCTTATTATTTCCATTTCATATATAAGGAAACTGAAATTCAGAGAGGGTTGCTCTCTGAACAACAATG |
| GAGGGTTGCTCCCTCCATTCATCCTCCCATCCATGCAATAAAAATATTGAATTCTTCCCACAGTATGTTCAGGGTA |
| ACCAATCAGAAATAGTCCCTGCCTGAATGGAGCTTCCATTCTACCAGGAAACAGACATCAAATGTAGAATTACACA |
| GAAACACTCGTTAGAAGTGCAATCAAGCAGAAGCCCTGGGTATTATGAGAATAAACCACGTGGGATCTGATCCAGC |
| CTGAGATGTGTGTATGTGTGTGTCAGGGAATGCTTCCTGGAGGAAGTAACATTGAAGCTGAAAACTGCATTGTCAC |
| CTGAGCCAAGGAATGAGTGTGTTTCAAGGAGGGTGAAGCTGACAACTCTAAATGCTGCTGATTTACTCTTGAGGAG |
| ATCACTGGGATGATATAGGCACAAGCCAGACTTTGTTGGGTGGGGGAGTGAGTGAAAGGTGAAGAAGTAAAGGCAG |
| CCCGTGTAGAAAACTGGAAAAGTTCAGGAAGCGGACAAAAGACGTGGTAGTAGTTAGGGAGGGTGTAAATCTGAGG |
| GAATCATCCCTCATCCCCAAGATAGGAGAGACTTAGCATGTTAAATGCTGCTAGGAAAGAGCTAGCAGCAACGCA |
| CAGAGGGGGGAAGTCAAGGTAGGAATGGAGGGCTCAACCTGCCATCATTTCTTCACTGAAGAGATACCATTGAACA |
| CATACCATGTGCCAGGTGTTTTGAAAAAGGCTGACAAGGTCTATGCTCCCCCAACCCCCCAGCTAATTTTTTTGCA |
| TTTTCTGTAGAGATGGGGTCTTGCCGTGTTGTCCAGGTTGAGCTCAAACTCCTGAGCTCAATTGATCCGCCCAAAG |
| TGCTGGGATTACAGGCGTGAGCCACTGTGCCTGGCCTCGTCTGTGCTTTTACGGAGCTTATTTTCTAGGGAGGGAG |
| GCAGGAGGTGAGTTACAGATCAACAAGAAAACTTCAGCTAATGATAAGTGTAATGATGAGATAAAATGAGGTATGT |
| GGTAACCTGAAGGGTGTAACCCAGGAAAAGGTGAGGTCACGAGGCCTAGAGTGCTGTGCCGTGGGATGTGGTGCGGG |
| TGACAAGTGGCCTGGGGGAGCTGAAGATATGGGGGAGAGCTGGAGTTCATGAAGGTGGAGTGGGGGCTATGGAAGA |
| AAATGGTCAGAAAAGAGGCAGAAGGACAGAGGAGGGCTGGTCTGGAGGCCCCAGGGAGATGACAGAGTGTTACAGA |
| GTGGGCAACTTCAGGGTCACCCTTAGTCAACTGCTGACCTCGCATCTGTTCCTTTAGACCCTCGGGTACTCAGACT |
| CAACATTACCAACCATGAATTCAGTTCCTTCCCACCCTAACCTGCTGCCCTGGCTTCCTGGTCTGGAGGGCAA |
| AGGCGCCATTCTCCTGGGTACAGTGACTTGCAGTCTCAGTGATGACCATTGAGATGGAGACTGGATGGAGGCCCCT |
| GAGGAGAGCAGAATGGTTCCCACATCAGGGCCCCTCTGCACCACTTTTCCAGTCTCCTCATGTCTTCTCTGTTCCT |
| CGTCTGGGAAGTCATCTCCCTTACCCCCACAACTCCCCTCCACCAGCAGGGAGAGTCAATAGACTGGGGAGGCTGG |
| AACCCCGGATCAGAGTCATGGCCTTGCTTTGGAGTCAAGGGGGAAGCCCAGCTGGGCGGGCTGGTCTCATGTCCTG |
| GCATCATCTCCCCTGGGGTGGATGCCTGATGAGCCCTGCCCGCTCCTCCAGGTGTTCTTTCCTTTCCTCTCTTCCT |
| GTCCCCCAGAACCTCCACTCTAGGCAAACATGGCCTGTTCAGTTCCACCTCCATGCGTCTGCTTATGCGGAACAAA |
| GGAGCTTTGGGAGAATCCTGAAGGCAATGGGAACCCCAGGAGCAACCCCATCCATAACTCCTGAGGGTTGGAGTAG |
| GGAATCTGAGGGGTGGGATCTGAGAGGTAGGATGGGTGGGAGTAGGATGTGACAGAGGTGAGGTCAGCTGCCCAGC |
| TGCAGGCTTGGGCCCTTCTTCAGGCTCGCTGCTAAAGCCTCTTCCTCTGCATGGCCCGGGAGATAGGGGTTTTGT |
| CGCCAGGAAGTCCAGATGGGGTAAGAACTAGGAGGAGGTTGATCACTGCCACACCCAGGGCCCGAGATGTGCGTGG |
| GTGCCCTGGCAGCATCGCTGACAAATACTCCTGAGGAAACAGCAGCTGGATTCACACAGGTCGTGCAATACCTAAG |
| GTGGCTTGGCTGTTTGACTCCCTGATGATGCTACTTCTGCTGGCCCTGCTGGGGGCTGGCCTACTGGGGGCTTCCC |
| TGCTCACCTCGTGGCATGCTCCAGCCCGGAACAAGATCCCCAGGGCCCAGAAGTGGAGGGAGGTAGCACTGCAGAA |
| GATGGAGGACCTGGCCCAGTGACTCCGGCAGCAGGTGAGTCGACACGGGGCTCGACAGGGCCCCAGCCACAGGGGGC |
| CTTGGCCCTCAATCCCAACAGGAGGACTACACCTCAGGATGCCCTCCCGTCCATGACCCCAGCCCCCGCAGACAC |
| AGGGAGCAGGTGGGCACTTCCCCACCCCCAGTTCTCCCCCATGCCAGCTCTGTGTGTGGTTGTCAGTTCTCCTCC |
| ATCCCCGGCCTTTGAGACCCTGGAGATTGGGGGCAGTGTATTCTTTCTCTGTTCTCCCAGCACTTGGCACGTGGCT |
| CAGTAACATGGGAGGTGCCCACTTAGGGTATTTGCGGAAATAAGATAAACTGATGGAGGCCATTGGAGGAGGGAGG |
| CTCGATCTCTTTTAGCCCCTGAGCACTCCAAAATCCCCCAAGACAGGAACCCTAGTCTACCTGTCCCCTCCTACCT |
| CCACCCCATTCAGCTCTGAAAACACTTGCTGAGCCCTGATAAGTGCAGAGCATGGGGGGCTGGGGATGGGGTCTCC |
| CAGGAAGCTGCAGGTCTTCAGAGGCAGCTTTGGCAACTCGGAGTGGGGGTATTTCACTGGGATAGCCTCTGTGGCT |
| GGCTGGGCTGAGACTGGCAGGCGAAGTGGCTGAGCCATAGATGTATCAGCAAAGCCTGCCCCAGGTGGCAGAGAGA |
| AGGGCGGGAAGGAGGGACATGGAGACAAACATAGACTGAGCCTGGGATTTGCTGTGTGGCCTGGAGGATGTGACAA |
| CCCGTCTCTGGGCCTTGGACTCCCCAGCTGTCTGAGGGGGGATGGCTCATGGTCTCTCGGGGTCTCCAGCTTTGG |
| TTGATGATGGTGGACTCAGTCTGGGAGCCCGGAGGTAGGGGCTGGGGCTAGTGCCTGAGGTGCTGTTCCCATGCTT |
| TGGAGTTCCTGAGTGTCCTCTGCTGTCCCCTGGATGGTGATTGATGGCCCCAATGGGCAGCTTCTCTGTCTGAGTT |
| GCTGCAGTTGCTGAGTATGTGTATTAATATTAATTAGGGCTAATTAGTTGGATAAATCAATCTGCCCCCAGAGAGC |
| AGCTGCCCCTCCCTGGTTGATGAGGAGGAAGTCTGGGCTAATGGGTTGCAGTGGTGAATGGGCATGATGGAGGCGT |
| CCTGTGTGCGTGTGGAGGCCCCATCTGTGTGCGGTGGTGGGTATAGCTTCCTTTACTGCGGACGAGGGCCTGCTTT |
| CTTGTGCCTCCTGCTGGCATTTCATTGTGTTGTGGTTGGTTGTGTCTGGTCTGGCTGTGTGGTTATGTGCCTGG |
| CTGGGTGTGCATGTGTTGGGTTATTGGTTGGAGTGTGTACATCTAGCTATGTGTGGCTGGTGTGGGTCTGAATGTC |
| TGGTAGAGAGTGTTTGTGTGTGGTTGTGTGTCTGATGTGTGGGGGCAGCTGGTTTGGTATGTGTCTGGGCATCTGG |
| TTGGTGAACATGTGGATGTCTGGGCTGTTGGGCTGGGGACCTGGAGGGGGTATATGTCTGGATGGCTGGAGGAGTG |
| GAAGAGGTTTTGGGGTGAGGTCACTCATGGTGTCTCCAGCCTCCCATTGTGGTTTCAGGCTTCTTGGCTCTCAGCA |
| CCTTGCTGTCTCCCCAACAAGCTATCAGGTCTGTCCTGGGCACCTTCTCAGTCATGTCACCCTCTCTCTCTGCCAGT |
| GACAACCTCGAGACCTCAGGTGTCCACCTTTATGTCCCGGGGAGGTGCAAGGCTGGGACACAGGTCAAACCCTCAC |
| AGGCTCAGCAAACAAATTCAATTCTGCTGAGTTTAGTAAAATTTCCCAGGGAATTTCTCCAGGTCTTGCCCTGTGC |
| TGAGCTCTGGGGACACATTCATTATAAAGATGAATCTGACCCCTGACTCACACTTGTGCTAAAAATGTTCCCAACC |
| TGGGAGGGGCGTGGTGGAGATAGAGCTGTGCAGACTATGCAGGGCAGCAGCACGGCAGAGTGTGGTGAGGCCAGAT |
| GCCCACAGAACTGGTGACTTGGCAGGAGGGTGGCTGGTCTGTCTGGTGCTGGCAGTCATGTTGGAGGGCTCCCCAGAC |
| GGGTGGTGAGTGAGCTGAACCTCATGGCACCTGTAGGACTTTTCTGAAAGGAGAAACGAGAAAGGCAGTACCAGGG |
| AGGGAGAAGCCCCAGATGAGGCAGTGTTTCTGTAGAACGTATAGAAAATAATATTCCTAGGACCCATTGGGTAAAT |
| GGACCAGCTGCTCATGGCTGGAACTGCTCAAGCTACTCATGGCCAGGAAGCTCTGCTCACCTCAGGCAGAGCCTGG |
| CCACCTTGAGAGTTGACGGTTTTTATGATACTAAACATTTAACCACCACATTGGAATTTTTTTTTTTTCAGACGG |
| AGTCTCACTTTGTTGCCCAGGCTGGAGTGCAGTGGCCTGATCTCGGCTCCCTGCAACCTCCACCTCCCGAGTTGAA |
| GCAATTCTCTTGCCTCAGCCTCCAGATGAGCTGGGATTACAGGCAAGTCCCACCAAGCCCAACTAATTTTTGTATT |
| TTTCGTAGACATGGGGTTTCACCATGTTGGCCAGGATGGTCTTGATCTCTTGACCTCGTGATCCTCCCACCTTGGC |
| CTCCCAAAGTGCTGGGATTACAGGCGTGAGCCACCGTGCCCGGCCATAAATATTAATAATACATTGATTCACTAAA |
| AACTTTAAATTACATTTTTTTGTTTTTCAAACTAGGCTGGAGGCAGCACCCTGAGTACAGAGAAGGCTGGATGTC |
| CGTGGGGCTGTGGGATGGAGCTGGAGGGAAGGGTTAGCTCCAAACTAAATTACATATTAAAAAGTGATATAACTTG |
| AGGCTCAATTTTTCATCAAATTATTCAAATAATTTGTTGATTTTTAGCTTTTTTTTTTTTTTTTGGAGACGGAG |

-continued

Sequences

SEQ ID NO: 8-primer
5'CCACCAGTGTGCTGGTGGCTAC

SEQ ID NO: 9-primer
5'AGCCTCTGGGGCACTTTGACTC

SEQ ID NO: 10-primer
5'TTAATGTCTGGAGTGATAACATGAC

SEQ ID NO: 11-primer
5'ACAACTTCTAATTAGTGTTAATGAC

SEQ ID NO: 12-primer
5'AAGGCCGGGCGCGGTGACTTAC

SEQ ID NO: 13-primer
5' CTCTGGGCCATGTTGCTGGTTAC

SEQ ID NO: 14-primer
5' CAACTGTCACACAGGCCAAAACAG

SEQ ID NO: 15-forward primer
5' CCAGAAGTGGAGGGAGGTAGCAC

SEQ ID NO: 16-reverse primer
5' GCTGTCATAGGTGTCCTTGAGGCTC

SEQ ID NO: 17-reverse primer
5' CAAAGTGAGACTCCGTCTGCTGC

SEQ ID NO: 18-forward primer
5' GGCAAAGGCGCCATTCTCCTGGGTACA

SEQ ID NO: 19-reverse primer
5'GCCAGTCAGAAAATGTTTATTGAGCTC

SEQ ID NO: 20-primer
5' ACTGACACAGGTGACAGCATCTG

SEQ ID NO: 21-primer
5' GTCCAGTCGGTACATGTCTTCAC

SEQ ID NO: 22-primer
5'CCTGGCACCCAGCACAAT

SEQ ID NO: 23-primer
5' GGGCCGGACTCGTCATACT

SEQ ID NO: 24-guide
CCCAGTGAGTACGATGGCCAG

SEQ ID NO: 25-guide
TTAGTGATATTGTTCCGTGRG

SEQ ID NO: 26-guide,
TCATGGCCTTTCCCCTTCTCA

SEQ ID NO: 27-guide
GTCACTTGCAGTCTGATTAAG

SEQ ID NO: 28-guide 'FOP1'
AAPAGGTGAGGTCACGAGGCC

SEQ ID NO: 39-genomic DNA sequence of wild-type human FAAH (without
hypomorphic rs324420 SNP), including 5kb either side of FAAH (FAAH exons
in bold)
TCTCCTGCCTCAGCCTCCCAAGTAGCTGGGACTACAGGTGCCTGCCACCATGCCCAGCTAATTTTTATATTTTTAG
TAGAGATGGGGTTTCACTGTGTTAGCTAGGATGGTCTCGATCTCCTGACCTTGTGATCCATCTGCCTTGGCCTCCC
AAAGTGCTGGGATTACAGGTGTGAGCCACCTCACCCGGCCTACTTTGACAATCTTTTTAAAAGTGTCCTTGTAGAC
TGCACTGGAAGCAAGCCCTATTAGGCATTCGATTTGCCCAGTTTTTCCCTTTTCCAGAGCCTCCAAAGTCCACTTG
CCTGAGGGCCATGACTAAAGTGGTGGCCTCTTTTTTATCCTGTTTGTCCCATTCCACCTGCTCCTCCTGATCTTTA
TTATAAAAACCAAGGTTTCCAAGTTCAATAGGGTTTCTAAGTTTTGCTCCAGGCCTAAGGCGGACTTTTGAAGTT
TTTTTCTAATGTCTGCAGCTGACTGAGTGATAAACTTATTCTTCAAGATTAGTTGGCCTTCAATAGAGTTAGGTGA
CAGAGAGGTATGCTTTCTCAATGCCTCCCTTAGTCTCTCCAGAAAGGCAGTAGGATTTTCTTCCTTTCCCTGTATT
ATAGTGGACATCATTGAATAATTCATAGGTTTCTTCCTAGTTTTCCTTAGTCCTTCTAGCACGCAAGTTAGCAAAT
GTCTGCTGCACCAATCTCCATGTTCTGATTCTGTGTCCCAGTGAGGGTCTACACTGGGAACTGCCTGCTGGCCTGT

| Sequences |
| --- |
| GGGGAATCGTTCTTTCCTCTGTTGTCATCTTGTCATTGACCTGACTGAGATACCAGAGATCACCAAACTCTCGGGC |
| TGCAGTTATGGCAGCACTTCTCTCATTTGGGTTTAGTGTCTGATTTAGCAATAACATTATATCTTTCCATGTCAGA |
| TCAAAGGATTGTCCTAACCCTTGGAAAACATCAATATAGCCATCAGGGTTATCTGAGAATTTACCTAGGCCTATTT |
| TAATTTGCTTTAAGTCTGAGAGAGAAAAAGGTACATGCACTCTGGCTGGGCCGAATTCTCCTCCTCCCATTGCTTG |
| GAGAGGGGCATAATTGGGGAATATTAGCACTCTTTGGTTCATTGTTTACCCCTTTGTCTATCTCCTTTTGGACGTT |
| TGGGTTGAAGGGGGGTCCTCATTAGTTGGGGAAGGAGTCGGGGGGACACCAGGGTAGGGAGGTAGACTCTAGGGCT |
| TCCTGTAGGACATAAATCACACTTTTTACATAATTGCGAGTTGTCTCTTAATGAAAAGAAAGTTTGTACATATGGC |
| ACTTCATTCCATTTGCCTTCTTCTCTACAAAAGAGGTCTCACTGTAAGATGGTGTTATAATTTATATTTCCCTCAG |
| GAGGCCAGGTTTCTCCCCCTTGAAGAGGATATCATGGCCAGGTGGTACTGCAGAAGAATATAAGTCATTTCTTTCT |
| TAGCGTCTGAGGGTCAAATTGGTCCCAAATCTCCAGAATACATCTTAGGGGCGTTTTTGCCTTGTGGGGAACGTTT |
| CCCATTGCTTTGGAGGTCCCTTCGTGGTCGCCAAATGTTACTGGGGGGTCCTTGCTCCCAGAGCTCCCAAGATGGT |
| GGCGGGCCGCTTCCAAGATGGTGGCAAGCCTGGTGTTCTCTGACCTGGGGTTCTTGGCCTCACGAATTCCAAGGAA |
| TGGAATCTTGGGCCATGCGGTGAGTTTTATAGCTCTATTAGAAGCGTGGGTCATGGAAGAGAACTGTGGAACCCA |
| GTGACTAGTGTTCAGCTTGATTAGGATGAACCTGGGCACTTAGCCGTGCAGGAACAATGGCAAACCTTTAGCCTGA |
| TTGGGAGCGGCAATGGGCGCCTCGCTGGATCAGGAGCACAGTAGACACCCTGCCGGATCCAGAGGGATGGAAGTCG |
| GCGGCGGGTCTGCGATGGCAGCAAACAGCAGTGGATGTCGAGCGAAAGCTCAGCTCCAGCCATAGCAAACACGGAC |
| CAGAAGAGAGTGCAGTTGCAAGATTAATAGAGTGAAAACAGAGCTCCCATACAAAGGGAGGGGACCCAAAGAGGG |
| TAGCCATTTTTTCACTTTTTTTTTTAACTTTTGTTGAAAACATTTTAAGTTTGGAATTTCAACTATTCTTTGCTA |
| TTAATAAGACCTCATTCAGTCCATATTAACTTAGAATTGGTATAGATGGGTCCTTCCTGATTCTGTAAGTGCTTTA |
| AGGCTTGGCTGAGTGCAAACAGCTCTCACATTTGAACAGGCCAATTATTAGGCAATTTTCCTAACTCTGCTTCTAC |
| AAGAGTTTCCTTATCACTTACTGAATACCCATTGTGTCTTTTTCCCTCAATTACCCAGGAGGAACCATCTATCATC |
| CTGTCCTGAAGGGAGTTCTTCCTAGGTCTGGTCGGACCTTTGTATGGTAATTAATTAAGATTTAGATCCCATGTTA |
| GGAAACCTGCTGGGTTAAGGGAATTTTCAGTGGTTAATATTAAATCATTTTTTTCTAACAGAACAGCCTCATACTT |
| TAAGGTTCTTGAGTCAGTAAGCTACCTTTTTTTTTTTTGACTTAGGATAGTTCTGACCTGATGAGGTGTGCTCAC |
| AATGAGGTTTCCTCTAAAAGTTGTTTTTCTACTTTCTTCTGTTAGCAAAGCAGTTGCTGCTACAGATTGAATGCAT |
| TTGGGCCATCTGCCGGTTACTGGGTTAAGGAGTTTTGATTAGGGAGGTTACGGGTTGTCAGTGGCCTCAGTGCTTT |
| TGGGCTACATCCTTGTTTACACTGACAACAAGGTGGTATTGGAGTGTTATAGGGTCATGGAGAAGACCTTCAATTA |
| TCAATTACAGGTTTTGAATTTTATCCTGGCTTTTAAAGGAATAGGGTACACTGTTTTCTCTTTACTACTTCTATCT |
| CTCTTTCTCTCTCTCTCTTTGACTCTCTCTCTCTTTCCCTGTCTCTGACTCCCTCTCTCTCTCTTTTTCTTT |
| TGAGACAGAGTCTAGCTCTATCACCCAGGCTGGAGTGCAGTGGCGCGATCTCGGCTCACTGCAAGCTCCGCCTCCC |
| AGGTTCACGCCATTCTCCTGCCTCAGCCTCCTGAGTAGCTGGGACTACAGGCGCCCGCCACCACGCCTGGCTAATT |
| TTTTTGTATTTTTAGTAGAGATGGGGTTTCACGGTGTTAGCCAGGATGGTCTTGATCTCCTGACCTCGTGATCCAC |
| CGGCCTTGGCCTCCCAAAGTGCTGGGATTACAGGCATGAGCCACCACGCCTGGCTTCTGTCTTTCTGTCTCTTTCT |
| CTCTCTGCCTCTCTTTCTCTCTTTGCCTCTCTCTTTCTCTCCAACTTCCTCTCCCAGTTTCTCTTTCCTCTCTG |
| CTGGTCTTTCCCTGCCTCTGCCAGCTGCTTATGCTGCTGTTCTCCCCTCTCCTTCCCCTTCCCTAGGGAAGGGAC |
| CGTCAGGAGTGCAGCTACTTTTCTTCCCCGAGAAGAAAGGAAAGGGGAATTCTGAATATTTTTCTTACTACCGGA |
| GGTTTGTGTGAGGTTTTTGATCCCCTGAAATTTGTGGAAGGCTCAACACCTCAAACCAGGGGGGTATCTTGCCTTGC |
| CTGACCTGGAAGGCTCAACCCCTCAAACCAGGGGGTGTTTTGCCTTGCTGCCCTGGAAGGCTCAATCCCTCAAACT |
| AGGAGGTGTCTTGCCTTGCTTCCTGGAAGGTTGACCTGTTTCCTCCCTTTCCCCCTCTGAAGGTCCTTTGCACAC |
| TTCCCACTCCGTGTTGTCCTCTCTGGCTGCTCCCCCAAGGGAGAATTAGGCCCCCCTCAGCATTGGCATTCCAGTAG |
| AAATCCCACCGCAGGATCCTCCCTAAGCCATATGAGGTAGCTACGGAAACGTGGAGAGGACCCCACTCACTCCGTCC |
| AGCAGTAGGACTTGTCATCATCCACACGAACAACACCACAGGTAGGGTTGTTTGTGATCATTCACGCACACACACA |
| TTTAGCCCTCCAGAATTTGACCACCAAGGAAGTACCTTACCGGCTCCCTCGGCTTCTTCCTTTGTCTGTGCACAGA |
| GTTGTCTCTGCAGTGTGTGAGGATGCTTTACCCTAGGTTGCCTGCTGGTTTCTTTTCACATTGCTGAGAGCTCAGG |
| TTATTTCTTGCACATGGGTGAGTCCTGATTTCTCACCCCTGAGGCCCATCACAAGAGGGTGGGGCATACCTCCTCAGG |
| AGAGAGAACCAGAGACTGCCCCTGAAGGGGAATGTAATCACGAGCAAGCCCCCAAATTGTTATAAATAAAGTTTCC |
| CCCCAGTGCCGCAAAAGAAATAGCACTCGAATATAAAATTTTCTTTTTTTCTTCTCAGCAAGGCAATTTACTTCT |
| ATAGAAGGGTGCGCCCTCACAGACGGAGCAAAGGTGAGCGCACACCTGGACAAGGGAGGGGAAGGTGGTTCTTATG |
| CCTGACCCACGTGATTCCTGATGCTGTGTCCTTCCCCTGTTGGCTAGGGTTAGACCTATAGGCTAAACTAATTCCG |
| ATTGGCTAATTTAAAGACAGTGAGGGGGTGAGTGGTTTGGCGGGAAAAATGGTTACCGCAGAGCAGGAAATCGGAA |
| TGAACCACGGTGAAGAATGAGTGAGGGAGGAGCAGGTAATCGAAAAATGTTGCTTTATGAGGAAGTTAAGTTTAAA |
| AGTAGAAGGCAAAGAATTGAAGATACTGACATATTGATTCTTTTAAGATAAATTTAGAACTCATATCTAACAGCTG |
| GCATGTCTGGCATGGGGCTCCGGCTGGGGCGCAGTCTTCAGCATTTGGGGCTCTGGGGTGCAGGGGGCAGAGGACG |
| GCCGGGGCTGTGGTGCCCAACCGGTGCTAAACTCAAGCTTGGGAGGTCGCCCACGAGAAACAGTCGCCCTTCCCCA |
| CCCGCCTGCTCGGCTTGGCGGGGAGCGGGATGTCGCTGGGGGCGATGCCAGGCGGGCCGCTCTGATAGCCTCTAG |
| GCTCTGGCGCGCTTCCCCGCCCCTCCCGCGCAGGCGGGCGTGGGATCCCGGCTGATCCAGTCCGGGTTTTGCGGCG |
| GAGCGGCGGCTGCGCGTGCGGCGGCTTCAACTGTCGCGGTAGGCAGCAGCAGGCTGAAGGGATCATGGTGCAGT |
| ACGAGCTGTGGGCCGCGCTGCCTGGCGCCTCCGGGGTCGCCCTGGCCTGCTGCTTCGTGGCGGCGGCCGTGGCCCT |
| GCGCTGGTCCGGGCGCCGGACGGCGCGGGGCGCGGTGGTCCGGGCGCGACAGAGGCAGCGAGCGGGCCTGGAGAAC |
| ATGGACAGGGCGGCGCAGCGCTTCCGGCTCCAGGTGACTGCCGGAGCGTAGTGGGATGGGCGCGGCCTGAGGGTAC |
| TCGCAGCGGCACTTTCAGCCGCCGGACCCGCCGAGGGACAGGGGATGGGGCGGGCGGGCAGAGCAGATGTGTAACTCTCC |
| AGAATCTCTCCTTGCCCTAAGATATTCCGCACTTTCTGAGCCAGGTAGAGCACGGGGGAAGAAAGGAAACGGTAGT |
| GTCAAGGCAGGTGGTGGAAGGCCTTTCCCTCACTGGGTCAAAGAGGAGTTTTGCTTTGTGCCAAAGAATCTCACGA |
| TTGCTGCCTATTGGAATGCGAAAACGCAAGCGTGACAACCAGTGGGATGCCAGGGGTTGAGGACTTTGGAATCGCA |
| GAGTGTAATGGCCAAGGGGATCTGGAGAGCTTAGAGTTTTGTTTTTGTTTTTTTTTGTTTTGTTTGAGACGGAG |
| TCTCGCTCTGACTCCCAGGCAAGAGTGCAGTGGTGCGATCTCGGCTCACTGCAACCTCCGCCTCCCGGGTGCAAGC |
| GATTCTTGCTGCCTCAGCATCCCCAGTAGCTGGGATTACAGGGGCCCGCCACTACGCCTGGCTAATTTTTGCATTT |
| TTAGTAGAGACTGGGTTTCACCATGTTGGCCAGGCTGATCTCAAACGCCTGACCTCAGTTGATACACCTGCCTCGG |
| CCTCCCAAAGTGCTGGGCGTGAGCCACCGCGCCTGGCTGAGTTCAAGCTTCTTGATTTGTGCATTTGGATCCTAAG |
| AGGGAGCCAGAAAGAAACCTGCCAAGTGCACAGGGAGATCTTGGCAAAGCCAGGCTAGAAGGGAAGTCTCTCTGGC |
| TCCTGCTGTGGTGTCCAACCCCTGGCAAGCCCTTTCCATGAGCAGGTTTAGTTCCAGCCCCTCCGTGGGTGGTCTGT |
| CAACAAGCTTTTCTCCCTGCGCTGCCTTTGGATCACCTCAGTATGTGGGTTTGGAGGCGTGGAAGGGCCTGGCTGA |
| GGGTTTGGAAGATGTGGCTTGAAGAGGGGCTTTTCCTCTGGGTGTGTGAAACACTGACCCCAGTTAAAGCCTTCTT |
| ATGTGCTGAGAGAGGGAGGGCTTGCTGTATCTGTGGGACCTGACAGGTGGGAAGGCTTTACAGGTTGGGAACCGCA |
| GGACTCAGGAGGGTGTGCCTGGGTGGGAGACAGAAAGAGTCACAGAAAATTGTGTTCAGCAGATGTTCCGCAAGTG |
| ATTTTTGAGTTGGGGCAGAGCTGGAACTAGAACCTAGGTGCCCGCTGCACTCTGCAGCCACACTTTCGTGGAGAGG |
| AACAGGAGAGAGATATGAGGAAGGCACCTTGCATGCCAGCCCAGGGTGTAGCCCTGCATGTTGAAGGGGGCCAGCC |

-continued

| Sequences |
|---|
| CCTCCACACCTGTGGGTATTTCTCCTCAGGTGGGACAAGAGACTGAGAAAAGAAATAAGACACAGAGACAAAGTAT |
| AGAGAAAGAACAGTGGGCCCAGGGGACCACCGCTCAGTATAGGGAGGACCCGCGCCAGCACTGGTCTCTGAGTTCC |
| GTCAGTATTTATTGATCACTATCTCTACCATCTCGGTGAGGGGGATGTGGCAGGACTATAGGGTAATGGTGGGGAA |
| AGGGTCAACAGGAAAACATGTGAGCAAAGGACTCTGTGTCATAAGTTTAAGGAAAGGTGCTGTGCCTTGATGTGTA |
| TGTAGGCCAGATTTATGTTTGACTTTATACAAGCATCTCAGTGCAGTAAACAACAGTATTGTCACCAGCATGTCTC |
| ACCTCCAGCCATAAGGTGGTTTTCTCCTATCTCAGTAAATAGAACGTAGGATCGGGTTTTACACTGACACATTCCA |
| TTCCCAGGGACGAGCAGGAGATAGATGCCTTCCTCTTATCTCAACTGCAAAGAGGCCTTCCTCTTTCACTGATCCT |
| CCTCAGCACAGACCCTTTACGGGTATCGGCTGAGGTATGGTCAGGTCTTTCCCTTCCCACAAGGCCGTATCTCAG |
| GCTGTCTCAGTGGGGAGAAACCTTGGAGAATACCCAGGCTTTCTTGGGCAGAGGTGCCTGCAGCCTTCCGCAGTGC |
| ATTGTGCCCCTGGGTACTCAAGACGGGAGAATGGCGATGACTTTTTGCCAAGCATACTGCCTGCAAACACATTTTT |
| AACAAAGCACATCCTGCACAGCCCTAATTAAACCTTGAGTCAACACAGCACATGTTTCTGCGAGCATAGGGTTGGG |
| GCTAGGTTTACAGATTACCAGCATCTCAAGGCAGAAGAATTTCTCTTAGTACAGAACAAAATGGAATTTCTTATGT |
| CTACTTCTTTTTACATAGACACAGTAACAGTCTGATCTCTCTTTTCCCCACACATGTGTTGCGGTTTTGGCTGGCT |
| GTAATGTATGAATTTACTCCAAACCATCCCTGGGGCAAGATATCTCATATTTATTTAGTAAGATAAAAAATATAT |
| CTGGTTCCAGCCTCCACTCACCAAGCTGGCTGAAAAGTCCACCATCAGTCAGTTTTTAGGGTTTCTTCCTTCCAGA |
| GTGAGAGGGCCCTGGTGGTCAACCCAAATTGGCCATCTCCCCTACACAAGCACAGGTTCTTCACTGTCTAGTTGCC |
| CTCTCTGGCTGGGCGCTGGAGGTCCTCCTTAGAGATCCTCCTGTTTATCCCTGGCTCTGTGCAGCCAGCTGAGTTC |
| TGCCAGCTCCAAGAGCAGCGTGGGCAGCACTAGCAGGGATCTGCTCACAGCTCTTGCCTGCAGAACTCCCCTCCTG |
| GTTGCAAGGAATCCACCTGGCTGGCAGGGGTGTGGGATGGTAGCAGGATGGGTCTTCCTGCACTTCGGCTCCAAAC |
| AGCAGCATCTATATGGTTTTCCTCTGGAACAACTGCTCTTCATTATTTTTACGAACAGATTATTCCAGGACAGAAG |
| TTTTGGCTCTGAAAGCTTGGCTCTTTCAGGAGGAGAAGCGGGAAATTACCTTTCAGGTTTCCAGTGATTGTGGTTT |
| TGAGTAATCAGCAAAGGGGTGGGGTCCTGATTGACAATAGCTTTGTAGGCTTTGCGGGGGAGTAGGATTTTTTTTT |
| GGTTTTTGTTATTTTGTTTTTGTTTTTGAGACGGAGTCTTGCTCTGTCGCCCAGGCTGGAGTGCAATGGTGCGA |
| TCTCGGCTTACTGCAACCTCTGCCTCCCAGGTTCAAGCGATTCTCCTGCCTCAGCCTCCCGAGTAGCTGGGATTAC |
| AGGCGCCTGCCACCATGCCTGGCTAATTTTTGCATTTTTAGTAGAGACGGGGCTTCACCATGTTGGCCATGGCTGG |
| CCTCGACCTCCCGACCTCAGGTGATCGCCCGCCTCGGCCTCCCAAAGTGCTGGGATTATAGGCATGAGCCACCGC |
| GCCTGGCCAATGCCTGGCTAATTTCTGTAGTTTTAGTATAAACGGTTTCGTCATGTTGGCCAGGCTAGTCTTGAAC |
| TCTTTTTTTTTTTTTTTTGAGATGAAGTCTCACTTTGTTGCCCCAGCTGGAGTGCACTGGTGCAATCTCGGCT |
| CACTGCAACCTCCACCTCCCGGGTTCAAGCAATTCTCCTGCCTCAGCCTCCCTAGTAGCTGGGGTTACAGGTGCCT |
| GCCACCATGCCCGGCTAATTTTTGTATTTTTTAGTAGAGATGGGATTTCACCATCTTGGCCAGGCTGGTCTTGAAC |
| TCCTGACCTCAGGTGATCCCCCTGCCTTGGCTTCCCAAAGTGTTGGGATAACAGGTGTGAGCCACCTCACCCGGCC |
| AGGACGTGGGAGTTTTAGCTGAACCCAGCCCAGGCTTGGGAACAGCTCTTTCCCCCGCCTCTCCTCCCTTCTGCCT |
| ACAACTCCTAAGGCACCCTTCTGTTTGGCTCTGGAGTCCTTGAATGATGGGCAGGTAGGATCTGTGACTGTCTGGG |
| CAACCTTTCTTCTGGGGCTCTTAGCCCAGCCCTGAATCACAAGGGGGCACCTGAGATAAGCAGGGCTCCAGCAGGC |
| CCTGGGAGAACACAGCGATTTGTAGTAAAGCTCCTGTCTGATAGATTCTGGACAAAGCGATTTGGCAACCAAGATT |
| CTTTTTTTTTTTGAGTCAGAGTCTTGCTCTGTTGCCCAGGCTGGAGTGTAGTGCGTCAATCTTGGCTCACTGCAA |
| CCTCCGCCTCCCGGGTTCAAGTGATTCTCCTGCCTCAGCCTCCTGGAGTAGCTAGGACTACAGGTGCCTGCCACCA |
| CATCCAGCTAATTTTTGCATTTTTGGTAGAGACAGGGTTTCGCCATGTTGGCCAGGCTGGTCTCGAACTCCTGACC |
| TCAGGTGATCCGCCTGCCTCGGCCTCCCAAAGTGCTGGGATTACAGGTGTGAGCCACCACTCCCGGATTCTTGGCT |
| GTGTCCAAGGAGGACACAGCTGGATGAAGGGGTACCTAAACACCTTCTGAATTTTCACAAAATAGTTCACCTCTCT |
| CTAAACTCTTGAGCAAATCTAGAGAAAAATGTGTTTCTGGTAATTCTGTTGACGCTTCACCCATTTTTTCCCACCC |
| TGCCCCCTGAATAAGTTTTGATATCTTTTCTAGACCGAAGAGAAGGACCACCATCAATAGAATAGTATAGCTGGGA |
| GAGACATCACAGAACACCTATTTATGCCCTTATGCCTTTGTACATGCAGTTTTGTTTTACCCTGAATGGTTTTTCC |
| TACATCTCTTACAACCCGCTTATCAATCCCACTGGCATTGTGGTTCAGAAGGAGAAAACAAAACAGATGGAGGAGG |
| GGCAATGCCTCCTAAGTGATTGGTAGAGTATCCCTCTCTTGAAAAATTGTGCATGCAGGTGGCCACAGGTTTAGAT |
| GTTACCTGTATACTATACTTCCCTGCATTCTCCGCAAAATCAGGTTTCCGCATGTTCACTGATTGGTCTTCTGGAG |
| GTGCAGACTTACTTTGGTGTCTAGGAGAAAATGTCTCAGCTGCCTGACACTAGTTGAAGATTTAAAAATAGCTGTT |
| AGCAGCTGTGTCATTAACTGTCAACAGGCAAGAACATAGGAAAGAATGAAAATGTGTGCTGAGCGTGGAGGGGAGC |
| ACATTGCTAGCTGCTAGCTGCCGTGCACAGGCACTCTGTGGGCGCCTTGTAGCGAGGTCGGGGGAGTTGGTGACCG |
| GACTGTCAGGTGGCAGTTATTCCAGGGTGGTGAATGCTCTGCTGATTTCGATGTCCTTCTCCATACTCTTAGGCAT |
| TTTTTAAAATACAATGAACCTGTATTTATATAATGAAAACAAAATAAAGCAAATTTGATTTTCATTGTGAGATG |
| GGAAAGGCAAGATGCAGTACTGTGTGTATAGTATGATTCCTTTGTGCAAAAAGAATATATATAGACAACTGTTGA |
| CATGGTGGGTTTTTCATAAATATTTTCTTTTCCTGTAAGAGTACACCAGAAACTGTTAATTATAGTTTTCCTTTAT |
| AGAGGAGGGACTGTGCAAGGAGAACCAGGGGTGGAGGGAATGCTCACTTTTCATTTTGTATACCTTTAAAGAATAT |
| ATCAAGAGGATTATCTAGTGTGTTTGGGGAGAAGTCTTGAACCCATTTTTTCTTCTTTGTAGCTCCTTGTGTTAGA |
| AAAAAAATCCAAAGTAAGTACTCTATCAGTTCAATGAATTCAGGGAAGTGCTCCTGACACTGAGGACATCAGGGGG |
| CAGAGGCTGTGGCATGTGCTCGGAGAGGGCAGGCGCCAGGCTCTGGGGTGTGGGGGGTGGGGGAGGGCAGTGGTGC |
| CTGGGTGGGGAGAGGTGCACATGAGTCTGAGAGGACCACAGCTTGGAAGCACCTCCTGGAATATGCTCTGGAGCCT |
| GTGGTGTGATGAGATGGGGATTTAAGGGGAGAGGCAAGGCCAGGTTGGGTTTTGCACTGTCTGGCCCTAGTGGAA |
| AGTGTGGGTTGGAGGTGCAGGACCTGGGCAGGGCAGCAGTTGGGTGGCCGCGTGTGACCTAGGAGACAAGGATGAG |
| TCTGAGGCCCGGTGAGGGCCTTGGTAGAGGGGATGGAGAGGTGACCATTTTTCAGAGGCTACTTAGCTTGGTGACTG |
| GATGCAGGTGGTGGTGGGAAGGAGGAGCCAGAAAGACACCTGTTTCATTTCCTGAACACCTGGATGGATGGCGGGG |
| CCTCCCCTGAGTACAGGGTACAGGATACATAAGGAGGAGCTGGTCAAAAGTCGGGCAGGTGATGAGCTTAGAGGAA |
| GGACAGGGAAGGTGGACAGGTGACAGGAATAGCCCAGTGAGCTGGTTTGGGCTCCATTGCCTCGGGCTGGGTAGGG |
| GATCTGGGGATGTGGGATGAGTGGAGAGCCTGGAGTCAGAGGTGCTTAGGGGAGGAGTGGAAGCCAGGGTAGGGG |
| AGGAGGGTAAGAGGGGAGGGGAGGGGAGGGAAGGGTAGAGGGGAGGAAGGGGAAGGAGGAGGGAGGTGAGGAAGGGAAG |
| GGGAGAAGGGAAAGGAAGGGAGGGAGGAAGGAAGGAAGGAAGGAGGAGGAGGAGGGAAGCAAGGGGAGGAGGGGAAG |
| AGGAAGGGAAGGGTAGAGGGGGAGGAGGGGAAGCCAGGGAGGGGAGGAGGGAAAGGGTAGAGGGGAGGAGGGAAA |
| CCAGGGGAGGGGAGGAGGGGAAATTGGGGAGGGAAGAGGGGGAAGTGGGAGGGGAGGAGGGGAAGCAGGCCAGG |
| GGAGGAGGGGGAGTAGGGGAGGGGAGTAGGGGATTAGGGGAGGGGAGGAGTAGAAGCAGGGTTGGAGGGGTGG |
| GAGGAATGGAAGCAGGAGGAGGGGAAGCCTTCTCCCAGAATCAGAGAGGGAGAAGGTACCCAGAGCTCTGTCT |
| CTCCCCACATCTGGCATCTTCTTATCCTTCAAATCACAGCTGAAATGTGGTTTCTTCAGATAGGCAGCCTTTAAGA |
| ACTGGAACACTCACTGTGAGGGTCTGCGGCTTCATTCTTGAAGTCAGTGAGACCAAGAACCCACCAATTCCGGACA |
| CAGAATGAATGTGTAAACCCTTCCTTTTGGGTGTGGCCTTCAGTCACAGACCCAGCCTCCCAAGATGGGGTCTTCT |
| TGTTTTTGCCCTTCCCTGCTAGAGGTTGGCAACCCCCTGAGTAGTGTTCAGAGCTGCTCTGTGGGTGTGGGGATGG |
| CATGGGGTCAGGTCAGGCAGATGGCTGGTGGGCAAGAAGGCACCTCTCTCTCAGCCTCAGTTTATCTGTGCAATG |
| GGAATGGCAGTAAGACTTAATCAAAACATGGATGACATCAGCGTGGTGTTGGCACACAGAAGGCAGCCACTGCTGG |

```
TGTATATTTGTAGTGGTTTAATCATCAGTCTGGAGCTAGGCACAGTAGCATGTGCCTGTAGTTCCAGCTACTCGGG
AGGCTGAAGTGGGAGGATCACTTGAGCCCAGGAGTTCAAGTCTAGCCTGGGCAACACGGCCAGACACTGTCTCTAA
GGAAAAAAAAAACCTACTTGGGCAGGTCGGCTCGCTGGGCACCCCTTCAACAAGCTTCTGGAGGAGACAGAGCTGC
ATTCTCTAGGGATGGCAAGGGCCTGCCCAGGCTGGGCCATGTCAGAGCTGCTGGGGCATGGGCCACTGGTGTCTGC
TGCAGGCCCATGAGACTTCGGCGAGTAGGGGACTGATCCGAGTTTGTTCCCCACAGAACCCAGACCTGGACTCAGA
GGCGCTGCTAGCCCTGCCCCTGCCTCAGCTGGTGCAGAAGTTACACAGTAGAGAGCTGGCCCCTGAGGCCGTGCTC
TTCACCTATGTGGGAAAGGTAAGGCCAGCCAAGGCCAGCCCCTCCCTGGGAAAGGTAAGGCCAGCCAAGGCCAGCC
CCTCCCTTTCCCCTCCCTCTGTCCGCACAGGCTGTGGGGAAAACCTGGCCTGGAGTTAGTCCTGCTGGGGGCCATG
GTGGGACCTACAGTGCCAGGGACTGCCAGGGAGGGAAGGAGCCAGAGCGTGTGCGTGTGTATGTATGTGTGTAT
GAGACACTGAGCATGCTGTCTTAGCTAGTAACCTGGCTTTTAGCCCAGACTTCCCTCTCCCTCCTGCCTCCACCCC
ATTGGGCAACAAGTCTGGTCTGTTCCCTTCTTTTTTTTTGAGATGGAGTTTCGCTCTTGTTGTTCAGGCTGGAGTG
CAATGGCACAATCTTGGCGCACTGCAACCTCCACCTCCTGGGTTCAAGCAATTCTCCTGCCTCAGCCTCCCAAGTA
GCTGGGATTACAGGCATGCACCACTACACCCGGCTAATGAAAAGAAAAAAAATTTTTTTTTTTTTTTGAGATGGA
GTCTCGCTCTGTTGCCCAGGCTGGAATGCAGTGGCATGATCTTGGCTCACTGCAGCCTCCACCTCCTGGGTTCAAG
TGATTCTTCTGCCTCAGCCTCCTGAGTAGCTGGGAGTACAGGCACCTGCTAACACACCCAGCTAATTTTTGTATTT
TTAGTAGAGATGGGGATTTTTACCATGTTGGTCAGGCTGGTCTGGAACTCCTGACCTCAAGTGATCCACCCGCCTCGG
TCTCCCAAAGTGCTGGGGTTACAGCTGTGAGCCACTGCAGCTGGCCCCCAACTAATTTTTTGTATTTAGTAGAGAC
GGGGTTTCACCATGTTGATCAGGCTGGTCTCAAACTCCTGACCTCAGGTGATCCACCCGCCTCGGCCTTCCAAAGT
GCTAGGATTACAGGCGTGAGCCACCATGCCCGACCCCGTCTTTTTTTTGAGATGGGAGTCTTGCTCTGTCGCCCA
GGCTGGAGTGCAGTGGCATGATCTTGGCTCACTACAACCTCCACCTCCCGGGTTCAAGTGATTCTCATACCTCAGC
CTCCCGAGTAGCTGGGATTATAGACATGCACCCCCATGCTTGGCTAATTTTTGTATTTTTATTTGGCGGGCTGGT
CTGGAACTCCCAACCTCAGGTGATCCTCTGAAAGTGCTGGGATTACAGGCGTGAGCCACCGCGCCTGGCCTGTTCT
CTTCTTTTACCCAGCCCTCTCCTGTCTCCATCCCCTTTGGCCACCCTGGCCCGCCACCACCATCTCCCGCCATGCC
CAAGCACCACCAGCCTCCTGGTCAGGTGCCCTCTTGTGTCCCCAGCTCTTCAGGCCATCTCTTGTACTCCTCCTCTGTG
TGTGGCATCACCTCTGGCCAAGGCCTTCTGGAGCTTGGGTGTCAGCAGCTCTGCACTGGCTTGGGTGGGGCTCCTT
TACCTGGAAGGCTGTTTCCCTCTTCTTTGCCCCTGTCCGTGCCACGGGCTCCCCTGGCTGAGCCTTCGGGGCTCAG
AGCAGGAGGCACCGTCTTCCATTCGCCACCTGAGGTAGGGTTTCCTCTTCCAGGCCTACTCTCATTCTAATAGCAC
ATTTCTCATCACAGTGTCAGGCTTGTCTTCTCTATCTCTTTCCCATGGGGGGTCTTTGTGGACAGAGCTTGTCTCA
TTTGTCTTTGAACCTTAGTGCTCAACATGTTGCATTTCACGTAATAAATGCTCAAGAAATATGTTTGAAAAGAAAG
GGAGGGAGGGAGGGAAAGAAGGAGACAAATTGTGCTTTGAGTGTGGCCTGCATGATTTCTTGAAAGGGTGTGGGACA
GTGAGTGTGACCCCTAGGCAGGTGAACTTGTCTGGGTGCAGTGTATGTGACAATGCTGTGGGGGCTGCAGCTGAGG
AAGCGAGCGCATGCTGGGCTGGTGTCACTGAGAGGGGCACGTACATAGTCTCAGCAGATGGTCTTGCTTCTTCCC
TGTCAATGTCCCTGAAAGGCTCCTGCCCTTCCTAGTTAATCTAGTCTATCTGGTTAGATTAGCCTTCTCTGTTCCT
GCCTCGGGTACCCCGGGACAGATTTTGCACATGCCTGAATATGGCAACACAGCCCACCCTGTTTCCCCCAGATAC
TCCCCAGGAGCAGGAATATTTACTGAAAGCTGCATCTCACTCTGCCCTCACCTTTCCTTCTGTAGGACCCTGTGTG
GTGAGGTTTGAGCATTCTAGGCAGATTTCCACTATTAGCATGTTCTTCCCTTTTGTCAAGCTCCTACTCCACATGG
CTTGATTATCAAATTCAAGATTTCCTGGGTAAGGGGAGGCTTGACTGGGCTACATGTGGGGAAGGCGTGGGGTTGA
GGAGAGACTGCTGGGCTCCGGGAGGCAGGAGTCTGGTCTAGTCCTGCTCTGTGGTTGCCCTTCAGTGTGACCAGTG
ATGGGGCGCTGCCCCTGTCTGGTTTCTGTCTGCCTCACTGGCAGAGATGTGGCTTGGGGAGGTGAGGGAGTGGCC
AGTGGTCATCTTCCTCCCAGCTCACCCCCTACCTGGGGGGCACCTGAGGCCAGTATCTTGCTCCCTTGAGTGTCCC
GGTTGTGCCTGGTCCTGGTTGAAGGCCAGAGACAGCCAGGATGAGGCCTGGAGTGCACTGTAGTGCTTGCCCTAGT
GAGGCAGATGCTGAGCCCTAGGTCATCCTCTGTGCCCCAGGCTCTGGGCATGTTGCTGGTTACCCCTCTCCCTGGGTATACTT
TAAAAGGCCAGTTCTACATGATGTATATTTCACCACAATTTCTTAAAAAGGCCAGCCTCCTTTTATCTTATGTCTA
CTTCCCCTTCCTCAGGCCTGGGAAGTGAACAAAGGGACCAACTGTGTGACCTCCTATCTGGCTGACTGTGAGACTC
AGCTGTCTCAGGCCCCAAGGCAGGGCCTGCTCTATGGCGTCTTCAAGCCTCAAGGAGTGCTTCAAGGTCACCTACAAGGT
ATGCTCTGCCTCAGCGCCAGGCCTCCATCGTCCCCTCCATCCCTGCCAGCCTGCTCTGCATCTTGGGTCATTTTGG
GCCCTTAGAGGAGGTATCAGGTCCAGAGGCCTTCCGAGGGGACACTGGTATACCTGTTTTGGCCTGTGTGACAGTT
GTTGGAGTGGACCCTTGGCTGCCCACGGGCCCTGACTCACTCCCTTCTGGTGCCCATCCCTCCTCCCAGGGCCAGG
ACTCCACGCTGGGCTTGAGCCTGAATGAAGGGGTGCCGGCGGAGTGCACAGCGTAGTGGTGCATGTGCTGAAGCT
GCAGGGTGCCGTGCCCTTCGTGCACACCAATGTTCCACAGTCCATGTTCAGGTTGGGTCTTGGGGTGGGCGGGGC
GGGGCAGGGCACCGGTCCCAGCATGGCACGGGCTGACCCATTCTTGGCTCCTCAGCTATGACTGCAGTAACCCC
CTCTTTGGCCAGACCGTGAACCCATGGAAGTCCTCCAAAAGCCCAGGGGCTCCTCAGGGGGTGAAGGGCCCTCA
TCGGGTCTGGAGGCTCCCCCCTGGGCTTAGGCACTGATATCGGAGGCAGCATCCGCTTCCCCTCCCTTCCTCGCGG
CATCTGCGGCCTCAAGCCCACAGGGAACCGCCTCAGGTAAGGTGGGTGGAGGGCGCTTCTGGGCCCCTCGCTGTGT
GACCTTGCCTAGCTTCCAACCTCTCTGGGCTCCAGGCGGGATTCGGTCTCCGGGGTTTTGCTGGGAGGAAGCAT
TACAGTACCACTGGCCGGGCGTGGGTCCTAGTTTCCAAAGCGGTGAGTGTTCAGAGCTGCTCTGTGGGTGTGGGA
TGGCGGCGGGTGGCCATTTCCTGTTTCCAGCATCTTATGTTTCTTATCCAGCAAGAGTGGCCTGAAGGGCTGTGTC
TATGCAGGAGGCAGGTGAGGTCCGTGGTGCTCTCAGTGCCCCGAGGAGGGTGGGGGTCGGCCTGACCCGCTTCC
GCCCGTGCTTCTCAGGTGGCAGGGCAGTGTCTGGCCCCAGGCTGCTCTAGGTCTGGGTTCCTCGCTCCTTGTCTG
CTTACCTCCCTCACCTCTCTGCCCCACAGTGCGTCTCTCCGTGGGCCCCATGGCCCGGGACTGGAGAGCCTGGCA
CTGTGCCTGCGAGCCCTGCTGTGTGAGGACATGTTCCGCTTGGACCCCACTGGCCTCCCTTGCCCTTCAGAGAAG
AGGTGAGCAGGGCTGGGTGGGCATGAATGTGGACCGCTGAACCCAGACAGCCACCCCAGGCCTTGTGGGCAGGCCT
TGGAGCCCCTGTCTCCTGAGAACCGTCCCCCAGGCCTCTGAGGCCAGGGCGGTTGCCTCCACAGACGGCCACC
AGATGGAGCCCTTGCCTGCATTTTGAAATCCTCAGGCTTTTTTTTTTTTCCTTTTCTTTCTTTCTTTTTTTTTT
TTTTTTGAGACTGAGTATCGCTCTGTCCCTCAGGCTGGAGTGCAGTGGCGCGATCTCGGCTCACTGCAAGCTCCGC
CTCCCGGGTTCACGCCATTCTCCTGGGTTCACGCCATTCTCCTGCCTCAGCCTCCCGAGTAGCTGGGACTACAGGC
GCCCGCCACCACGCCCGGCTAATTTTTTTGTATTTTTAGTAGTAGACGGGGTTTCACCGTGTTGTATCCAGGATG
GTCTGGATCTCCTGACCTCGTGATCCGCCCGCCTCGGCCTCCCAAAGTGCTGGGATTACAGGCTTGAGTTACCGCG
CCGGCCGGAAATCCACAGGCTTTCAAAGGTGCCCAGCCTCAGCTGCTGGCACCAGGGATGCAGGAATCATTTCCCA
GCCTGCTGACCTTCAGCAAACAGCAGCCTTTCTAACAGTATTCCTGTCCACATTTTGGGAGCAGCACGCCACGCTG
CCTGCAGACCCCAGCTCATGTAGCCTGTTCCTGCCAGACTTGCTGCTACGTGAGCCAGGGTCTGCAAGCAGCGTGG
TGTGCTGCTCCCCAAAATACCACCACAGCAGCCTGTTGCTGAGACAGGCTGGGCTTGGTTGCTTTCTGTGGCGAGGC
AGCACTGTCTTGCAAAGCCTTAGGATCATCTCAGAGGGCAGGAAGGGTGGGGAGATCTGCTGAGATTTTGAAGTCT
GGTTTAAGGTGGATCTTTCAACATGGGGGTTGGTTAAGATTGGTTAAGTTGGTTAAGATTGGTTAAGATCCTTAA
TCCCCATGTTAAGGATTGGTGGGCACAGCAGGGTGTGGATTTTGAGGCGAGAGGTGTCAACCGATGCTTCCTGTTG
AAGAGTTGGAATGAATCGGAAGGTTATTTGTGTTATGTGTTATATTTGGAGGAGGTGGGGAGTGGCCAGTGGTCA
TCTTCCTCCCAGCTCATCCCCTACTGCGGGGCATCTGAGACCAGTATTTTGCTCTCTTGAGTGTTCTGGTTGTGCT
```

| Sequences |
|---|
| CTGGTCCTGGTACTCTCTCTCTCTGTCTCTGTGTGCGTTGGGGTTGAAGGCCAGAAACAGCCAGGTTGAGGCTG |
| GGGCCAGATGTCCCCAGTGAGGCAGGTGCTGGGCCCTAGGTCATCCTCTGTGCCCACTCCAACAGAGTGCAGGAGC |
| TGTAAAGTTAGATTGGTGCAGACAGAGGAAGAGTGAAGTCACGTTAATGTAGACAGTAAGCTGTGTGACGTAAGCT |
| CCGTTTCTCAGCAGTCCAGCGATTGTCTATCTTGTACAGACCTCTTGCCCTCGCCCCAGCCAAGGTTGCCTTGGAA |
| AGGCTGAGGGTTTGTGGACGGGAAGGAGAGTGGGCCTTGGTGTTTCTTGGGAGTGGGGCAGCAGGGCAGATCTGGG |
| CTGGGTAGGGTGAACTCCCCCTCCCCAGGCAGAGGGAGATATTCTAACCGAACCCACGGGGATAGGCAGCCGTGAA |
| GTCCTTCCTCGGAGGAGGAGGAGGAGATGAGGTCCCTGTCTGGAAGTCTGGAACAGTTTATCATGAGAGCCAGGACA |
| GGTGGTGGAGAGCCTCAGCTCAGAAGACAGGATGCCTGCATTCCAGACCTGTCTTGTCACTCTGCATTGGGTAGCT |
| TTGGGCAAGTCCCAGTCCCACCTAATCTCCCTATTGAGACCTCAAGCCTCAGTTTCCTCATATGACCAGTAGGAAT |
| CCTTATCCTTGCTCTGCCCACCTGAGTCACTGTGAAGGTGTTTTATGAAAGGGTCAGATGCAGAAGGGGCTGGCCT |
| CGCTGACTGCAGCCTCGCAGCTGTGTCTGGGGGTGAGTAGTTTCTCTGATCTCTAGGGGTCCTGCCTAGGGTTGTC |
| TTCTCCTGACCTGCCCCTGTCCCCTGTGTTTTCCCTCCAGGTCTACACCAGCTCTCAGCCCCTGCGTGTGGGGTAC |
| TATGAGACTGACAACTATACCATGCCCTCCCCGGCCATGAGGCGGGCCGTGCTGGAGACCAAACAGAGCCTTGAGG |
| CTGCGGGGCACACGGTATGACTGCAGGGTCCTGGAAGTACTGGCATCTCCTCCCCTCACGGGAAGCCTTCCTGGTA |
| CCCATGGCTACTCCATCCCTGGCATCCTGGCACTCTGACGATGTTGTCGTCGGGGTGAACTGTGACCCTGTGGGAC |
| AAGTATATAGAGGGCTGATCAAGAGTATTGGAGTGAGTGATTGATGGAGAACTTTAGCCCTGTGCTGTGTGATGTG |
| TGAGCACTGCATGTGGGGAGGCTCTTCAGCTCTAAACAGTGGTGCACAGCTGTCCAGAGGCTCCCAGGGCCAGTGG |
| GTTTTGGTCTGGTCATTACACAACTTTATGTGTGGCTCCAGACTTCTCTCATGCTGTGCATTCCACAGTGAGTTTT |
| CATGGGTCAGTAAGGCTGCCTTTGTAGCTCTAGTGAGAGCTATCTTGTGGGCAGGGTTGGTCCAATCCATCCTCAG |
| GGCCGCCCAGACAGCATGGGGATCATGAAGCCAGTTGTTAGGTCAGGAGGCCTTACACCCCTCAATCCCTGCAGCT |
| GGTTCCCTTCTTGCCAAGCAACATACCCCATGCTCTGGAGACCCTGTCAACAGGTGGGCTCTTCAGTGATGGTGGC |
| CACACCTTCCTACAGAACTTGTGAGTGATAGTGGGCTTTGGGGTCTTGGTGGGATCAGACAAGTAGGCAGACCTGG |
| GGGAGCAGCAGGGTGTGGTGATGCCTGGATGGGCCTTAGCTGAATCCAACAAAGGCCTGAGCACTCTGGGCAGGGA |
| CCTCGCTGTCCCTCCAGCTGGGCACATTGAGCCTGGAGATCCCTTGCCAGGGTGCCAGCCCGAGGGGAGGCTGGGT |
| TGAGTATCTGTGGCCTACCCCTGATCTGAGCTTGTTGTGAGGTAGGAGGTGGGCAGGAGGTTGCCTCTCTGTTTGG |
| GAAGGATTTGGGCCAAGGGCAGGATCCAGGCAGGAGGGTGGGGTTTGGACTTGATGCTGTGACTCCAGGCTCTGT |
| CTGACTTGAGCCAAGTCTTCTTTTTGAGCAGGACCTCAGCTTTCTCTCCTGTAAAGTGGGTGGGTTGGACCAGACT |
| CCCTTTAAGGGACTTTGCAGAGCTCATTTTTAGAGAAGTTCGTTCCTCTGGGATGCTTCTAGTCATTAAAGGTGTC |
| AGGGGCAGAGAACAGGCCTGCAAAGGTGCCTCCTGGTGACATACCTCTGCTGGATGGACTGGAACCCTTCAGAACA |
| CAGTCCCCCTTCCTCCACTTCACTGATGGAGAACTTGGCCCTGCAGCCTGGAGCTTGGCCCTGCAGCTTCACTCAG |
| TCAAGGGCCCAGCCTGTCATGTTCCTTTCCTTCCCCTAGCAGCCAAGTGTGGTCCAGGCTTCAGTGGAAGGGGTCA |
| CTCCTCACTCTGGCCCTGGGAATGAGTCCCCAGGATCAGCTGCCTGAGACCTTTCCCTGAGATCTTGAGCCAGAGA |
| TAGCCTCAGAGCCCTGCTTCATGGGCAGCCCACCCTCGATTTCCCCACCTGTGCCTCCAGGCTGTACCTCCCTAAG |
| GGGAGGTACCCTCAGGGAGGCCTCATCAGGGAGATGTTGCCCTCAGTTCTTAGAGCTCTGAGCTGGGTTTGCTGGA |
| GAGGGATACCCTGAGTCCTGCCTTGGGGAGCTCCCGTGGATGTGGGTTGCAGCCCAGGCATCCCAAAGGATCAGCA |
| GAAACAAACGGCATGTTTGGAAGGAGGGAGCTGAGTCTGGTGAGGAGGGAGGTGGACAGGATCCCTGCATAGAGAAT |
| GGGATTGCTGTGGGCCGGGCGAGCAAGCTGGGAAGGATGTGGGGATGGGAGTGCCTGGACCGAGCATTTTGTTTCC |
| CAGCAAAGGTGATTTCGTGGACCCCTGCCTGGGGGACCTGGTCTCAATTCTGAAGCTTCCCCAATGGCTTAAAGGA |
| CTGCTGGCCTTCCTGGTGAAGCCTCTGGTGAGGGCACAAGGAGTGGAGGGGCTAGGATGGCTGGGGGGGAACCTAG |
| GGCCTCCTATCGCATGATCCCCCATGGCCTCCCTCAGCCTCTCTTGGTTTGGGCAGGCATGGCCTCCTCTTCTCTC |
| CAGTCCCCACCCAGACTGCTCTCCTCCTCTGTCCCCTGCGATCTTCAGCCAACCCGCATGCTGAAAGGGGTGCCGA |
| CCTGGGCCCTGGGGGAGGCATGGAGGGAGGGGTCCCCAGTGGCTTGGCCTGAAGAAGGTTGACGTCTGCCGTGGC |
| CCAGAGCTGAGTCACCGACCCTGCGTCTGTCCTGTGCAGCTGCCAAGGCTGTCAGCTTTCCTCAGCAACATGAAGT |
| CTCGGTAAGGGTTCTTCTGTGTCTAGCTGCCGGCCCCTGCCTGTCCTGATCCGAGTCTGGGTCTGGGTAGTTTCTG |
| ACAGGAAAGGACTTGAGGGAAGTAGCCTCTGAGGCTGGAAGTGGCCCAGGCAGGGGGCAACCTTTGTGGCCTTCA |
| GATGGGACTTTGAAGTTGTCTTGGCAAGGTCCAGTTCTGGCTGGAGAGCAAAGGCCTGAGGGGGACAAGAGGATGG |
| GGGAGTTGGAGGGGAGGAGGTTGACCTGGCTGGGGCATGAGTGGAAAGGACCAGGAAGTGGGGGTTGGCCTGGGCC |
| AAGGGTGGGGCACCCGGGAGAGATGCCACTGTTAGAGATCTGAGCTGACCTGAGCTGCGCCAGGCCCTACTTGCCC |
| CTTAGTGCTTGGGGCTGGAAAAGCAGGGCGTAAACCTCCCTGTTTCATGCCCTGACGTCCCATGGACTCACTCCTT |
| CCCTTACCACCAGGCTTCAGGACTGGCAGCAGCTATGGCCTCTCCCGTGTCCTGAGGGTAGCGAGGAATCGGGCCT |
| GGGCTAGTCCTGGCTCTGCTGTGGAGTCACCAAGTGCCAGCCTGTGCCCCTCGGGGCCTGATTTTCTCATCCAGA |
| CAGTAGGGGTTTGAACTTCCCTCTCAGAGCTCCCATGGGGTTGTGAAGGGTCCACGGAGGGGTGAGATCTAGAGGG |
| TTGGCAGTAGGGGTCTGATGTTGCTGATCTCCGTGGCTGTGACCATCATGGCTGGTGACCACACTCCTTCTGCCCA |
| GTTCGGCTGGAAAACTCTGGGAACTGCAGCACGAGATCGAGGTGAGGCCAGAGCCTCTGGATTGGAGCAGGGTGGT |
| GGGGGGAGGGTGGAGTTGGACAGGGTACCCGCTAGCAGTGTCTCGTGGCCACTGCCCCATGGGGCTCCTAGACTG |
| GCCTGTCATCCCCCTTCCACTCCCTGGACCACCACTTGGGCCCAGCTCTCTGACCCTTACTTGCCTAGATGCCCAT |
| CCTTTGAGGCTGGGTCAGCCCCAGGCTCCTGTCCTGGCCGCCTTTTTGCCCCTCTGGAGCTGCCTTTGTGTGGCTC |
| CGCCTCAGCGGGAAGAGGTGTATCCACAATTCATTCTGGAGGCAGAACGACTGATGCCCTCTGAGAGGCAGCACTG |
| CCTGCCCGGAGGACCTGTGTCCCACTGTGCTCTGTTCAGATCCAGGGCAGGTGCTGGGGCAGAGCCACCCCAG |
| CCACAGTCCCTGAGTTAAAGAGCCTGGGGTGGGCTAGGTCTGAGTGCTTTCACCTGGTGTGTTGTGTCCTCCGCAG |
| GTGTACCGCAAAACCGTGATTGCCCAGTGGAGGGCGCTGGACCTGGATGTGGTGCTGACCCCCATGCTGGCCCCTG |
| CTCTGGACTTGAATGCCCCAGGCAGGGCCACAGGTGAGGCCCGACACCCTGCCTGTCCCTTCTGTGAATCTGGCCA |
| TGTGCCCTGCAGGGCTGCGAGGAAATGGAAGAAGAGCCCTCTGGGAGGACCCTGCCCTCTCGGGGCCCACAGTCTG |
| GCTGACTGGAGACATGGCAGTCATGTGGGTTGCCCTGGCAGGGATTGATTTTCCTGTCATCAGCACTATTCAAGTT |
| GGGGATCTTGAGTTACAGAATCTAGTTTGGGGAGGTGATGGTTTGAAGTCCAGGTGGGATTTAGATAAATCAAGAA |
| AATAGGGGCCAGGGCGGTGGCTCACACCTATAATCCGAGCACTTTGGGAGGCTGAGGCTGGAGGATCAGTTTGAGCC |
| CAGGAGCTCAAGAGCAGTCCAGGCAACATAGTGAGGCTCCTGTTGCTACAAAAAATAGAAAATTAGCTGGGTGTG |
| GTTGCATGTTCCTGTAGTCCTGGCTACTCGGGGGCTGAGGCAGGAGGATTGCTTGAGCCCAGGAGGTCAAGGCTG |
| CAGTGAGTTATGATCACACCACTGCACTCCAGCCTGGGTGACAGAGTGAGACTGTCTCAAAAAAAGGAAAAGGAAA |
| AGAAAACAGGAACAGCATTCCCAGTGGAGAAAGTACATGGGCAAAGGCATGGGGCAAACATCAGTGGGTTGTCCAG |
| CCCGGCCCTGAAATCTGAATTCCTGGGCTTTGTCACTCAGACCTCAGTCCTGGGAGAGCCTTTCTCTGGCTGTA |
| GACACAGGGTGCCATTTCATATGAGGTTTGACTCAGGCCCGGAGTTGGCACTGAAGATTCTCAGGGCCTGCTGCAG |
| CTGCCTGTAATGTGTTCCAGGGGCCGTCAGCTACACTATGCTGTACAACTGCCTGGACTTCCCTGCAGGGGTGGTG |
| CCTGTCACCACGGTGACTGCTGAGGACGAGGCCCAGATGAACATTACAGGGGCTACTTTGGGGATATCTGGGACA |
| AGATGCTGCAGAAGGTGAGGACTGACCTGCCCCTCAACTGGACTCACTCCCCACCCTGACTCTGGCCGCTGTGGAG |
| GAAACAGTACCAGCACTGCGGGTTTGCCAGCCTTTCTTAAGCAAGACCTGAAGGACTATGGCCTGGCCCTACGTTG |
| TGGCCTCTCTCTAGCTGGGTGCTTCCTGGGCCTGGGGTGGGGAGTCCTGCCTTGCTAACCCTATCCTGATGCCTG |

-continued

Sequences

```
TATCCCCTATAGGGCATGAAGAAGAGTGTGGGGCTGCCGGTGGCCGTGCAGTGTGTGGCTCTGCCCTGGCAAGAAG
AGTTGTGTCTGCGGTTCATGCGGGAGGTGGAGCGACTGATGACCCCTGAAAAGCAGTCATCCTGATGGCTCTGGCT
CCAGAGGACCTGAGACTCACACTCTCTGCAGCCCAGCCTAGTCAGGGCACAGCTGCCCTGCTGCCACAGCAAGGAA
ATGTCCTGCATGGGGCAGAGGCTTCCGTGTCCTCTCCCCAACCCCCTGCAAGAAGCGCCGACTCCCTGAGTCTGG
ACCTCCATCCCTGCTCTGGTCCCCTCTCTTCGTCCTGATCCCTCCACCCCCATGTGGCAGCCCATGGGTATGACAT
AGGCCAAGGCCCAACTAACAGTCAAGAAACAGCTCCTCGTCTGTGTGGTTTCTGGGCGTCATCGTGAGGGTGGGGT
TTGGAGCCTGTTGAGAGCAGGGCTGGCTTGACTGTGCATACCCAGGCTCCAGCCATGCCAGTCTCCTGCTCCACAA
CCTCCCCTGGTGCCCATCACCCACAGGAGGGGTGCAGGCTTGTATCCCCAGCACTTCGGCCGTGCCCCTCCTCTC
TCACCTACACTAAGCCCTGCTCTGCTGGACACTGCCCTTGGTCTCCTTCCTTCTTCTGCTTCTTTCCCTGCCTAGA
AAGCTCTTTCTGTTCCTCTGCTTTCTATCCTTTGAGACCTGACTCAGATCCTTCTCTCTCCAGGACACCTTTCCTC
CTCCCTCTGGGCCCTGGAGTATATGGGCTATTTCTTCCCAGTCTGCCCTGTGTGGTGGGCATTGGTGGGTGTGTCT
GCCTGCCTTAGCACACTGGCTTTCCTTGACGGCAGGGAACCCATTGCCACATCTCTGTCTTCTGTGGCCAGCACGG
CAGCAGGGGAAGCACTGAGTTGGGTTGCAGAGAGTCCGAAGTGCTGGCCCTGAGCTGCTGCTGTTTGGGAGAGGAG
CCCATGGGCCTGGGGAGGCCGGCATGAGACAAGGCTGACCTGGTAGAGTGTGCTCTCAGGGCTGGCCAAGGCCTGGA
TTGCCCTGGGAAGGTTTCCTGAAGGAGGTGGACGTGTGTTGAGTCTAGAAGTTTTCCAGAGACTGAGCTAGGGGTT
GAGGACATCTCAGAGAGAAGGGACAGTATGCCCAAAGATCAGGGTGGGTTTGCTAAATGGCAGGCATGTTGAATGG
GCACAGGGGAAGCAGAGATATAGGTGAGGACAGATCAAGGTGGACTTGGGCAGCCAGGTCAGGAACTTGAGTTCTG
TCTCAAGGACAGTGGGACTCTGGAAAGATCATAGCTCGGCCTGAGGACTAGACTCGTGGGGCAAAACCTGTAGAAG
GGTAAAGAAGCTGCTCCATGATCCCTAATTTGGGGAGAGGGGCCTAAAGCCTGAACCTTGGCCCAGGGGTAAAGAG
GGGCCCTTTGGGAATTGACAGGATGGAGGTGAGCTGTCTCAGCTCGTCTGCTATCCACCTCTTACTGGACTATGTC
ACCTGGCTGGTAGAAAGGTGGCATCTGTAGCCGACCCTAGGAGTTTCCTTCTTTTTTTTTTTTTTTTTAGCAGAGTT
TCGCTCTTGTTGCTCAGGCTGGTGTGCAATGGTGTGATCTCGGCTCACTGCAACTCCGCCTCCTGGGTTCAAGCAA
TTTTCCACCTCTTGGGTTCAAGTGATTCTCCTGCCTCAGCCTCCTGAGCAGCTGGGATTACAGGCATGCGCCACCA
TGCCCGGCTAATTTTGTATTTTTAGTAGAGACGGGGTTTCTCCATGTTGGTCAGACTGGTCTTGAACTCCCGACCT
CAGGTGATCCGCCCACCTCGGCCTCCCAAAGTGCTGGGATTACAGGTGAAAGCCACCATGCCCGGCTGACCCTAGG
AGTTTCTTAACCCCATTAGCCCAGTTGCTTTGCTCTTCCCTGGCCCCAGCCCTAATTCTCCTGCTGGCTGGAGATG
TTTCAGAGCCTGAGCCCTCTAGGTAGGGCAGGTCCACGGCTCCTACCTGTCTGTCTCAGATTCTTTCTAGAAGAGT
TGCCTTCCCAAGACTTCCTTCTCCACCCTGGTTTTCATACTCCTCCAGAAGTGCTTTGCCCTCCAGGTTGCCACAC
CCATTGGCGCCTGCACCATCTCCCAGTGCCATCCCTGCCTCTGTGGGGCCATTTTCAGGGCAGAGGTGAGGTCCCA
ACCTACATGGGGACACCCAGATTGGGACATCTAGGTAGATGCTGCACTTTGCCCTGATTTCTTGTAACCACTGCTG
TAATTTTGCCTTTTTCATAAAACCACTACCATCTGCCCCAGCTTCCTCCTCCTGCCCCATTTCTCTCTTTCAGTTA
CCGATATCTTTGTGCCTTCAGACACGAGGCTGCAGAGTGGAGGTGCCTTCACTCGTTCATTGATTCAGCCCTTGGA
GCCTCAGCATGGCCATGTCCAGACCTCAGCTGACCTGAGTCAAGCCTGGGCTTCTGGGGACGTGGACATTGACACA
AACACATCTGTTCCTCCTGTGATTAGGGCTGGGGGACAGGATAGACAAGGGGTCAAATGCTGCCAAGGGGAGGGGG
AAGTGGTCACTGAGGCTAGTACATGGCCACTGTGTTTCATCTCCACCACCATGCTCTAGTCCAAGCCACCTCCCTC
ATCTGGACGCTGCAGTGACTTCCCTTCTGGGCTCCCTGCTTTCAACCCTGGCTGCCCTCTAATCCATTCTCCACAC
AGAGCTGGAATGATCTTTTAAAAGTATAAATCAGGCTAGGCGCAGTGGCTCATGCCTGTAATCCTCGCACTTTGGG
AGGCTGAGGCGGGTGGATCACCGAGGTCAGGAGCTCCAGACTAGCCTGGCCAACATGGCGAAACCCTGTCTCTACT
AAAAGTACAAAAAGTCTTGACAGGCATGGTGGCGTGCATCTGTAGTCCCAGCTACTGAGGAGGCTTGGAACGTGGC
TCCAATGTCACCTTCCCTGCTCACCCATTTATAAAACGGCCTCCTTTATTTCTTTTTCTTTTTTTGAGACGGAGTC
TAGTTCTGTTGCCAGGCTGGAGTGCAGTGGCGCGATCTCAGCTCACTGCAACCTCCACCTCCTGGGTTCAAGCAAT
TCTCTTGCCTCAGCCTCCTGAATAGCTGGGATTATAGGCAAGCGACACCACGCCCAGGTAGTTTTTTTTTTTTTTT
TGAGATAGAGTCTTGCTCTGTTGCCCAGGCTGGAGTGCAGTGGCGCGATCTTGGCTCGCTGCAACCTCCCTCTGCC
TCCCGGGTTCAAGCGATTCTATTGCCTCAGCCTCCTGAGTAGATTGAATTACAGGCACGCGCCACCATGCCCAAGC
TAATTTTTGTATTTTTAGTAGAGACAGGGTTTCACCATGTCACCAGGATGGTCTTGATCTCCTTACCTCGTGATC
TGCCCGCCTCGGCCTCTCAAAGTGCTGGGATTACAGGTATGAGCCACCACGCCCGGCCTTGGTTTCTTGATTATCT
CAAGCTGGGCCCTGCTTCAGAGCTTTCATGTTAGCTCTTCTCTCTGCTTGGAACACGCAGCTCCAATGTCACCTTC
CCTGCTCACCCATTTATAAAATGGCCTCCCTTGTTACTCTCTTTTCTTTTTCTTTTTTTCTTTTTTCTGAGACG
GAGTCTTGCTCTGTTACCCAGGCTGGAGTGCAGTGGCATGATTTTGGCTTACTGCAACCTCTGCCTCCCGGATTCA
ACCAATTCTCCTGCCCCAGCCTCCCAAGTAGCTGGGATTACAGGTGTCTGCCACCATACTCAGCGAATTTTTGTAT
TTTTAGTTGGGACGGGGTTTCAACATGTTGGTCTGGCTGGTCTTGAGCTTGTGATCTGCCTGCCTGGGCCTCCCAA
AGTGCTGGGATTACAGGGGTAAGCCACTGCACCCGAGCCCTTGTTTCTTTCTTTTTTTTTTTTTTGTTTTTT
TTTGACAGAGTCTCACTCTGTCGCCCACGCTGGAGTGCAGTGGCACGATCTTGGCTCACTGCAACCTCCGCCTCCT
GGGTTCAAGCGGTTCTCCTGCCTCAGCCTCCTGAGTAGCTGGTATTACAGGCGTGCGCCACCACGCCCAGCTAATT
TTTGTATTTTAGTAGAGATGGGGTTTCACCATGTTGGTCAGGCTGGCCTCGAACTCCTGACCTCATGATCTGCCTG
CCTGGGCCTTACAGGCATGAGCCACCACGCCCTGCCCCTTGTTACTTTCTAATAGGTTACCCTTTGTTCTTTTTT
TTTTTTTTTTTTATTAAGACAGGATTTTGCTCTTGTTGCCCAGGTTGGAGTGTAATGGCAGGATCTTGGCTCACT
GCAAACTCTGCCTCCTGGGTTCAAGCAATTCTCCTGCCTCAGCCTCCCAAGTAGCTGGGATTACAGGCATGCGCCA
CCATGCCCAGCTAATTTTGTATTTTTAGTAGAGACAGGGTTTCTCCATGTTGGTCAGGCTGGTCTTGAACTCCCGA
CCTCAGGTGATCCACCCTCCTGGGCCTCCCAAAGTGCTGGGATTACAGGTGTGAGCCACCTCGCCTGGCCACCCTT
TGTTCTTTGTAGCATTATCACTCTCTGAGCTCTTTGATGTTTTTTGCTCCTCCACTAAACCATAAGCTTCCTGA
GAGCTGTGCTTTGTCTTGTTCATCACTTGTTCTTGGCTTAGAGGATGGTGCTCCACAAATTCTGGGATGATAAAGT
GTGGCTGTGTGAGGGGCCAAGGCACTGTGCTGGGTGCTGGCAGTGACAAATGAGGCAGCCCTGGCCCTGTCCTCG
TGGAGCTCACATTCTGGAGGGATTTGTTGAATGAACAGAAGGGGGACAGAGAGTTGTGCTAATGAAGACCTCTAAA
TATTTAATGTCTGGAGTGATAACATGACTTTTGATCCGGAAAAAGGGGAAAGGGAATTCTAGACCACATTTACTG
AGTACCTACTATGAGCCATCTACTTTCTGGGCACTTCACAGTCATGCCATTTAATCCTCTGTGAACCCTATGATGG
GCATTTTTGCCCCCCTTTTACAGAAAGTTTACGTATCTTGCCCAGGGTCCCACAGCTAGAAGTTGGGGGCTTGAA
CCGAAAGCTAGGCCCAGTCTGTCAGCAACTGCATGAGGTCTTTCTGTTGATGCCAAGCCCCAGTGAGTACGATGCC
AGAAGAGTGAGAGCACAAATCAGCCTCCTCCTCATACCTCTCTGACCACCAGTGTGCTGGTGGCTACTGCCTGTTT
TCATGGCCTTTCCCCTTCTCACCGGGTCCACTGCCACAGCTTCTTTTTTTTTTCGAGACGGAGTTTCGCTCTTGT
TGTGCAGGCTGGAGTGCAATGGCGAGATCTCAGCTCACTGCAACCTCTGCCTACCGGATTCAAGTGATTCTCCTGC
CTCAGCCTCCCGAGTATC
```

SEQ ID NO: 40-amino acid sequence of wild-type human FAAH (without hypomorphic rs324420 SNP)
MVQYELWAALPGASGVALACCEVAAAVALRWSGRRTARGAVVRARQRQRAGLENMDRAAQRFRLQNPDLDSEALLA
LPLPQLVQKLHSRELAPEAVLFTYVGKAWEVNKGTNCVTSYLADCETQLSQAPRQGLLYGVPVSLKECFTYKGQDS

| Sequences |
|---|
| TLGLSLNEGVPAECDSVVVHVLKLQGAVPFVHTNVPQSMFSYDCSNPLFGQTVNPWKSSKSPGGSSGGEGALIGSG<br>GSPLGLGTDIGGSIRFPSSFCGICGLKPTGNRLSKSGLKGCVYGQEAVRLSVGPMARDVESLALCLRALLCEDMER<br>LDPTVPPLPFREEVYTSSQPLRVGYYETDNYTMPSPAMRRAVLETKQSLEAAGHTLVPFLPSNIPHALETLSTGGL<br>FSDGGHTFLQNFKGDFVDPCLGDLVSILKLPQWLKGLLAFLVKPLLPRLSAFLSNMKSRSAGKLWELQHEIEVYRK<br>TVIAQWRALDLDVVLTPMLAPALDLNAPGRATGAVSYTMLYNCLDEPAGVVPVTTVTAEDEAQMEHYRGYFGDIWD<br>KMLQKGMKKSVGLPVAVQCVALPWQEELCLRFMREVERLMTPEKQSS |
| SEQ ID NO: 41-amino acid sequence of human FAAH that contains the<br>hypomorphic SNP rs324420 (bold)<br>MVQYELWAALPGASGVALACCEVAAAVALRWSGRRTARGAVVRARQRQRAGLENMDRAAQRFRLQNPDLDSEALLA<br>LPLPQLVQKLHSRELAPEAVLFTYVGKAWEVNKGTNCVTSYLADCETQLSQATRQGLLYGVPVSLKECFTYKGQDS<br>TLGLSLNEGVPAECDSVVVHVLKLQGAVPFVHTNVPQSMFSYDCSNPLFGQTVNPWKSSKSPGGSSGGEGALIGSG<br>GSPLGLGTDIGGSIRFPSSFCGICGLKPTGNRLSKSGLKGCVYGQEAVRLSVGPMARDVESLALCLRALLCEDMER<br>LDPTVPPLPFREEVYTSSQPLRVGYYETDNYTMPSPAMRRAVLETKQSLEAAGHTLVPFLPSNIPHALETLSTGGL<br>FSDGGHTFLQNFKGDFVDPCLGDLVSILKLPQWLKGLLAFLVKPLLPRLSAFLSNMKSRSAGKLWELQHEIEVYRK<br>TVIAQWRALDLDVVLTPMLAPALDLNAPGRATGAVSYTMLYNCLDEPAGVVPVTTVTAEDEAQMEHYRGYFGDIWD<br>KMLQKGMKKSVGLPVAVQCVALPWQEELCLRFMREVERLMTPEKQSS |

The invention claimed is:

1. A method of treatment of nociceptive, neuropathic, inflammatory or idiopathic pain, comprising administering an effective amount of an inhibitor of fatty-acid amide hydrolase pseudogene (FAAH-OUT) to an individual with nociceptive, neuropathic, inflammatory or idiopathic pain, wherein FAAH-OUT is defined by SEQ ID NO: 5, and wherein the inhibitor is a guide RNA comprising a guide sequence that hybridizes to FAAH-OUT and targets a CRISPR-Cas enzyme to FAAH-OUT.

2. The method according to claim 1, wherein the guide sequence targets the CRISPR-Cas enzyme to a regulatory region of FAAH-OUT.

3. The method according to claim 1, wherein the guide sequence targets the CRISPR-Cas enzyme to a promoter of FAAH-OUT.

* * * * *